United States Patent
Saito et al.

(10) Patent No.: US 10,968,229 B2
(45) Date of Patent: Apr. 6, 2021

(54) SEVEN-MEMBERED RING COMPOUNDS

(71) Applicant: Idemitsu Kosan Co., Ltd., Chiyoda-ku (JP)

(72) Inventors: Masatoshi Saito, Sodegaura (JP); Hideaki Nagashima, Basel (CH)

(73) Assignee: Idemitsu Kosan Co., Ltd., Chiyoda-ku (JP)

( * ) Notice: Subject to any disclaimer, the term of this patent is extended or adjusted under 35 U.S.C. 154(b) by 265 days.

(21) Appl. No.: 16/092,834

(22) PCT Filed: Apr. 12, 2016

(86) PCT No.: PCT/IB2016/052066
§ 371 (c)(1),
(2) Date: Oct. 11, 2018

(87) PCT Pub. No.: WO2017/178864
PCT Pub. Date: Oct. 19, 2017

(65) Prior Publication Data
US 2019/0119291 A1 Apr. 25, 2019

(51) Int. Cl.
| | | |
|---|---|---|
| *C07D 487/14* | (2006.01) | |
| *C07D 487/18* | (2006.01) | |
| *C07D 403/10* | (2006.01) | |
| *C07D 513/14* | (2006.01) | |
| *C07D 519/00* | (2006.01) | |
| *H01L 51/00* | (2006.01) | |
| *H01L 51/50* | (2006.01) | |

(52) U.S. Cl.
CPC ......... *C07D 487/14* (2013.01); *C07D 403/10* (2013.01); *C07D 487/18* (2013.01); *C07D 513/14* (2013.01); *C07D 519/00* (2013.01); *H01L 51/0059* (2013.01); *H01L 51/0067* (2013.01); *H01L 51/0072* (2013.01); *H01L 51/0073* (2013.01); *H01L 51/0074* (2013.01); *H01L 51/5016* (2013.01); *H01L 51/5096* (2013.01); *H01L 51/5072* (2013.01)

(58) Field of Classification Search
CPC .. C07D 403/10; C07D 487/14; C07D 487/18; C07D 513/14; C07D 519/00; H01L 51/0059; H01L 51/0067; H01L 51/0072; H01L 51/0073; H01L 51/0074; H01L 51/5016; H01L 51/5072; H01L 51/5096
See application file for complete search history.

(56) References Cited

U.S. PATENT DOCUMENTS

| | | |
|---|---|---|
| 2009/0288707 A1 | 11/2009 | Lee et al. |
| 2011/0198579 A1 | 8/2011 | Martin et al. |
| 2012/0068170 A1 | 3/2012 | Pflumm et al. |

FOREIGN PATENT DOCUMENTS

| | | |
|---|---|---|
| DE | 10 2009 023 155 A1 | 12/2010 |
| EP | 2 110 376 A1 | 10/2009 |
| EP | 3 070 144 A1 | 9/2016 |
| SU | 385970 A1 | 6/1973 |
| WO | WO 2010/043693 A1 | 4/2010 |
| WO | WO 2014/044722 A1 | 3/2014 |
| WO | WO 2014/206863 A1 | 12/2014 |

OTHER PUBLICATIONS

International Search Report and Written Opinion dated Jul. 11, 2016, in PCT/IB2016/052066 filed Apr. 12, 2016.
Krasovskii, A. et al., "Synthesis of derivatives of a new heterocyclic system of dibenzimidazo[1,2,2',1'-b,f][1,3,6]thiadiazepine", XP002758746, 1976, 2 pages.
Munz, D. et al., "ortho-Phenylene bridged palladium bis-N-heterocyclic carbene complexes: synthesis, structure and catalysis", Dalton Transactions, RSC Publishing, vol. 42, XP-002758747, 2013, pp. 7297-7304.

*Primary Examiner* — Dawn L Garrett
(74) *Attorney, Agent, or Firm* — Oblon, McClelland, Maier & Neustadt, L.L.P.

(57) ABSTRACT

The present invention relates to compounds of formula (I); a process for their production and their use in electronic devices, especially electroluminescent devices. When used as charge transport material and/or host material for phosphorescent emitters in electroluminescent devices, the compounds of formula I may provide improved efficiency, stability, manufacturability and/or spectral characteristics of electroluminescent devices.

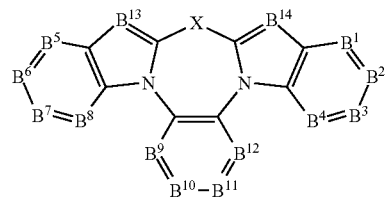

29 Claims, No Drawings

SEVEN-MEMBERED RING COMPOUNDS

The present invention relates to compounds of formula I, a process for their production and their use in electronic devices, especially electroluminescent devices. When used as charge transport material and/or host material for phosphorescent emitters in electroluminescent devices, the compounds of formula I may provide improved efficiency, stability, manufacturability and/or spectral characteristics of electroluminescent devices.

A. N. Krasovskii et al.; Khimiya Geterotsiklicheskikh Soedinenii (1976) 856 (ISSN: 0132-6244) report the synthesis of derivatives of a heterocyclic system of dibenzimidazo[1,2,2',1'-b,f][1,3,6]thiadiazepine

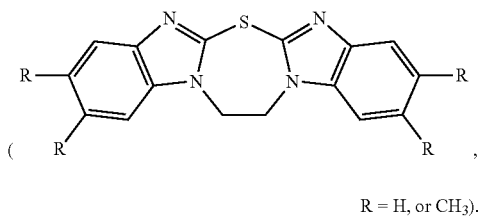

R = H, or CH$_3$).

SU385970 relates to bisbenzimidazo[2,1-b:1',2'-f][1,3,6]thiadiazepine derivatives of formula

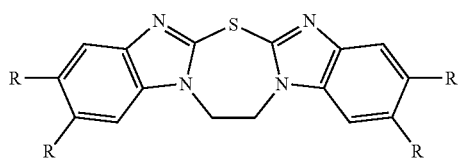

(R=H, lower alkyl), which are prepared by treating the 2-halobenzimidazoles with XCH$_2$CH$_2$X (X=halogen) in an organic solvent containing alkali, followed by cyclization of the intermediate 1,2-bis(2-halobenzimidazol-1-yl)ethanes with a thiolating agent.

Accordingly, it is an object of the present invention, with respect to the aforementioned prior art, to provide further materials suitable for use in OLEDs and further applications in organic electronics. More particularly, it should be possible to provide charge transport materials, charge/exciton blocker materials and matrix materials for use in OLEDs. The materials should be suitable especially for OLEDs which comprise at least one phosphorescence emitter, especially at least one green emitter or at least one blue emitter. Furthermore, the materials should be suitable for providing OLEDs which ensure good efficiencies, good operative lifetimes and a high stability to thermal stress, and a low use and operating voltage of the OLEDs.

Certain seven-membered ring compounds are found to be suitable for use in organo-electroluminescent devices. In particular, said derivatives are suitable charge transport materials, or host materials for phosphorescent emitters having good solubility in organic solvents, high glass transition temperature ($T_g$), wide triplet energy and a potential as ambi-polar materials for OLED.

Said object has been solved by compounds of the formula

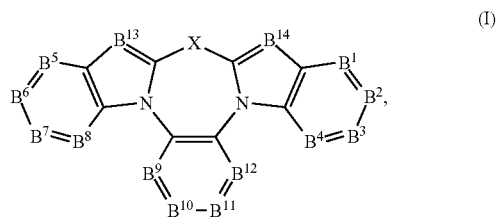

wherein
$B^1$ is N, or CR$^{81}$,
$B^2$ is N, or CR$^{82}$,
$B^3$ is N, or CR$^{83}$,
$B^4$ is N, or CR$^{84}$,
$B^5$ is N, or CR$^{85}$,
$B^6$ is N, or CR$^{86}$,
$B^7$ is N, or CR$^{87}$,
$B^8$ is N, or CR$^{88}$,
$B^8$ is N, or CR$^{89}$,
$B^{10}$ is N, or CR$^{90}$,
$B^{11}$ is N, or CR$^{91}$,
$B^{12}$ is N, or CR$^{92}$,
$B^{13}$ is N, or CR$^{93}$,
$B^{14}$ is N, or CR$^{94}$,
X is NR$^{95}$, S, or O,
R$^{81}$, R$^{82}$, R$^{83}$, R$^{84}$, R$^{85}$, R$^{86}$, R$^{87}$, R$^{88}$, R$^{89}$, R$^{90}$, R$^{91}$, R$^{92}$, R$^{93}$ and R$^{94}$ are independently of each other H, F, CN, a C$_1$-C$_{25}$alkyl group, which can optionally be substituted by E and or interrupted by D; a C$_6$-C$_{24}$aryl group, which can optionally be substituted by G, a C$_2$-C$_{30}$heteroaryl group, which can optionally be substituted by G; or a group of formula -(A$^5$)$_s$-(A$^6$)$_t$-(A$^7$)$_u$-(A$^8$)$_v$-R$^{17}$;
R$^{95}$ is a group of formula -(A$^1$)$_o$-(A$^2$)$_p$-(A$^3$)$_q$-(A$^4$)$_r$-R$^{16}$,
o is 0, or 1, p is 0, or 1, q is 0, or 1, r is 0, or 1,
s is 0, or 1, t is 0, or 1, u is 0, or 1, v is 0, or 1,
R$^{16}$ and R$^{17}$ are independently of each other H, —NR$^{10}$R$^{11}$, —C(=O)R$^{15}$, —Si(R$^{12}$)(R$^{13}$)(R$^{14}$), a C$_6$-C$_{24}$aryl group, which can optionally be substituted by G; or a C$_2$-C$_{30}$heteroaryl group, which can optionally be substituted by G;
R$^{10}$, R$^{11}$ and R$^{15}$ are independently of each other a C$_6$-C$_{24}$aryl group, which can optionally be substituted by G; or a C$_2$-C$_{30}$heteroaryl group, which can optionally be substituted by G;
A$^1$, A$^2$, A$^3$, A$^4$, A$^5$, A$^6$, A$^7$ and A$^8$ are independently of each other —Si(R$^{12'}$)(R$^{13'}$)—, a C$_6$-C$_{24}$arylene group, which can optionally be substituted by G, or a C$_2$-C$_{30}$heteroarylene group, which can optionally be substituted by G;
R$^{12}$, R$^{13}$, R$^{12'}$, R$^{13'}$ and R$^{14}$ are independently of each other a C$_1$-C$_{25}$alkyl group, which can optionally be substituted by E and or interrupted by D; a C$_6$-C$_{24}$aryl group, which can optionally be substituted by G; or a C$_2$-C$_{30}$heteroaryl group, which can optionally be substituted by G; D is —CO—, —COO—, —S—, —SO—, —SO$_2$—, —O—, —NR$^{65}$—, —SiR$^{70}$R$^{71}$—, —POR$^{72}$—, —CR$^{63}$=CR$^{64}$—, or —C≡C—, E is —OR$^{69}$, —SR$^{69}$, —NR$^{65}$R$^{66}$, —COR$^{68}$, —COOR$^{67}$, —CONR$^{65}$R$^{66}$, —CN, or F, G is E, —Si(R$^{73}$)(R$^{74}$)(R$^{75}$), or a C$_1$-C$_{18}$alkyl group, a C$_6$-C$_{24}$aryl group, a C$_6$-C$_{24}$aryl group, which is substituted by F, C$_1$-C$_{18}$alkyl, or C$_1$-C$_{18}$alkyl which is interrupted by O; a C$_2$-C$_{30}$heteroaryl group, or a C$_2$-C$_{30}$heteroaryl group, which is substituted by F, C$_1$-C$_{18}$alkyl, or C$_1$-C$_{18}$alkyl which is interrupted by O;
R$^{63}$ and R$^{64}$ are independently of each other H, C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—;

$R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring, $R^{67}$ is a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{68}$ is H; a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl, $R^{73}$, $R^{74}$ and $R^{75}$ are independently of each other a $C_1$-$C_{25}$alkyl group, which can optionally be interrupted by O; a $C_6$-$C_{24}$aryl group, which can optionally be substituted by one, or more $C_1$-$C_{18}$alkyl groups; or a $C_2$-$C_{30}$heteroaryl group, which can optionally be substituted by one, or more $C_1$-$C_{18}$alkyl groups; with the proviso that not more than two of the groups $B^1$, $B^2$, $B^3$ and $B^4$ represent N;

not more than two of the groups $B^5$, $B^6$, $B^7$ and $B^8$ represent N; and $R^{16}$ is different from H, or —$NR^{10}R^{11}$, if o is 0, p is 0, q is 0 and r is 0.

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices, such as, for example, organic light-emitting diodes (OLEDs).

Accordingly, a further subject of the present invention is directed to an electronic device, comprising a compound according to the present invention. The electronic device is preferably an electroluminescent device.

The compounds of formula I can in principal be used in any layer of an EL device, but are preferably used as host, charge transport and/or charge/exciton blocking material. Particularly, the compounds of formula I are used as host material for green, especially blue light emitting phosphorescent emitters.

Hence, a further subject of the present invention is directed to a charge transport layer, comprising a compound of formula I according to the present invention.

A further subject of the present invention is directed to an emitting layer, comprising a compound of formula I according to the present invention. In said embodiment a compound of formula I is preferably used as host material in combination with a phosphorescent emitter.

A further subject of the present invention is directed to a charge/exciton blocking layer, comprising a compound of formula I according to the present invention.

D is preferably —CO—; —COO—, —S—, —SO—, —$SO_2$—, —O—, —$NR^{65}$—, wherein $R^{65}$ is $C_1$-$C_{18}$alkyl, such as methyl, ethyl, n-propyl, iso-propyl, n-butyl, isobutyl, or sec-butyl, or $C_6$-$C_{14}$aryl, such as phenyl, tolyl, naphthyl, or biphenylyl, or $C_2$-$C_{30}$heteroaryl, such as, for example, benzimidazo[1,2-a]benzimidazo-2-yl

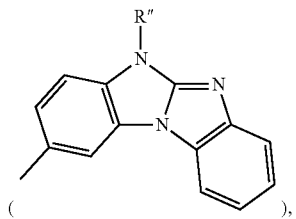

carbazolyl, dibenzofuranyl, which can be unsubstituted or substituted especially by $C_6$-$C_{10}$aryl, or $C_6$-$C_{10}$aryl, which is substituted by $C_1$-$C_4$alkyl; or $C_2$-$C_{14}$heteroaryl.

E is preferably —$OR^{69}$; —$SR^{69}$; —$NR^{65}R^{65}$; —$COR^{68}$; —$COOR^{67}$; —$CONR^{65}R^{65}$; or —CN; wherein $R^{65}$, $R^{67}$, $R^{68}$ and $R^{69}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl.

G is preferably —$OR^{69}$; —$SR^{69}$; —$NR^{65}R^{65}$; CN, a $C_1$-$C_{18}$alkyl group, a $C_6$-$C_{14}$aryl group, a $C_6$-$C_{14}$aryl group, which is substituted by F, or $C_1$-$C_{18}$alkyl; a $C_2$-$C_{14}$heteroaryl group, or a $C_2$-$C_{14}$heteroaryl group, which is substituted by F, or $C_1$-$C_{18}$alkyl; or —$Si(R^{73})(R^{74})(R^{75})$; wherein $R^{65}$, $R^{67}$, $R^{68}$ and $R^{69}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl; $R^{73}$, $R^{74}$ and $R^{75}$ are preferably independently of each other a $C_6$-$C_{14}$aryl group, which can optionally be substituted by $C_1$-$C_{18}$alkyl; or a $C_2$-$C_{10}$heteroaryl group, which can optionally be substituted by $C_1$-$C_{18}$alkyl, such as, for example, a phenyl group.

A $C_2$-$C_{14}$heteroaryl group is for example, benzimidazo[1,2-a]benzimidazo-5-yl

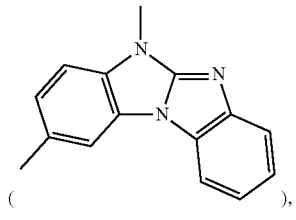 [SMILES: Cc1ccc2c(c1)n1c3ccccc3nc1n2C]

benzimidazo[1,2-a]benzimidazo-2-yl

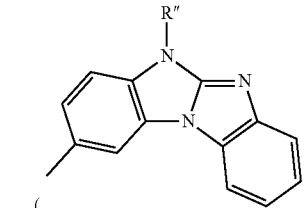

; R″ is $C_6$-$C_{10}$aryl, or $C_6$-$C_{10}$aryl, which is substituted by $C_1$-$C_4$alkyl; or $C_2$-$C_{14}$heteroaryl)

benzimidazolo[2,1-b][1,3]benzothiazolyl, carbazolyl, dibenzofuranyl, which can be unsubstituted or substituted, especially by $C_6$-$C_{10}$aryl, or $C_6$-$C_{10}$aryl, which is substituted by $C_1$-$C_4$alkyl; or $C_2$-$C_{10}$heteroaryl.

In a preferred embodiment the present invention is directed to compounds of formula

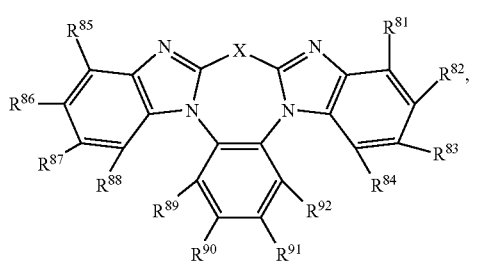
(I')

wherein X, $R^{81}$, $R^{82}$, $R^{83}$, $R^{84}$, $R^{85}$, $R^{86}$, $R^{87}$, $R^{88}$, $R^{89}$, $R^{90}$, $R^{91}$ and $R^{92}$ are defined above, or below.

X is preferably $NR^{95}$, or S, more preferably $NR^{95}$.

The compound of formula (I') is preferably a compound of formula

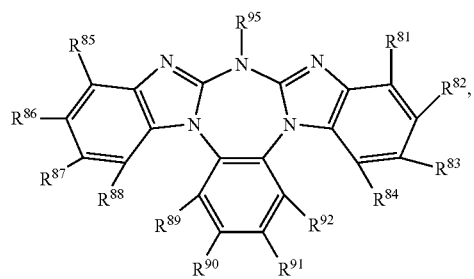
(Ia)

or a compound of formula

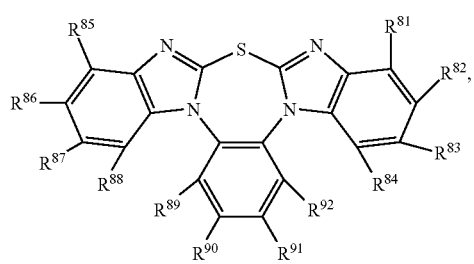
(Ib)

wherein $R^{95}$, $R^{81}$, $R^{82}$, $R^{83}$, $R^{84}$, $R^{85}$, $R^{86}$, $R^{87}$, $R^{88}$, $R^{89}$, $R^{90}$, $R^{91}$ and $R^{92}$ are defined above, or below.

$R^{81}$, $R^{82}$, $R^{83}$, $R^{84}$, $R^{85}$, $R^{86}$, $R^{87}$, $R^{88}$, $R^{89}$ and $R^{92}$ are preferably H.

$R^{95}$ is a group of formula -$(A^1)_o$-$(A^2)_p$-$(A^3)_q$-$(A^4)_r$-$R^{16}$.

$R^{81}$, $R^{82}$, $R^{83}$, $R^{84}$, $R^{85}$, $R^{86}$, $R^{87}$, $R^{88}$, $R^{89}$, $R^{90}$, $R^{91}$, $R^{92}$, $R^{93}$ and $R^{94}$ can be a group of formula -$(A^5)_s$-$(A^6)_t$-$(A^7)_u$-$(A^8)_v$-$R^{17}$.

For the groups of formula -$(A^1)_o$-$(A^2)_p$-$(A^3)_q$-$(A^4)_r$-$R^{16}$ and -$(A^5)_s$-$(A^6)_t$-$(A^7)_u$-$(A^8)_v$-$R^{17}$ the following preferences apply.

$A^1$, $A^2$, $A^3$, $A^4$, $A^5$, $A^6$, $A^7$ and $A^8$ are independently of each other a $C_6$-$C_{24}$arylene group, which can optionally be substituted by G, or a $C_2$-$C_{30}$heteroarylene group, which can optionally be substituted by G.

The $C_6$-$C_{24}$arylene groups, $A^1$, $A^2$, $A^3$, $A^4$, $A^5$, $A^6$, $A^7$ and $A^8$, which optionally can be substituted by G, are typically phenylene, naphthylene, especially 1-naphthylene, or 2-naphthylene, biphenylylene, terphenylylene, pyrenylene, 2- or 9-fluorenylene, phenanthrylene, or anthrylene, which may be unsubstituted or substituted.

The $C_2$-$C_{30}$heteroarylene groups, $A^1$, $A^2$, $A^3$, $A^4$, $A^5$, $A^6$, $A^7$ and $A^8$, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated-electrons such as, for example, benzofuro[2,3-b]pyridylene

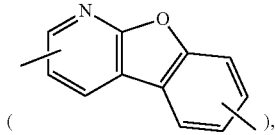
( ), benzothiopheno[2,3-b]pyridylene

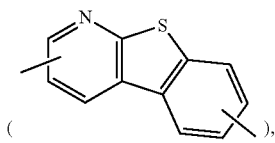
( ), pyrido[2,3-b]indolylene

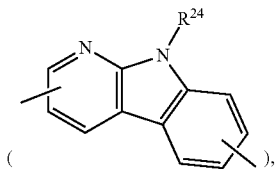
( ), benzofuro[2,3-c]pyridylene

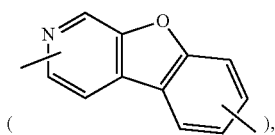
( ), benzothiopheno[2,3-c]pyridylene

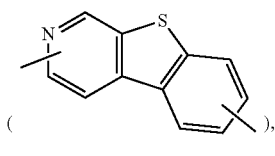
( ), pyrido[2,3-c]indolylene

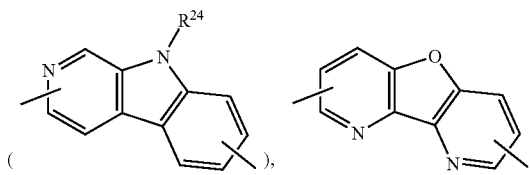

furo[3,2-b:4,5-b']dipyridylene, benzofuro[3,2-b]pyridylene

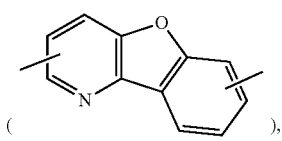

benzothiopheno[3,2-b]pyridylene

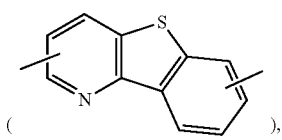

thieno[3,2-b:4,5-b']dipyridylene

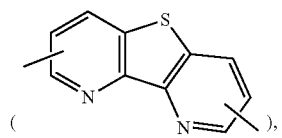

pyrrolo[3,2-b:4,5-b']dipyridylene

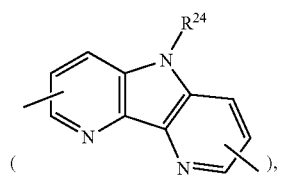

thienylene, benzothiophenylene, thianthrenylene, furylene, furfurylene, 2H-pyranylene, benzofuranylene, isobenzofuranylene, dibenzofuranylene

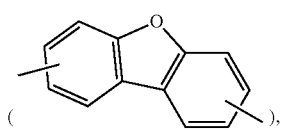

dibenzothiophenylene

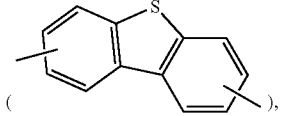

phenoxythienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, chinoxalinylene, chinazolinylene, cinnolinylene, pteridinylene, carbolinylene, benzotriazolylene, benzoxazolylene, phenanthridinylene, acridinylene, pyrimidinylene, phenanthrolinylene, phenazinylene, isothiazolylene, phenothiazinylene

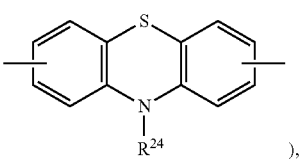

isoxazolylene, furazanylene, carbazolylene

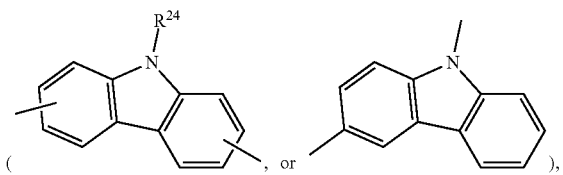

benzimidazo[1,2-a]benzimidazo-2,5-ylene

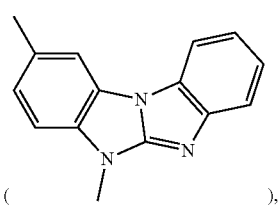 [SMILES: Cc1ccc2c(c1)n1c3ccccc3nc1n2C]

benzimidazo-1,2-ylene

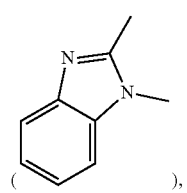

9,9-dialkylacridinylen

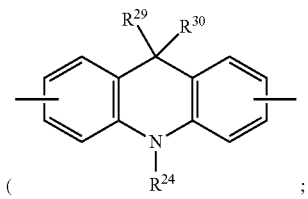

$R^{29}$ and $R^{30}$ are $C_1$-$C_{25}$alkyl), or phenoxazinylene

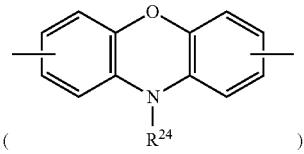

which can be unsubstituted or substituted. $R^{24}$ is a $C_6$-$C_{24}$aryl group, or a $C_2$-$C_{30}$heteroaryl group, which can optionally be substituted by G, wherein G is as defined in above. Preferred $C_6$-$C_{24}$arylene groups are 1,3-phenylene, 3,3'-biphenylylene, 3,3'-m-terphenylene, 2- or 9-fluorenylene, phenanthrylene, which may be unsubstituted or substituted, especially by $C_6$-$C_{10}$aryl, $C_6$-$C_{10}$aryl which is substituted by $C_1$-$C_4$alkyl; or $C_2$-$C_{14}$heteroaryl.

Preferred $C_6$-$C_{24}$arylene groups are 1,2-phenylene, 1,3-phenylene, 1,4-phenylene, 3,3'-biphenylylene, 3,3'-m-terphenylene, 2- or 9-fluorenylene, phenanthrylene, which may be unsubstituted or substituted, especially by triphenylsilyl, $C_6$-$C_{10}$aryl, $C_6$-$C_{10}$aryl which is substituted by $C_1$-$C_4$alkyl; or $C_2$-$C_{14}$heteroaryl.

More preferred $C_2$-$C_{30}$heteroarylene groups are thienylene, benzothiophenylene, thianthrenylene, furylene, furfurylene, 2H-pyranylene, pyridinylene, benzofuranylene, isobenzofuranylene, dibenzofuranylene, dibenzothiophenylene, phenoxythienylene, pyrrolylene, phenothiazin-10-ylene, imidazolylene, indolizinylene, isoindolylene, indolylene, indazolylene, carbazolylene, benzimidazo[1,2-a]benzimidazo-2,5-ylene, phenoxazin-10-ylene, or 9,9-dialkylacridin-10-ylen, which can be unsubstituted or substituted.

The $C_6$-$C_{24}$arylene and $C_2$-$C_{30}$heteroarylene groups may be substituted by G.

G is preferably $C_1$-$C_{18}$alkyl, such as methyl, ethyl, n-propyl, iso-propyl, n-butyl, isobutyl, sec-butyl, hexyl, octyl, or 2-ethyl-hexyl, —$CF_3$, CN, triphenylsilyl, a $C_6$-$C_{14}$aryl group, a $C_6$-$C_{14}$aryl group, which is substituted by F, or $C_1$-$C_{18}$alkyl; a $C_2$-$C_{14}$heteroaryl group, or a $C_2$-$C_{14}$heteroaryl group, which is substituted by F, or $C_1$-$C_{18}$alkyl.

Benzimidazo[1,2-a]benzimidazo-5-yl, benzimidazo[1,2-a]benzimidazo-2-yl, carbazolyl and dibenzofuranyl are examples of a $C_2$-$C_{14}$heteroaryl group. Phenyl, 1-naphthyl and 2-naphthyl are examples of a $C_6$-$C_{14}$aryl group.

Most preferred, $A^1$, $A^2$, $A^3$, $A^4$, $A^5$, $A^6$, $A^7$ and $A^8$ are independently of each other a group of formula

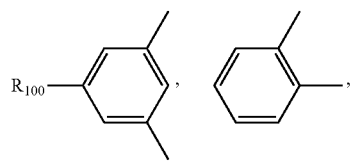

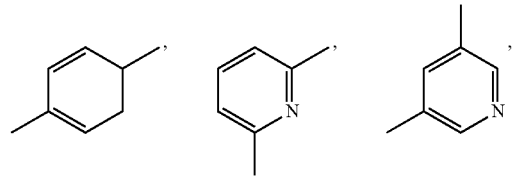

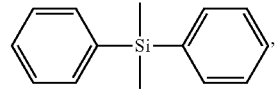

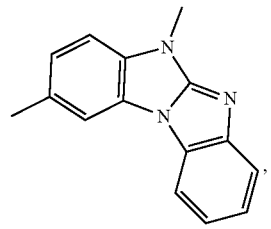

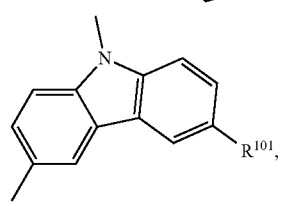

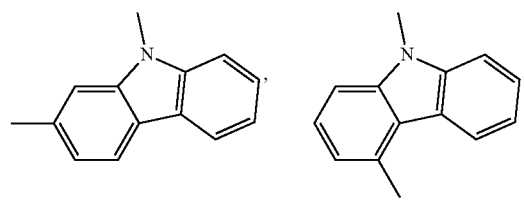

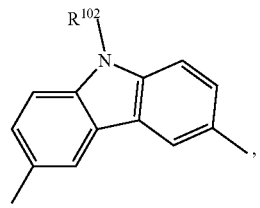

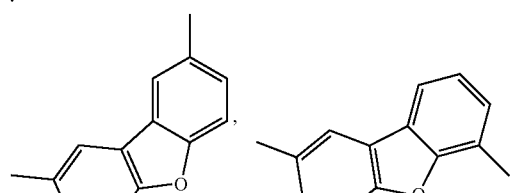

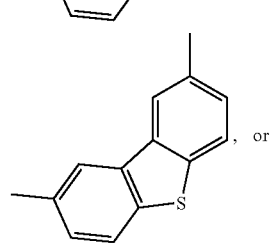

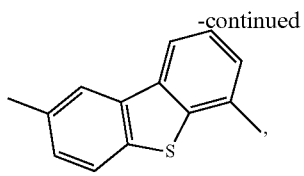

wherein
R$^{100}$ is H, Si(Ph)$_3$, or

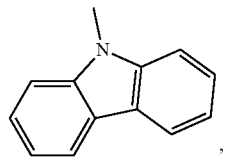

R$^{101}$ is H, or CN, and
R$^{102}$ is a phenyl group.

R$^{16}$ and R$^{17}$ are independently of each other H, —NR$^{10}$R$^{11}$, —C(=O)R$^{15}$, —Si(R$^{12}$)(R$^{13}$)(R$^{14}$), a C$_6$-C$_{24}$aryl group, which can optionally be substituted by G; or a C$_2$-C$_{30}$heteroaryl group, which can optionally be substituted by G Examples of a group of formula Si(R$^{12}$)(R$^{13}$)(R$^{14}$) are a trimethylsilyl group, a triethylsilyl group, a tert-butyldimethylsilyl group, a propyldimethylsilyl group, a triisopropylsilyl group, a triphenylsilyl group, a phenyldimethylsilyl group, a t-butyldiphenylsilyl group, a tritolylsilyl group, a trixylylsilyl group, or a trinaphthylsilyl group.

Examples of the group N(R$^{10}$)(R$^{11}$) include diphenylamino and a phenylnaphthylamino group.

Examples of the group —C(=O)R$^{15}$ include 1-phenyl carbonyl and naphthyl carbonyl.

The C$_6$-C$_{24}$aryl groups, R$^{16}$ and R$^{17}$, which optionally can be substituted by G, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, or triphenylenyl (especially triphenylen-2-yl), which may be unsubstituted or substituted.

The C$_2$-C$_{30}$heteroaryl groups, R$^{16}$ and R$^{17}$, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated π-electrons such as 9H-pyrido[2,3-b]indolyl, benzofuro[2,3-b]pyridyl, benzothiopheno[2,3-b]pyridyl, 9H-pyrido[2,3-c]indolyl, benzofuro[2,3-c]pyridyl, benzothiopheno[2,3-c]pyridyl, furo[3,2-b:4,5-b']dipyridyl, pyrrolo[3,2-b:4,5-b']dipyridyl, thieno[3,2-b:4,5-b']dipyridyl, thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, benzimidazolyl, benzimidazo[1,2-a]benzimidazo-5-yl, benzimidazo[1,2-a]benzimidazo-2-yl, benzimidazolo[2,1-b][1,3]benzothiazolyl, carbazolyl, 9-phenylcarbazolyl, azabenzimidazo[1,2-a]benzimidazolyl, or phenoxazinyl, which optionally can be substituted by G, or a group of formula

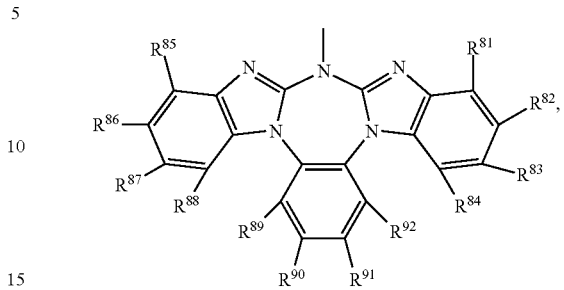

wherein R$^{81}$ to R$^{92}$ are defined above, or below.

The C$_6$-C$_{24}$aryl and C$_2$-C$_{30}$heteroaryl groups may be substituted by G.

G is preferably C$_1$-C$_{18}$alkyl, such as methyl, ethyl, n-propyl, iso-propyl, n-butyl, isobutyl, sec-butyl, hexyl, octyl, or 2-ethyl-hexyl; —CF$_3$, a C$_6$-C$_{14}$aryl group, a C$_6$-C$_{14}$aryl group, which is substituted by F, or C$_1$-C$_{18}$alkyl; a C$_2$-C$_{14}$heteroaryl group, or a C$_2$-C$_{14}$heteroaryl group, which is substituted by F, or C$_1$-C$_{18}$alkyl.

Preferred C$_2$-C$_{30}$heteroaryl groups are pyridyl, triazinyl, pyrimidinyl, 9H-pyrido[2,3-b]indolyl, benzofuro[2,3-b]pyridyl, benzothiopheno[2,3-b]pyridyl, 9H-pyrido[2,3-c]indolyl, benzofuro[2,3-c]pyridyl, benzothiopheno[2,3-c]pyridyl, furo[3,2-b:4,5-b']dipyridyl, pyrrolo[3,2-b:4,5-b']dipyridyl, thieno[3,2-b:4,5-b']dipyridyl, benzimidazol-2-yl

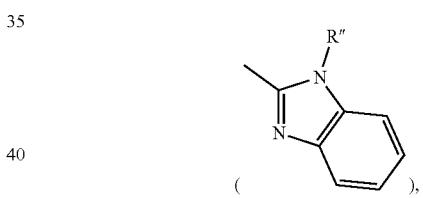

benzimidazol-1-yl

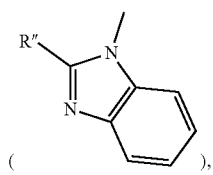

benzimidazo[1,2-a]benzimidazo-5-yl

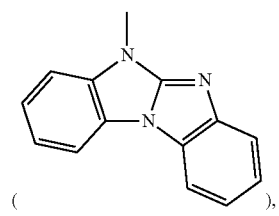 [SMILES: Cn1c2ccccc2n2c3ccccc3nc12]

benzimidazo[1,2-a]benzimidazo-2-yl

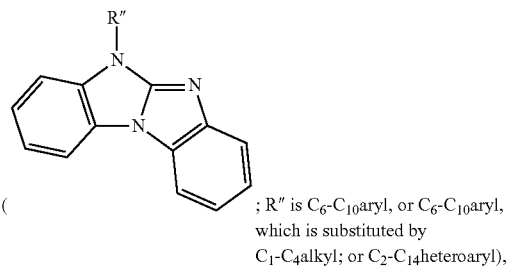

( ; R″ is $C_6$-$C_{10}$aryl, or $C_6$-$C_{10}$aryl, which is substituted by $C_1$-$C_4$alkyl; or $C_2$-$C_{14}$heteroaryl), benzimidazolo[2,1-b][1,3]benzothiazolyl

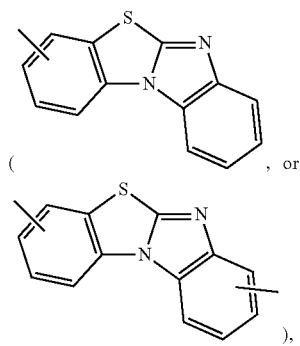

( , or ), carbazolyl, dibenzofuranyl, dibenzothiophenyl, 4-azabenzimidazo[1,2-a]benzimidazo-6-yl

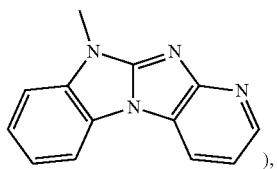 [SMILES: Cn1c2ccccc2n2c3cccnc3nc12]

( ), 3-azabenzimidazo[1,2-a]benzimidazo-6-yl

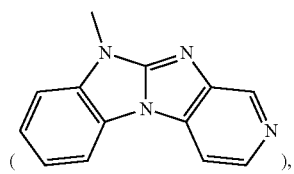 [SMILES: Cn1c2ccccc2n2c3ccncc3nc12]

( ), 2-azabenzimidazo[1,2-a]benzimidazo-6-yl

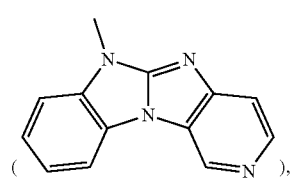 [SMILES: Cn1c2ccccc2n2c3cnccc3nc12]

1-azabenzimidazo[1,2-a]benzimidazo-6-yl

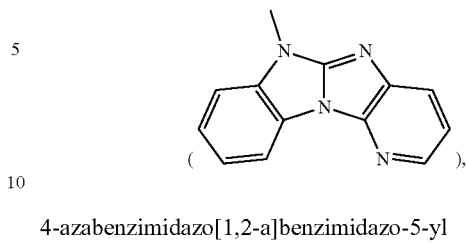

( ), 4-azabenzimidazo[1,2-a]benzimidazo-5-yl

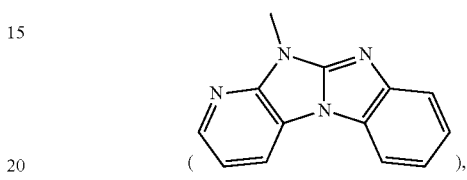

( ), 3-azabenzimidazo[1,2-a]benzimidazo-5-yl


( ), 2-azabenzimidazo[1,2-a]benzimidazo-5-yl

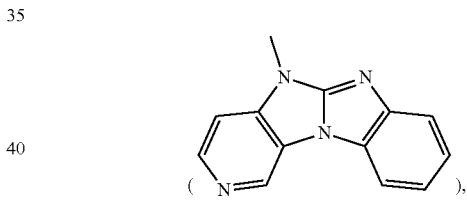

( ), 1-azabenzimidazo[1,2-a]benzimidazo-5-yl

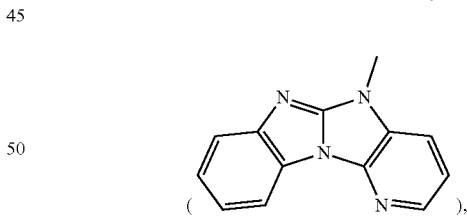

( ), which can be unsubstituted or substituted especially by $C_6$-$C_{10}$aryl, or $C_6$-$C_{10}$aryl, which is substituted by $C_1$-$C_4$alkyl; or $C_2$-$C_{14}$heteroaryl.

Most preferred, $R^{16}$ is a group of formula CN,

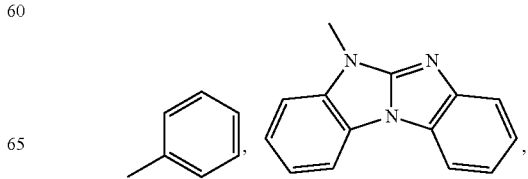

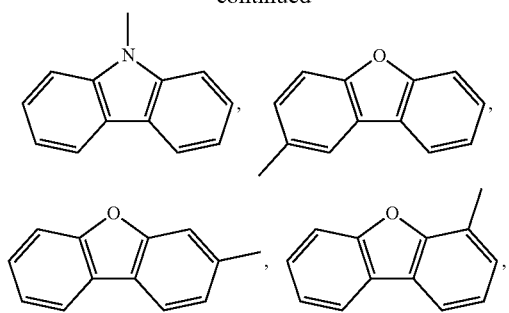
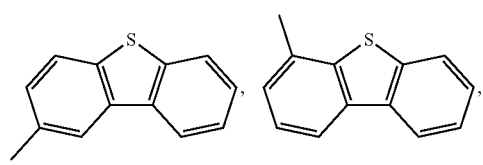
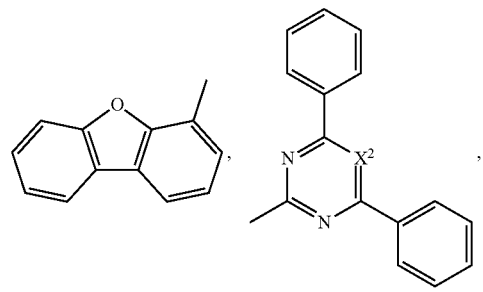
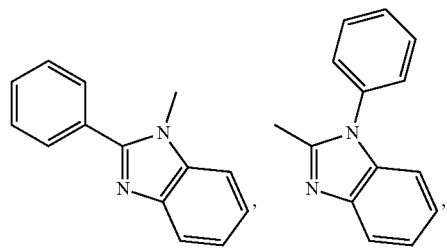
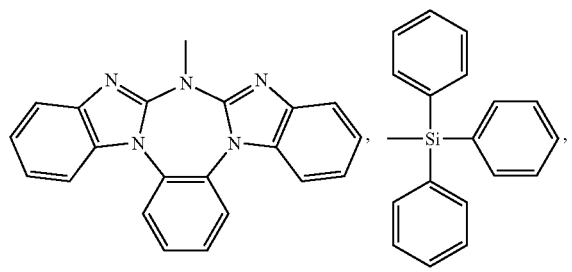
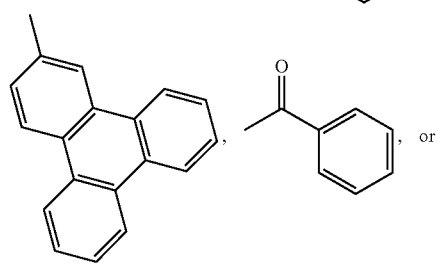
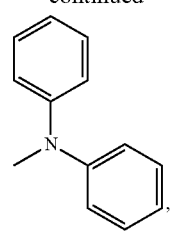
wherein $X^2$ is N, or CH, with the proviso that o is different from 0, if $R^{16}$ is CN, a group of formula
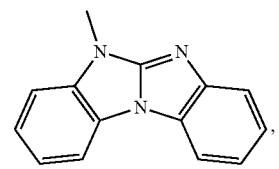
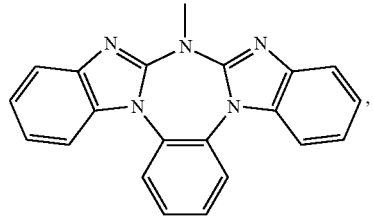
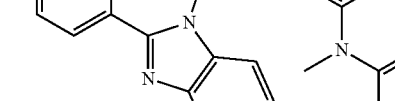, or
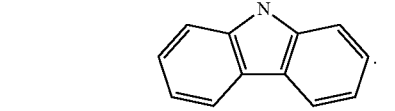
Most preferred, $R^{17}$ is a group of formula CN,
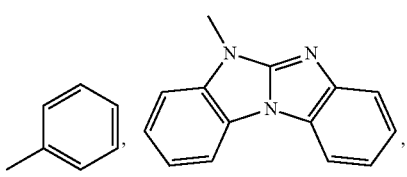
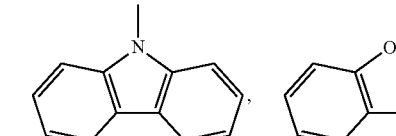
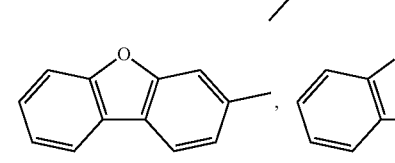

-continued
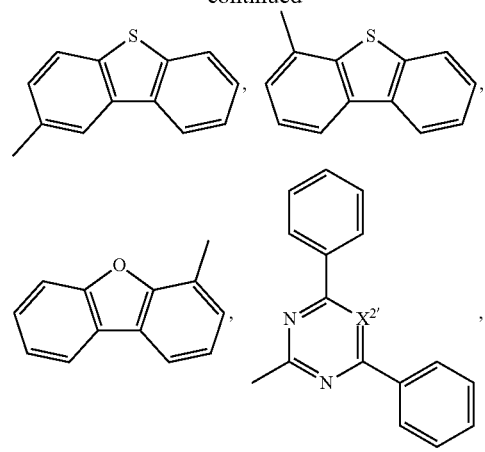
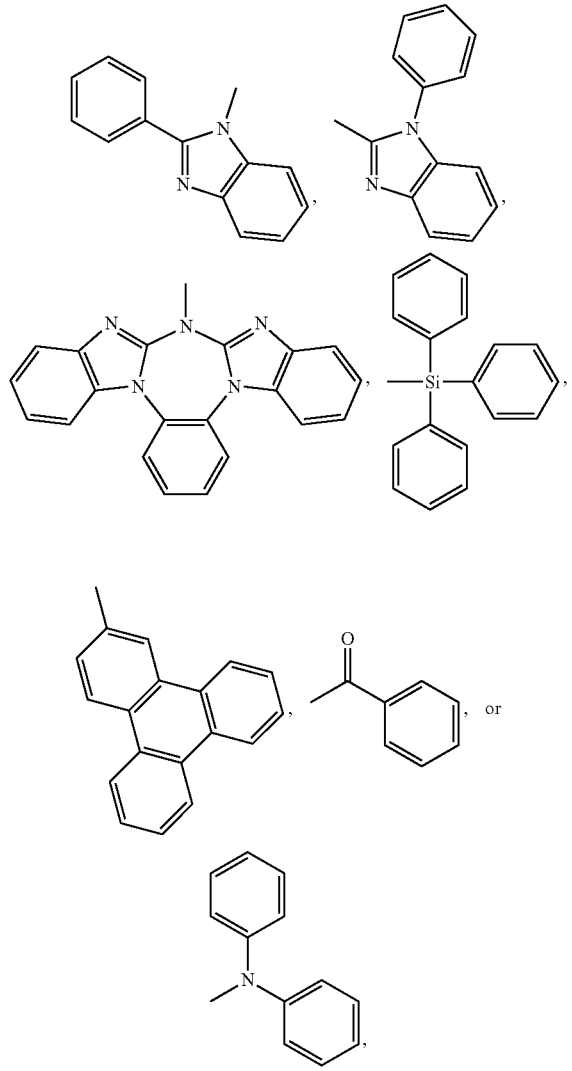
wherein X$^{2'}$ is N, or CH.
In a particularly preferred embodiment, the present invention is directed to compounds of formula
(Ia-1)
wherein
R$^{95}$ is a group of formula -(A$^1$)$_o$-(A$^2$)$_p$-(A$^3$)$_q$-(A$^4$)$_r$-R$^{16}$,
R$^{16}$ is a group of formula CN,

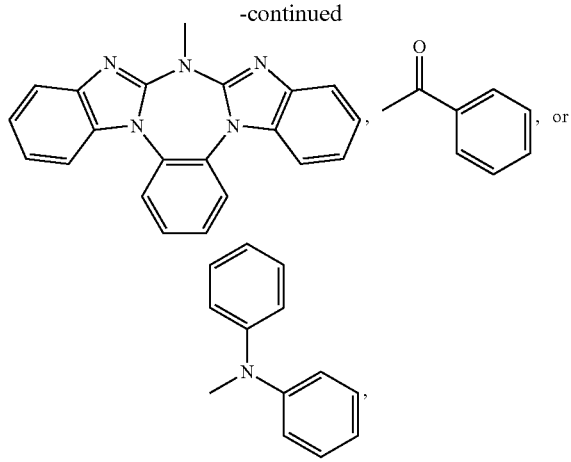

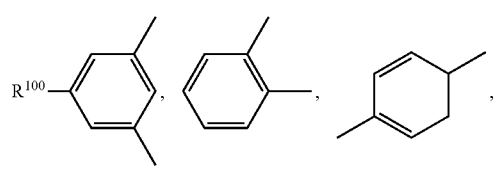

wherein X² is N,
or CH, o is 0, or 1, p is 0, or 1, q is 0, or 1, r is 0, or 1, with the proviso that o is different from 0, if $R^{16}$ is CN, a group of formula

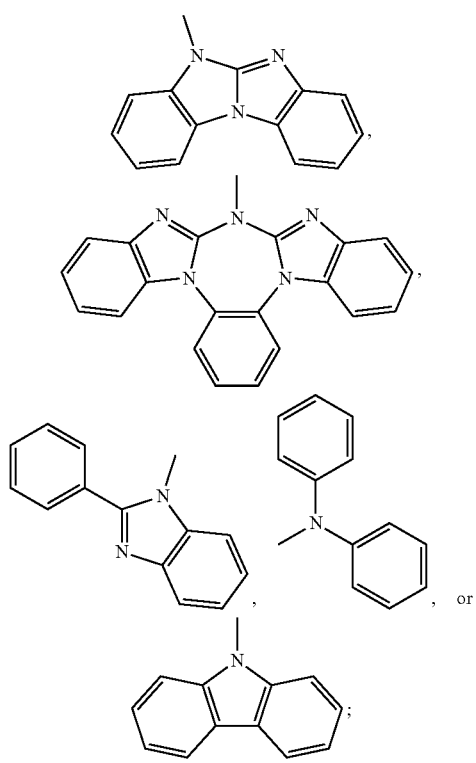

$R^{90}$ and $R^{91}$ are H, or $R^{90}$ and $R^{91}$ are CN, or one of $R^{90}$ and $R^{91}$ is H and the other is CN, one of $R^{90}$ and $R^{91}$ is H and the other is a group of formula $-(A^5)_s\text{-}(A^6)_t\text{-}(A^7)_u\text{-}(A^8)_v\text{-}R^{17}$, s is 0, or 1, t is 0, or 1, u is 0, or 1, v is 0, or 1, $A^1, A^2, A^3, A^4, A^5, A^6, A^7$ and $A^8$ are independently of each other a group of formula

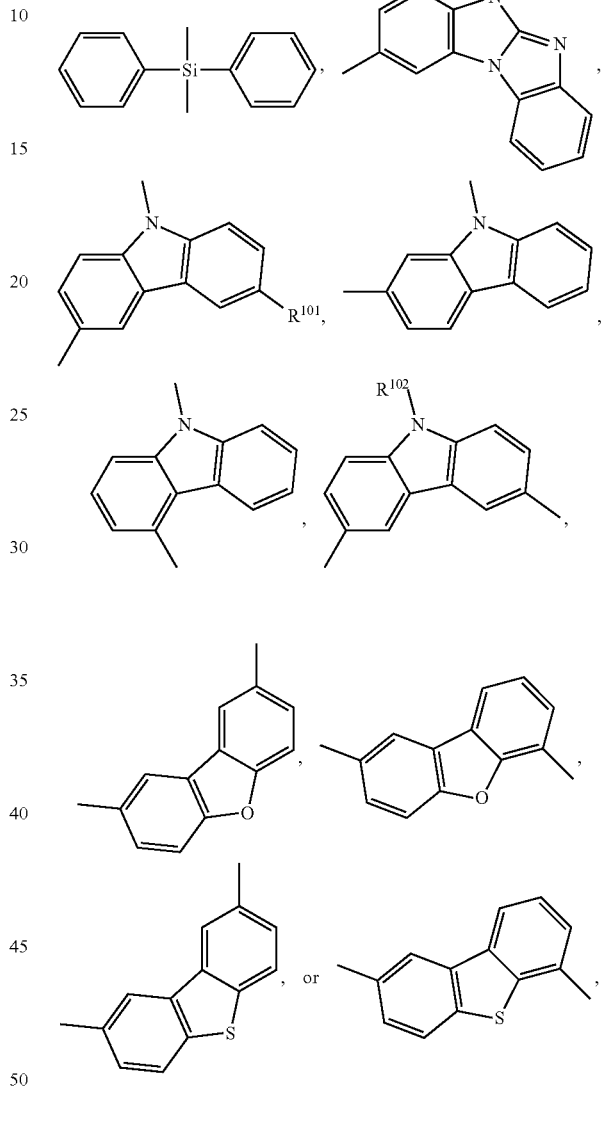

wherein $R^{100}$ is H, Si(Ph)₃, or

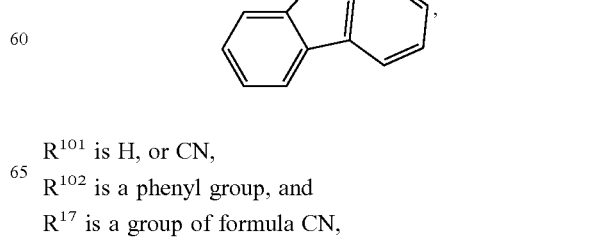

$R^{101}$ is H, or CN, $R^{102}$ is a phenyl group, and $R^{17}$ is a group of formula CN,

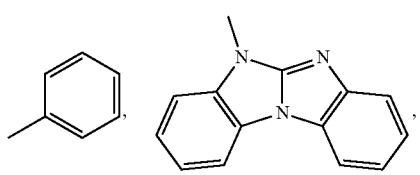
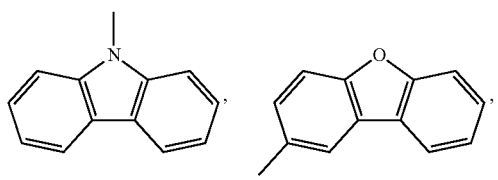
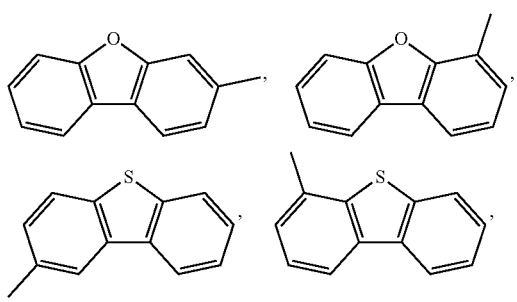
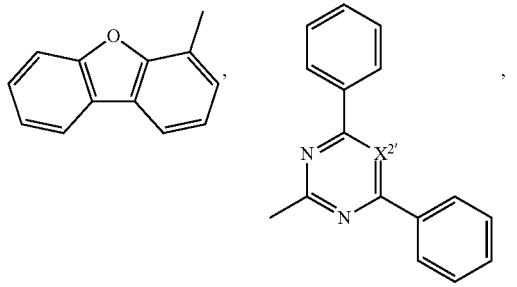
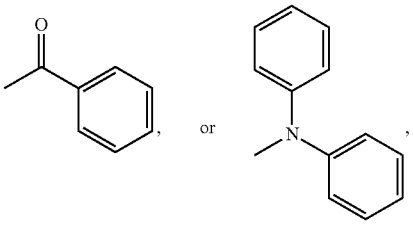
wherein X²' is N, or CH.
Examples of compounds of formula
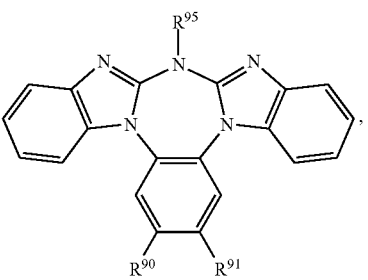
(Ia-1)
wherein R⁹⁰ and R⁹¹ are H, or one of the groups R⁹⁰ and R⁹¹ is a group of formula -(A⁵)$_s$-(A⁶)$_t$-(A⁷)$_u$-(A⁸)$_v$-R¹⁷ and the other is H; are shown below:
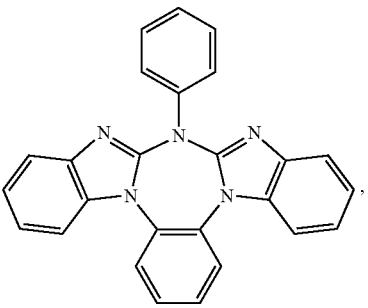
(A-1)
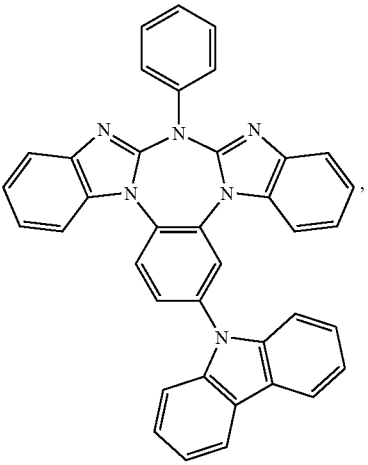
(A-2)

(A-3)
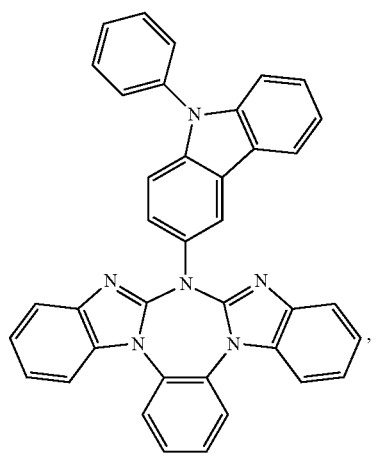
(A-4)
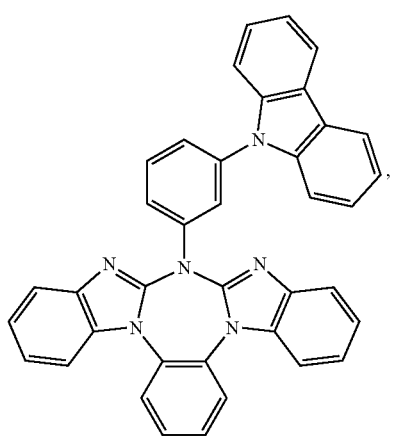
(A-5)
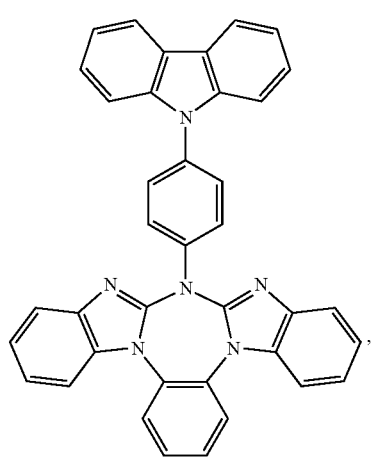
(A-6)
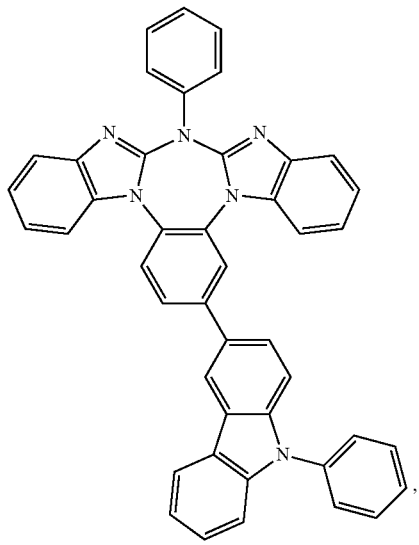
(A-7)
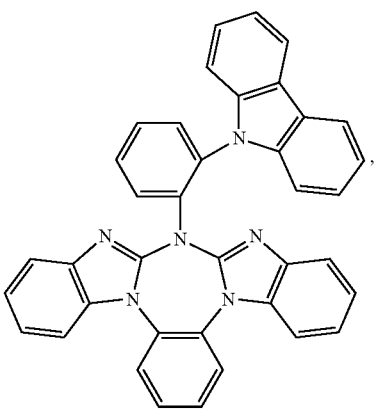
(A-8)
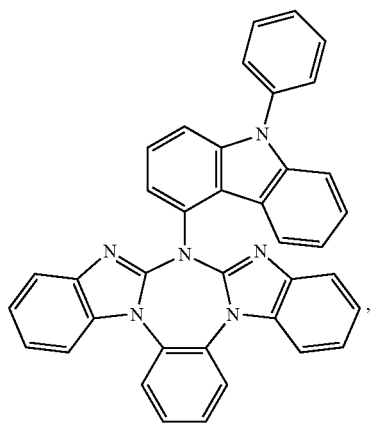

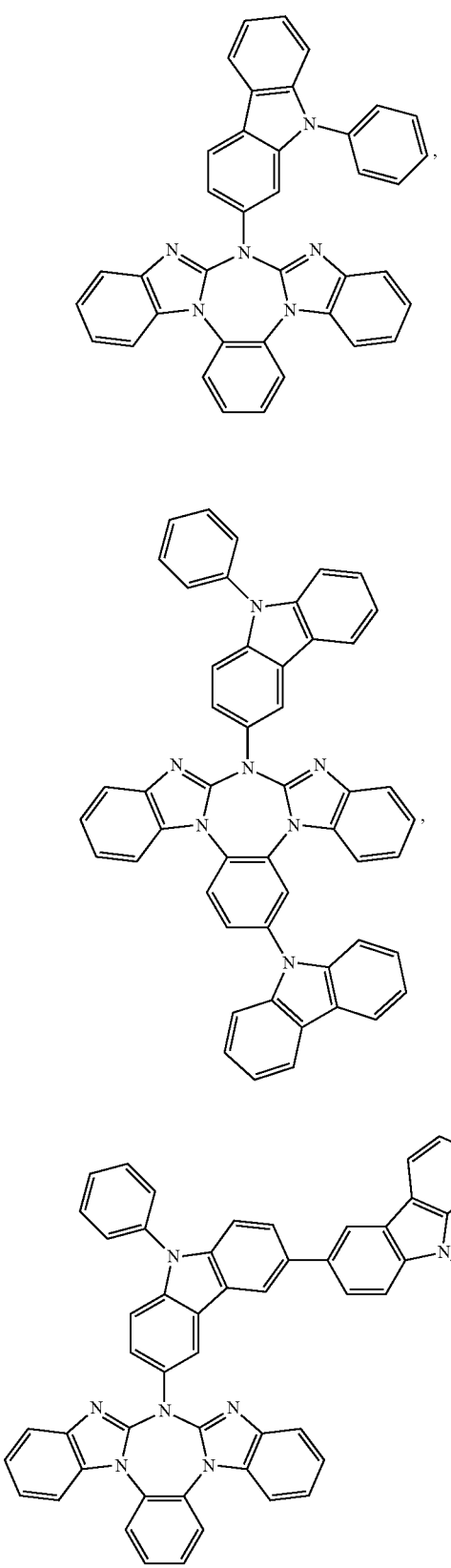
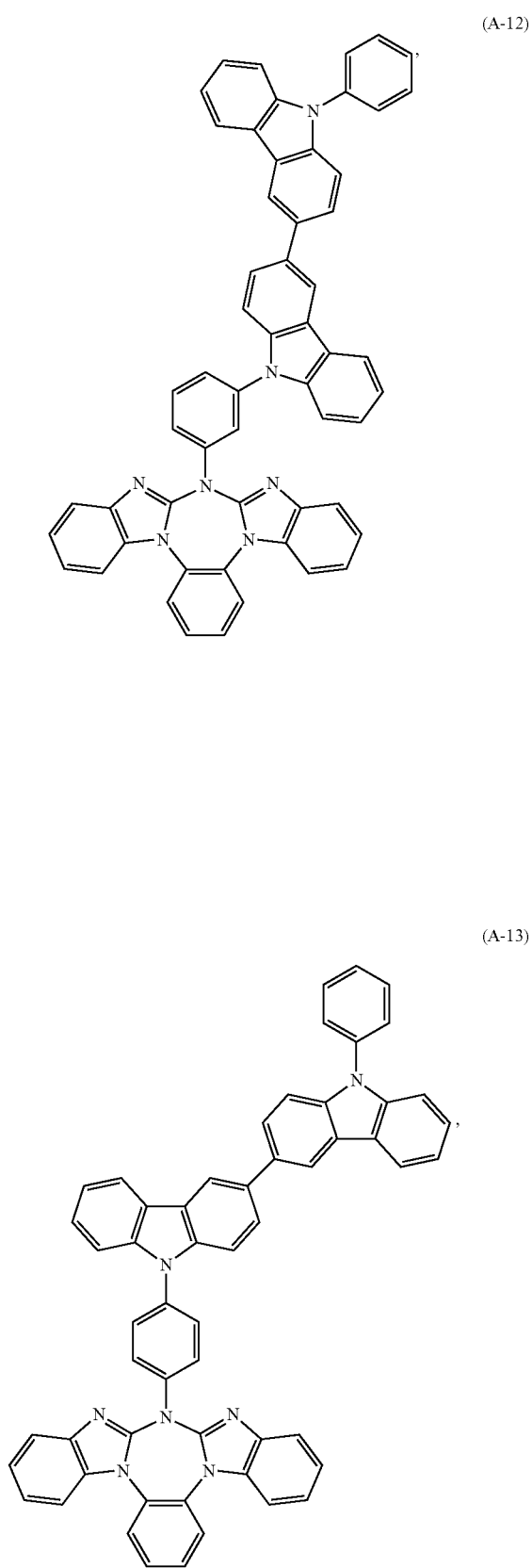

(A-14)
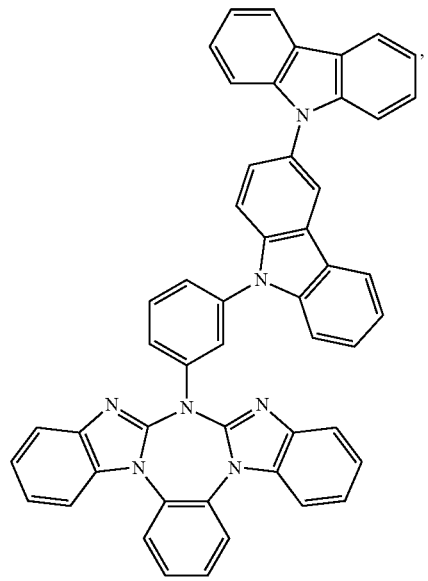
(A-15)
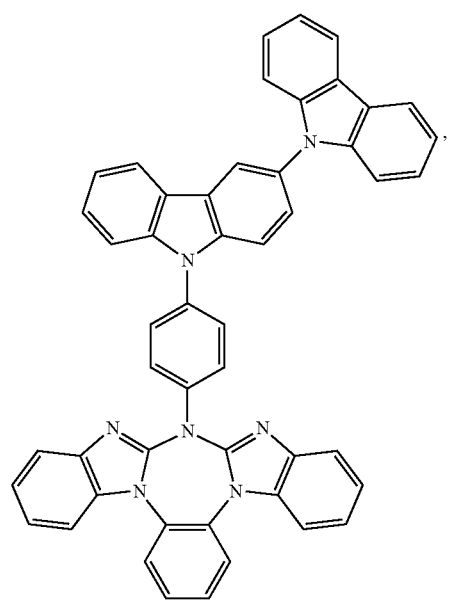
(A-16)
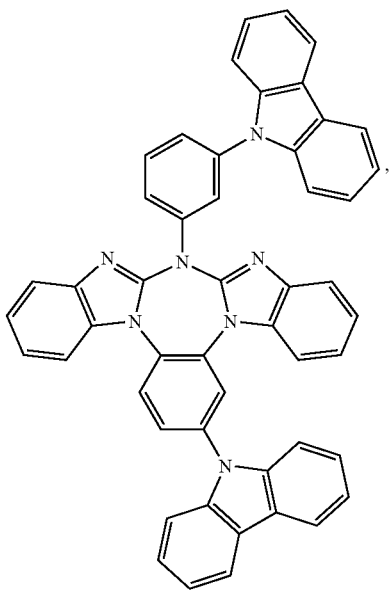
(A-17)
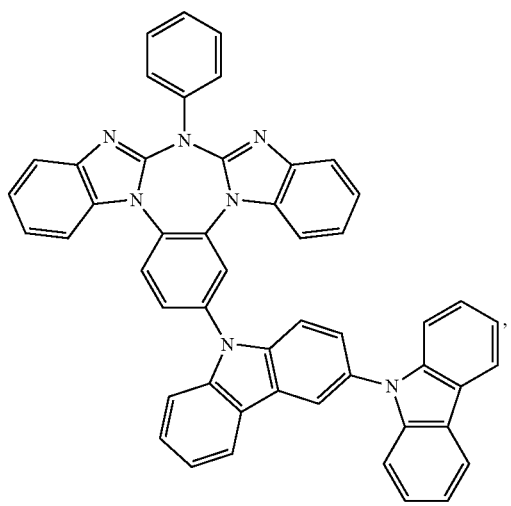
(A-18)
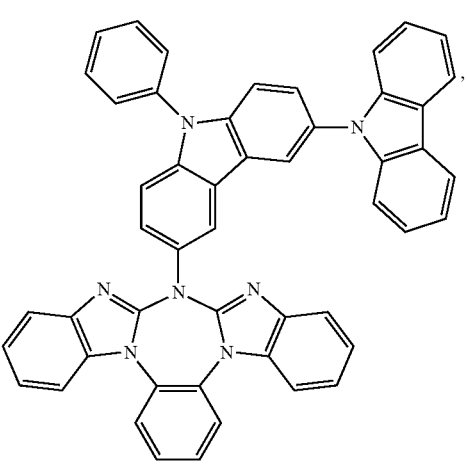

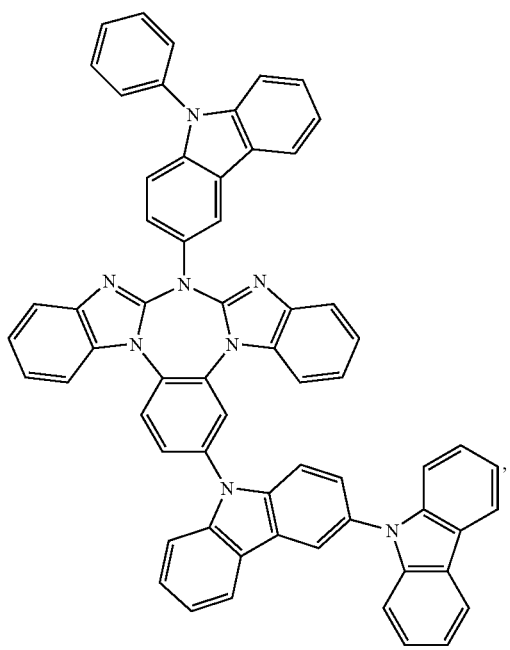
(A-19)
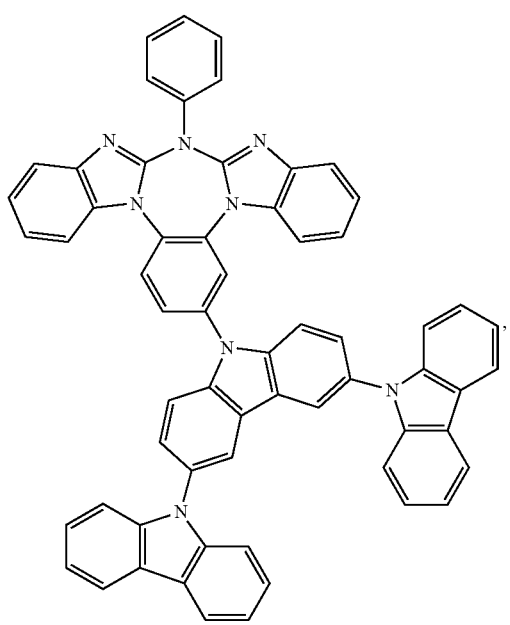
(A-20)
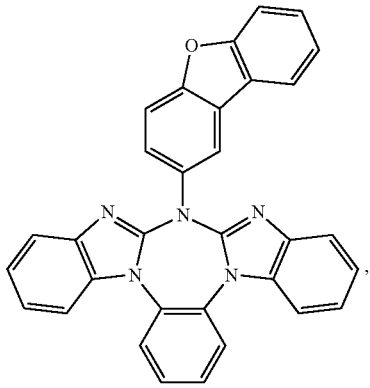
(A-21)
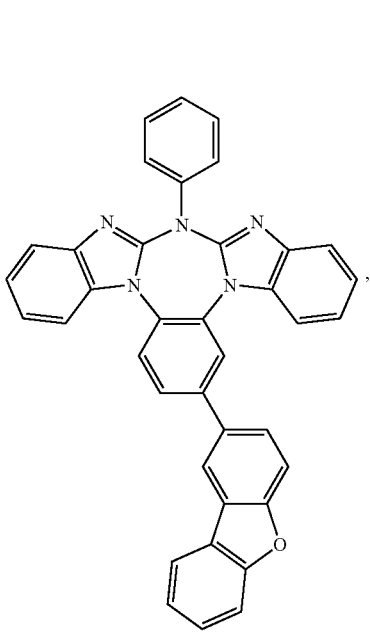
(A-22)
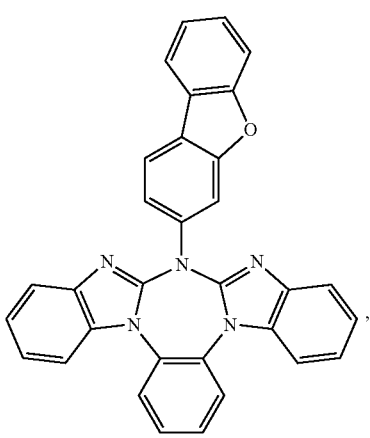
(A-23)

(A-24)
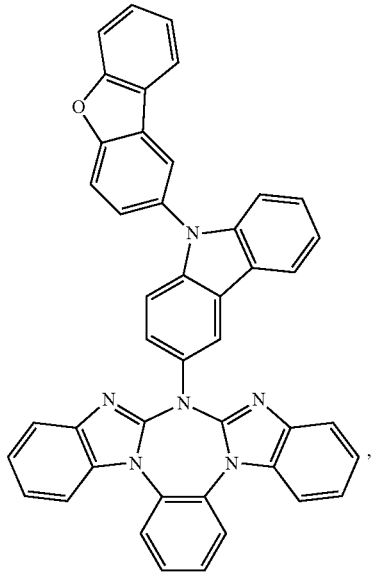
(A-25)
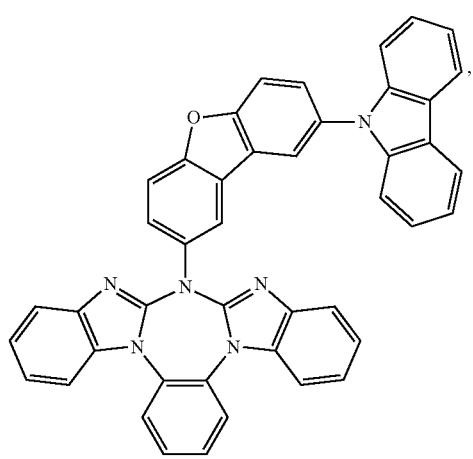
(A-26)
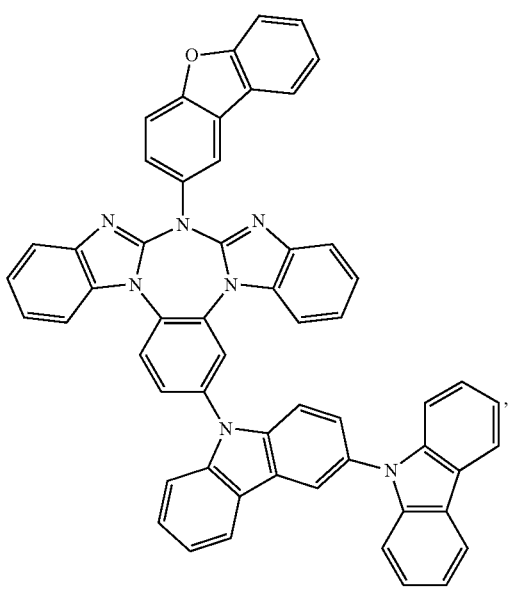
(A-27)
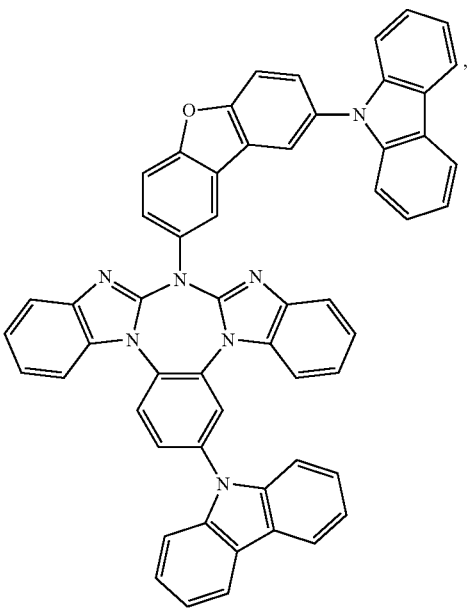
(A-28)
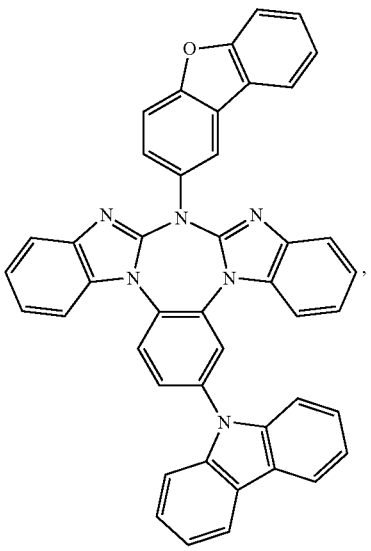

(A-29)
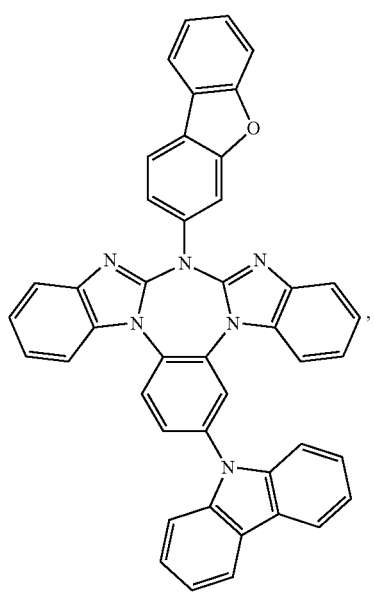
(A-30)
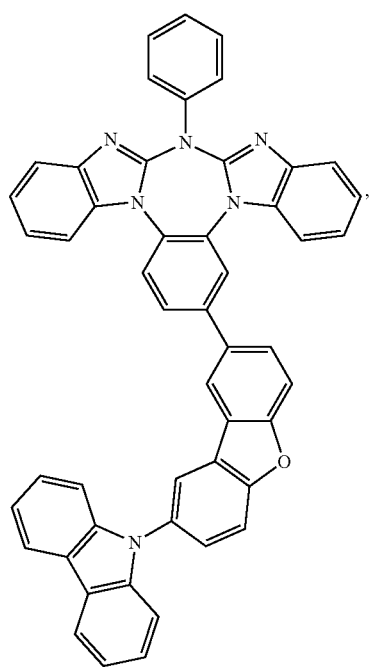
(A-31)
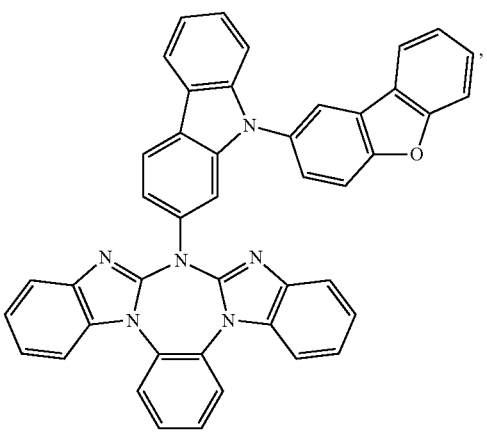
(A-32)
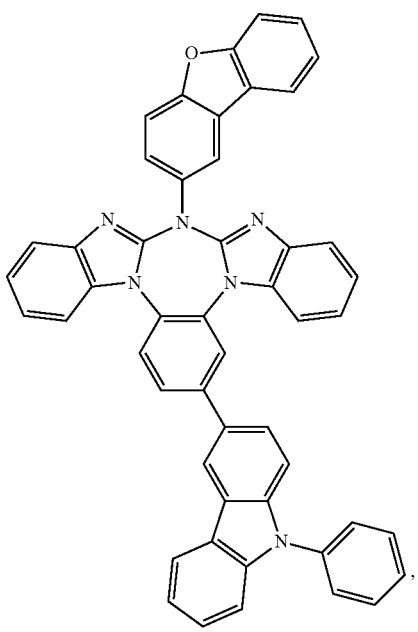

(A-33)
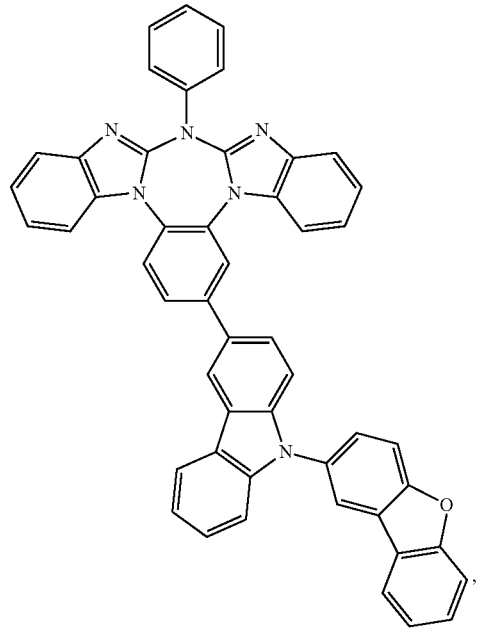
(A-34)
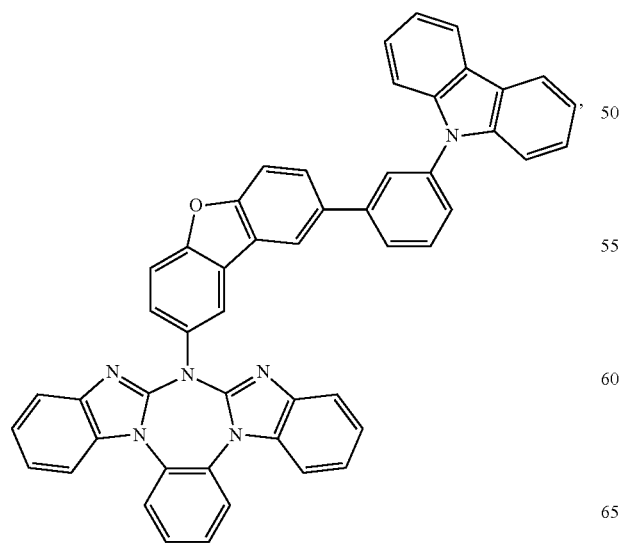
(A-35)
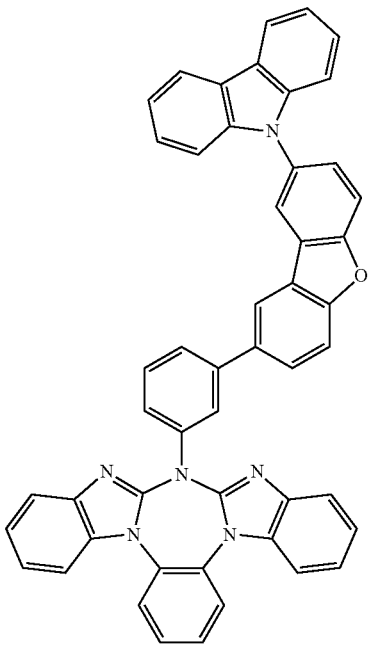
(A-36)
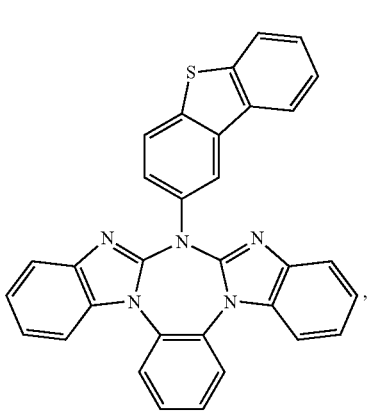
(A-37)
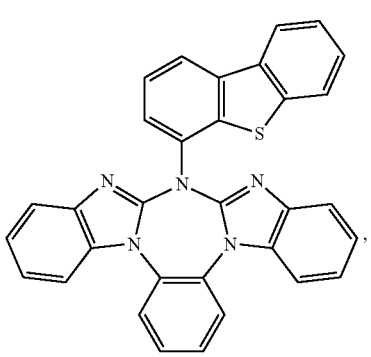

-continued
(A-38)
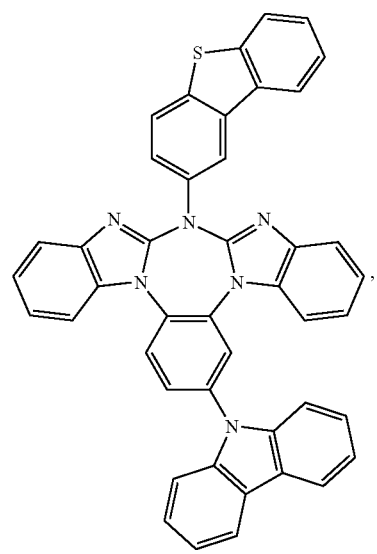
(A-39)
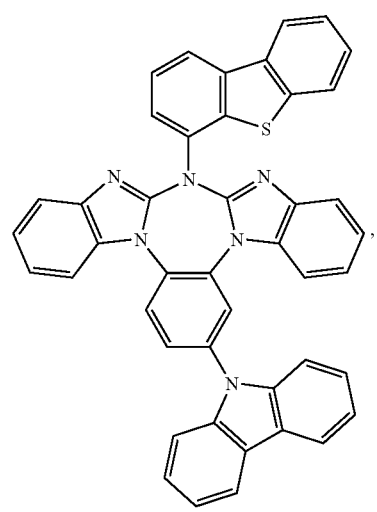
(A-40)
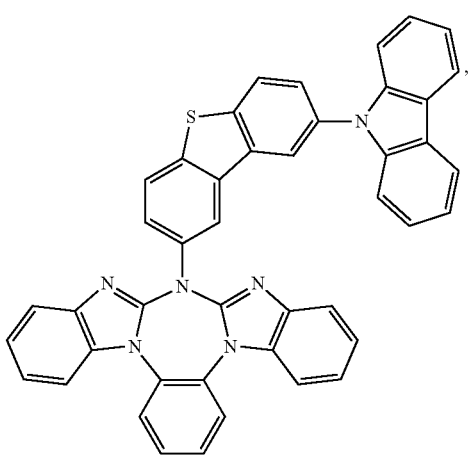
-continued
(A-41)
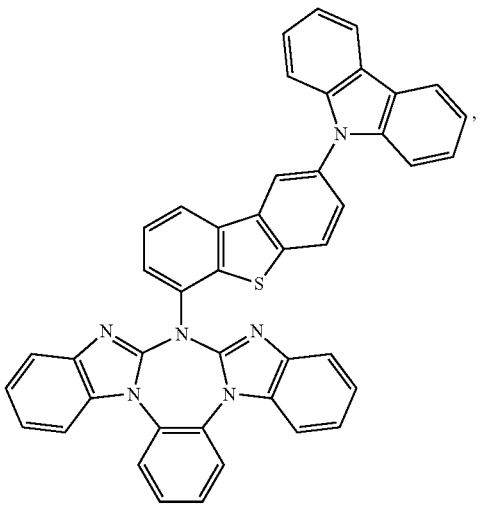
(A-42)
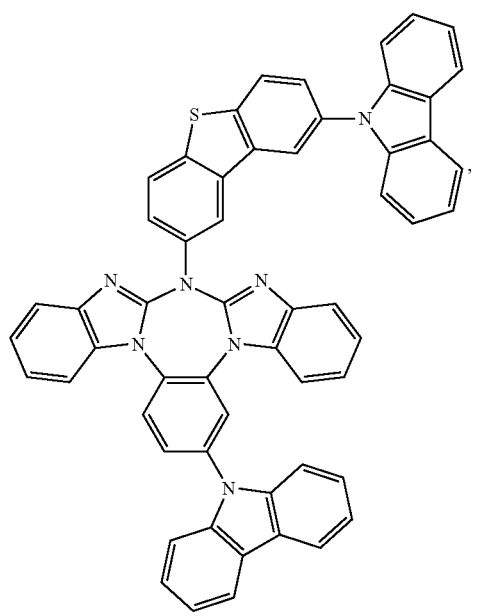

(A-43)
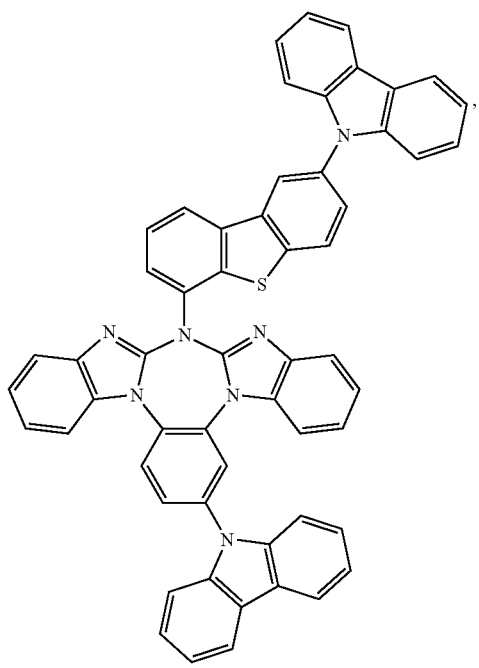
(A-46)
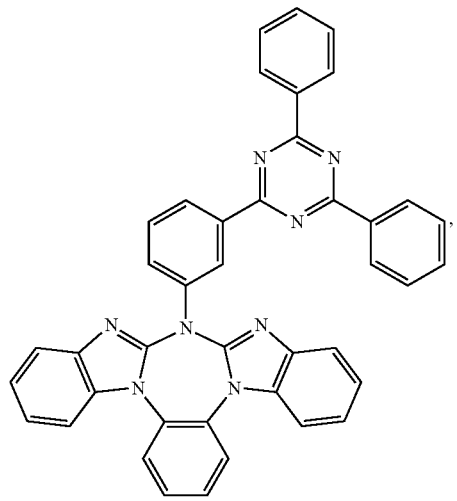
(A-44)
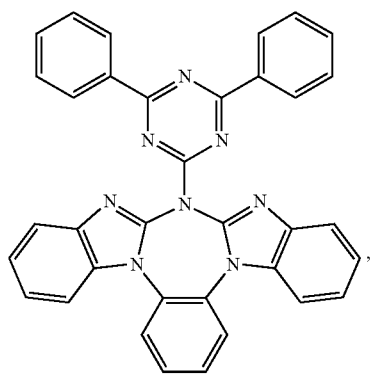
(A-47)
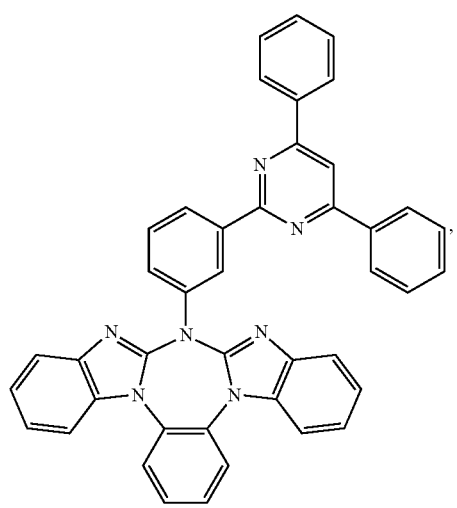
(A-45)
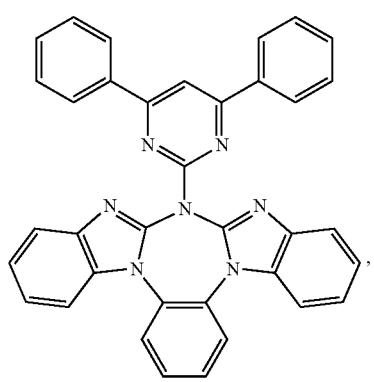
(A-48)
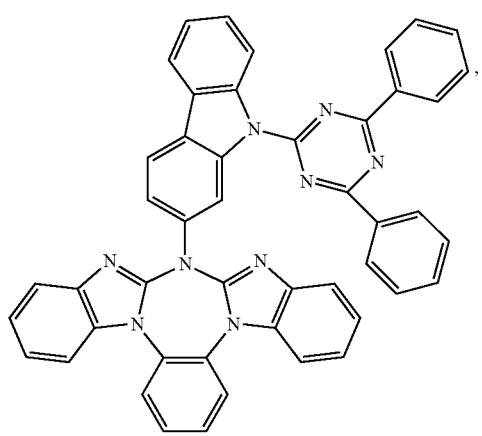

-continued
(A-49)
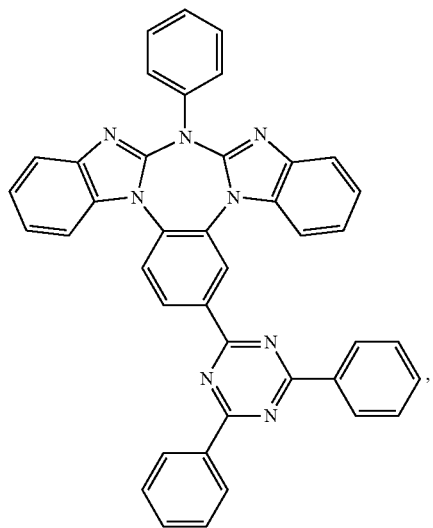
(A-50)
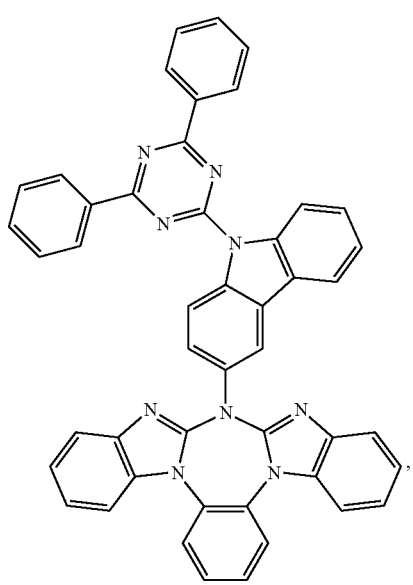
(A-51)
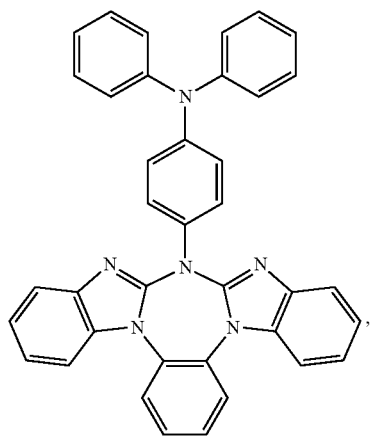
(A-52)
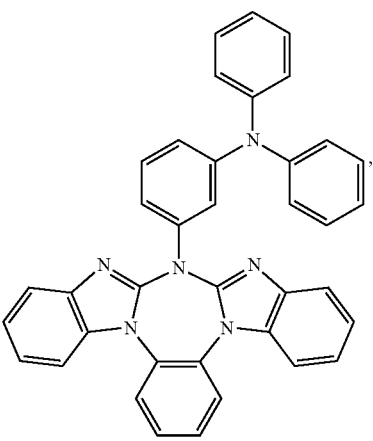
(A-53)
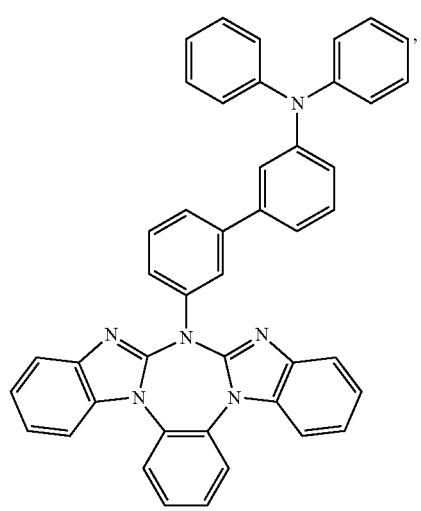
(A-54)
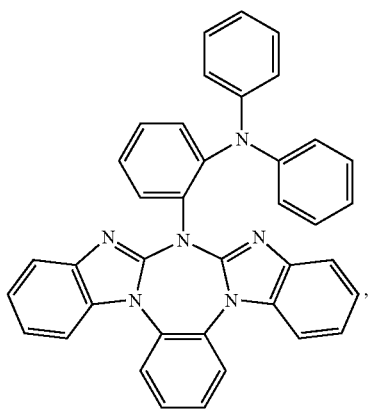

(A-55)
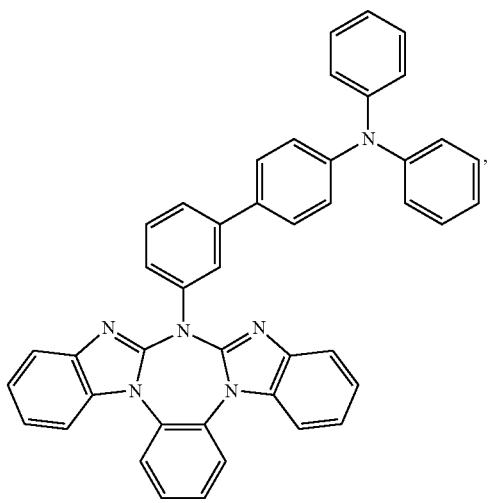
(A-56)
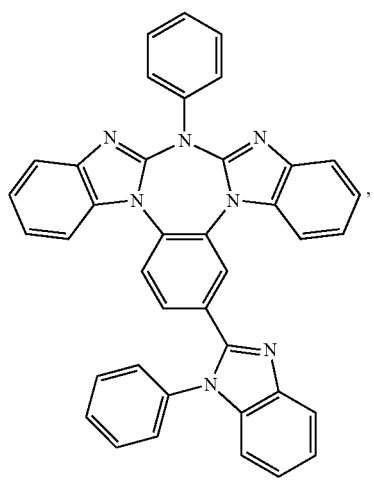
(A-57)
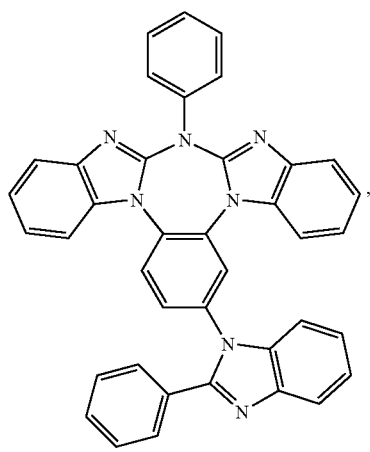
(A-58)
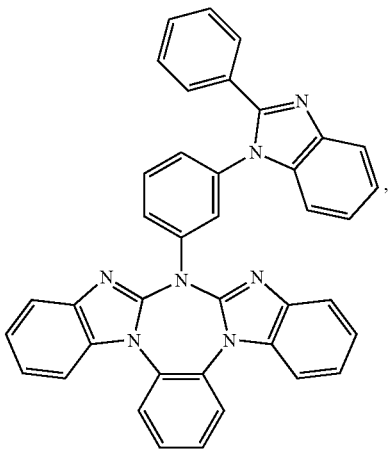
(A-59)
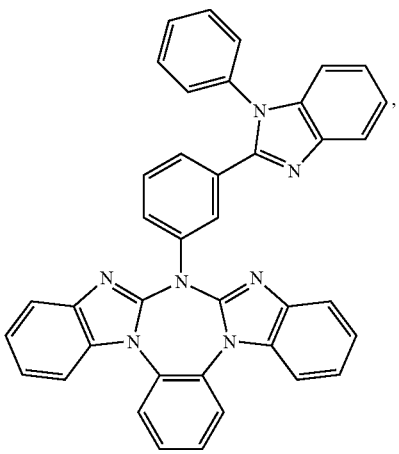
(A-60)
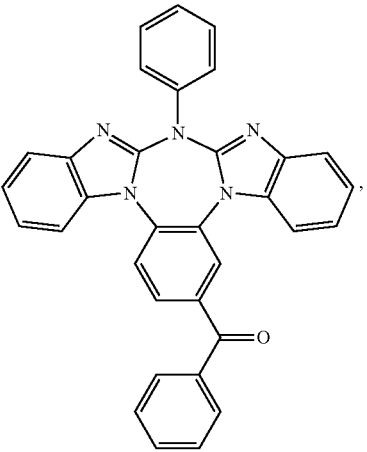

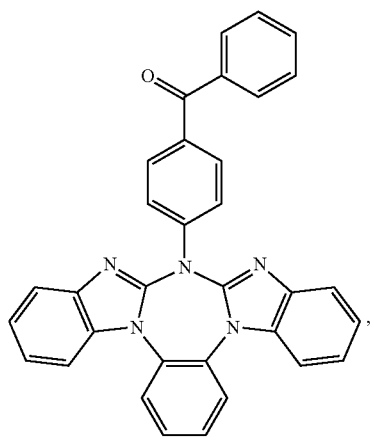
(A-61)
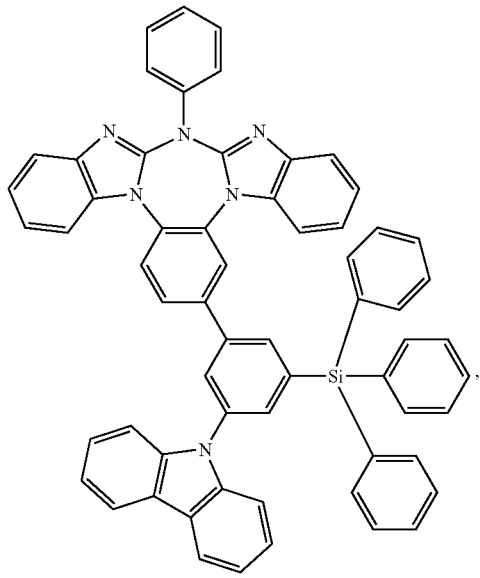
(A-64)
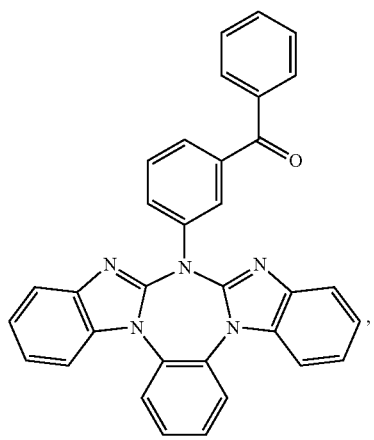
(A-62)
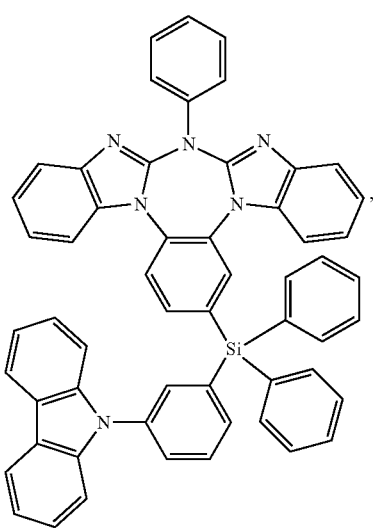
(A-63)
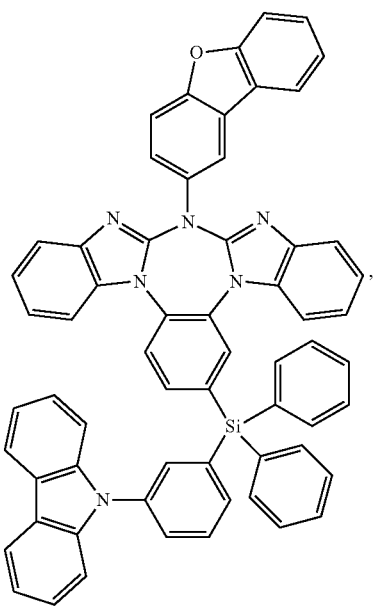
(A-65)

(A-66)
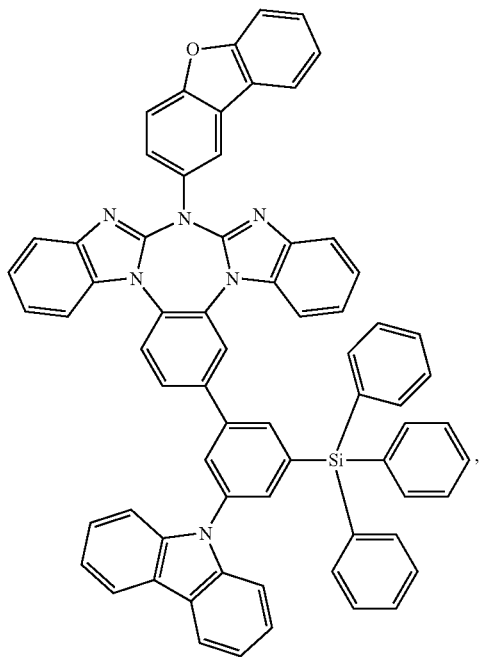
(A-67)
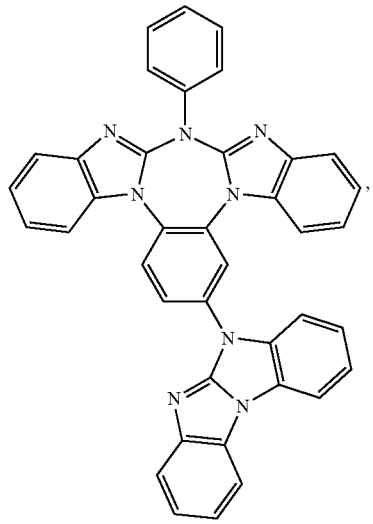
(A-68)
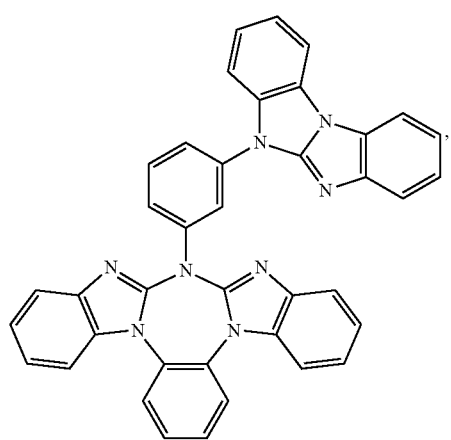
(A-69)
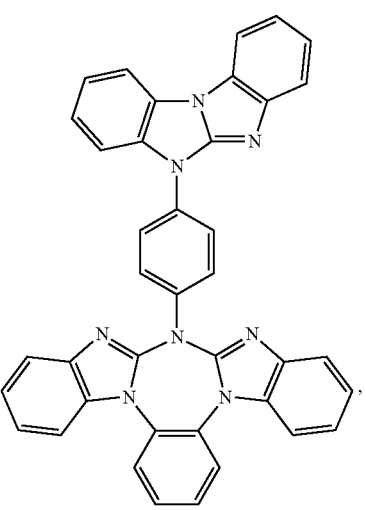
(A-70)
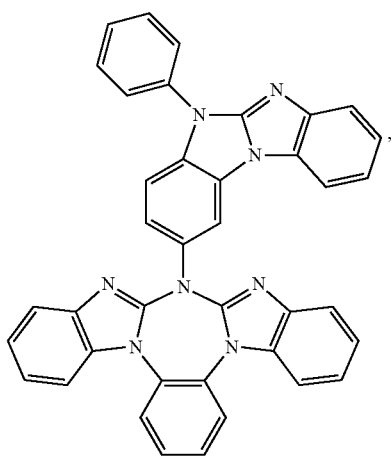
(A-71)
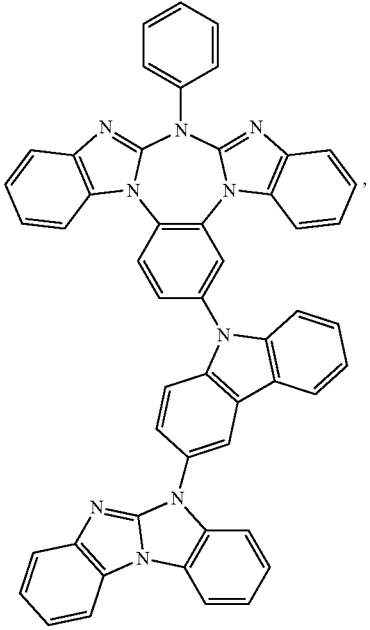

(A-72)
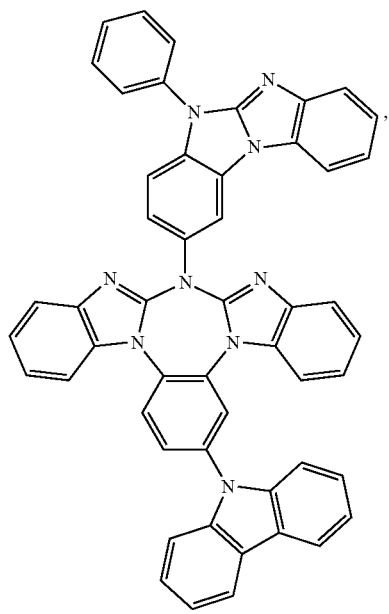
(A-73)
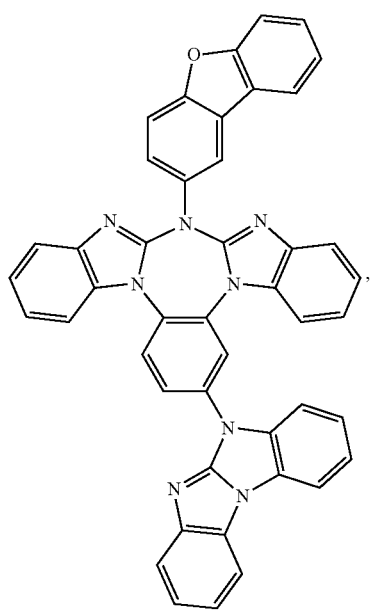
(A-74)
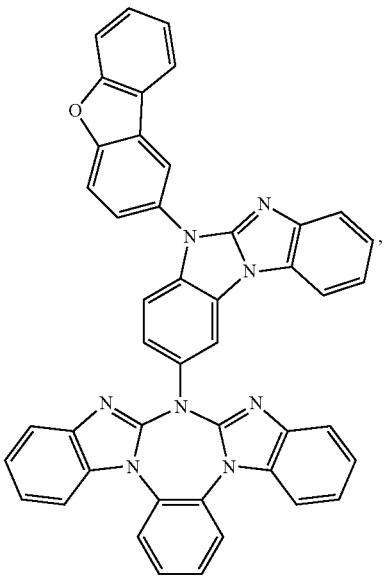
(A-75)
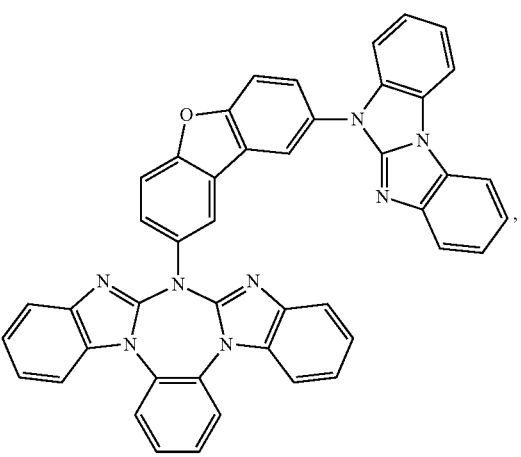
(A-76)
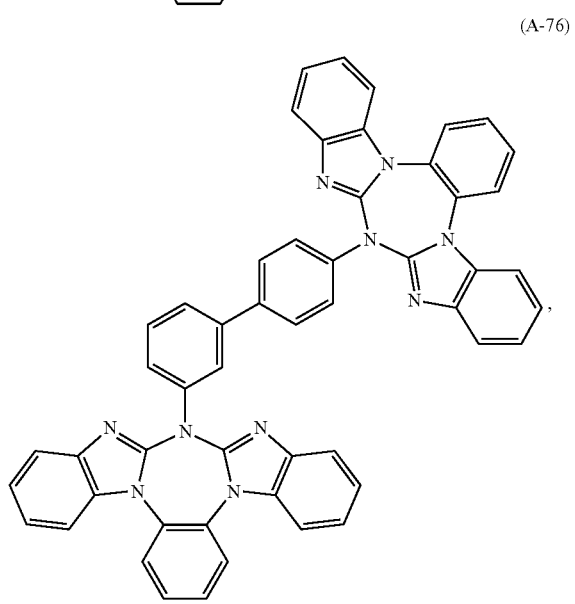

-continued
(A-77)
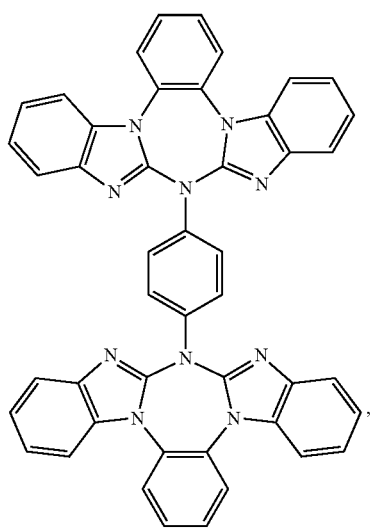
(A-78)
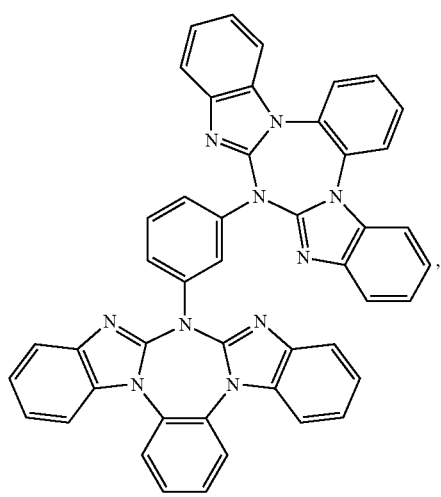
(A-79)
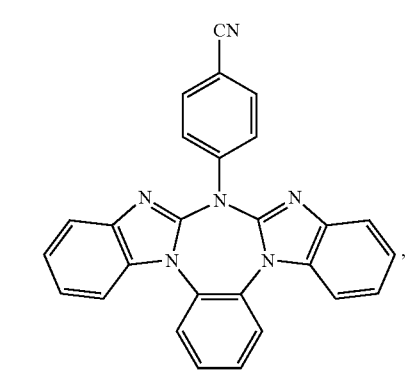
-continued
(A-80)
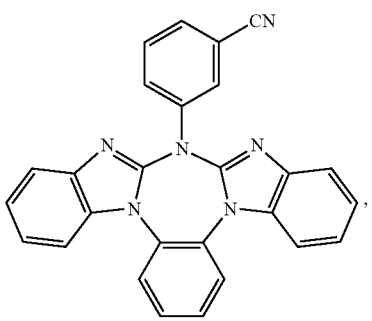
(A-81)
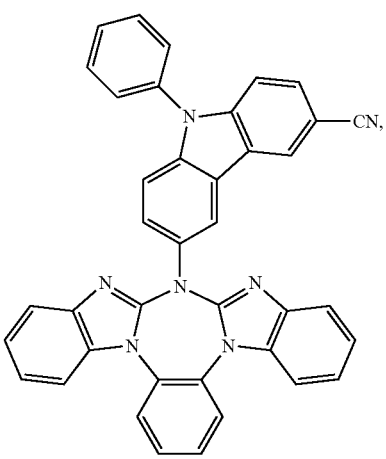
(A-82)
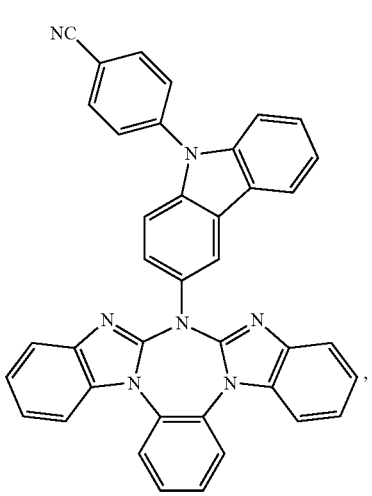

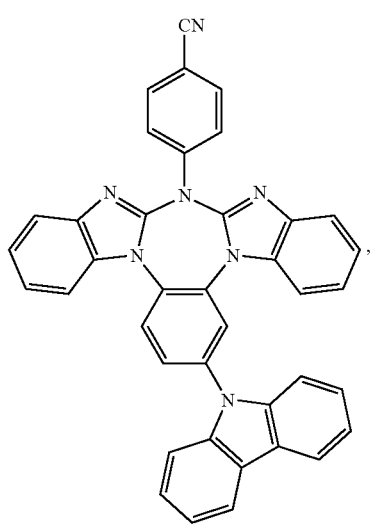
(A-83)
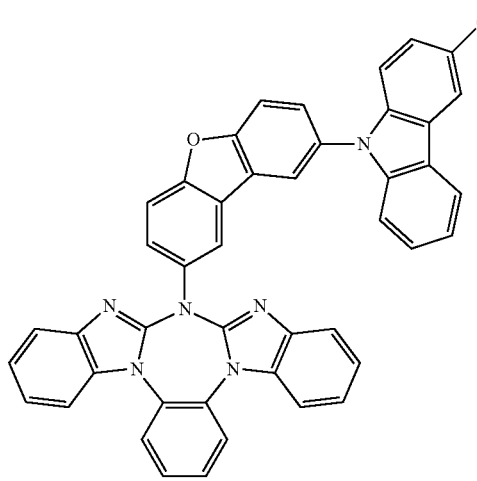
(A-86)
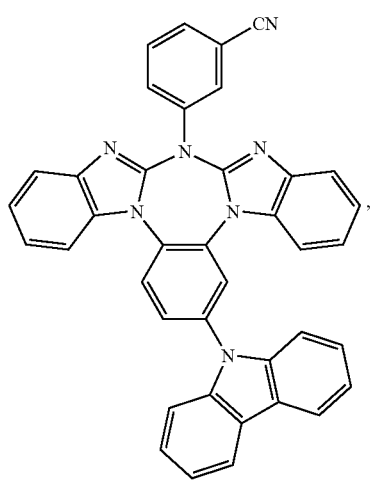
(A-84)
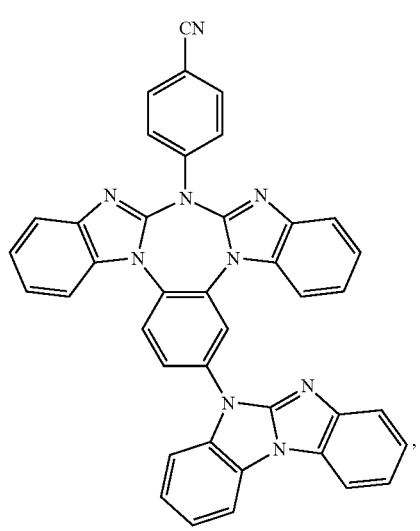
(A-87)
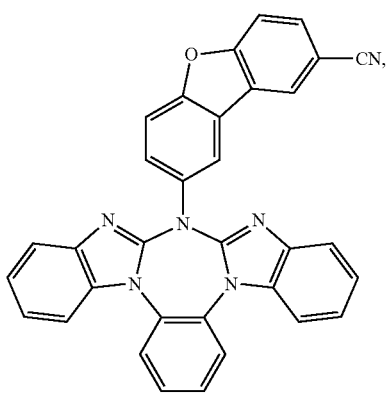
(A-85)
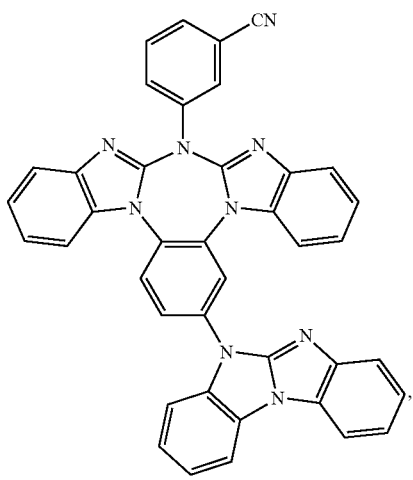
(A-88)

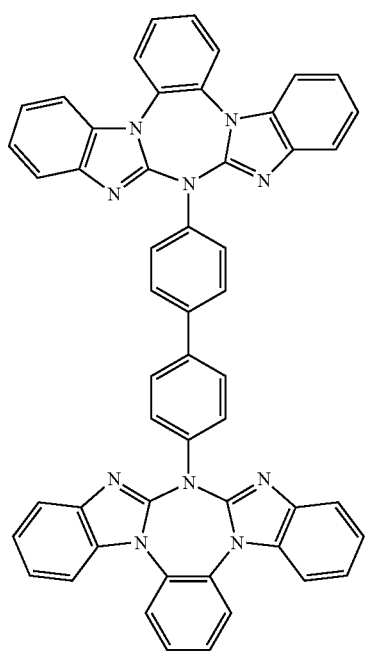
(A-89)
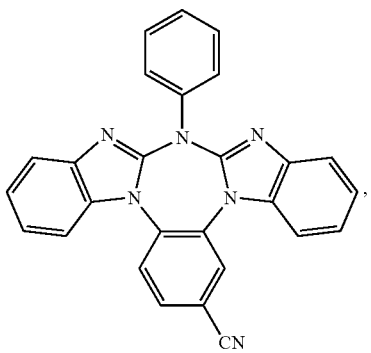
(B-1)
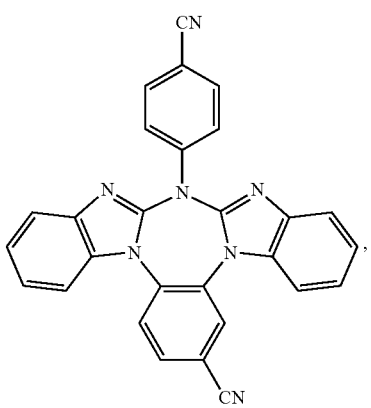
(B-2)
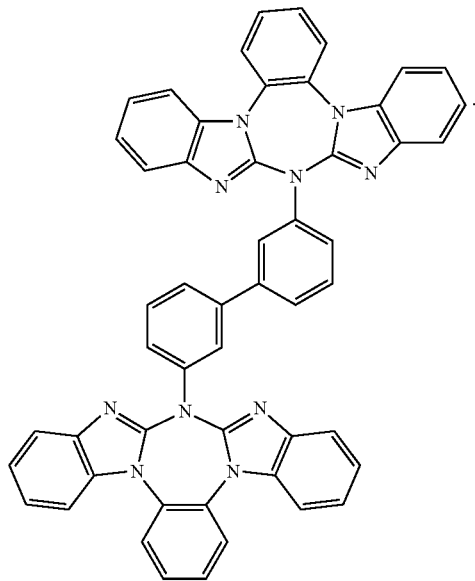
(A-90)
Examples of compounds of formula (Ia-1), wherein one of the groups $R^{90}$ and $R^{91}$ is CN and the other is H, are shown below:
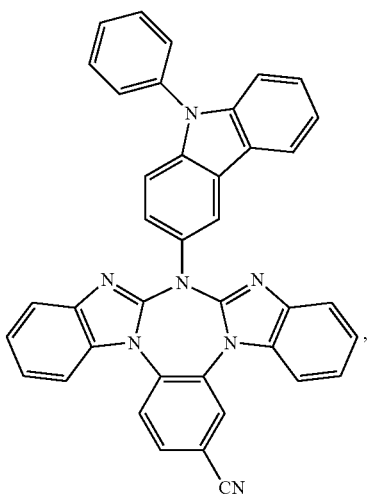
(B-3)

-continued
(B-4)
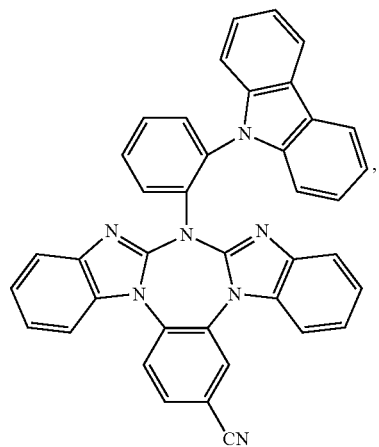
(B-5)
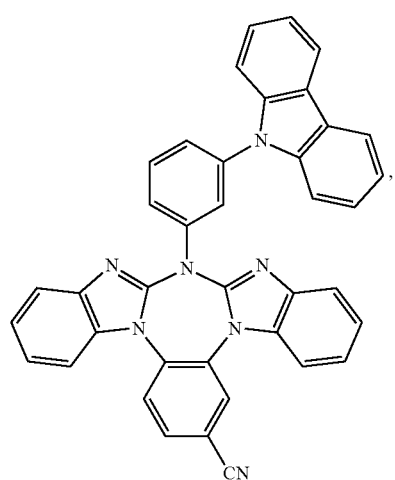
(B-6)
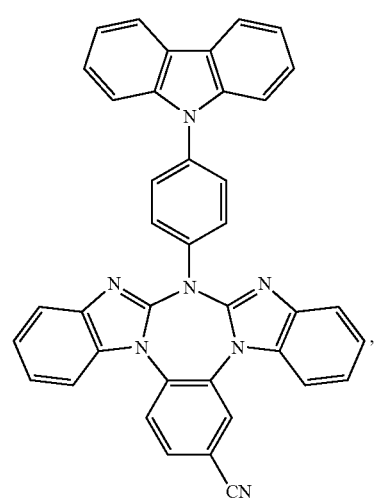
(B-7)
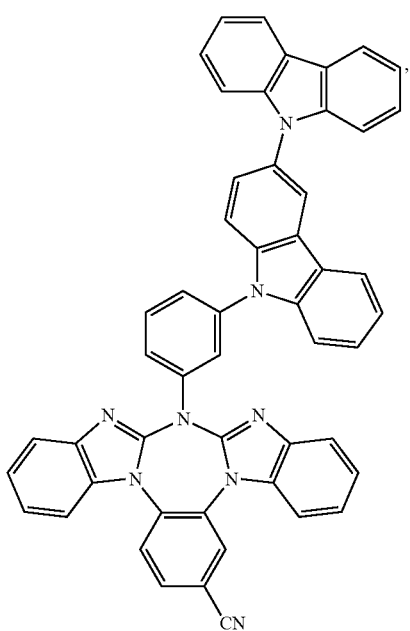
(B-8)
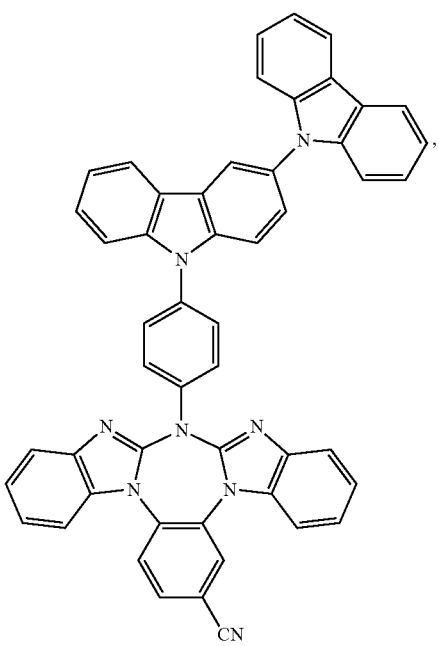

(B-9)
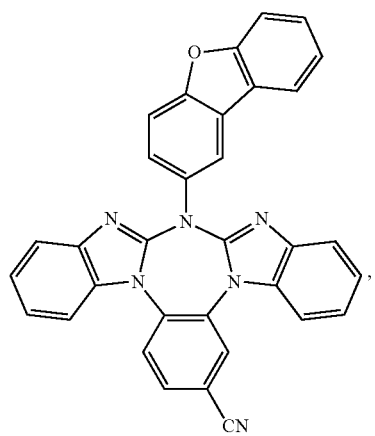
(B-10)
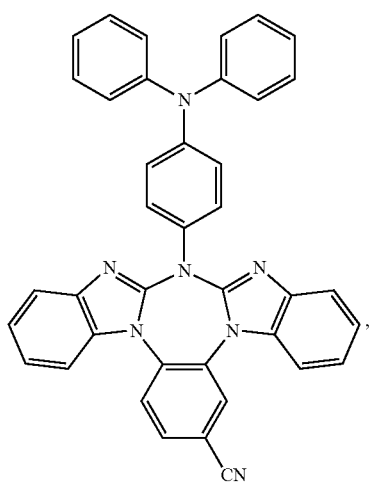
(B-11)
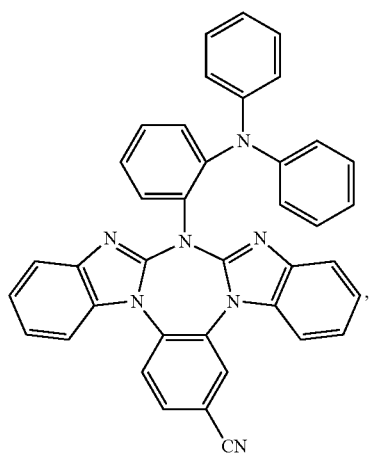
(B-12)
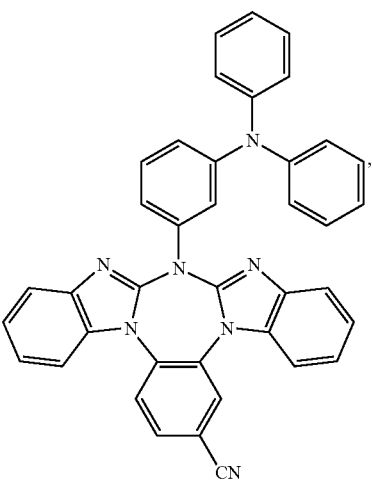
(B-13)
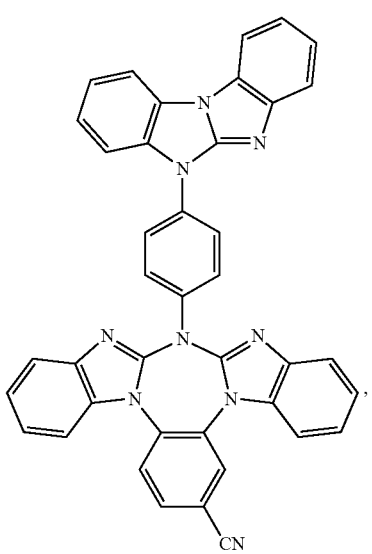
(B-14)
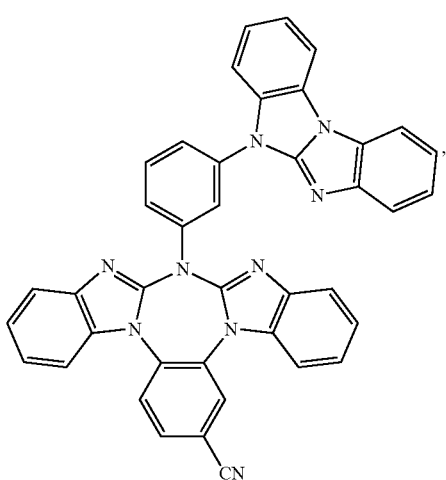

(B-15)
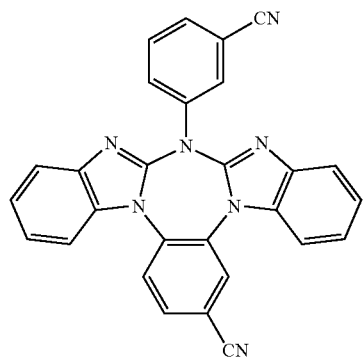
(B-16)
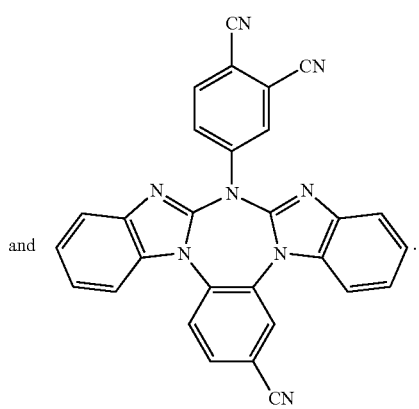
Examples of compounds of formula (Ia-1), wherein $R^{90}$ and $R^{91}$ are CN, are shown below:
(B-17)
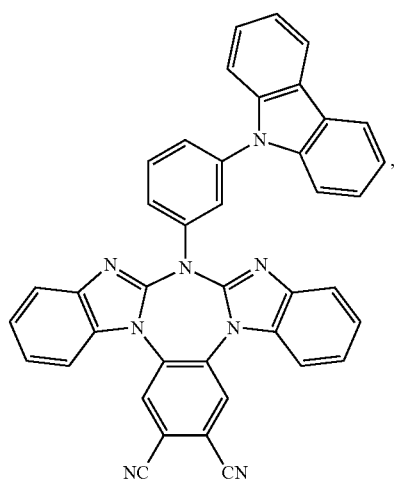
(B-18)
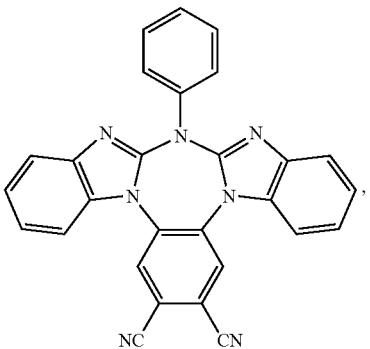
(B-19)
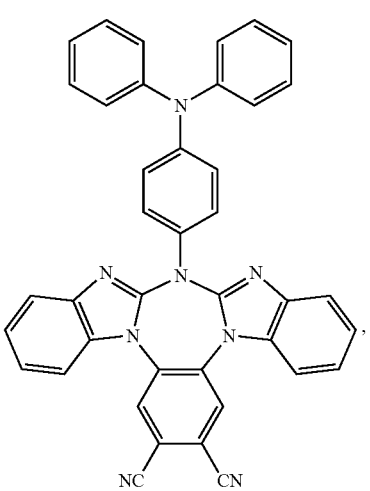
(B-20)
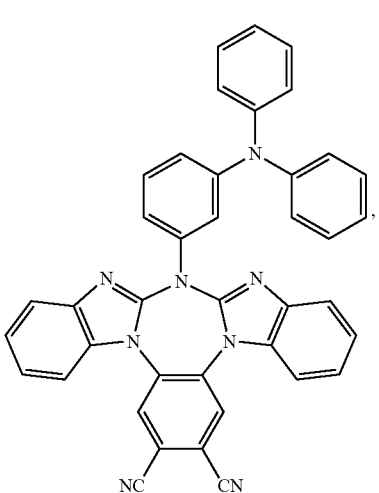

-continued (B-21)
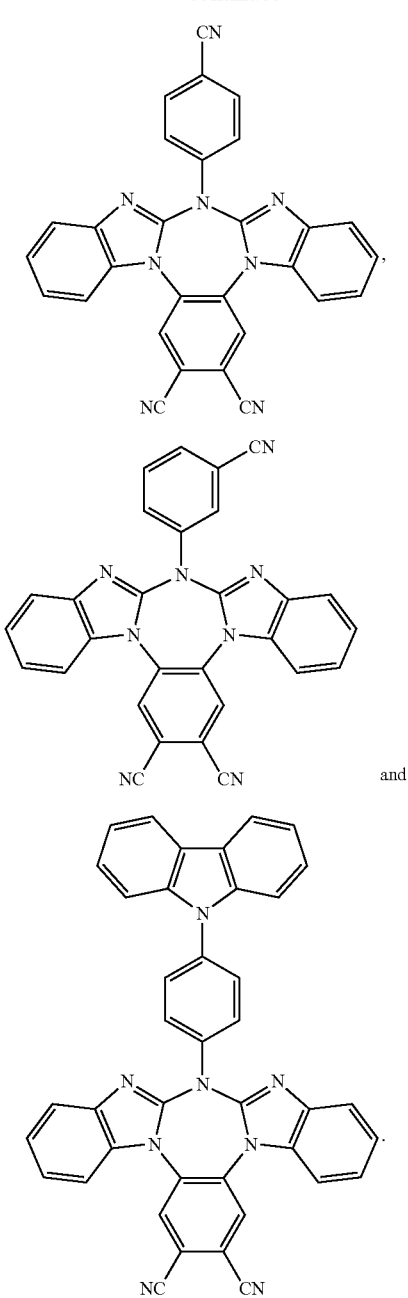

(B-22)

and (B-23)

In another particularly preferred embodiment the present invention is directed to compounds of formula (Ib-1)
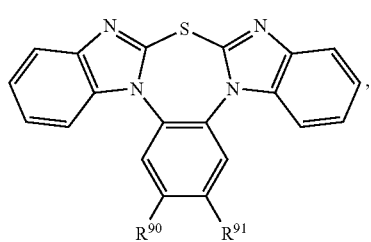

wherein
$R^{90}$ and $R^{91}$ are H, or
$R^{90}$ and $R^{91}$ are CN, or
one of $R^{90}$ and $R^{91}$ is H and the other is CN,
one of $R^{90}$ and $R^{91}$ is H and the other is a group of formula $-(A^5)_s-(A^6)_t-(A^7)_u-(A^8)_v-R^{17}$,
s is 0, or 1, t is 0, or 1, u is 0, or 1, v is 0, or 1,
$A^5, A^6, A^7$ and $A^8$ are independently of each other a group of formula

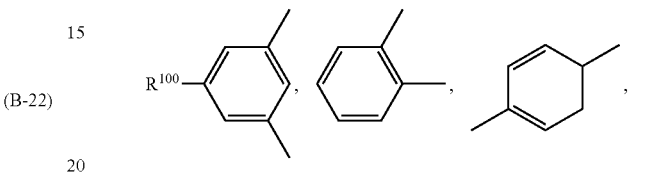

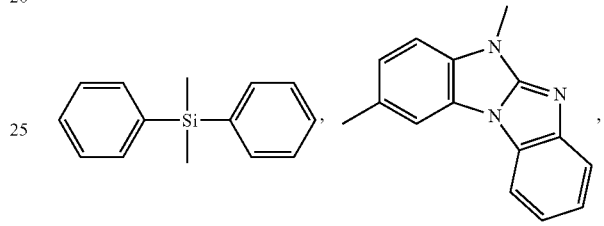

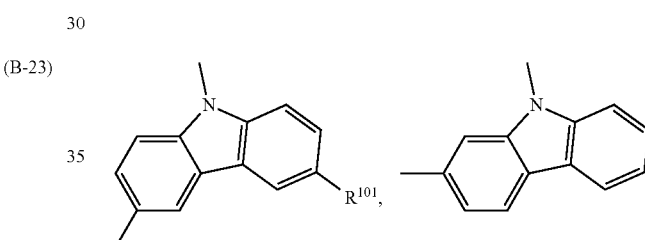

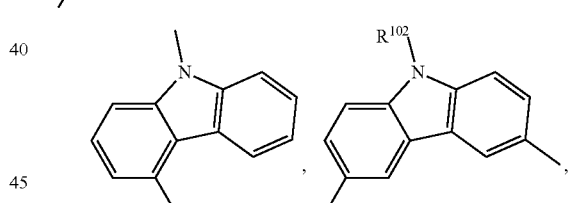

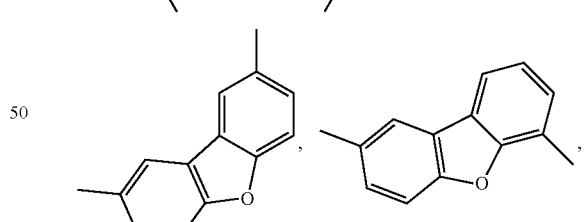

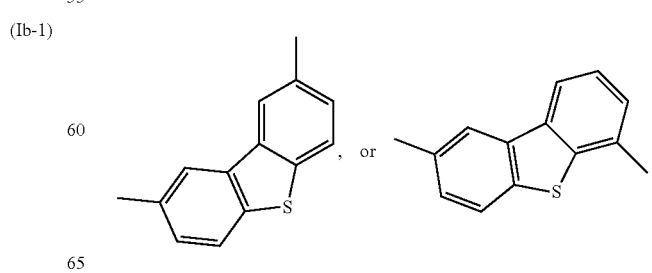

wherein
R$^{100}$ is H, Si(Ph)$_3$, or
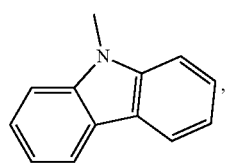
R$^{101}$ is H, or CN,
R$^{102}$ is a phenyl group, and
R$^{17}$ is a group of formula CN,
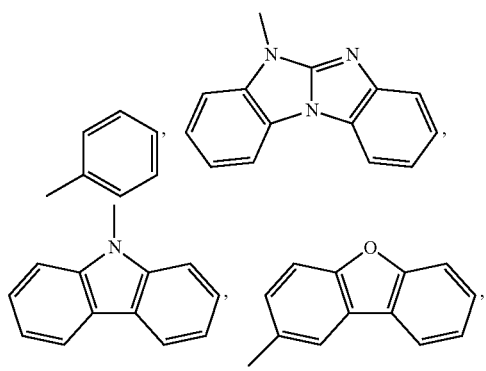
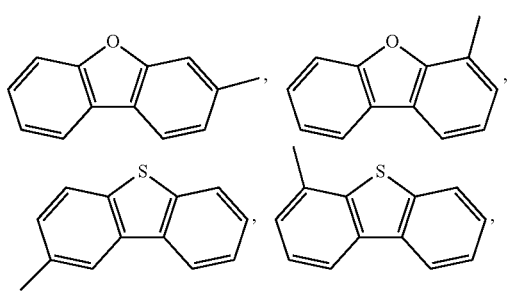
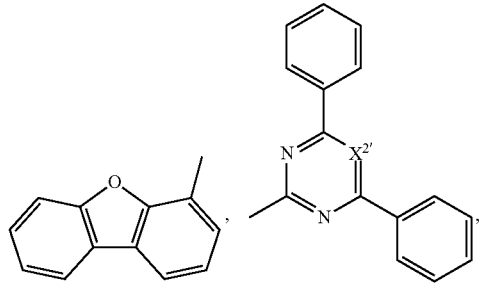
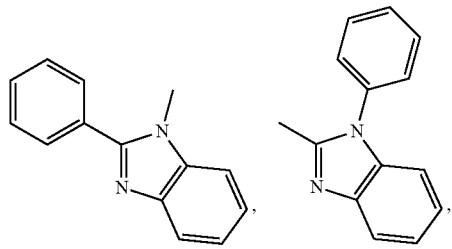
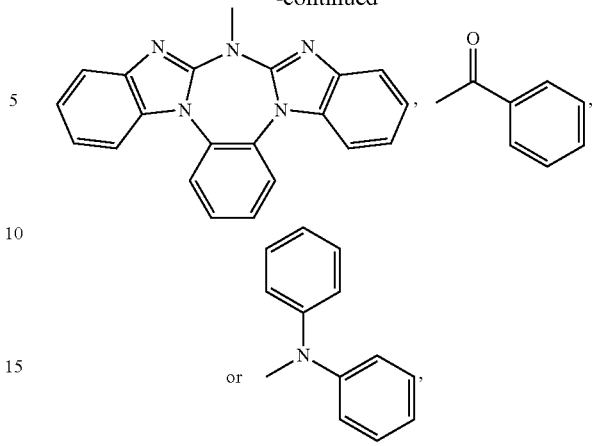
wherein X$^{2'}$ is N, or CH.
Examples of compounds of formula (I-1b), wherein R$^{90}$ and R$^{91}$ are H, or one of the groups R$^{90}$ and R$^{91}$ is a group of formula -(A$^5$)$_s$-(A$^6$)$_t$-(A$^7$)$_v$-(A$^8$)$_v$-R$^{17}$ and the other is H, are shown below:
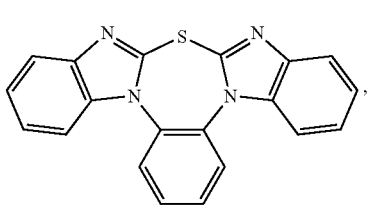
(C-1)
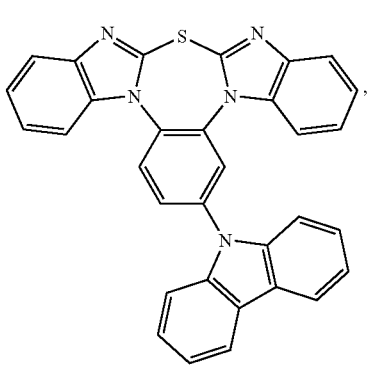
(C-2)
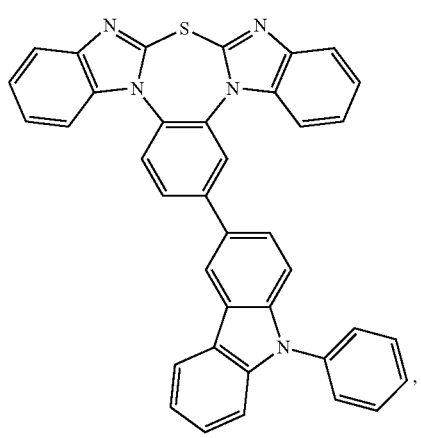
(C-3)

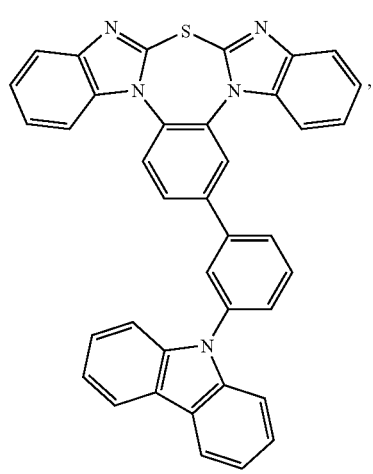
(C-4)
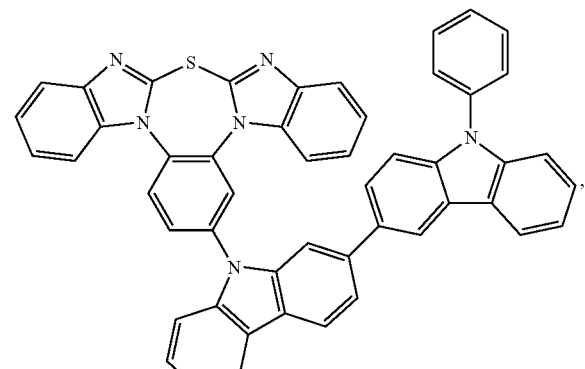
(C-7)
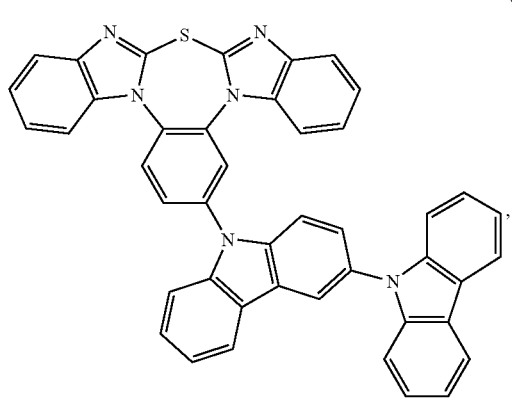
(C-5)
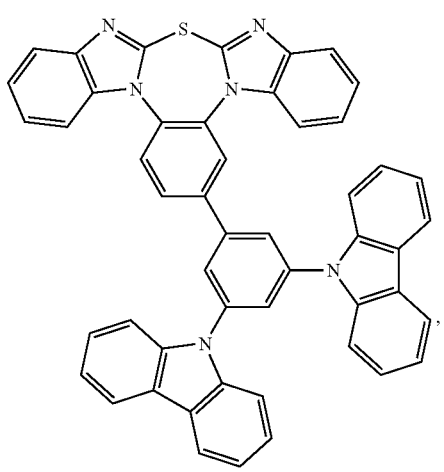
(C-8)
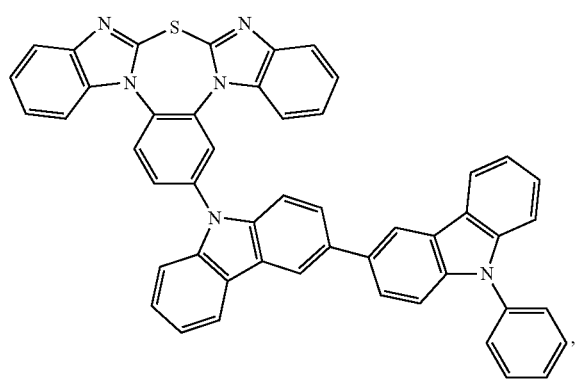
(C-6)
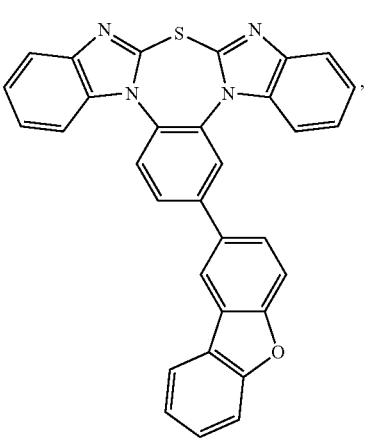
(C-9)

-continued
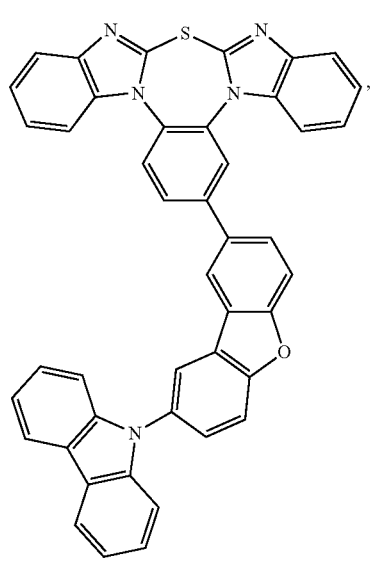 (C-10)
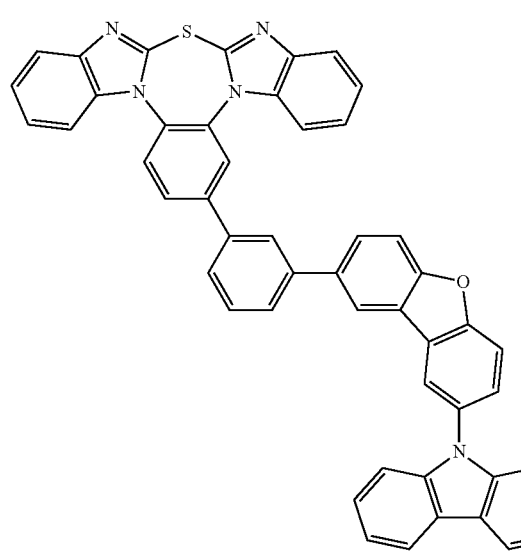 (C-11)
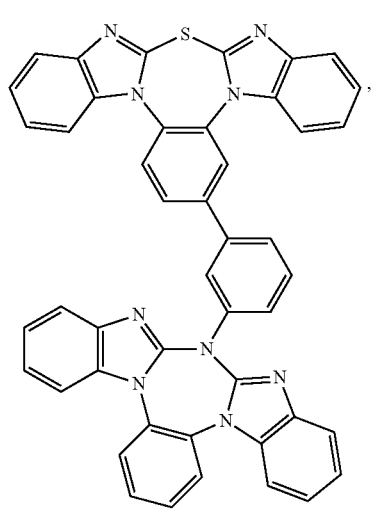 (C-12)
-continued
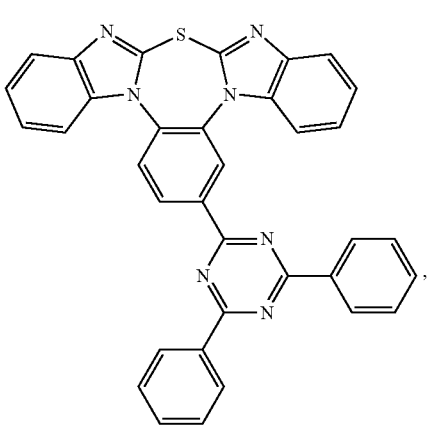 (C-13)
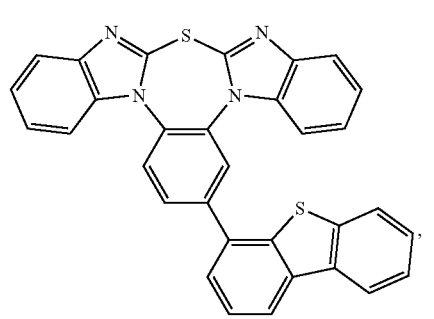 (C-14)
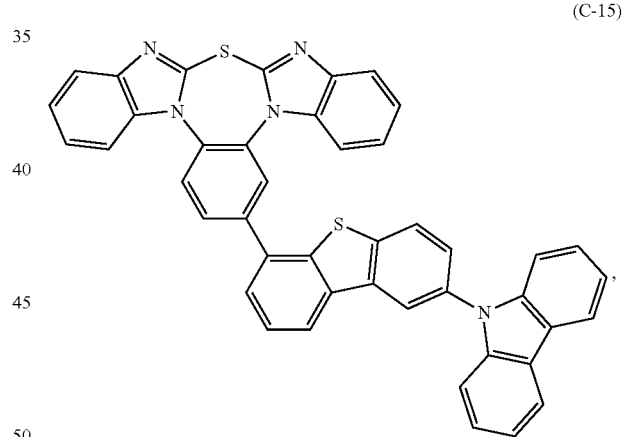 (C-15)
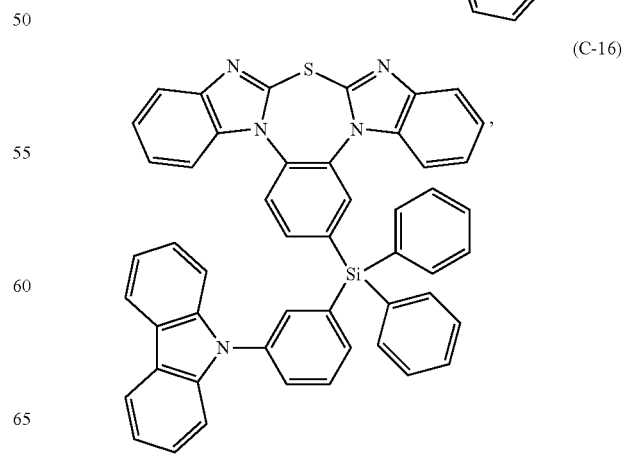 (C-16)

-continued
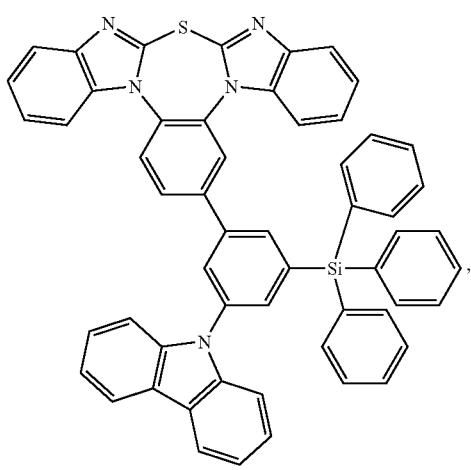
(C-17)
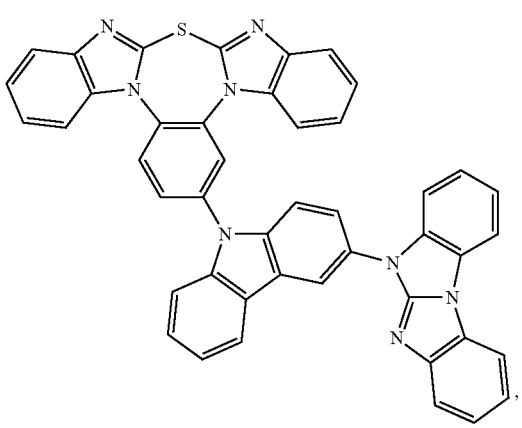
(C-18)
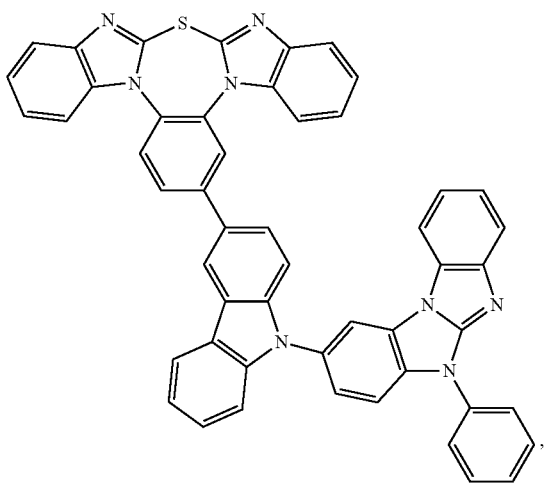
(C-19)
-continued
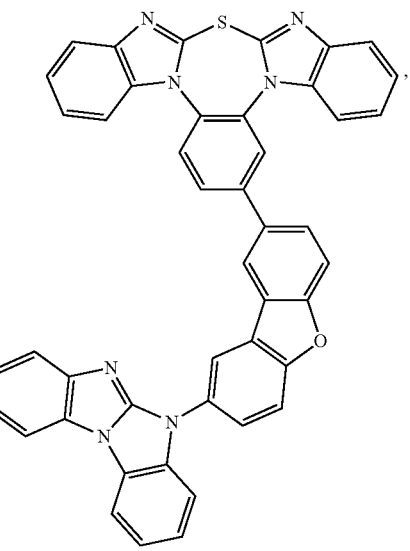
(C-20)
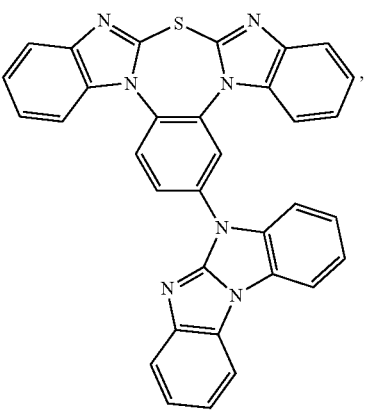
(C-21)
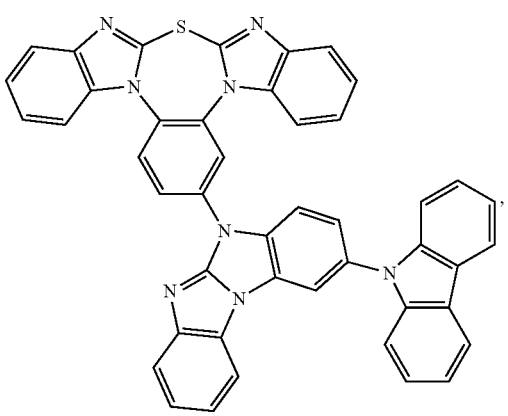
(C-22)

-continued

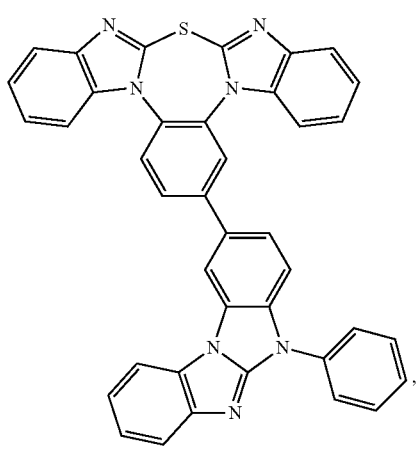

(C-23)

(C-24)

(C-25)

and

Compounds of formula (Ia) are preferred. Compounds of formula (Ia-1) are more preferred. Compounds of formula (Ia-1), wherein one of the groups $R^{90}$ and $R^{91}$ is CN and the other is H, are most preferred.

Compounds of the formula

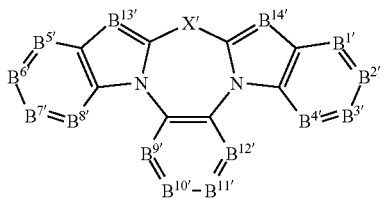

(IX)

are new, intermediates in the production of the compounds of formula (I) and form a further subject of the present invention;

$B^{1'}$ is N, or $CR^{81'}$, $B^{2'}$ is N, or $CR^{82'}$, $B^{3'}$ is N, or $CR^{83'}$, $B^{4'}$ is N, or $CR^{84'}$, $B^{5'}$ is N, or $CR^{85'}$, $B^{6'}$ is N, or $CR^{86'}$, $B^{7'}$ is N, or $CR^{87'}$, $B^{8'}$ is N, or $CR^{88'}$, $B^{9'}$ is N, or $CR^{89'}$, $B^{10'}$ is N, or $CR^{90'}$, $B^{11'}$ is N, or $CR^{91'}$, $B^{12'}$ is N, or $CR^{92'}$, $B^{13'}$ is N, or $CR^{93'}$, $B^{14'}$ is N, or $CR^{94'}$,

X' is $NR^{95'}$, S, or O, $R^{81'}$, $R^{82'}$, $R^{83'}$, $R^{84'}$, $R^{85'}$, $R^{86'}$, $R^{87'}$, $R^{88'}$, $R^{89'}$, $R^{90'}$, $R^{91'}$, $R^{92'}$, $R^{93'}$ and $R^{94'}$ are independently of each other H, CN, a $C_1$-$C_{25}$alkyl group, which can optionally be substituted by E and or interrupted by D; a $C_6$-$C_{24}$aryl group, which can optionally be substituted by G, a $C_2$-$C_{30}$heteroaryl group, which can optionally be substituted by G; or a group of formula -$(A^5)_s$-$(A^6)_t$-$(A^7)_u$-$(A^8)_v$-$R^{17'}$;

$R^{95'}$ is a group of formula -$(A^1)_o$-$(A^2)_p$-$(A^3)_q$-$(A^4)_r$-$R^{16'}$;

o is 1;

$R^{16'}$ and $R^{17'}$ are independently of each other F, Cl, Br, I, —B(OH)$_2$, —B(OY$^1$)$_2$,

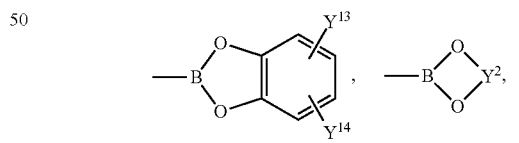

—BF$_4$Na, or —BF$_4$K, wherein Y$^1$ is independently in each occurrence a $C_1$-$C_{18}$alkyl group and Y$^2$ is independently in each occurrence a $C_2$-$C_{10}$alkylene group, and Y$^{13}$ and Y$^{14}$ are independently of each other hydrogen, or a $C_1$-$C_{10}$alkyl group, and p, q, r, s, t, u, v, D, E, G, $A^1$, $A^2$, $A^3$, $A^4$, $A^5$, $A^6$, $A^7$ and $A^8$ are as defined above, or below, with the proviso that at least one of $B^{1'}$ to $B^{14'}$ is different from N and at least one of $R^{81'}$, $R^{82'}$, $R^{83'}$, $R^{84'}$, $R^{85'}$, $R^{86'}$, $R^{87'}$, $R^{88'}$, $R^{89'}$, $R^{90'}$, $R^{91'}$, $R^{92'}$, $R^{93'}$ and $R^{94'}$ is a group of formula -$(A^5)_s$-$(A^6)_t$-$(A^7)_u$-$(A^8)_v$-$R^{17'}$ and/or $R^{95'}$ is a group of formula -$(A^1)_o$-$(A^2)_p$-$(A^3)_q$-$(A^4)_r$-$R^{16'}$.

Compounds of the formula

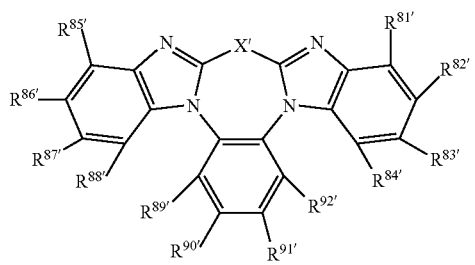

are preferred. Compounds of the formula

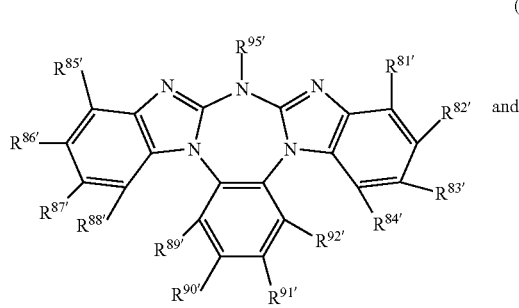

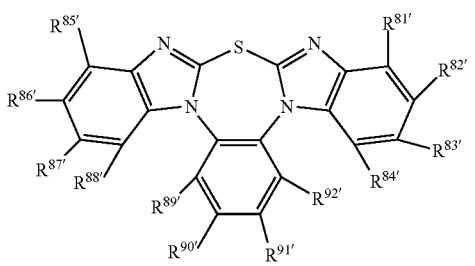

are more preferred.

$R^{81'}$, $R^{82'}$, $R^{83'}$, $R^{84'}$, $R^{85'}$, $R^{86'}$, $R^{87'}$, $R^{88'}$, $R^{89'}$ and $R^{92'}$ are preferably H.

$R^{90'}$ and $R^{91'}$ are preferably H, or a group of formula $-(A^5)_s-(A^6)_t-(A^7)_u-(A^8)_v-R^{17'}$.

$R^{95'}$ is a group of formula $-(A^1)_o-(A^2)_p-(A^3)_q-(A^4)_r-R^{16'}$. The group of formula $(A^1)_o-(A^2)_p-(A^3)_q-(A^4)_r-R^{16'}$ includes groups of formula

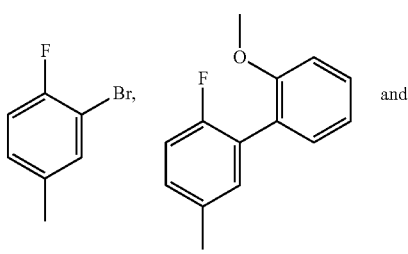

and

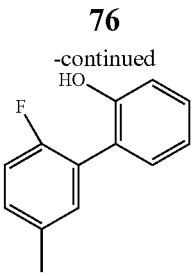

For D, E, G, $A^1$, $A^2$, $A^3$, $A^4$, $A^5$, $A^6$, $A^7$ and $A^8$ the same preferences apply as in case of the compounds of formula (I).

Examples of the intermediates of formula (IX) are shown below:

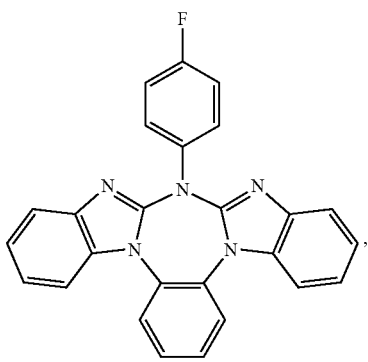

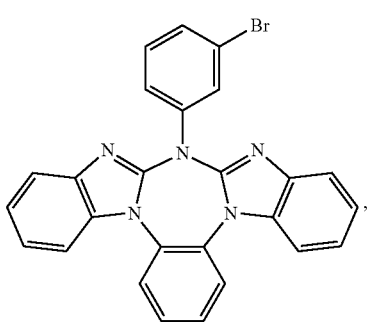

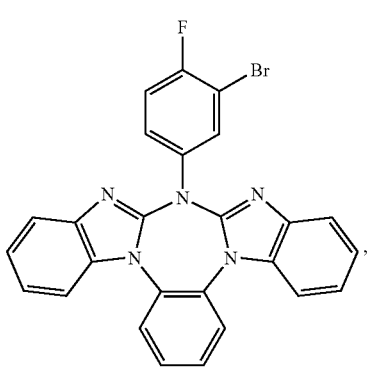

(I-4)
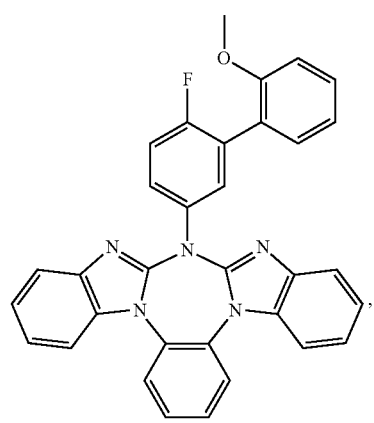
(I-5)
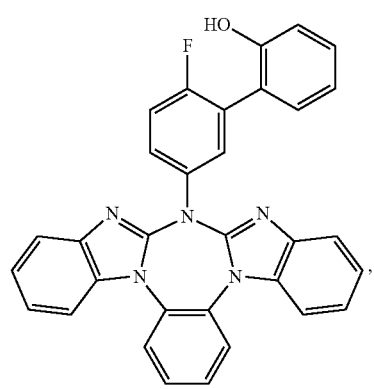
(I-6)
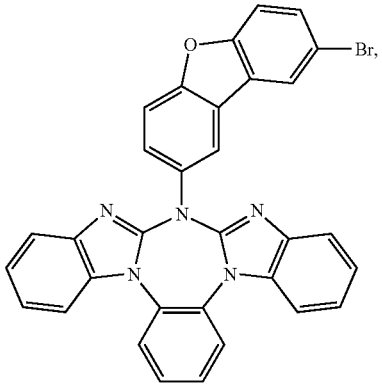
(I-7)
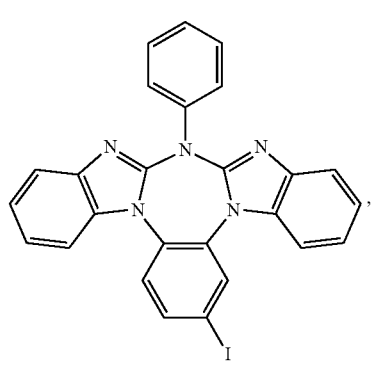
(I-8)
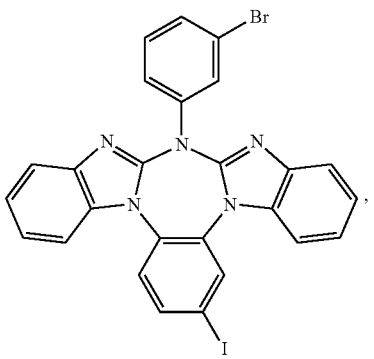
(I-9)
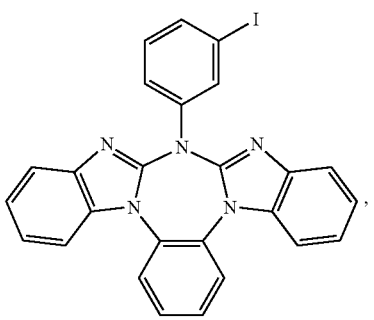
(I-10)
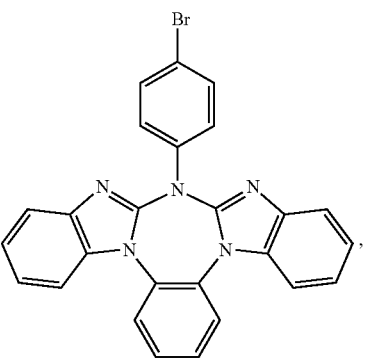
(I-11)
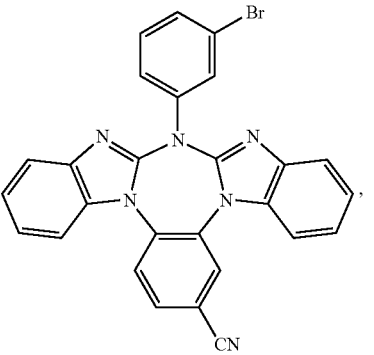
(I-12)
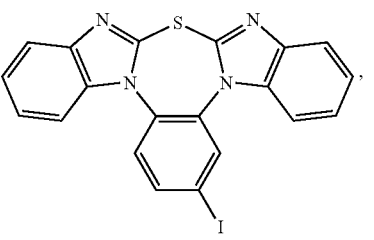

-continued (I-13)
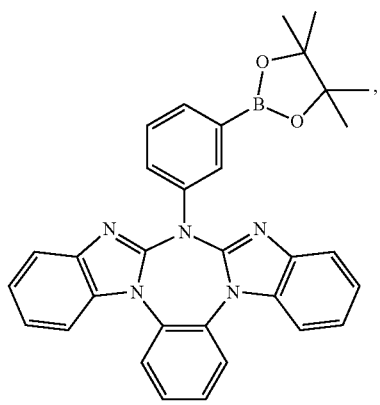

(I-14)
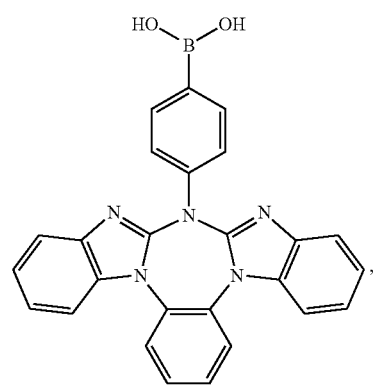

(I-15)

(I-16)

-continued (I-17)
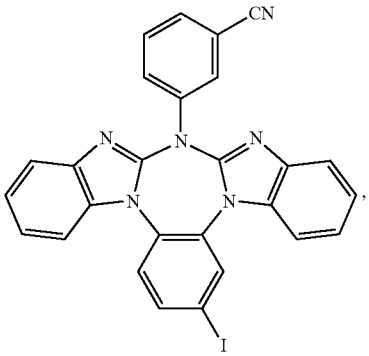

(I-18)
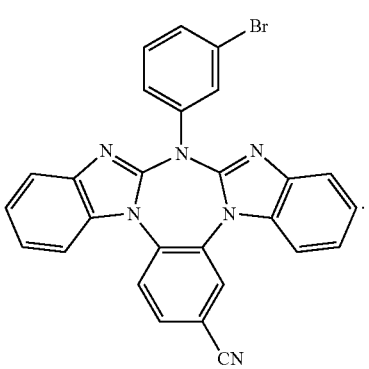

Compounds of the formula

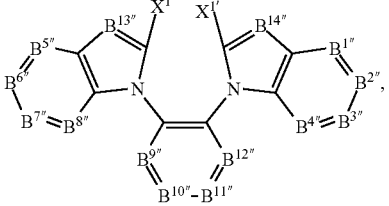
(X)

are new, intermediates in the production of the compounds of formula (IX), or (I) and form a further subject of the present invention; $X^1$ and $X^{1'}$ are independently of each other Cl, Br, or I, $B^{1''}$ is N, or $CR^{81''}$,
$B^{2''}$ is N, or $CR^{82''}$,
$B^{3''}$ is N, or $CR^{83''}$,
$B^{4''}$ is N, or $CR^{84''}$,
$B^{5''}$ is N, or $CR^{85''}$,
$B^{6''}$ is N, or $CR^{86''}$,
$B^{7''}$ is N, or $CR^{87''}$,
$B^{8''}$ is N, or $CR^{88''}$,
$B^{9''}$ is N, or $CR^{89''}$,
$B^{10''}$ is N, or $CR^{90''}$,
$B^{11''}$ is N, or $CR^{91''}$,
$B^{12''}$ is N, or $CR^{92''}$,
$B^{13''}$ is N, or $CR^{93''}$,
$B^{14''}$ is N, or $CR^{94''}$,
$R^{81''}$, $R^{82''}$, $R^{83''}$, $R^{84''}$, $R^{85''}$, $R^{86''}$, $R^{87''}$, $R^{88''}$, $R^{89''}$, $R^{90''}$, $R^{91''}$, $R^{92''}$, $R^{93''}$ and $R^{94''}$ are independently of each other H, CN, a $C_1$-$C_{25}$alkyl group, which can optionally be substituted by E and or interrupted by D; a $C_6$-$C_{24}$aryl group, which can optionally be substituted by G, a $C_2$-$C_{30}$heteroaryl group, which can optionally be substituted by G; or a group of formula -$(A^5)_s$-$(A^6)_t$-$(A^7)_u$-$(A^8)_v$-$R^{17'}$, or -$(A^5)_s$-$(A^6)_t$-$(A^7)_u$-$(A^8)_v$-$R^{17}$;

$R^{17'}$ are independently of each other F, Cl, Br, I, —B(OH)$_2$, —B(OY$^1$)$_2$,

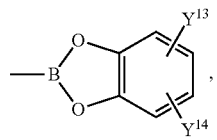

—BF$_4$Na, or —BF$_4$K, wherein Y$^1$ is independently in each occurrence a $C_1$-$C_{18}$alkyl group and Y$^2$ is independently in each occurrence a $C_2$-$C_{10}$alkylene group, and Y$^{13}$ and Y$^{14}$ are independently of each other hydrogen, or a $C_1$-$C_{18}$alkyl group, and s, t, u, v, D, E, G, $R^{17}$, $A^5$, $A^6$, $A^7$ and $A^8$ are as defined above, or below.

$X^1$ and $X^{1'}$ are preferably Br because of synthetic access.

The compound of the formula (X) is preferably a compound of formula

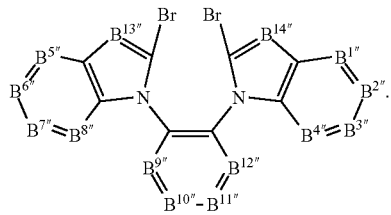
(X')

Compounds of formula

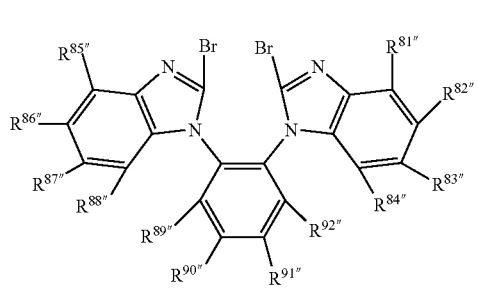
(Xa)

are more preferred.

$R^{81''}$, $R^{82''}$, $R^{83''}$, $R^{84''}$, $R^{85''}$, $R^{86''}$, $R^{87''}$, $R^{88''}$, $R^{89''}$ and $R^{92''}$ are preferably H.

$R^{90''}$ and $R^{91''}$ are preferably H, or a group of formula -$(A^5)_s$-$(A^6)_t$-$(A^7)_u$-$(A^8)_v$-$R^{17'}$, or -$(A^5)_s$-$(A^6)_t$-$(A^7)_u$-$(A^8)_v$-$R^{17}$. For D, E, G, $R^{17}$, $A^5$, $A^6$, $A^7$ and $A^8$ the same preferences apply as in case of the compounds of formula (I).

Examples of compounds of formula (X) are shown below:

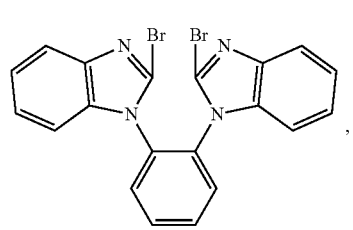
(IN-1)

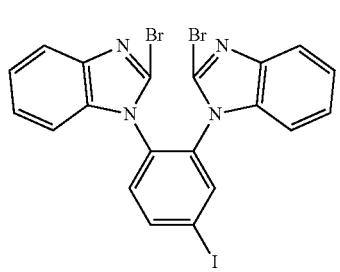
(IN-2)

and

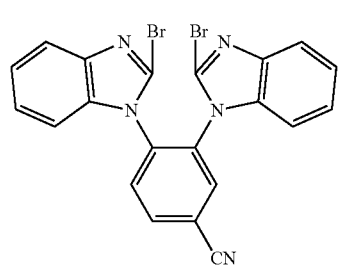
(IN-3)

A process for the production of the compounds of formula

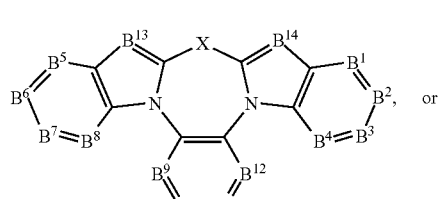
(I)

or

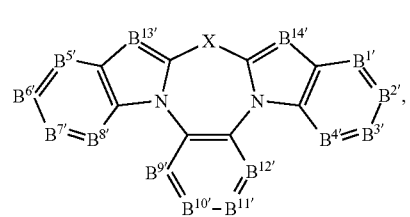
(IX)

wherein
X is $NR^{95}$, or S, X' is $NR^{95'}$, or S, comprises
a) reacting a compound of formula

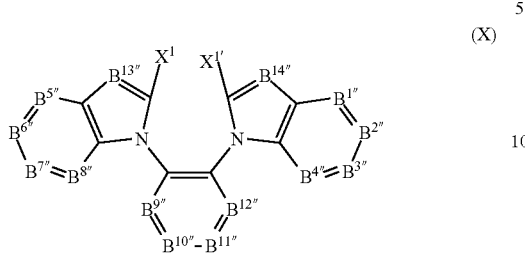
(X)

with a compound of formula $NH_2R^{95}$(XIIIa), wherein $R^{95}$ is a group of formula $-(A^1)_o-(A^2)_p-(A^3)_q-(A^4)_r-R^{16}$, or $NH_2R^{95'}$ (XIIIb), wherein $R^{95'}$ is a group of formula $-(A^1)_o-(A^2)_p-(A^3)_q-(A^4)_r-R^{16'}$, optionally in a solvent at elevated temperature, or
b) reacting a compound of formula (X) with natrium hydrogensulfite in a solvent at elevated temperature, wherein o, $R^{16}$, $R^{95}$, $R^{95'}$, $A^1$, $A^2$, $A^3$, $A^4$, $R^{16'}$, $B^{1'}$ to $B^{14'}$, $B^{1''}$ to $B^{14''}$ are defined above and $X^1$ and $X^{1'}$ are independently of each other Cl, Br, or I.

The synthesis of the compounds of formula (I) can be done in analogy to methods known in the literature.

The introduction of the group

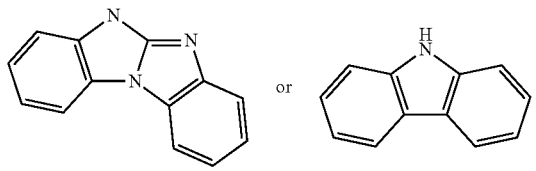 [SMILES: c1ccc2c(c1)nc1[nH]c3ccccc3n12 ; c1ccc2c(c1)[nH]c1ccccc12]

is performed in the presence of a base in a solvent at room temperature to reflux temperature of the solvent. Suitable bases are preferably selected from the group consisting of alkali metal and alkaline earth metal hydroxides such as NaOH, KOH, Ca(OH)$_2$, alkali metal hydrides such as NaH, KH, alkali metal amides such as NaNH$_2$, alkali metal or alkaline earth metal carbonates such as K$_2$CO$_3$ or Cs$_2$CO$_3$, alkali metal phosphates, such as, for example, K$_3$PO$_4$, and alkali metal alkoxides such as NaOMe, NaOEt. In addition, mixtures of the aforementioned bases are suitable. Particular preference is given to K$_3$PO$_4$ and K$_2$CO$_3$. Suitable solvents are, for example, (polar) aprotic solvents such as dimethyl sulfoxide, dimethylformamide, N-methyl-2-pyrrolidone (NMP), tridecane or alcohols.

The synthesis of

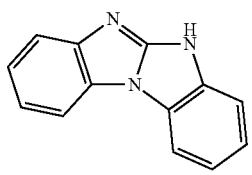 [SMILES: c1ccc2c(c1)nc1[nH]c3ccccc3n12]

is described, for example, in Achour, Reddouane; Zniber, Rachid, Bulletin des Societes Chimiques Beiges 96 (1987) 787-92.

Suitable base skeletons of the formula

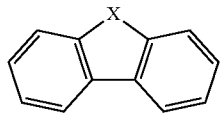

are either commercially available (especially in the cases when X is S, O, NH), or can be obtained by processes known to those skilled in the art. Reference is made to WO2010079051 and EP1885818.

The halogenation can be performed by methods known to those skilled in the art. Preference is given to brominating or iodinating in the 3 and 6 positions (dibromination) or in the 3 or 6 positions (monobromination) of the base skeleton of the formula 2,8 positions (dibenzofuran and dibenzothiophene) or 3,6 positions (carbazole).

Optionally substituted dibenzofurans, dibenzothiophenes and carbazoles can be dibrominated in the 2,8 positions (dibenzofuran and dibenzothiophene) or 3,6 positions (carbazole) with bromine or NBS in glacial acetic acid or in chloroform. For example, the bromination with Br$_2$ can be effected in glacial acetic acid or chloroform at low temperatures, e.g. 0° C. Suitable processes are described, for example, in M. Park, J. R. Buck, C. J. Rizzo, Tetrahedron, 54 (1998) 12707-12714 for X=NPh, and in W. Yang et al., J. Mater. Chem. 13 (2003) 1351 for X=S. In addition, 3,6-dibromocarbazole, 3,6-dibromo-9-phenylcarbazole, 2,8-dibromodibenzothiophene, 2,8-dibromodibenzofuran, 2-bromocarbazole, 3-bromodibenzothiophene, 3-bromodibenzofuran, 3-bromocarbazole, 2-bromodibenzothiophene and 2-bromodibenzofuran are commercially available.

Monobromination in the 4 position of dibenzofuran (and analogously for dibenzothiophene) is described, for example, in J. Am. Chem. Soc. 1984, 106, 7150. Dibenzofuran (dibenzothiophene) can be monobrominated in the 3 position by a sequence known to those skilled in the art, comprising a nitration, reduction and subsequent Sandmeyer reaction.

Monobromination in the 2 position of dibenzofuran or dibenzothiophene and monobromination in the 3 position of carbazole are effected analogously to the dibromination, with the exception that only one equivalent of bromine or NBS is added.

Alternatively, it is also possible to utilize iodinated dibenzofurans, dibenzothiophenes and carbazoles. The preparation is described, inter alia, in Tetrahedron. Lett. 47 (2006) 6957-6960, Eur. J. Inorg. Chem. 24 (2005) 4976-4984, J. Heterocyclic Chem. 39 (2002) 933-941, J. Am. Chem. Soc. 124 (2002) 11900-11907, J. Heterocyclic Chem, 38 (2001) 77-87.

For the nucleophilic substitution, Cl- or F-substituted dibenzofurans, dibenzothiophenes and carbazoles are required. The chlorination is described, inter alia, in J. Heterocyclic Chemistry, 34 (1997) 891-900, Org. Lett., 6 (2004) 3501-3504; J. Chem. Soc. [Section] C: Organic, 16 (1971) 2775-7, Tetrahedron Lett. 25 (1984) 5363-6, J. Org. Chem. 69 (2004) 8177-8182. The fluorination is described in J. Org. Chem. 63 (1998) 878-880 and J. Chem. Soc., Perkin Trans. 2, 5 (2002) 953-957.

Halogen is fluorine, chlorine, bromine and iodine.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

$C_6$-$C_{24}$aryl ($C_6$-$C_{18}$aryl), which optionally can be substituted, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted. Phenyl, 1-naphthyl and 2-naphthyl are examples of a $C_6$-$C_{10}$aryl group.

$C_2$-$C_{30}$heteroaryl represents a ring with five to seven ring atoms or a condensed ring system, wherein nitrogen, oxygen or sulfur are the possible hetero atoms, and is typically a heterocyclic group with five to 30 atoms having at least six conjugated π-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazoyl, 5-benzimidazo[1,2-a]benzimidazoyl, benzimidazolo[2,1-b][1,3]benzothiazolyl, carbazolyl, or phenoxazinyl, which can be unsubstituted or substituted. Benzimidazo[1,2-a]benzimidazo-5-yl, benzimidazo[1,2-a]benzimidazo-2-yl, carbazolyl and dibenzofuranyl are examples of a $C_2$-$C_{14}$heteroaryl group.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, or a cyano group. The $C_6$-$C_{24}$aryl ($C_6$-$C_{18}$aryl) and $C_2$-$C_{30}$heteroaryl groups are preferably substituted by one, or more $C_1$-$C_8$alkyl groups.

If a substituent occurs more than one time in a group, it can be different in each occurrence.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$) $C_4H_9$), $CH_2$—CH($OR^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H;

$C_1$-$C_8$alkylene-COO—$R^z$, e.g. $CH_2COOR^z$, $CH(CH_3)COOR^z$, $C(CH_3)_2COOR^z$, where $R^z$ is H, $C_1$-$C_{18}$ $(CH_2CH_2O)_{1-9}$—$R^x$, and $R^x$ embraces the definitions indicated above;

$CH_2CH_2$—O—CO—CH=$CH_2$; $CH_2CH(OH)CH_2$—O—CO—$C(CH_3)$=$CH_2$.

An alkyl group substituted by E is, for example, an alkyl group where at least one of the hydrogen atoms is replaced by F. Examples are —$CF_3$, —$CF_2CF_3$, —$CF_2CF_2CF_3$, —$CF(CF_3)_2$, —$(CF_2)_3CF_3$, and —$C(CF_3)_3$.

The compounds of the formula I can be used as matrix material and/or charge/exciton blocker material and/or charge transport material (charge conductor material). The inventive compounds of the formula I are preferably used as matrix materials in organic electronics applications, especially in OLEDs.

In the emission layer or one of the emission layers of an OLED, it is also possible to combine an emitter material with a matrix material of the compound of the formula I and a further matrix material. This may achieve a high quantum efficiency of this emission layer.

When a compound of the formula I is used as matrix (host) material in an emission layer and additionally as charge/exciton blocker material, owing to the chemical identity or similarity of the materials, an improved interface between the emission layer and the adjacent charge/exciton blocker material, which can lead to a decrease in the voltage with equal luminance and to an extension of the lifetime of the OLED. Moreover, the use of the same material for charge/exciton blocker material and for the matrix of an emission layer allows the production process of an OLED to be simplified, since the same source can be used for the vapor deposition process of the material of one of the compounds of the formula I.

Suitable structures of organic electronic devices are known to those skilled in the art and are specified below.

The organic transistor generally includes a semiconductor layer formed from an organic layer with charge transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or charge transport capacity. In addition, it is possible for further layers known to those skilled in the art to be present in the organic solar cell. The layers with charge transport capacity may comprise the compounds of formula I.

It is likewise possible that the compounds of the formula I are present both in the light-emitting layer (preferably as matrix material) and in the blocking layers (as charge/exciton blockers).

The present invention further provides an organic light-emitting diode comprising an anode (a) and a cathode (i) and a light-emitting layer (e) arranged between the anode (a) and the cathode (i), and if appropriate at least one further layer selected from the group consisting of at least one blocking layer for holes/excitons, at least one blocking layer for electrons/excitons, at least one hole injection layer, at least one hole transport layer, at least one electron injection layer and at least one electron transport layer, wherein the at least one compound of the formula I is present in the light-emitting layer (e) and/or in at least one of the further layers. The at least one compound of the formula I is preferably present in the light-emitting layer and/or the charge/exciton blocking layers.

In a preferred embodiment of the present invention, at least one compound of the formula (I), especially a compound of formula (Ia-1), very especially a compound of the formula (Ia-1), is used as charge transport material.

In another preferred embodiment of the present invention, at least one compound of the formula (I), especially a compound of formula (Ia-1), very especially a compound of the formula (Ia-1), is used as charge/exciton blocker material.

Compounds of formula (Ia) are preferred. Compounds of formula (Ia-1) are more preferred. Compounds of formula (Ia-1), wherein one of the groups $R^{90}$ and $R^{91}$ is CN and the other is H, are most preferred.

The present application further relates to a light-emitting layer comprising at least one compound of the formula I.

Structure of the Inventive OLED

The inventive organic light-emitting diode (OLED) thus generally has the following structure: an anode (a) and a cathode (i) and a light-emitting layer (e) arranged between the anode (a) and the cathode (i).

The inventive OLED may, for example—in a preferred embodiment—be formed from the following layers:
1. Anode (a)
2. Hole transport layer (c)
3. Light-emitting layer (e)
4. Blocking layer for holes/excitons (f)
5. Electron transport layer (g)
6. Cathode (i)

Layer sequences different than the aforementioned structure are also possible, and are known to those skilled in the art. For example, it is possible that the OLED does not have all of the layers mentioned; for example, an OLED with layers (a) (anode), (e) (light-emitting layer) and (i) (cathode) is likewise suitable, in which case the functions of the layers (c) (hole transport layer) and (f) (blocking layer for holes/excitons) and (g) (electron transport layer) are assumed by the adjacent layers. OLEDs which have layers (a), (c), (e) and (i), or layers (a), (e), (f), (g) and (i), are likewise suitable. In addition, the OLEDs may have a blocking layer for electrons/excitons (d) between the hole transport layer (c) and the Light-emitting layer (e).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole transport layer, in one embodiment, may simultaneously block excitons and/or electrons.

Furthermore, the individual layers of the OLED among those specified above may in turn be formed from two or more layers. For example, the hole transport layer may be formed from a layer into which holes are injected from the electrode, and a layer which transports the holes away from the hole-injecting layer into the light-emitting layer. The electron conduction layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used in accordance with the invention.

In a preferred embodiment the OLED according to the present invention comprises in this order:
(a) an anode,
(b) optionally a hole injection layer,
(c) optionally a hole transport layer,
(d) optionally an exciton blocking layer
(e) an emitting layer,
(f) optionally a hole/exciton blocking layer
(g) optionally an electron transport layer,
(h) optionally an electron injection layer, and
(i) a cathode.

In a particularly preferred embodiment the OLED according to the present invention comprises in this order:
(a) an anode,
(b) optionally a hole injection layer,
(c) a hole transport layer,
(d) an exciton blocking layer
(e) an emitting layer,
(f) a hole/exciton blocking layer
(g) an electron transport layer, and
(h) optionally an electron injection layer, and
(i) a cathode.

The properties and functions of these various layers, as well as example materials are known from the prior art and are described in more detail below on basis of preferred embodiments.

Anode (a):

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (a) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

Hole Injection Layer (b):

Generally, injection layers are comprised of a material that may improve the injection of charge carriers from one layer, such as an electrode or a charge generating layer, into an adjacent organic layer. Injection layers may also perform a charge transport function. The hole injection layer may be any layer that improves the injection of holes from anode into an adjacent organic layer. A hole injection layer may comprise a solution deposited material, such as a spin-coated polymer, or it may be a vapor deposited small molecule material, such as, for example, CuPc or MTDATA. Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrene-sulfonate) also called PEDOT/PSS.

Hole Transport Layer (c):

Either hole-transporting molecules or polymers may be used as the hole transport material. Suitable hole transport materials for layer (c) of the inventive OLED are disclosed, for example, in Kirk-Othmer Encyclopedia of Chemical Technology, 4th Edition, Vol. 18, pages 837 to 860, 1996, US20070278938, US2008/0106190, US2011/0163302 (triarylamines with (di)benzothiophene/(di)benzofuran; Nan-Xing Hu et al. Synth. Met. 111 (2000) 421 (indolocarbazoles), WO2010002850 (substituted phenylamine compounds) and WO2012/16601 (in particular the hole transport materials mentioned on pages 16 and 17 of WO2012/16601). Combination of different hole transport material may be used. Reference is made, for example, to WO2013/022419, wherein

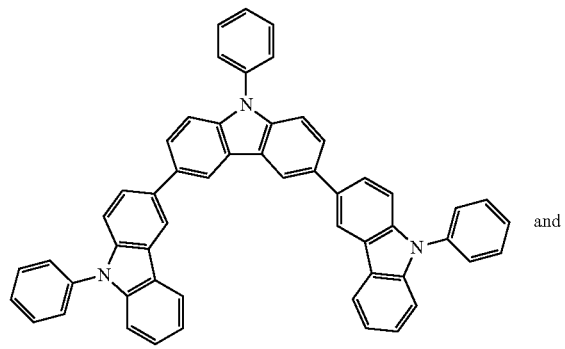

(HTL1-1)

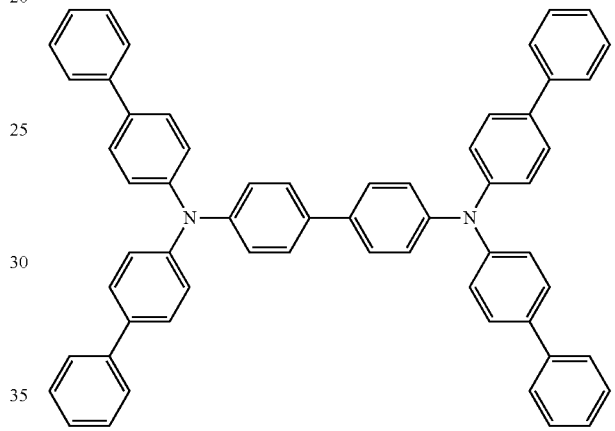

(HTL2-1)

and constitute the hole transport layer. Customarily used hole-transporting molecules are selected from the group consisting of

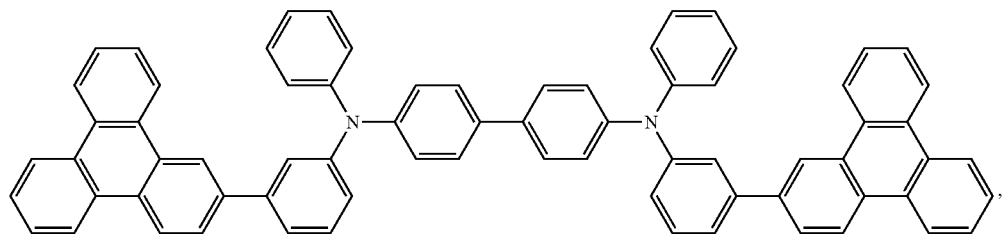

,

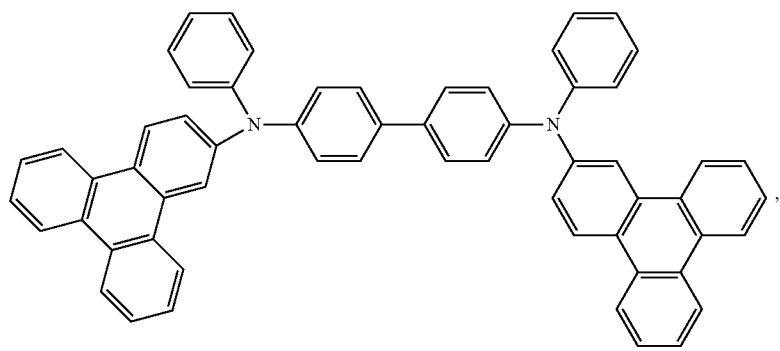

,

-continued

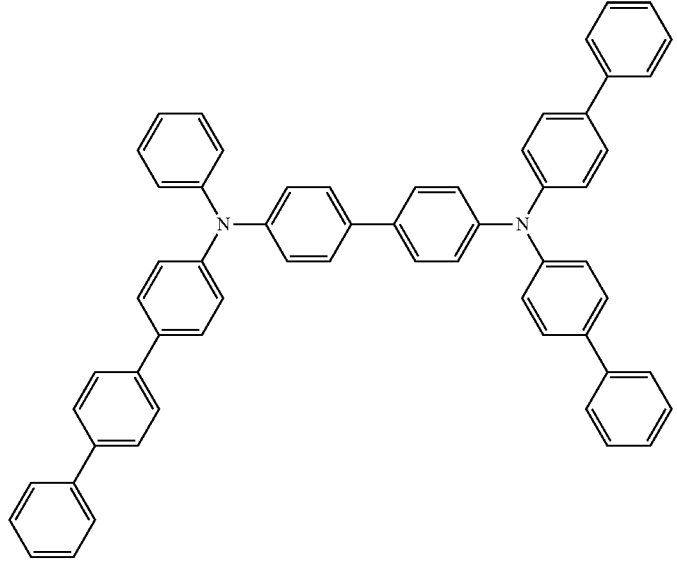

(4-phenyl-N-(4-phenylphenyl)-N-[4-[4-(N-[4-(4-phenyl-phenyl)phenyl]anilino)phenyl]phenyl]aniline),

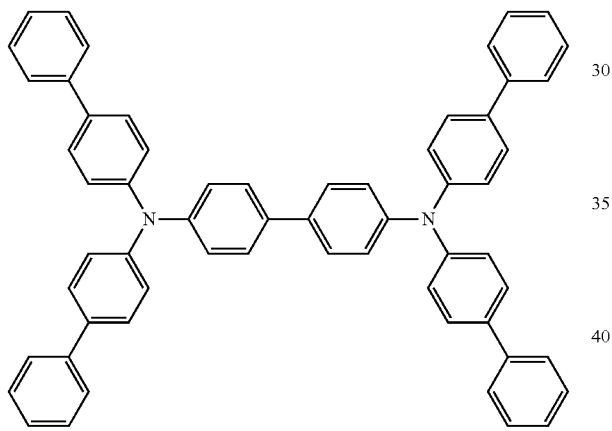

(4-phenyl-N-(4-phenylphenyl)-N-[4-[4-(4-phenyl-N-(4-phenylphenyl)anilino)phenyl]phenyl]aniline),

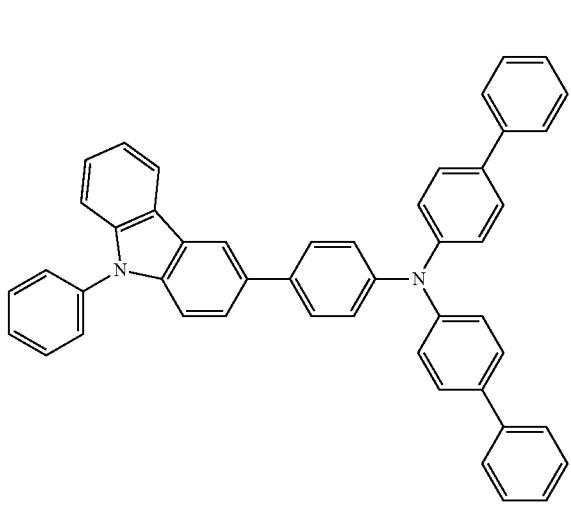 [SMILES: c1ccc(-c2ccc(N(c3ccc(-c4ccccc4)cc3)c3ccc(-c4ccc5c(c4)c4ccccc4n5-c4ccccc4)cc3)cc2)cc1]

(4-phenyl-N-[4-(9-phenylcarbazol-3-yl)phenyl]-N-(4-phenylphenyl)aniline),

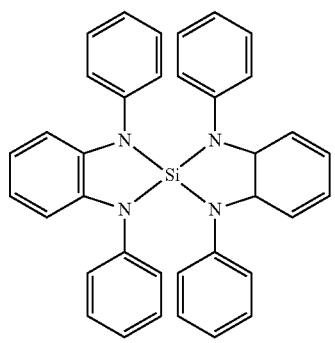 [SMILES: C1=CC2C(C=C1)N(c1ccccc1)[Si]1(N(c3ccccc3)c3ccccc3N1c1ccccc1)N2c1ccccc1]

(1,1',3,3'-tetraphenylspiro[1,3,2-benzodiazasilole-2,2'-3a,7a-dihydro-1,3,2-benzodiazasilole]),

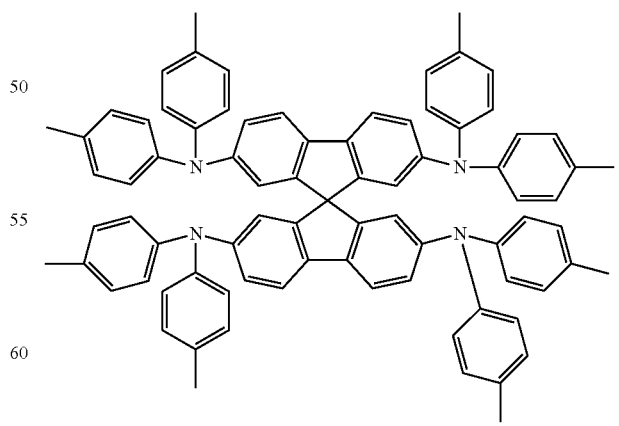

(N2,N2,N2',N2',N7,N7,N7',N7'-octakis(p-tolyl)-9,9'-spirobi[fluorene]-2,2',7,7'-tetramine), 4,4'-bis[N-(1-naphthyl)-N-phenylamino]biphenyl (α-NPD), N,N'-diphenyl-N,N'-bis(3- methylphenyl)-[1,1'-biphenyl]-4,4'-diamine (TPD), 1,1-bis [(di-4-tolylamino)phenyl]-cyclohexane (TAPC), N,N'-bis(4-methylphenyl)-N,N'-bis(4-ethylphenyl)-[1,1'-(3,3'-dimethyl)-biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)2-methylphenyl](4-methylphenyl)methane (MPMP), 1-phenyl-3-[p-(diethylamino)styryl]5-[p-(diethylamino)phenyl]pyrazoline (PPR or DEASP), 1,2-trans-bis(9H-carbazol9-yl)-cyclobutane (DCZB), N,N,N',N'-tetrakis(4-methylphenyl)-(1,1-biphenyl)-4,4'-diamine (TTB), fluorine compounds such as 2,2',7,7'-tetra(N,N-di-tolyl)amino9,9-spirobifluorene (spiro-TTB), N,N'-bis(naphthalen-1-yl)-N,N'-bis(phenyl)9,9-spirobifluorene (spiro-NPB) and 9,9-bis(4-(N,N-bis-biphenyl-4-yl-amino)phenyl-9Hfluorene, benzidine compounds such as N,N'-bis(naphthalen-1-yl)-N,N'-bis(phenyl)benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrene-sulfonate) also called PE-DOT/PSS. Preferred examples of a material of the hole injecting layer are a porphyrin compound, an aromatic tertiary amine compound, or a styrylamine compound. Particularly preferable examples include an aromatic tertiary amine compound such as hexacyanohexaazatriphenylene (HAT).

In a preferred embodiment it is possible to use metal carbene complexes as hole transport materials. Suitable carbene complexes are, for example, carbene complexes as described in WO2005/019373A2, WO2006/056418 A2, WO2005/113704, WO2007/115970, WO2007/115981, WO2008/000727 and PCT/EP2014/055520. One example of a suitable carbene complex is Ir(DPBIC)$_3$ with the formula:

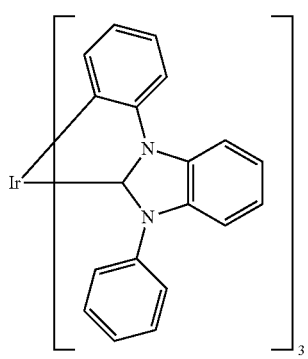

(HTM-1)

Another example of a suitable carbene complex is Ir(ABIC)$_3$ with the Ia:

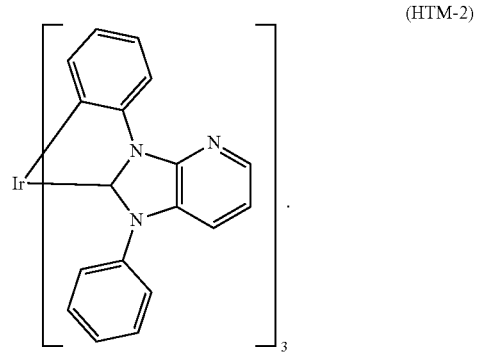

(HTM-2)

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, 2003, 359 (p-doped organic layers); A. G. Werner, F. Li, K. Harada, M. Pfeiffer, T. Fritz, K. Leo, Appl. Phys. Lett., Vol. 82, No. 25, 2003, 4495 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide, for example $MoO_2$, $MoO_3$, $WO_x$, $ReO_3$ and/or $V_2O_5$, preferably $MoO_3$ and/or $ReO_3$, more preferably $MoO_3$, or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho2,6-quinodimethane, 2-fluoro-7,7,8,8-tetracyanoquino-dimethane, 2,5-difluoro-7,7,8,8etracyanoquinodimethane, dicyanomethylene-1,3,4,5,7,8-hexafluoro-6H-naphthalen-2-ylidene)malononitrile (F6-T NAP), Mo(tfd)3 (from Kahn et al., J. Am. Chem. Soc. 2009, 131 (35), 12530-12531), compounds as described in EP1988587, US2008265216, EP2180029, US20100102709, WO2010132236, EP2180029 and quinone compounds as mentioned in EP2401254. Preferred mixtures comprise the aforementioned carbene complexes, such as, for example, the carbene complexes HTM-1 and HTM-2, and $MoO_3$ and/or $ReO_3$, especially $MoO_3$. In a particularly preferred embodiment the hole transport layer comprises from 0.1 to 10 wt % of $MoO_3$ and 90 to 99.9 wt % carbene complex, especially of the carbene complex HTM-1 and HTM-2, wherein the total amount of the $MoO_3$ and the carbene complex is 100 wt %.

Exciton Blocking Layer (d):

Blocking layers may be used to reduce the number of charge carriers (electrons or holes) and/or excitons that leave the emissive layer. An electron/exciton blocking layer (d) may be disposed between the first emitting layer (e) and the hole transport layer (c), to block electrons from emitting layer (e) in the direction of hole transport layer (c). Blocking layers may also be used to block excitons from diffusing out of the emissive layer. Suitable metal complexes for use as electron/exciton blocker material are, for example, carbene complexes as described in WO2005/019373A2, WO2006/056418A2, WO2005/113704, WO2007/115970, WO2007/115981, WO2008/000727 and PCT/EP2014/055520. Explicit reference is made here to the disclosure of the WO applications cited, and these disclosures shall be considered to be incorporated into the content of the present application. One example of a suitable carbene complex is compound HTM-1 and HTM-2.

Emitting Layer (e)

The light-emitting layer (e) comprises at least one emitter material. In principle, it may be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula I can be used as the matrix in the light-emitting layer.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO2010129323, WO2010056669, WO10086089, US2011/0057559, WO2011/106344, US2011/0233528, WO2012/048266 and WO2012/172482.

Further suitable metal complexes are the commercially available metal complexes tris(2-phenylpyridine)indium (III), iridium(III) tris(2-(4-tolyl)pyridinato-N,C$^{2'}$), bis(2-phenylpyridine)(acetylacetonato)iridium(III), indium(III) tris(1-phenylisoquinoline), indium(III) bis(2,2'-benzothienyl)pyridinato-N,C$^{3'}$)(acetylacetonate), tris(2-phenylquinoline)indium(III), indium(III) bis(2-(4,6-difluorophenyl)pyridinato-N,C$^{2}$)picolinate, iridium(III) bis(1-phenylisoquinoline)(acetylacetonate), bis(2-phenylquinoline)(acetylacetonato)iridium(III), indium(III) bis(di-benzo[f,h]quinoxaline)(acetylacetonate), indium(III) bis(2-methyldi-benzo[f,h]quinoxaline)(acetylacetonate) and tris(3-methyl-1-phenyl-4-trimethylacetyl-5-bis[1-(9,9-dimethyl-9H-fluoren-2-ypisoquinoline](acetyl-acetonato) iridium(III), bis(2-phenylbenzothiazolato)(acetylacetonato) iridium(III), bis(2-(9,9-dihexylfluorenyl)-1-pyridine) (acetylacetonato)indium(III), bis(2-benzo[b]thiophen-2-yl-pyridine)(acetylacetonato)iridium(III).

In addition, the following commercially available materials are suitable: tris(dibenzoylacetonato)mono (phenanthroline)europium(III), tris(dibenzoylmethane)-mono(phenanthroline)europium(III), tris (dibenzoylmethane)mono(5-aminophenanthroline)-europium(III), tris(di-2-naphthoylmethane)mono (phenanthroline)europium(III), tris(4-bromobenzoylmethane)mono(phenanthroline)europium (III), tris(di(biphenyl)methane)-mono(phenanthroline) europium(III), tris(dibenzoylmethane)mono(4,7-diphenyl-phenanthroline)europium(III), tris(dibenzoylmethane)mono (4,7-di-methyl-phenanthroline)europium(III), tris (dibenzoylmethane)mono(4,7-dimethylphenan- throlinedisulfonic acid)europium(III) disodium salt, tris[di (4-(2-(2-ethoxyethoxy)ethoxy)-benzoylmethane)]mono (phenanthroline)europium(III) and tris[di[4-(2-(2-ethoxy-ethoxy)ethoxy)benzoylmethane)]mono(5-aminophenanthroline)europium(III), osmium(II) bis(3-(trifluoromethyl)-5-(4-tert-butylpyridyl)-1,2,4-triazolato) diphenylmethylphosphine, osmium(II) bis(3-(trifluoromethyl)-5-(2-pyridyl)-1,2,4-triazole) dimethylphenylphosphine, osmium(II) bis(3-(trifluoromethyl)-5-(4-tert-butylpyridyl)-1,2,4-triazolato) dimethylphenylphosphine, osmium(II) bis(3-(trifluoromethyl)-5-(2-pyridyl)-pyrazolato) dimethylphenylphosphine, tris[4,4'-di-tert-butyl(2,2')-bipyridine]ruthenium(III), osmium(II) bis(2-(9,9-dibutylfluorenyl)-1-isoquinoline(acetylacetonate).

Preferred phosphorescence emitters are carbene complexes. Suitable phosphorescent blue emitters are specified in the following publications: WO2006/056418A2, WO2005/113704, WO2007/115970, WO2007/115981, WO2008/000727, WO2009050281, WO2009050290, WO2011051404, US2011/057559 WO2011/073149, WO2012/121936A2, US2012/0305894A1, WO2012/170571, WO2012/170461, WO2012/170463, WO2006/121811, WO2007/095118, WO2008/156879, WO2008/156879, WO2010/068876, US2011/0057559, WO2011/106344, US2011/0233528, WO2012/048266, WO2012/172482, PCT/EP2014/064054 and PCT/EP2014/066272.

Preferably, the light emitting layer (e) comprises at least one carbine complex as phosphorescence emitter. Suitable carbine complexes are, for example, compounds of the formula

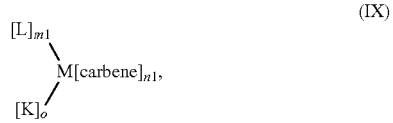

(IX)

which are described in WO 2005/019373 A2, wherein the symbols have the following meanings:

M is a metal atom selected from the group consisting of Co, Rh, Ir, Nb, Pd, Pt, Fe, Ru, Os, Cr, Mo, W, Mn, Tc, Re, Cu, Ag and Au in any oxidation state possible for the respective metal atom;

Carbene is a carbene ligand which may be uncharged or monoanionic and monodentate, bidentate or tridentate, with the carbene ligand also being able to be a biscarbene or triscarbene ligand;

L is a monoanionic or dianionic ligand, which may be monodentate or bidentate;

K is an uncharged monodentate or bidentate ligand selected from the group consisting of phosphines; phosphonates and derivatives thereof, arsenates and derivatives thereof; phosphites; CO; pyridines; nitriles and conjugated dienes which form a π complex with M$^{1}$;

n1 is the number of carbene ligands, where n1 is at least 1 and when n1>1 the carbene ligands in the complex of the formula I can be identical or different;

m1 is the number of ligands L, where m1 can be 0 or ≥1 and when m1>1 the ligands L can be identical or different;

o is the number of ligands K, where o can be 0 or 1 and when o>1 the ligands K can be identical or different;

where the sum n1+m1+o is dependent on the oxidation state and coordination number of the metal atom and on the denticity of the ligands carbene, L and K and also on the charge on the ligands, carbene and L, with the proviso that n1 is at least 1.

More preferred are metal-carbene complexes of the general formula

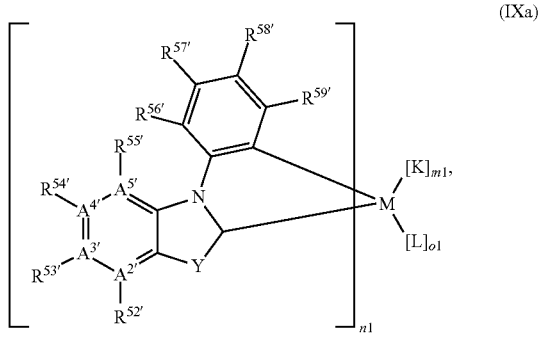

(IXa)

which are described in WO2011/073149,
where M is Ir, or Pt,
n1 is an integer selected from 1, 2 and 3,
Y is $NR^{51'}$, O, S or $C(R^{25'})_2$,
$A^{2'}$, $A^{3'}$, $A^{4'}$, and $A^{5'}$ are each independently N or C, where 2 A'=nitrogen atoms and at least one carbon atom is present between two nitrogen atoms in the ring,
$R^{51'}$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms,
$R^{52'}$, $R^{53'}$ $R^{54'}$ and $R^{55'}$ are each, if $A^{2'}$, $A^{3'}$, $A^{4'}$ and/or $A^{5'}$ is N, a free electron pair, or, if $A^{2'}$, $A^{3'}$, $A^{4'}$ and/or $A^{5'}$ is C, each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or
$R^{53'}$ and $R^{54'}$ together with $A^{3'}$ and $A^{4'}$ form an optionally substituted, unsaturated ring optionally interrupted by at least one further heteroatom and having a total of 5 to 18 carbon atoms and/or heteroatoms,
$R^{56'}$, $R^{57'}$, $R^{58'}$ and $R^{59'}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or
$R^{56'}$ and $R^{57'}$, $R^{57'}$ and $R^{58'}$ or $R^{58'}$ and $R^{59'}$, together with the carbon atoms to which they are bonded, form a saturated, unsaturated or aromatic, optionally substituted ring optionally interrupted by at least one heteroatom and having a total of 5 to 18 carbon atoms and/or heteroatoms, and/or
if $A^{5'}$ is C, $R^{55'}$ and $R^{56'}$ together form a saturated or unsaturated, linear or branched bridge optionally comprising heteroatoms, an aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms,
$R^{25'}$ is independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms,
K is an uncharged mono- or bidentate ligand,
L is a mono- or dianionic ligand, preferably monoanionic ligand, which may be mono- or bidentate,
m1 is 0, 1 or 2, where, when m1 is 2, the K ligands may be the same or different,
o1 is 0, 1 or 2, where, when o1 is 2, the L ligands may be the same or different.

The compound of formula IX is preferably a compound of the formula:

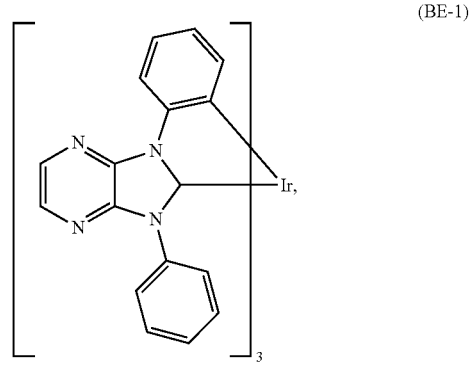

(BE-1)

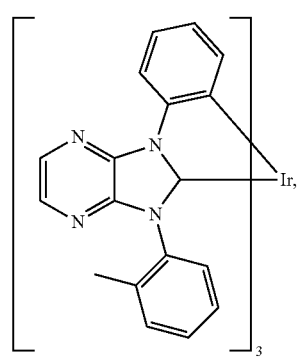
(BE-2)
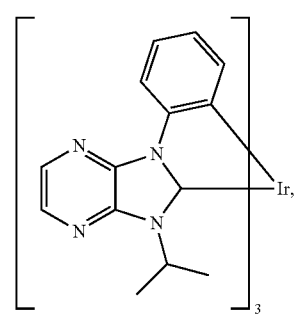
(BE-3)
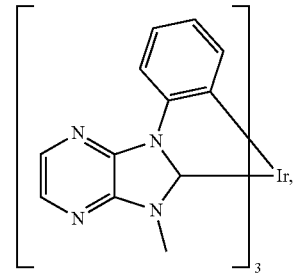
(BE-4)
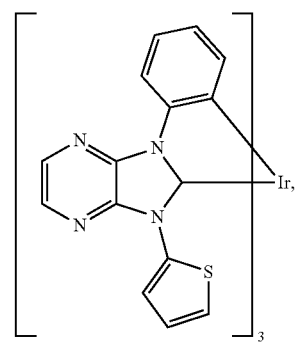
(BE-5)
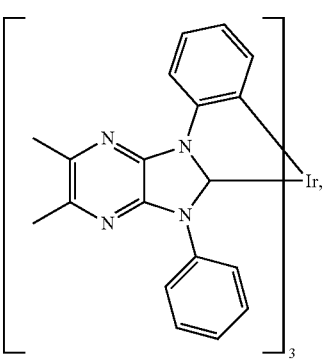
(BE-6)
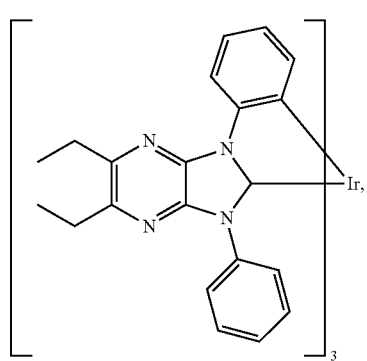
(BE-7)
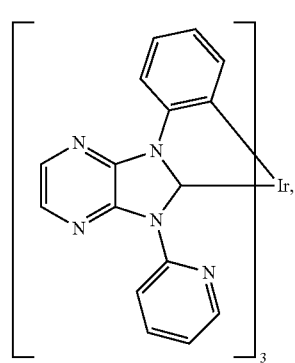
(BE-8)
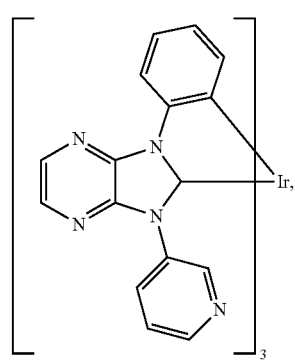
(BE-9)
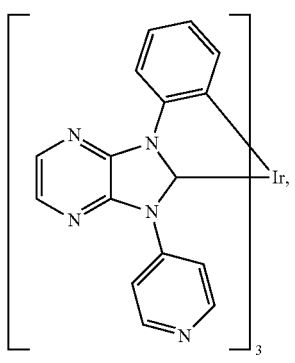
(BE-10)

(BE-11)
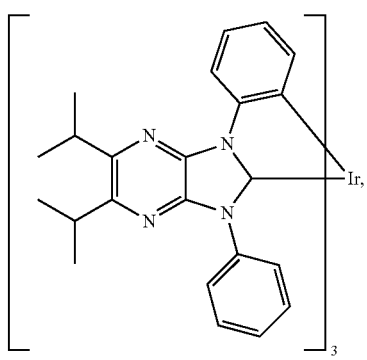
(BE-12)
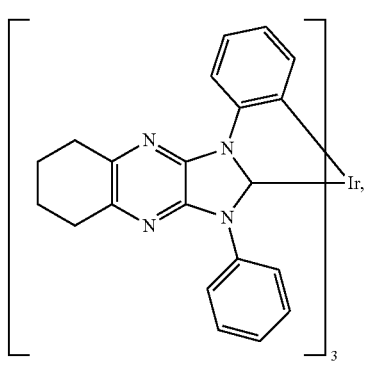
(BE-13)
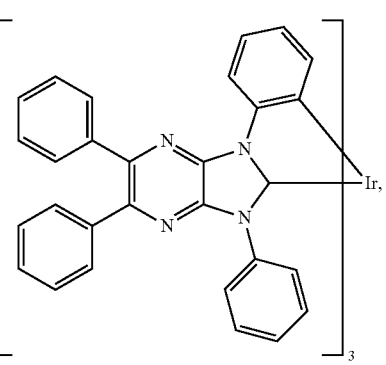
(BE-14)
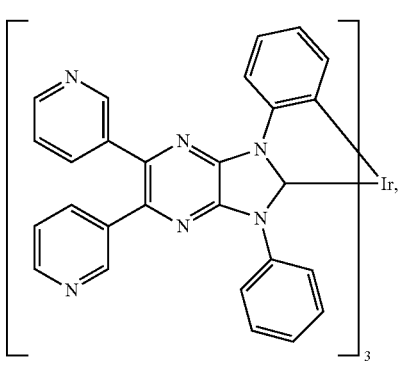
(BE-15)
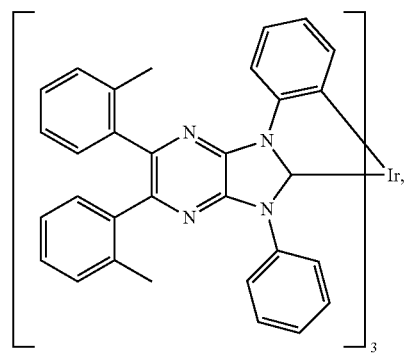
(BE-16)
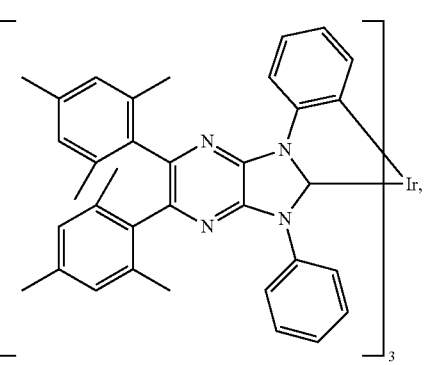
(BE-17)
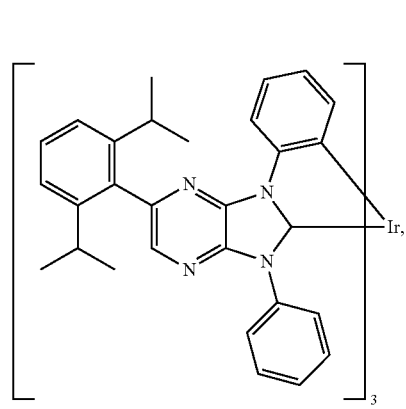
(BE-18)
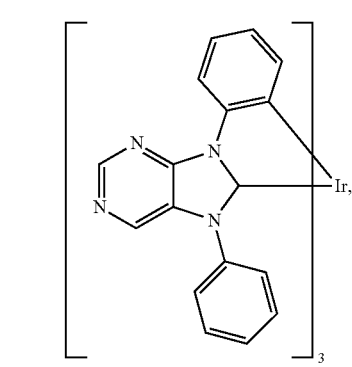

(BE-19)
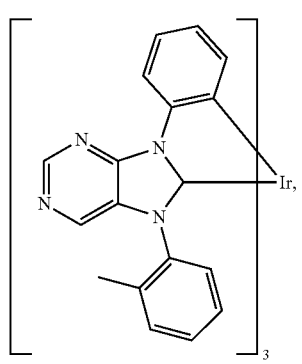
(BE-20)
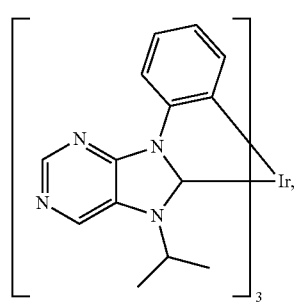
(BE-21)
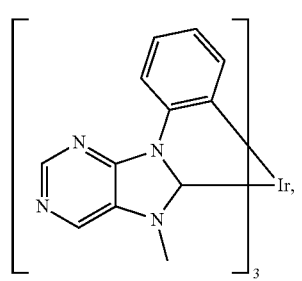
(BE-22)
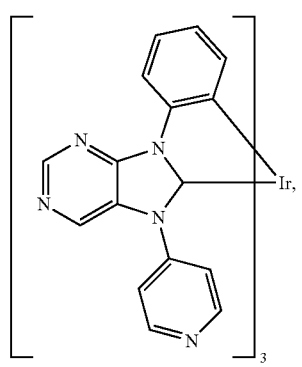
(BE-23)
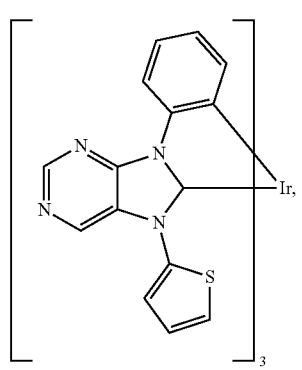
(BE-24)
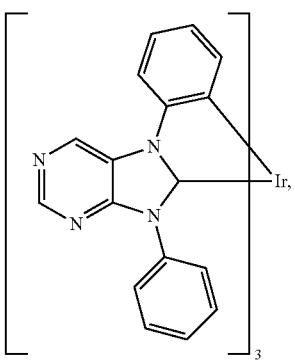
(BE-25)
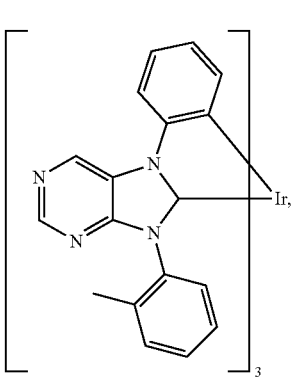
(BE-26)
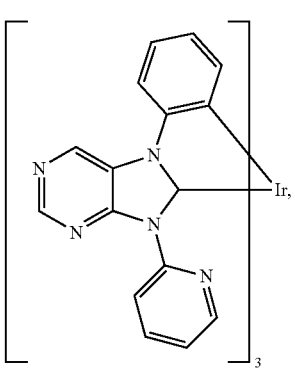
(BE-27)
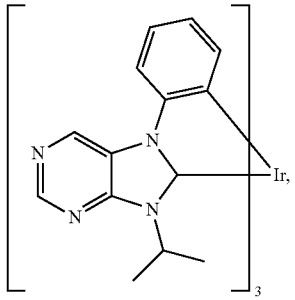

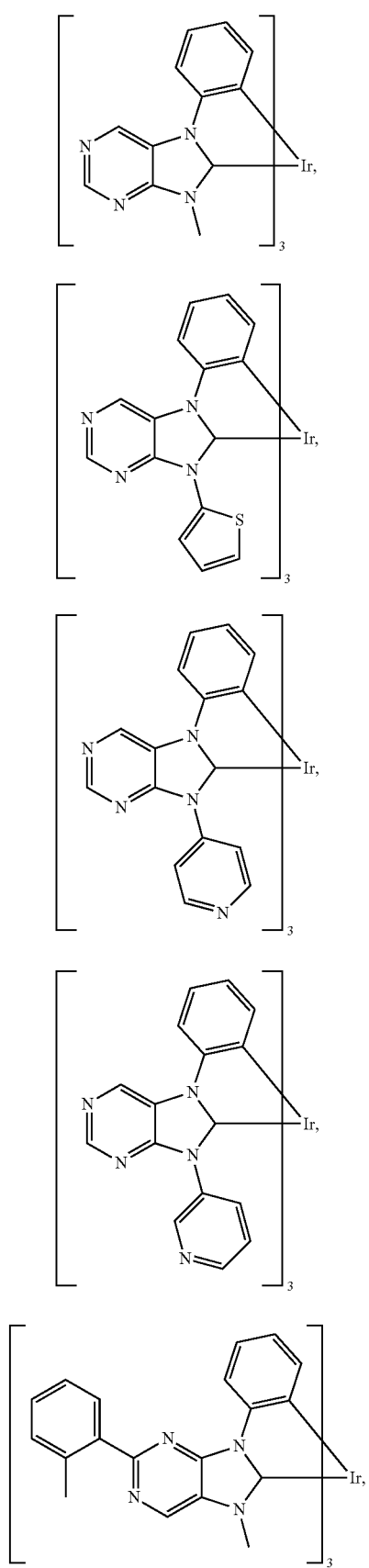
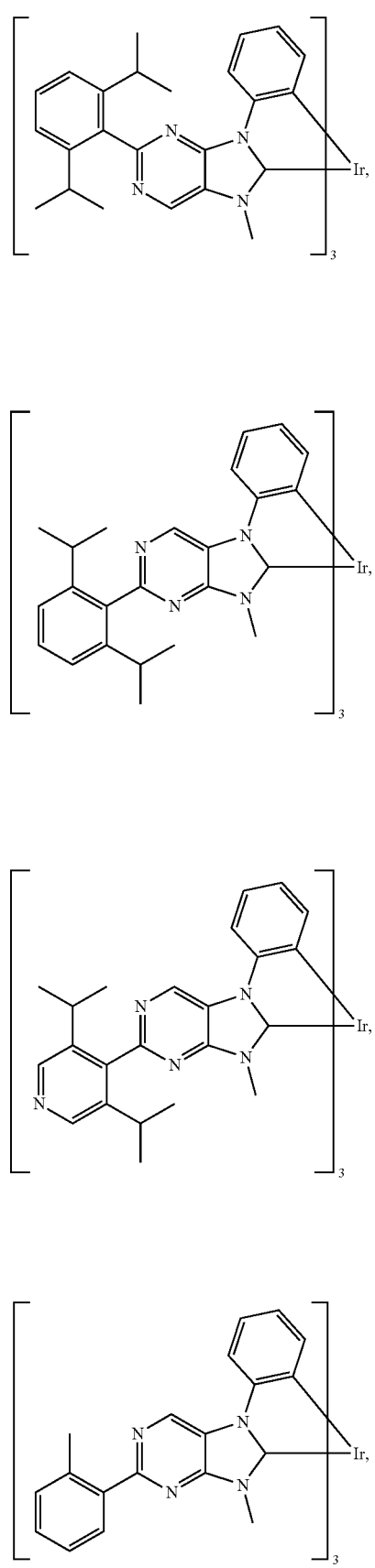

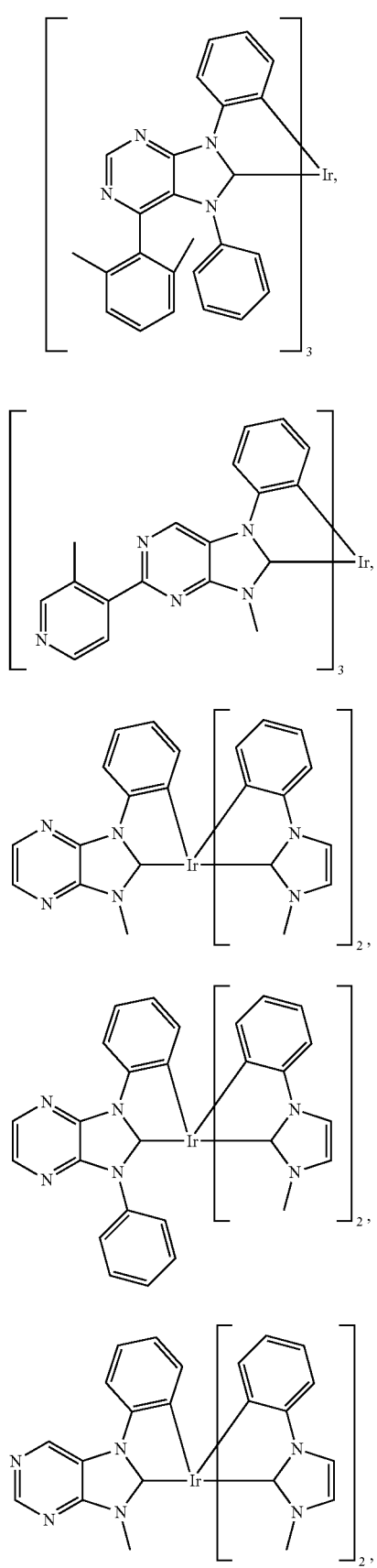
(BE-37)
(BE-38)
(BE-39)
(BE-40)
(BE-41)
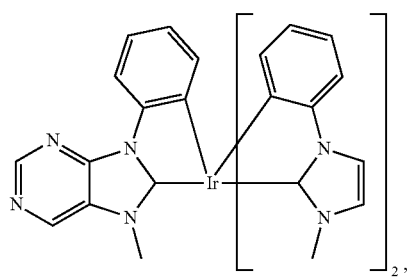
(BE-42)
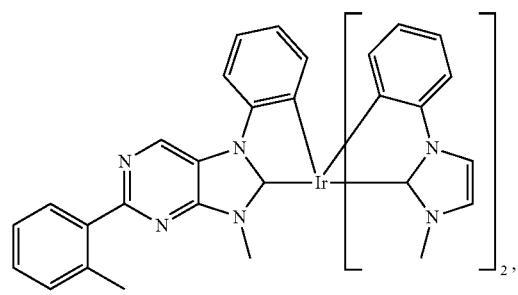
(BE-43)
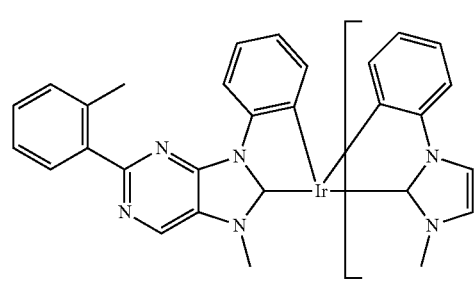
(BE-44)
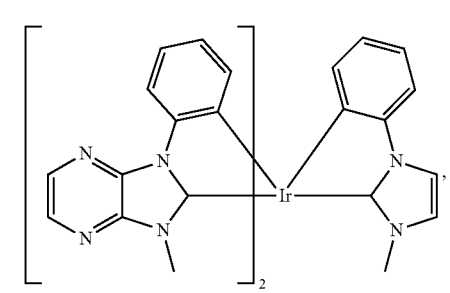
(BE-45)
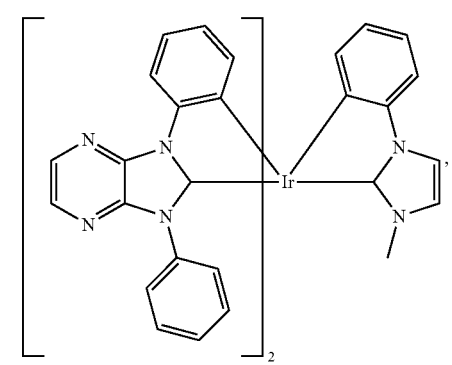
(BE-46)

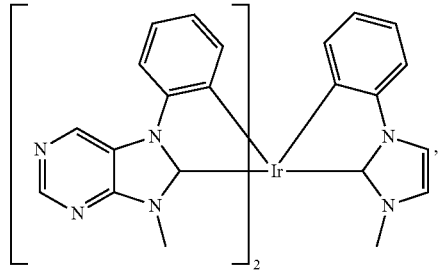
(BE-47)
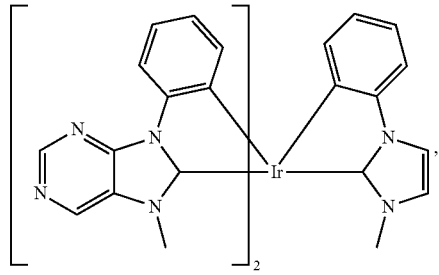
(BE-48)
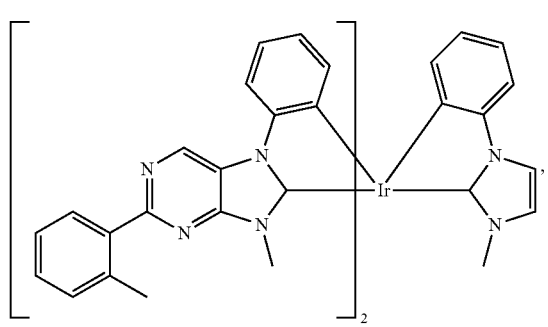
(BE-49)
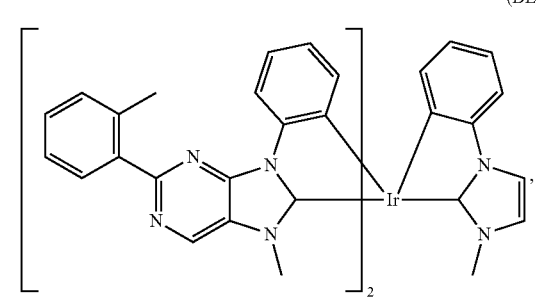
(BE-50)
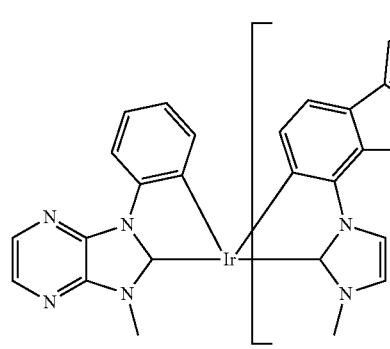
(BE-51)
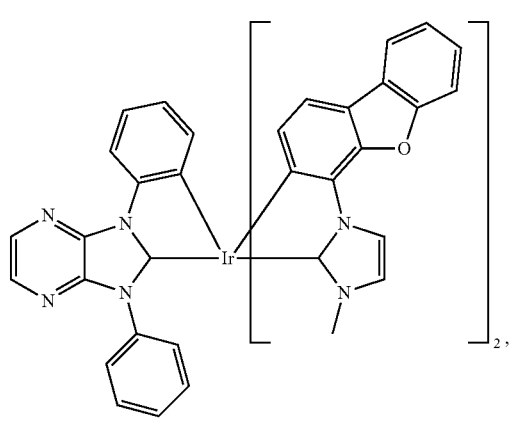
(BE-52)
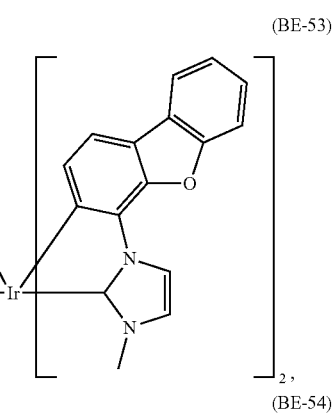
(BE-53)
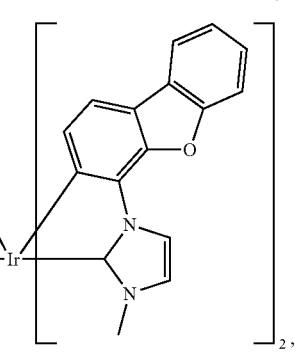
(BE-54)
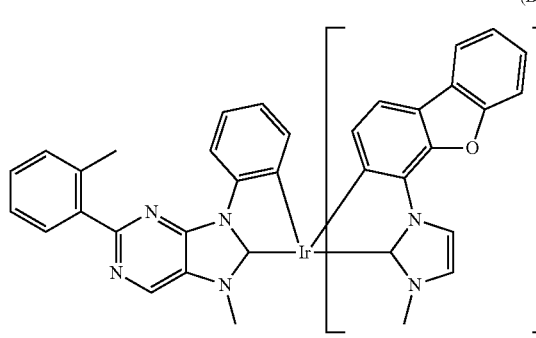
(BE-55)

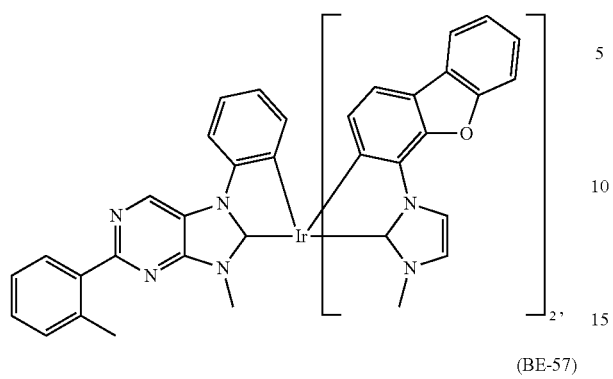
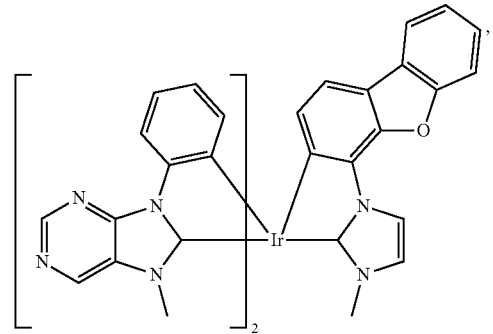
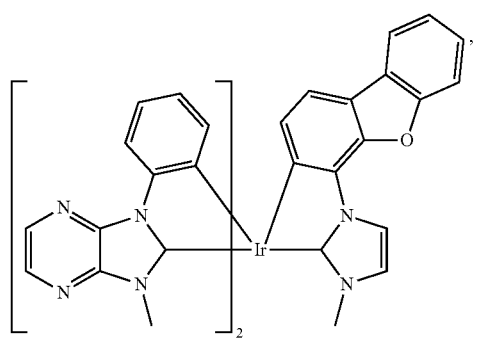
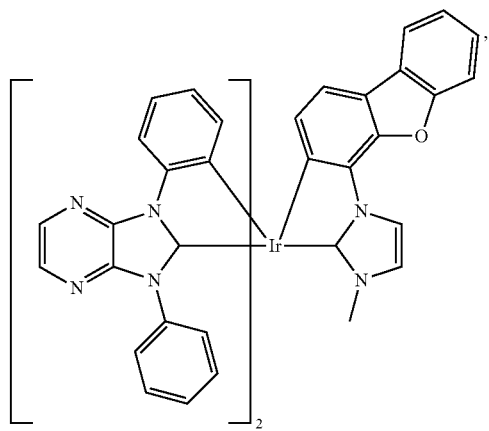
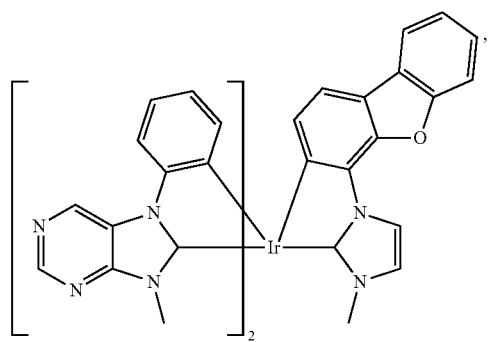

(BE-64)
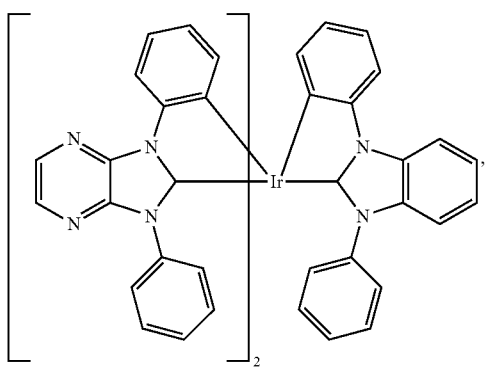
(BE-68)
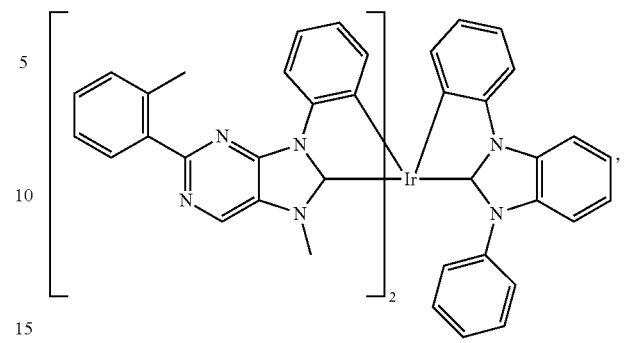
(BE-65)
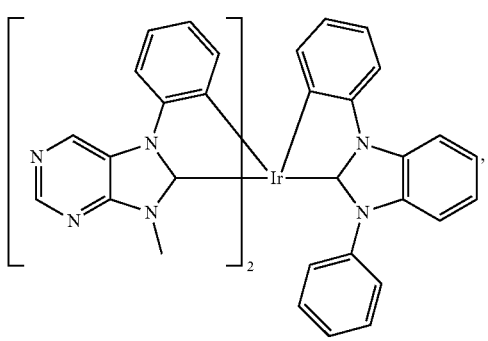
(BE-69)
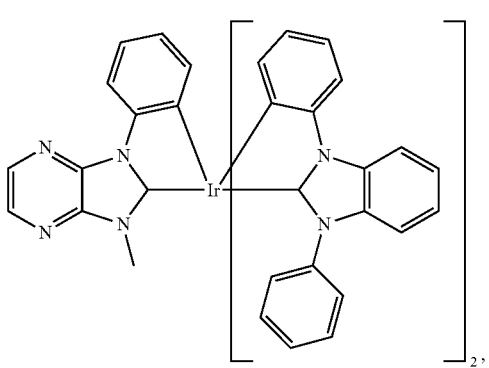
(BE-66)
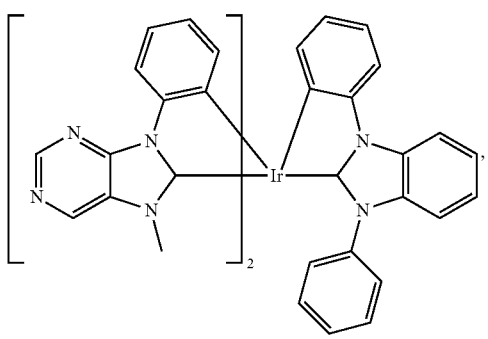
(BE-70)
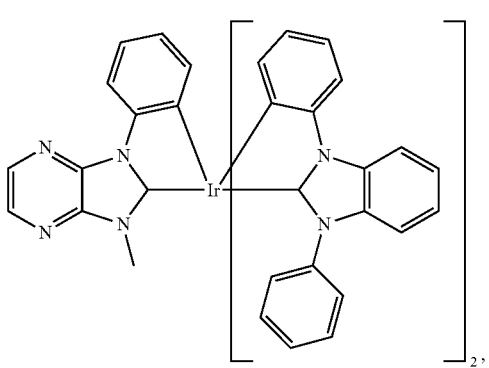
(BE-67)
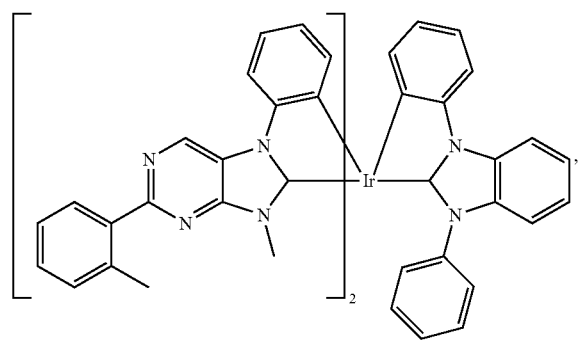
(BE-71)
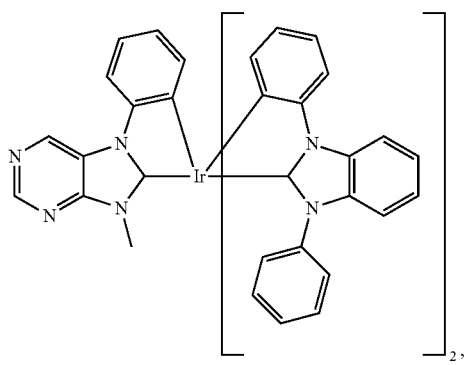

-continued
(BE-72)
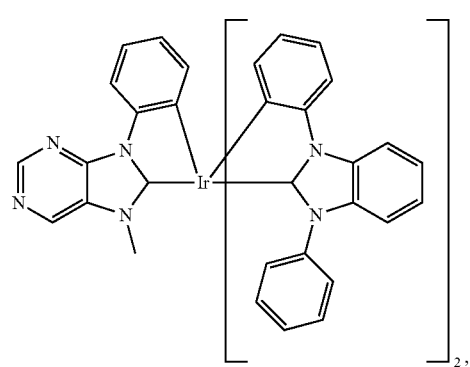
(BE-76)
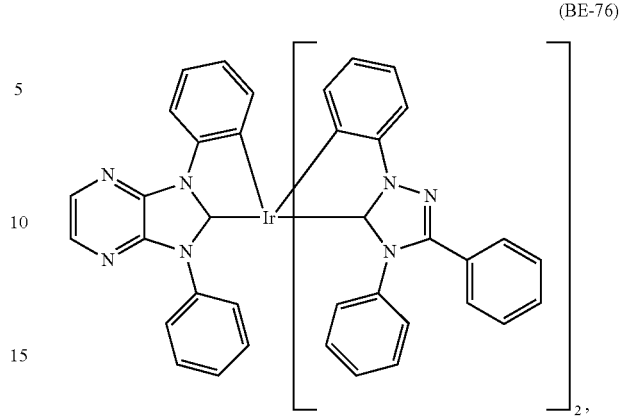
(BE-73)
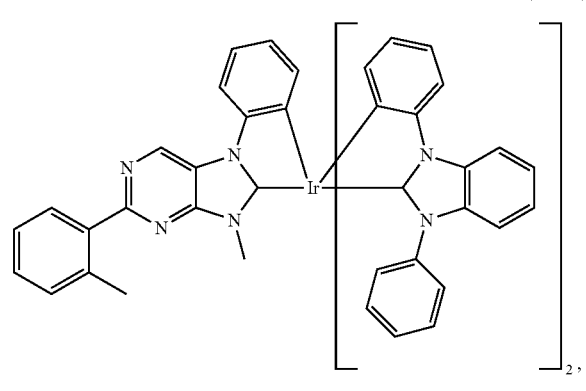
(BE-77)
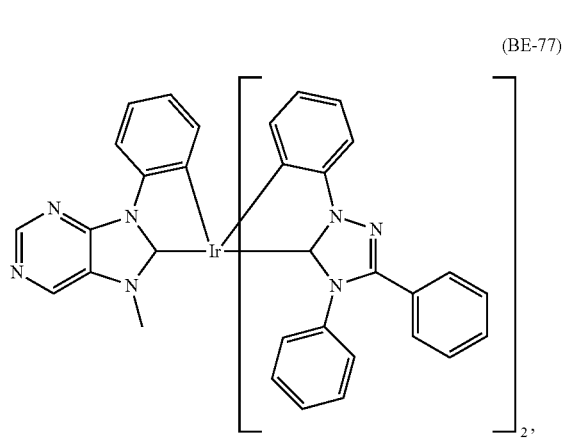
(BE-74)
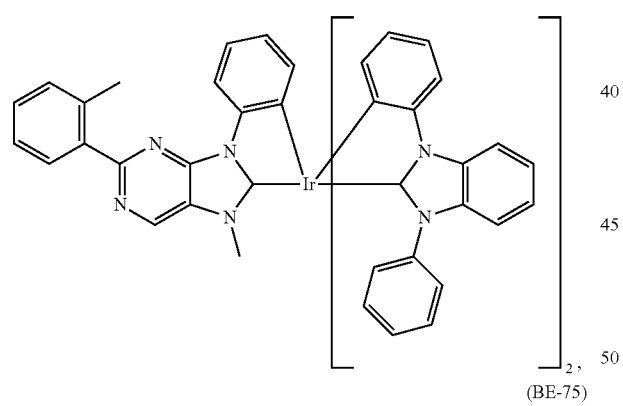
(BE-78)
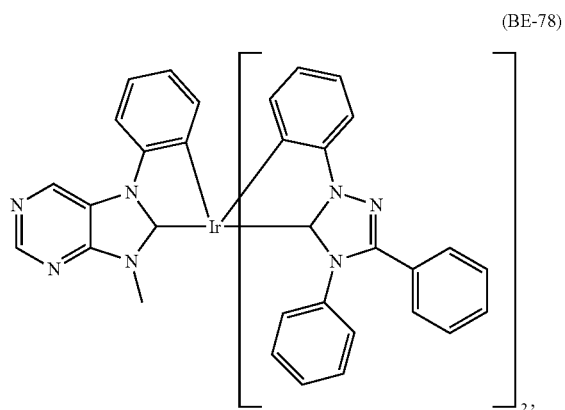
(BE-75)
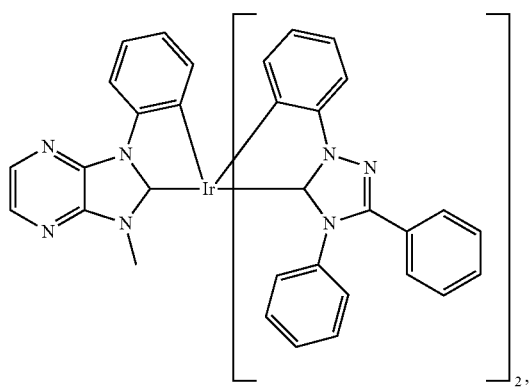
(BE-79)
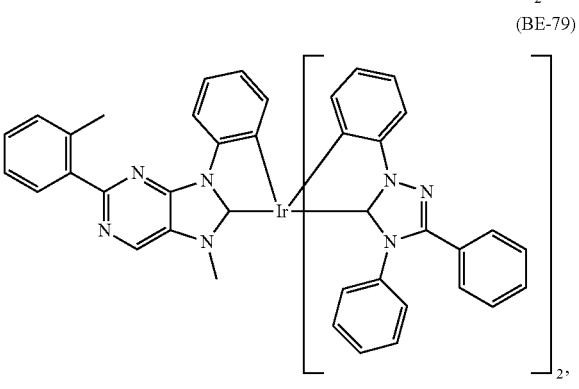

(BE-80)
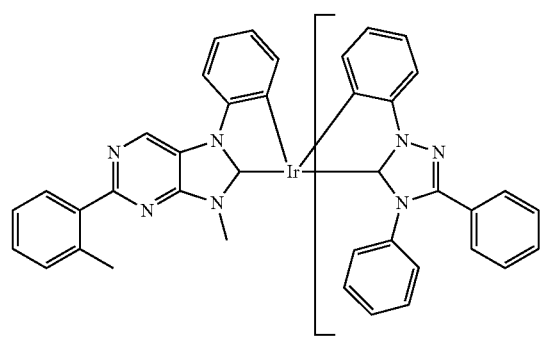
(BE-84)
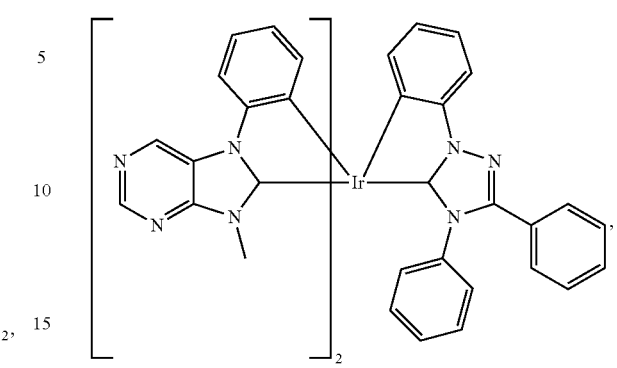
(BE-81)
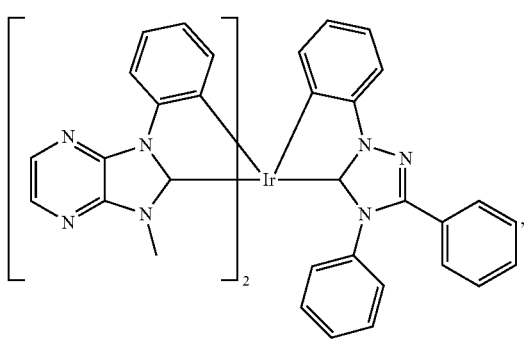
(BE-85)
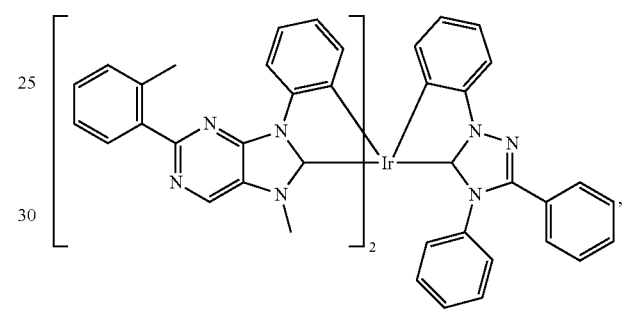
(BE-82)
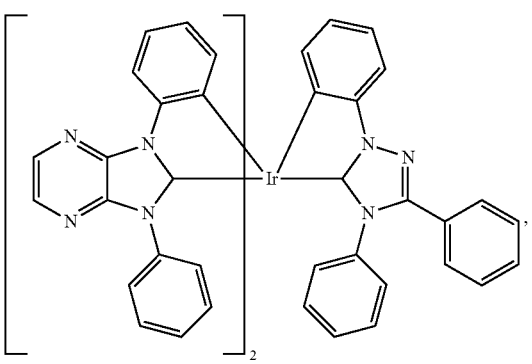
(BE-86)
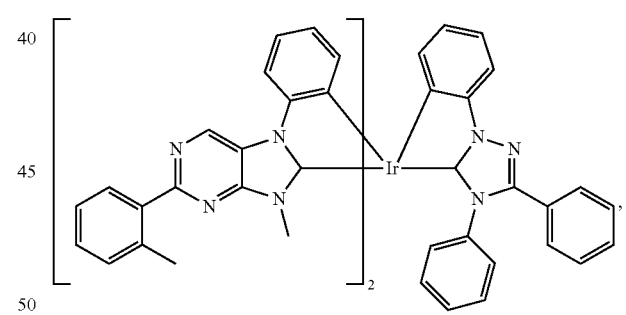
(BE-83)
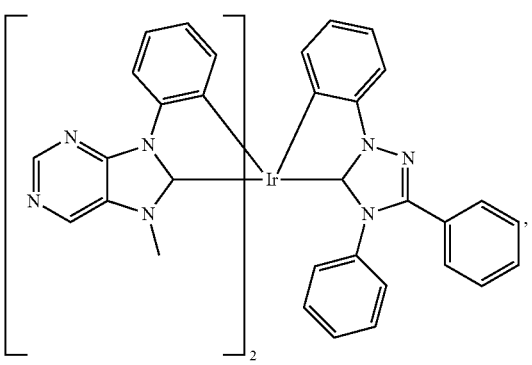
(BE-87)
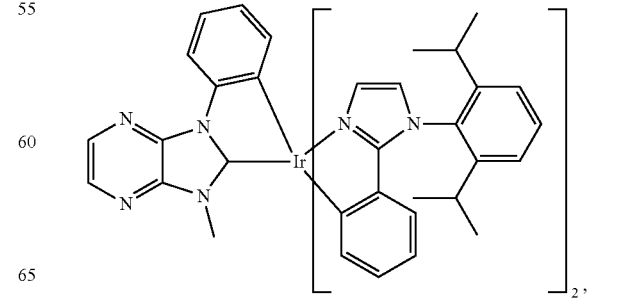

(BE-88)
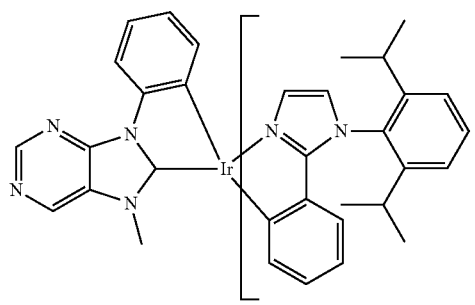
(BE-89)
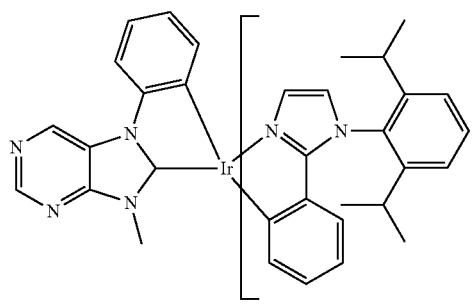
(BE-90)
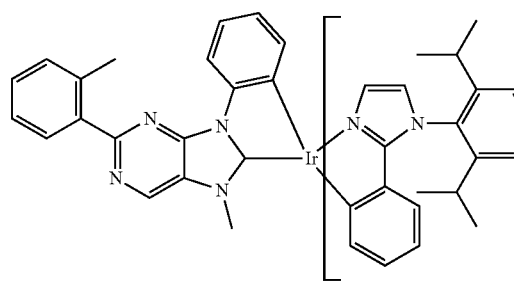
(BE-91)
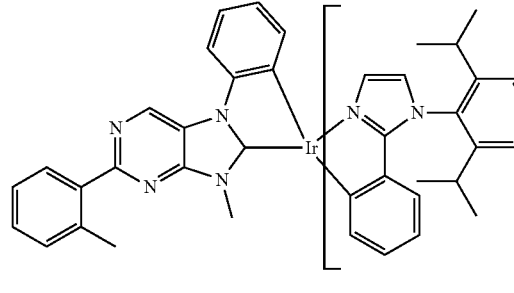
(BE-92)
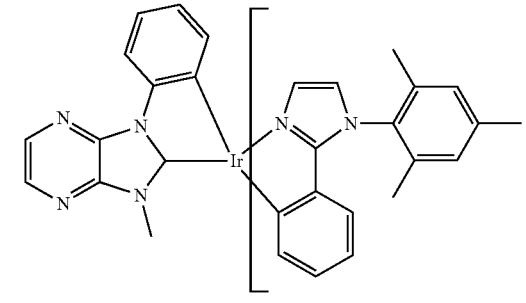
(BE-93)
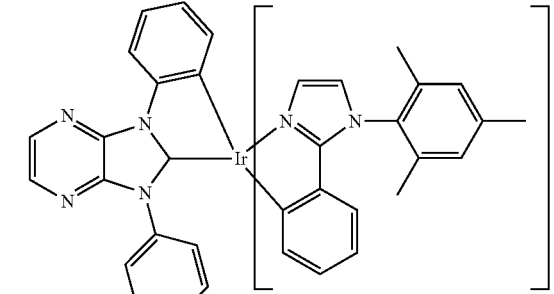
(BE-94)
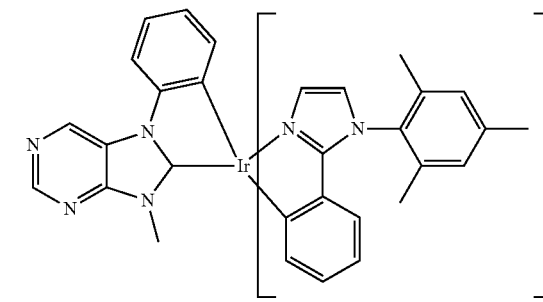
(BE-95)
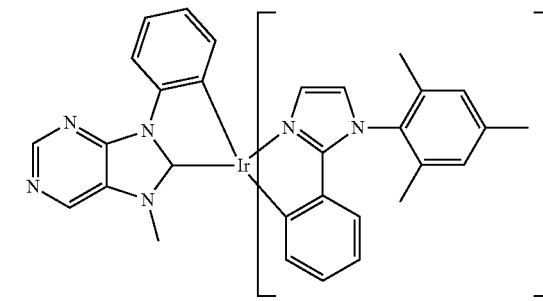
(BE-96)
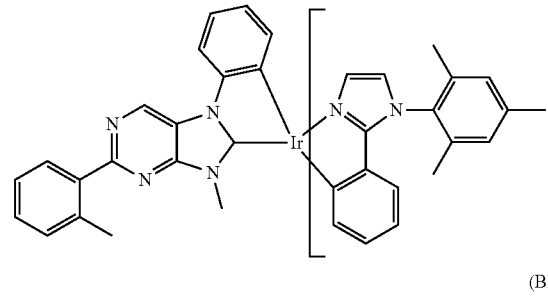
(BE-97)

(BE-98)
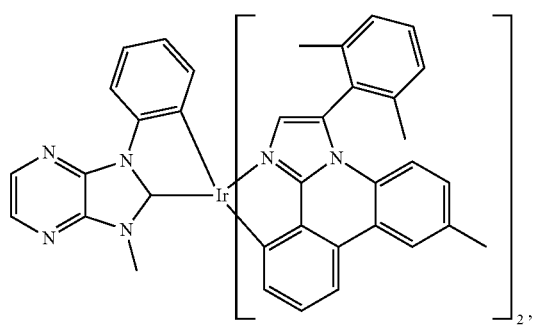
(BE-102)
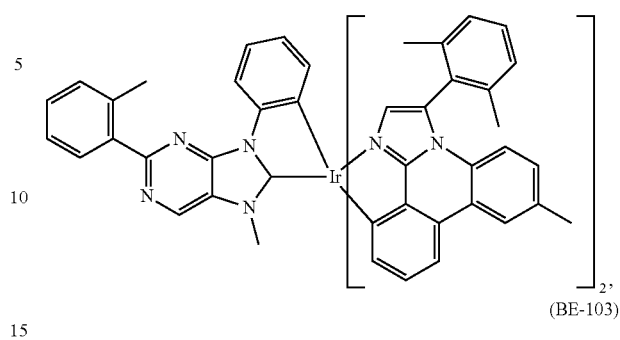
(BE-99)
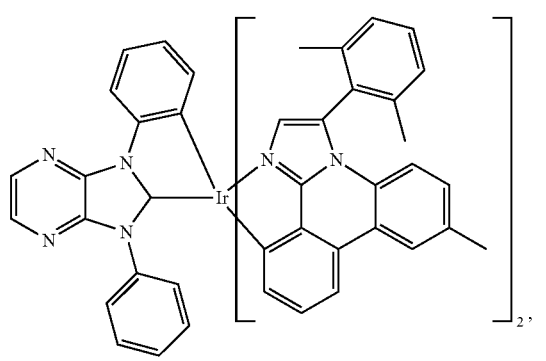
(BE-103)
(BE-104)
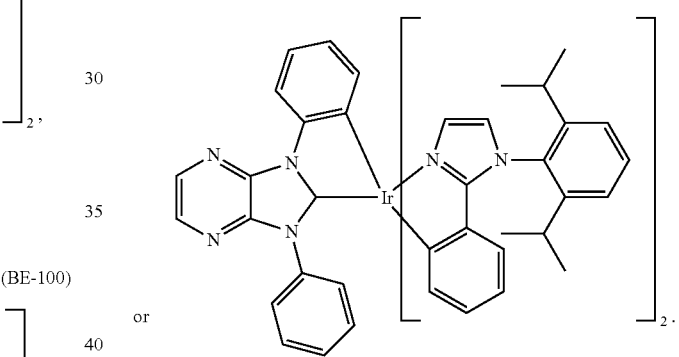
(BE-100)
or
Further suitable non-carbene emitter materials are mentioned below:
(BE-101)
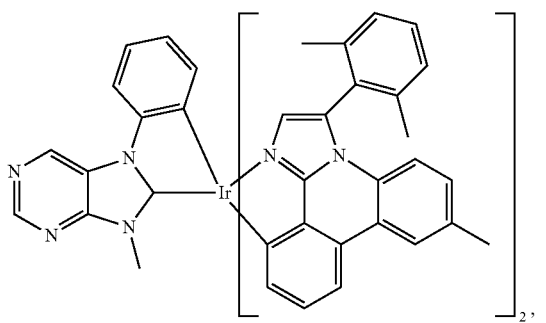
(BE-105)
(BE-106)
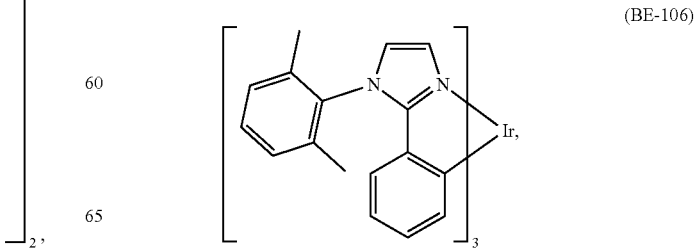

(BE-107)
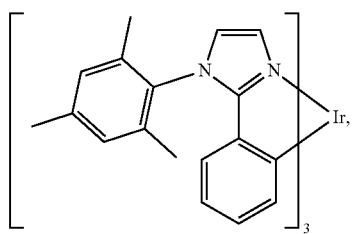
(BE-108)
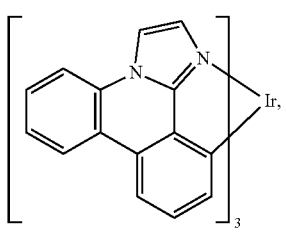
(BE-109)
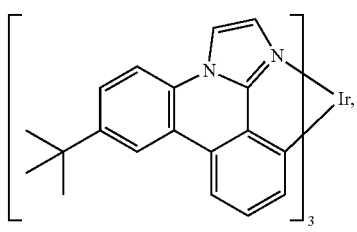
(BE-110)
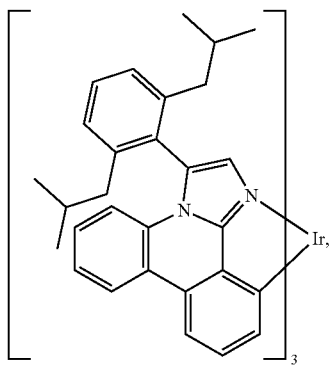
(BE-111)
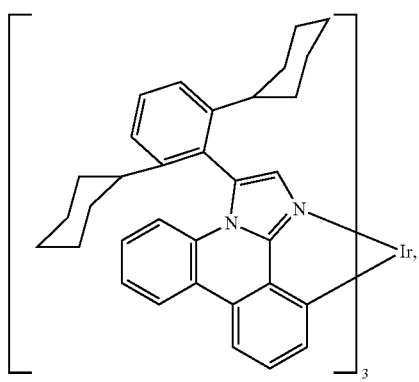
(BE-112)
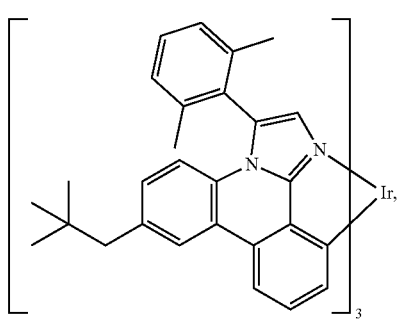
(BE-113)
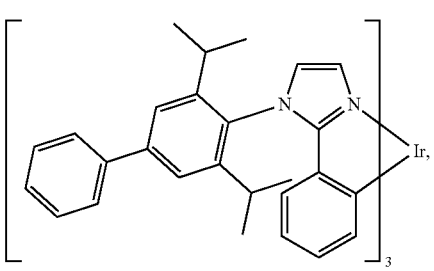
(BE-114)
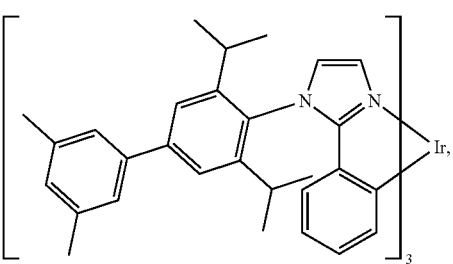
(BE-115)
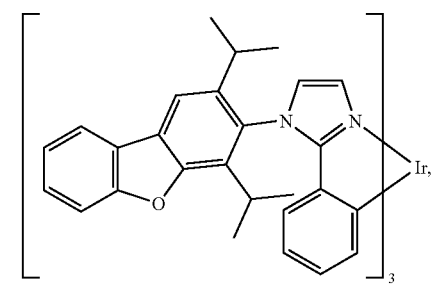
(BE-116)
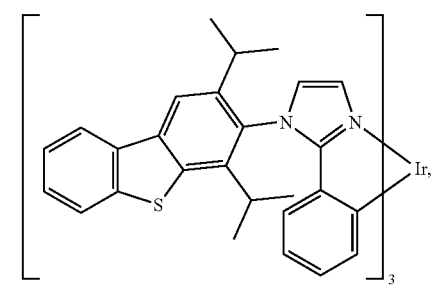

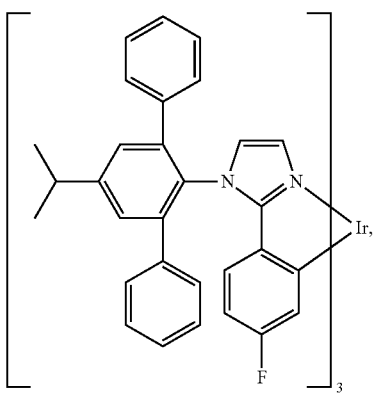
(BE-117)
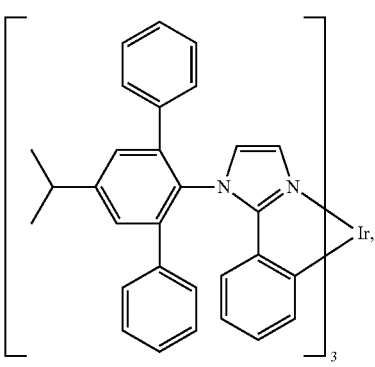
(BE-118)
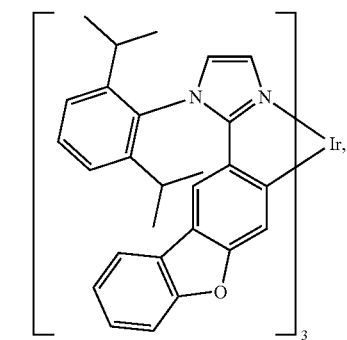
(BE-119)
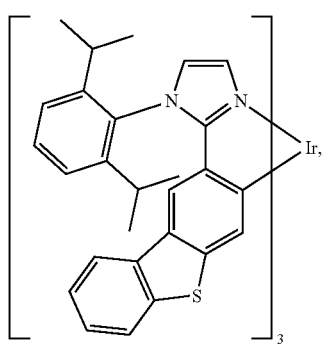
(BE-120)
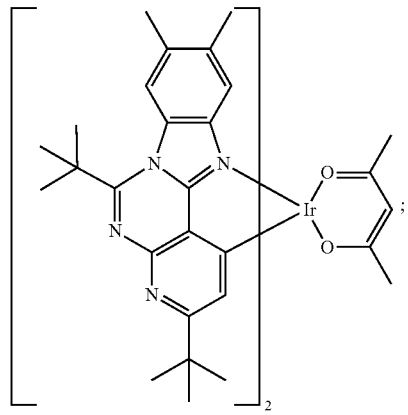
(BE-121)
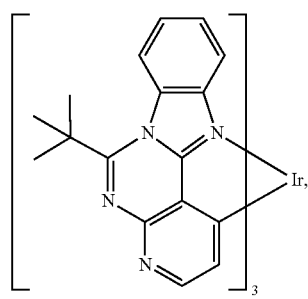
(BE-122)
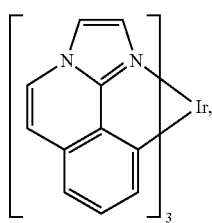
(BE-123)
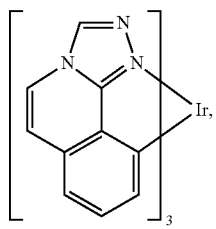
(BE-124)
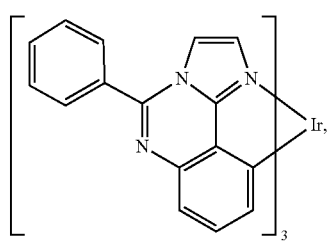
(BE-125)

(BE-126)

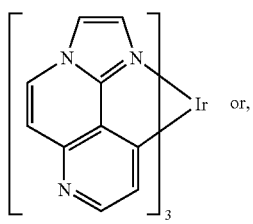

or, (BE-127)

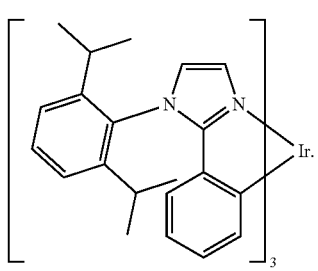

The compound of formula IX is more preferably a compound (BE-1), (BE-2), (BE-7), (BE-12), (BE-16), (BE-64), or (BE-70). The most preferred phosphorescent blue emitters are compounds (BE-1) and (BE-12).

The homoleptic metal-carbene complexes may be present in the form of facial or meridional isomers, preference being given to the facial isomers.

Suitable carbene complexes of formula (IX) and their preparation process are, for example, described in WO2011/073149.

The compounds of the present invention can also be used as host for phosphorescent green emitters. Suitable phosphorescent green emitters are, for example, specified in the following publications: WO2006014599, WO20080220265, WO2009073245, WO2010027583, WO2010028151, US20110227049, WO2011090535, WO2012/08881, WO20100056669, WO20100118029, WO20100244004, WO2011109042, WO2012166608, US20120292600, EP2551933A1; US6687266, US20070190359, US20070190359, US20060008670; WO2006098460, US20110210316, WO2012053627; US6921915, US20090039776; JP2007123392 and European patent application no. 14180422.9.

Examples of suitable phosphorescent green emitters are shown below:

(GE-1)

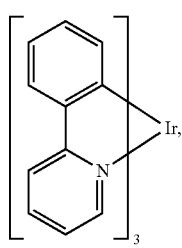

(GE-2)

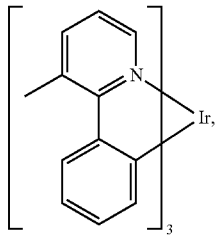

(GE-3)

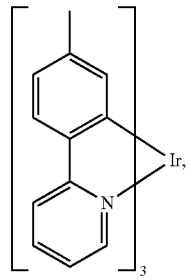

(GE-4)

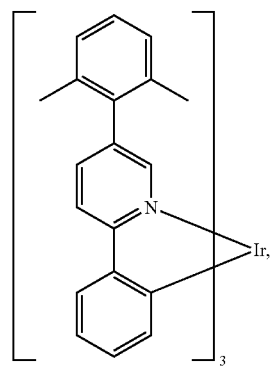

(GE-5)

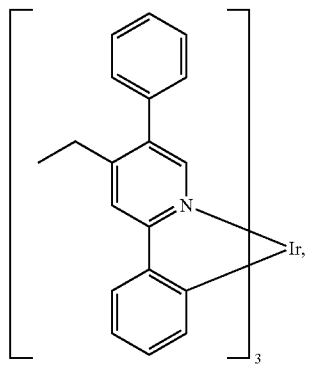

(GE-6)

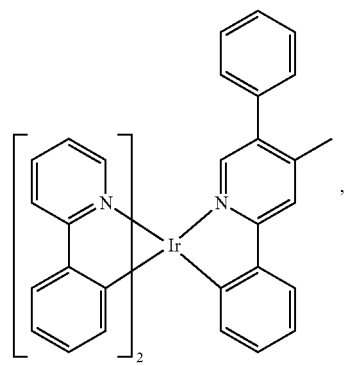

(GE-7)
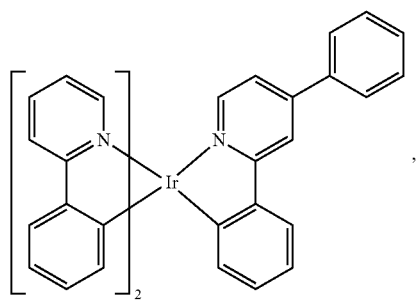
(GE-8)
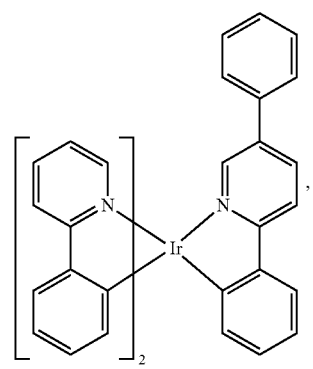
(GE-9)
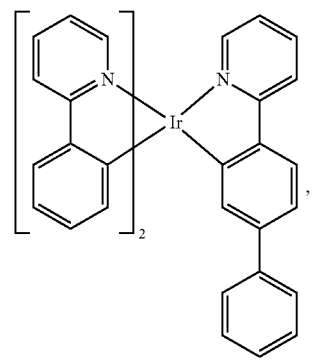
(GE-10)
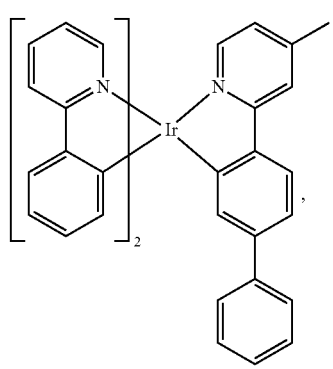
(GE-11)
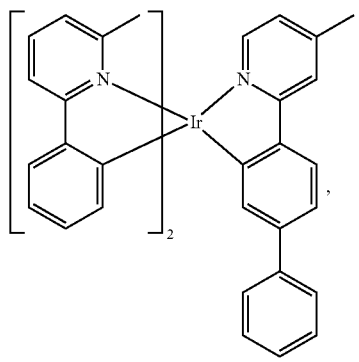
(GE-12)
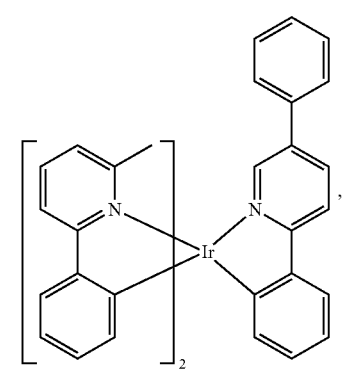
(GE-13)
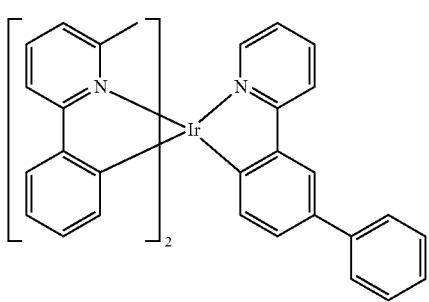
(GE-14)
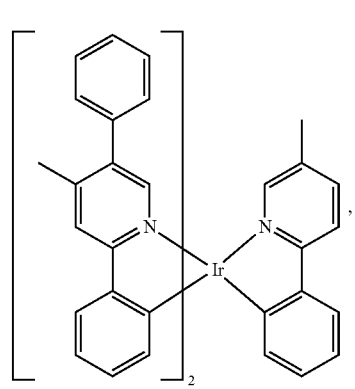

(GE-15)
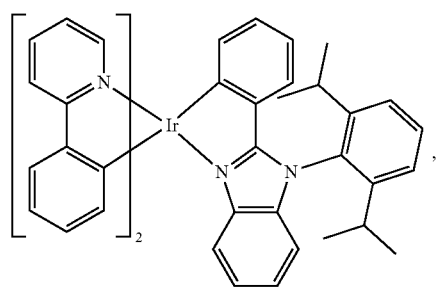
(GE-16)
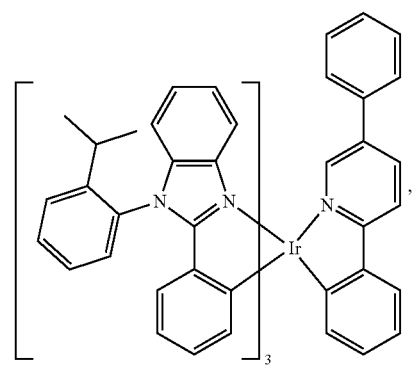
(GE-17)
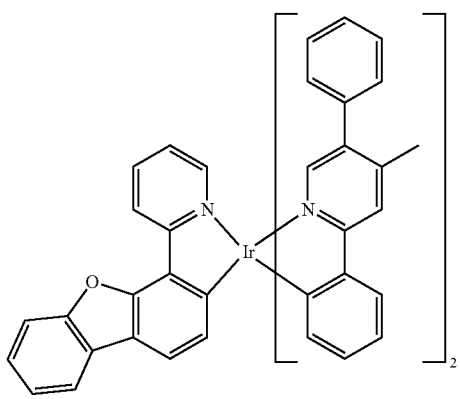
(GE-18)
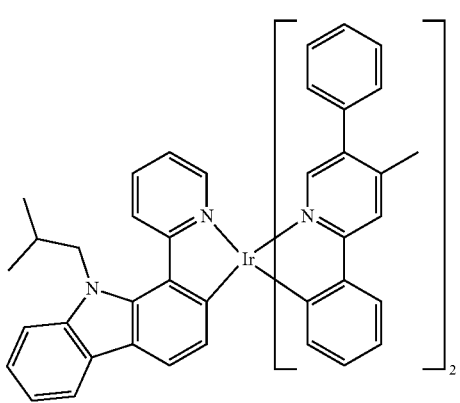
(GE-19)
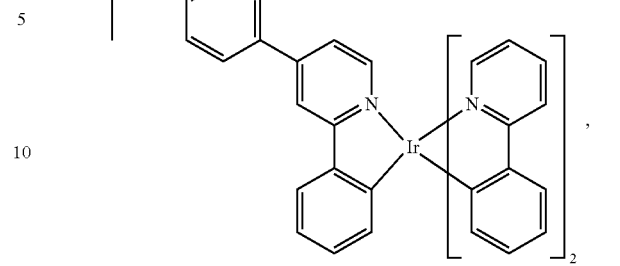
(GE-20)
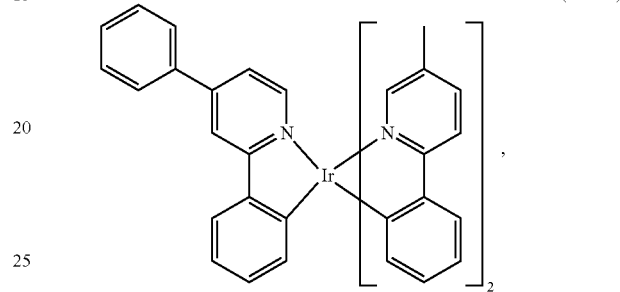
(GE-21)
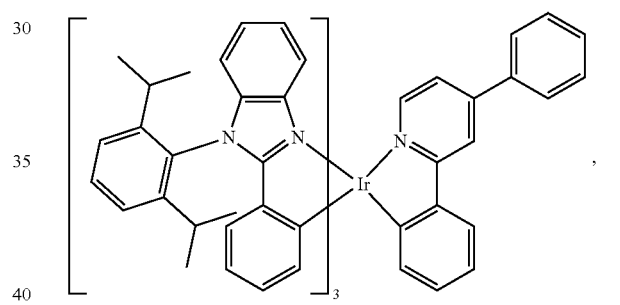
(GE-22)
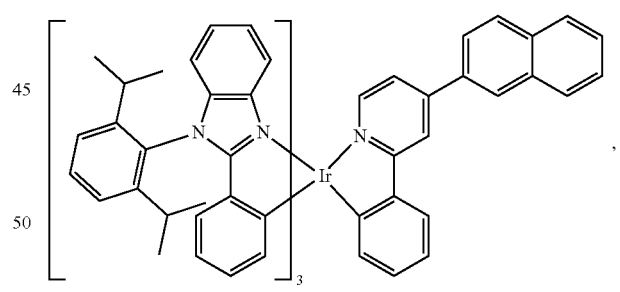
(GE-23)
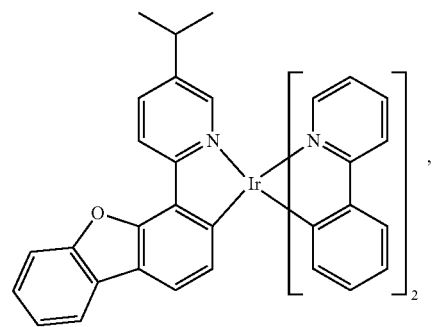

(GE-24)
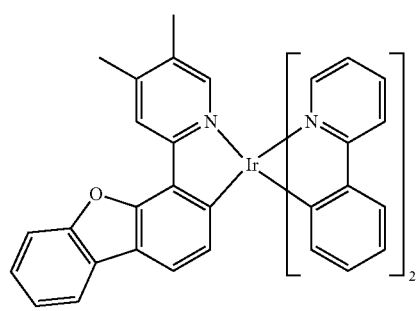
(GE-25)
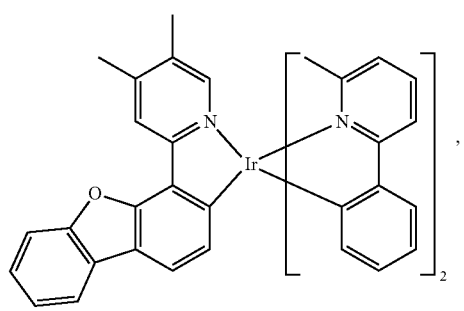
(GE-26)
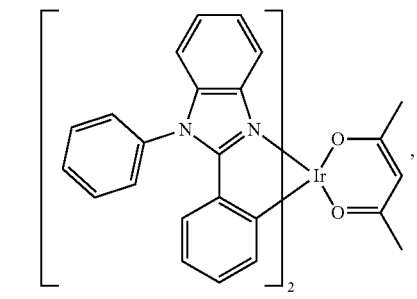
(GE-27)
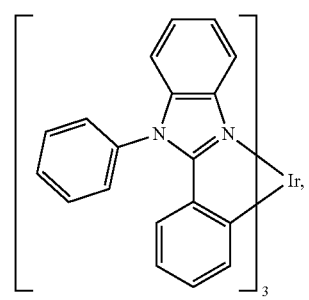
(GE-28)
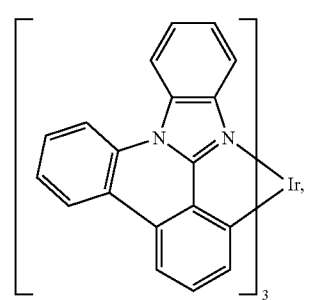
(GE-29)
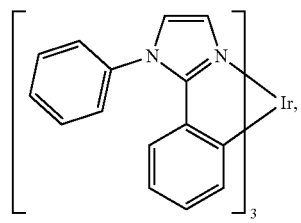
(GE-30)
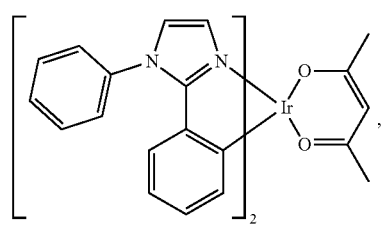
(GE-31)
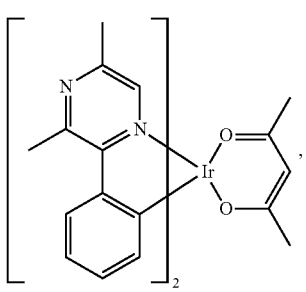
(GE-32)
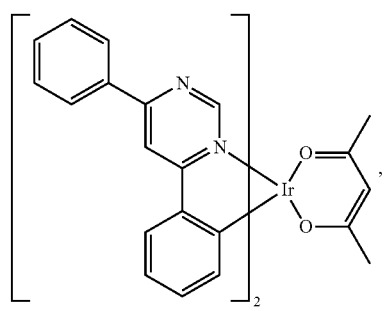
(GE-33)
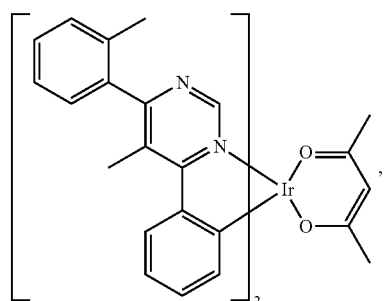
(GE-34)
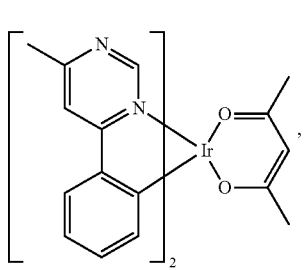

(GE-35)
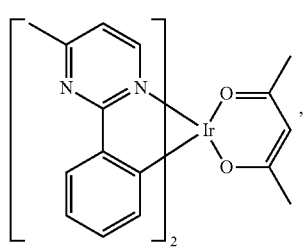

(GE-36)
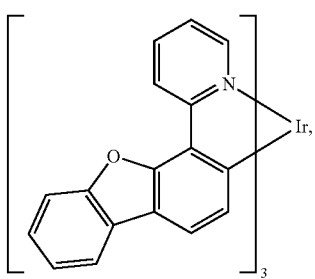

(GE-37)
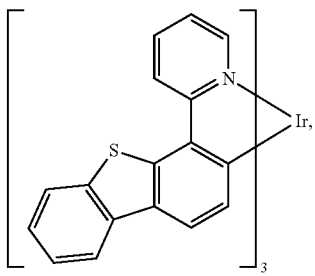

(GE-38)
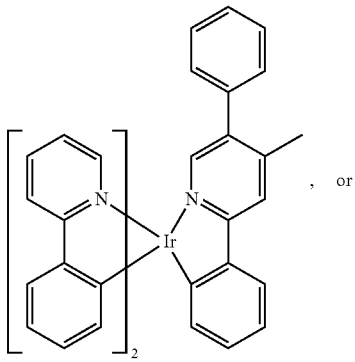
, or (GE-39)
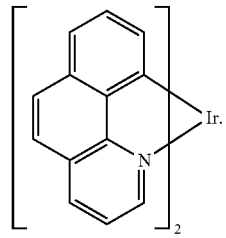

Host (Matrix) Materials

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example TCTA.

In another preferred embodiment of the present invention, at least one compound of the formula (I), especially a compound of formula (Ia-1), very especially a compound of the formula (Ia-1), is used as matrix material.

In a preferred embodiment, the light-emitting layer is formed from 2 to 40% by weight, preferably 5 to 35% by weight, of at least one of the aforementioned emitter materials and 60 to 98% by weight, preferably 75 to 95% by weight, of at least one of the aforementioned matrix materials—in one embodiment at least one compound of the formula I—where the sum total of the emitter material and of the matrix material adds up to 100% by weight.

In particularly preferred embodiment, the light-emitting layer comprises a compound of formula I, such as, for example, (E-3)
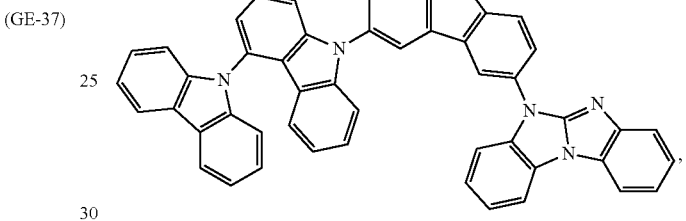

and two carbene complexes, preferably BE-1 and HTM-1, or HTM-2. In said embodiment, the light-emitting layer is formed from 2 to 40% by weight, preferably 5 to 35% by weight, of BE-1 and 60 to 98% by weight, preferably 65 to 95% by weight, of a compound of the formula I and HTM-1, or HTM-2, where the sum total of the carbon complexes and of the compound of formula I adds up to 100% by weight.

Suitable metal complexes for use together with the compounds of the formula I as matrix material in OLEDs are, for example, also carbene complexes as described in WO 2005/019373 A2, WO 2006/056418 A2, WO 2005/113704, WO 2007/115970, WO 2007/115981 and WO 2008/000727.

Further suitable host materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co) polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446, WO06128800, WO2012014621, WO2012105310, WO2012/130709 and European patent applications EP12175635.7 and EP12185230.5. and EP12191408.9 (in particular page 25 to 29 of EP12191408.9).

The above-mentioned small molecules are more preferred than the above-mentioned (co)polymers of the small molecules.

Further suitable second host materials, are described in WO2011137072 (for example,

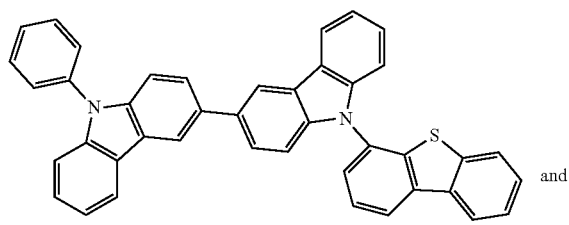

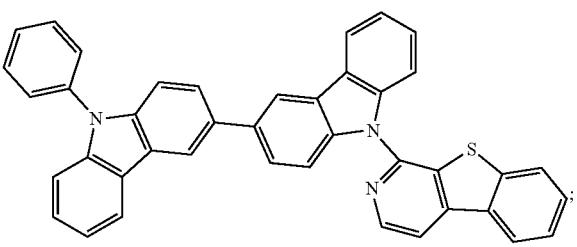

best results are achieved if said compounds are combined with

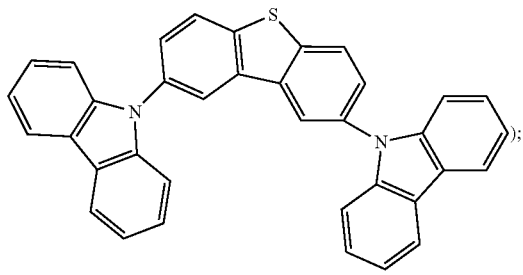 [SMILES: c1ccc2c(c1)c1ccccc1n2-c1ccc2sc3ccc(-n4c5ccccc5c5ccccc54)cc3c2c1]

WO2012048266 (for example,

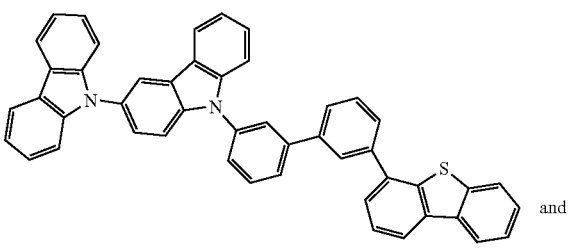

and

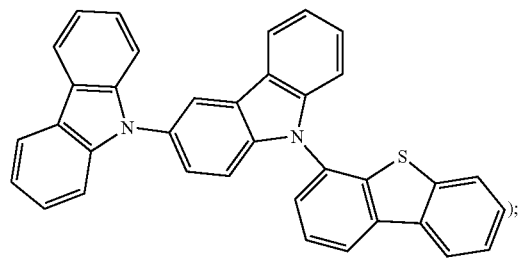

);

WO2012162325 (for example,

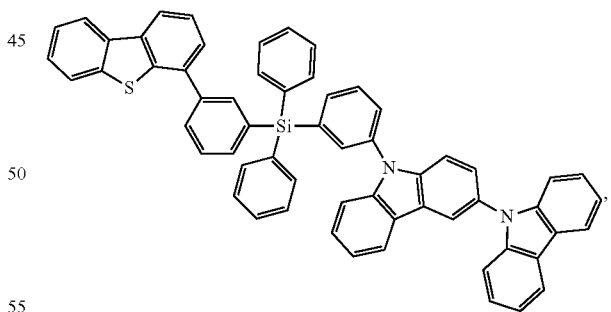

and

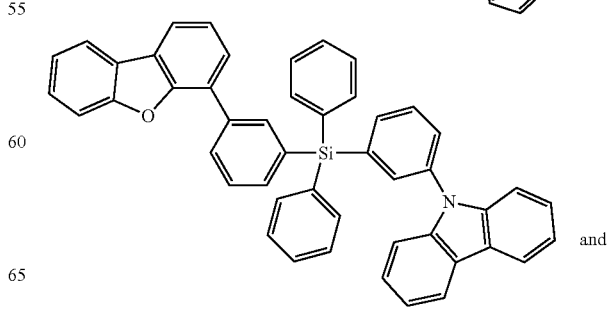

and

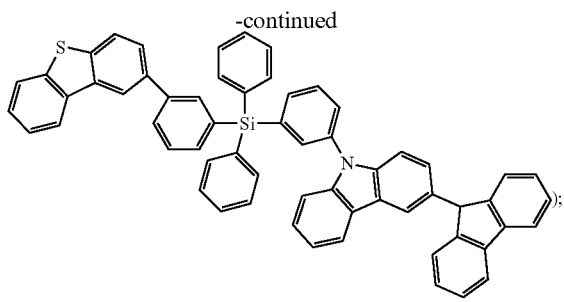

and EP2551932 (for example,

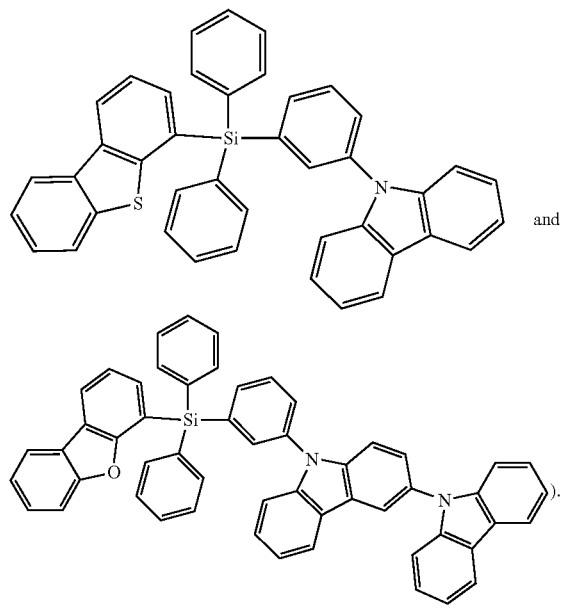

In a particularly preferred embodiment, one or more compounds of the general formula (X) specified hereinafter are used as second host material.

(X)

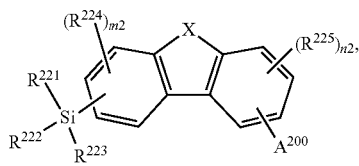

wherein
X is NR, S, O or PR;
R is aryl, heteroaryl, alkyl, cycloalkyl, or heterocycloalkyl;
$A^{200}$ is $-NR^{206}R^{207}$, $-P(O)R^{208}R^{209}$, $-PR^{210}R^{211}$, $-S(O)_2R^{212}$, $-S(O)R^{213}$, $-SR^{214}$, or $-OR^{215}$;
$R^{221}$, $R^{222}$ and $R^{223}$ are independently of each other aryl, heteroaryl, alkyl, cycloalkyl, or heterocycloalkyl, wherein at least on of the groups $R^{221}$, $R^{222}$, or $R^{223}$ is aryl, or heteroaryl; $R^{224}$ and $R^{225}$ are independently of each other alkyl, cycloalkyl, heterocycloalkyl, aryl, heteroaryl, a group $A^{200}$, or a group having donor, or acceptor characteristics;

n2 and m2 are independently of each other 0, 1, 2, or 3;
$R^{206}$ and $R^{207}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and $R^{208}$, $R^{209}$, $R^{210}$, $R^{211}$, $R^{212}$, $R^{213}$, $R^{214}$ and $R^{215}$ are independently of each other aryl, heteroaryl, alkyl, cycloalkyl, or heterocycloalkyl. Compounds of formula X, such as, for example, (SH-4)

(SH-5)

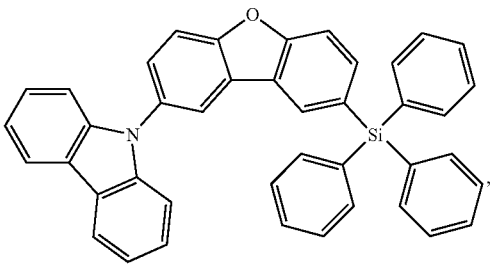

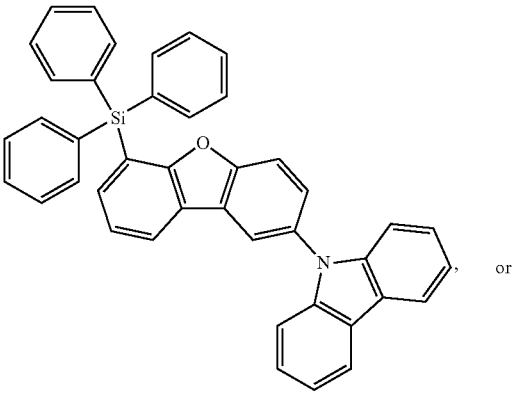

(SH-6)

are described in WO2010079051 (in particular pages on 19 to 26 and in tables on pages 27 to 34, pages 35 to 37 and pages 42 to 43).

Additional host materials on basis of dibenzofurane are, for example, described in US2009066226, EP1885818B1, EP1970976, EP1998388, EP2034538 and European patent application no. 14160197.1. Examples of particularly preferred host materials are shown below:

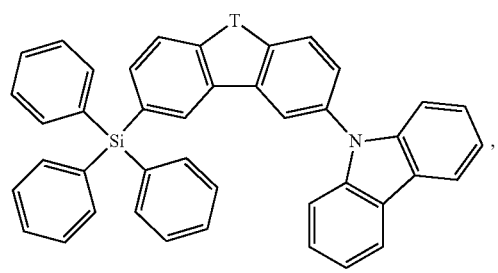
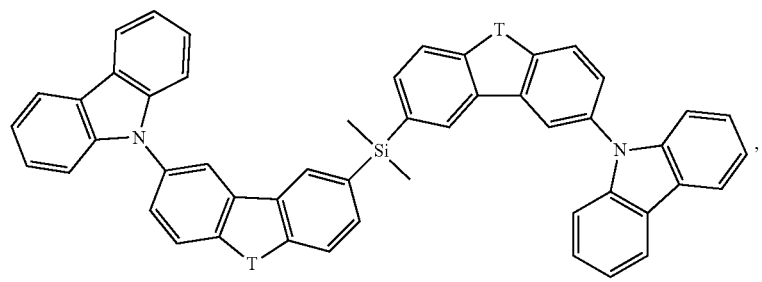
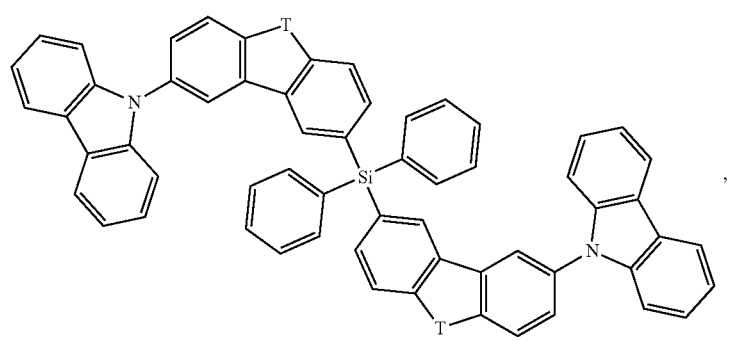
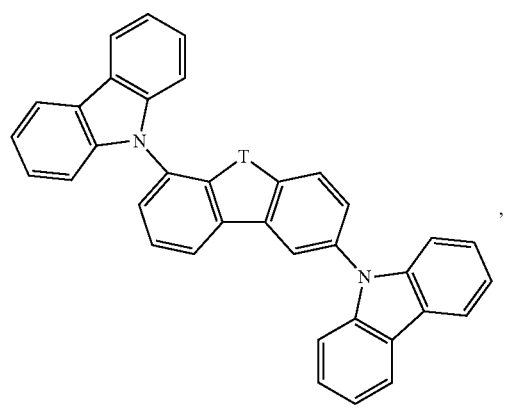
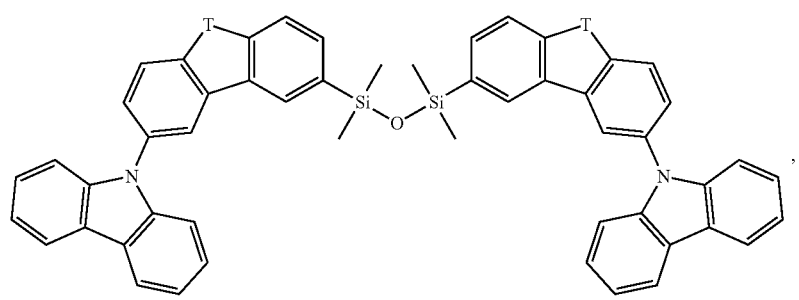

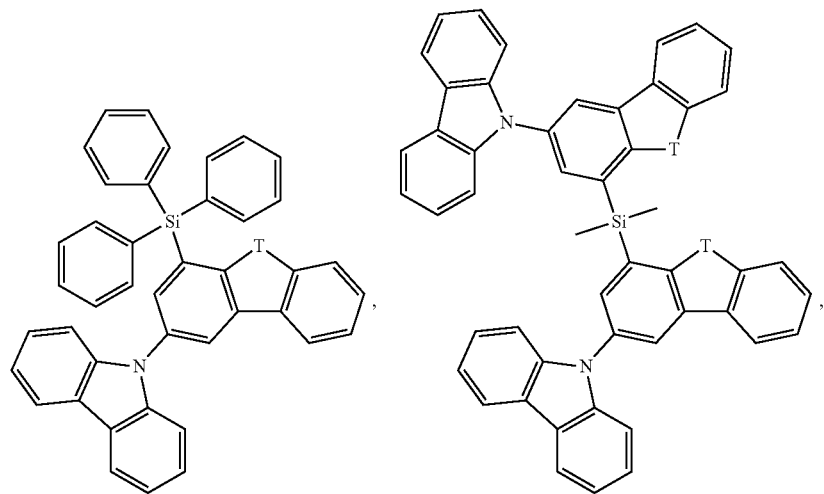
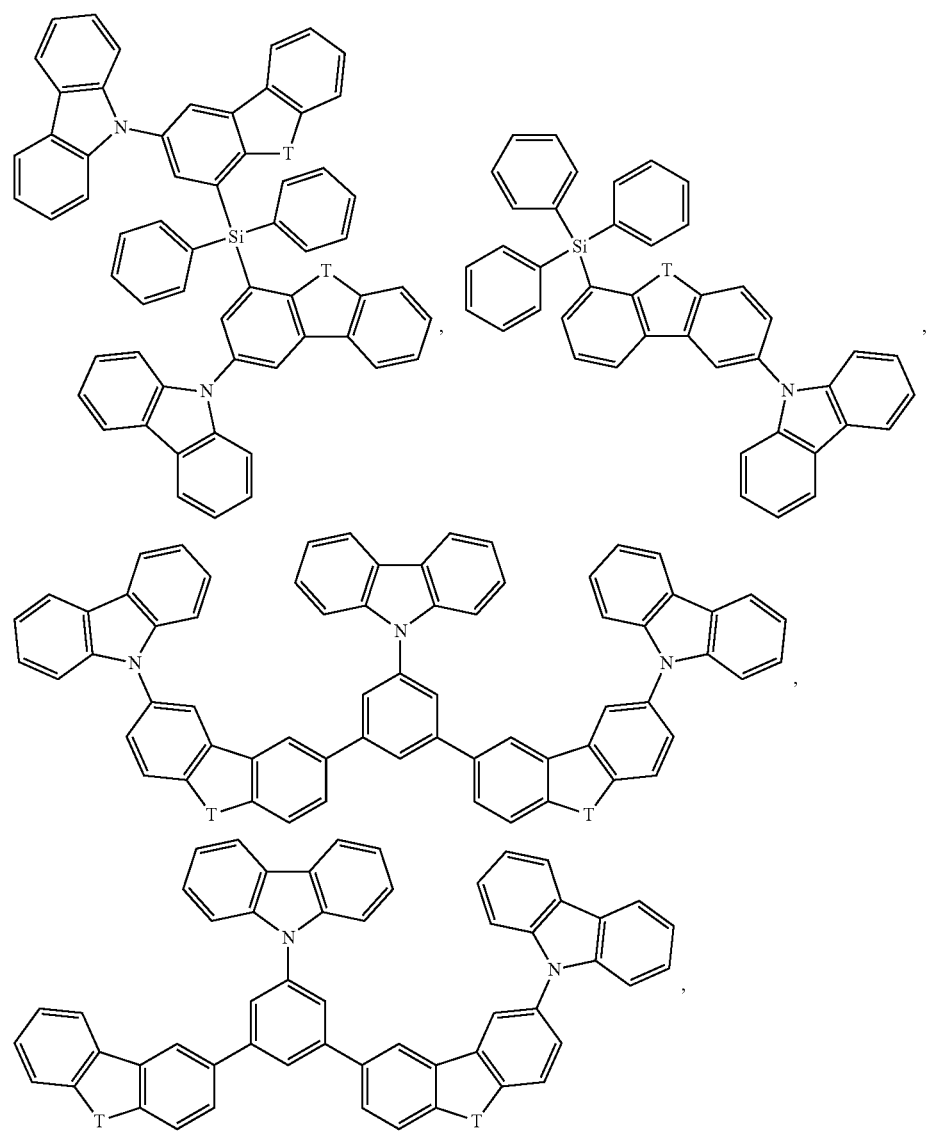

-continued
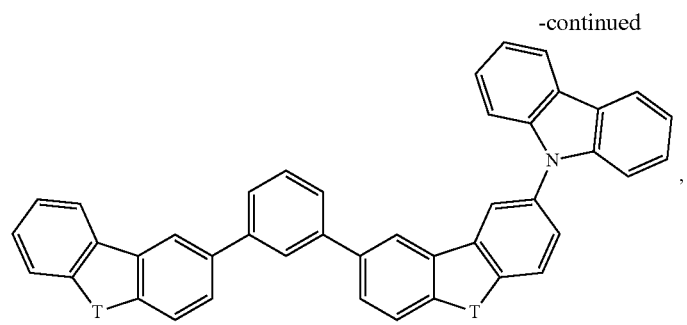,
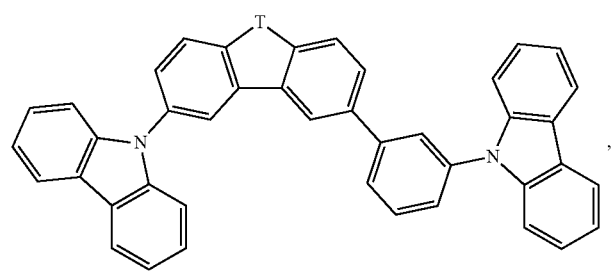,
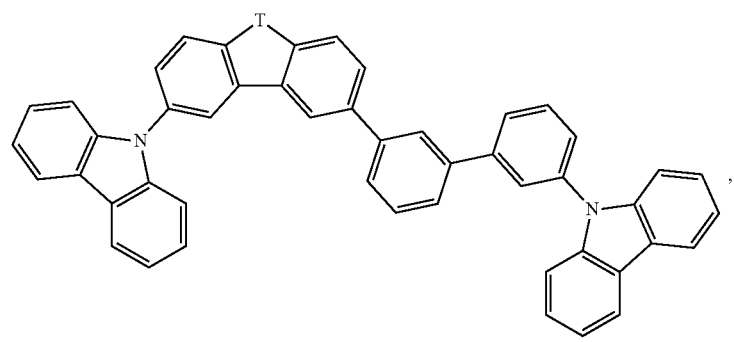,
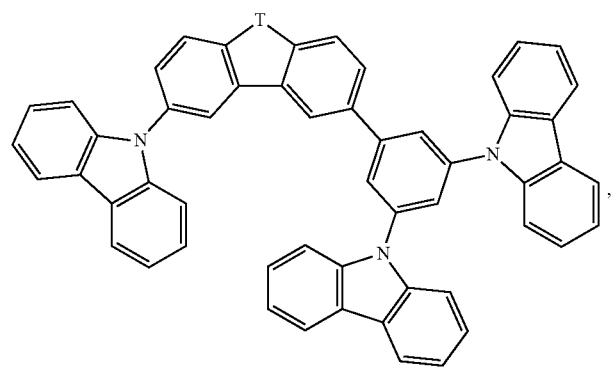,
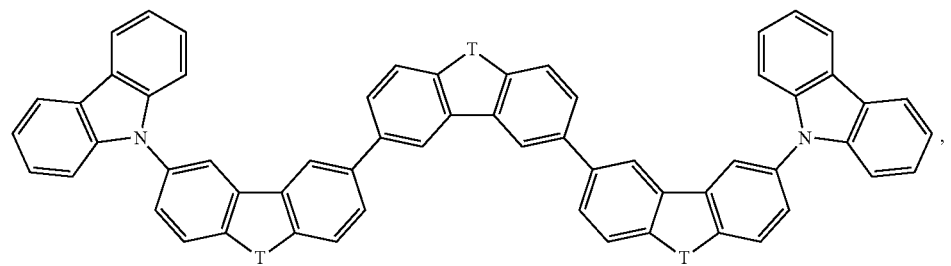,

-continued
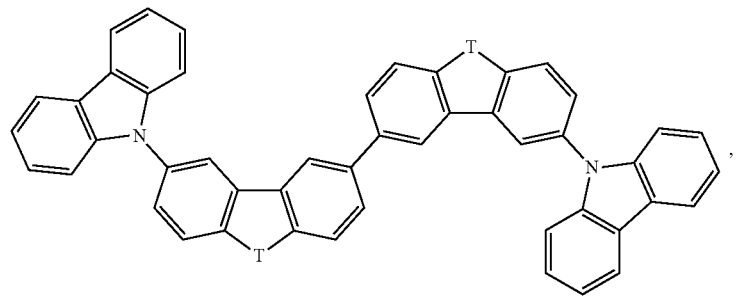
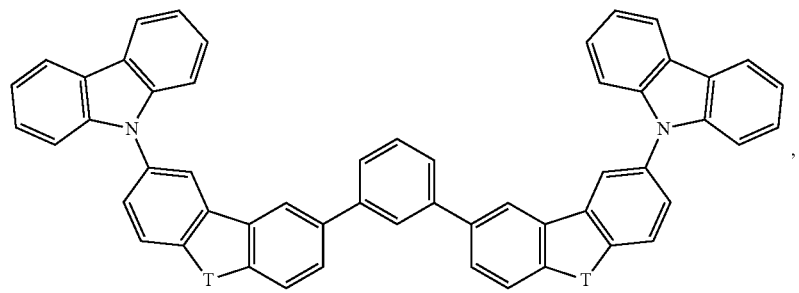
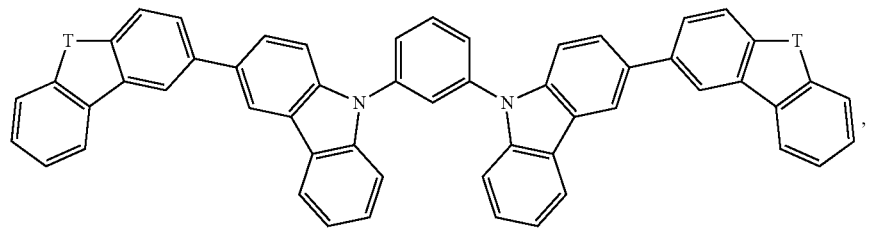
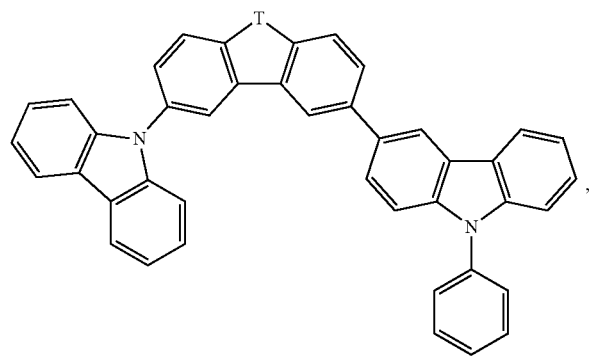
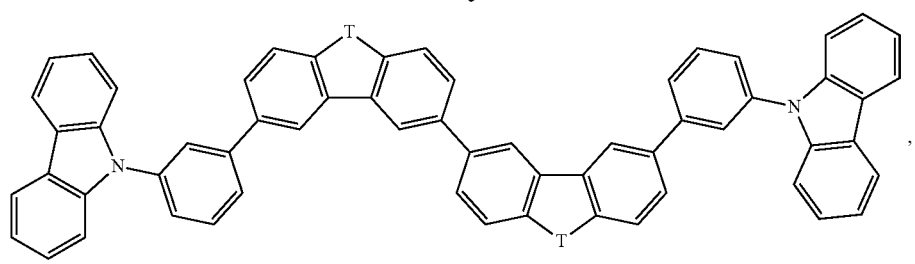

-continued
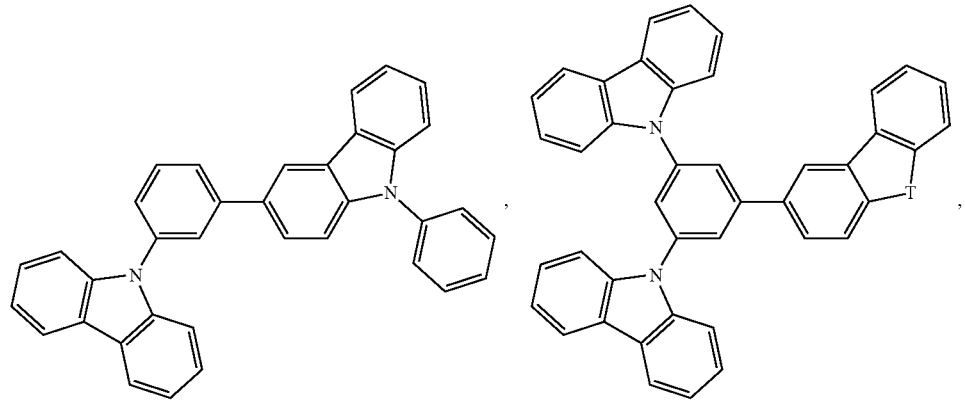
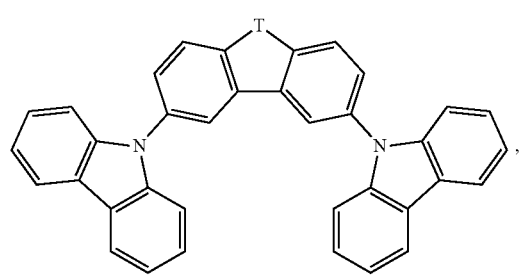
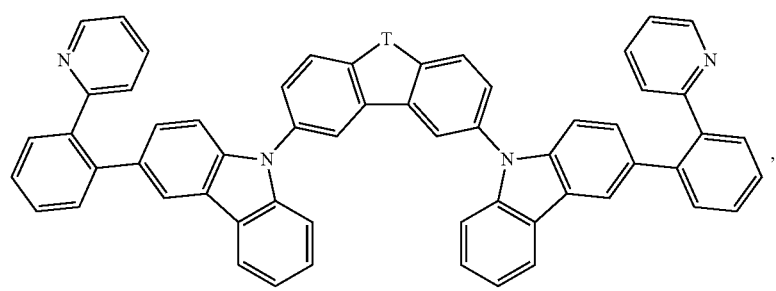
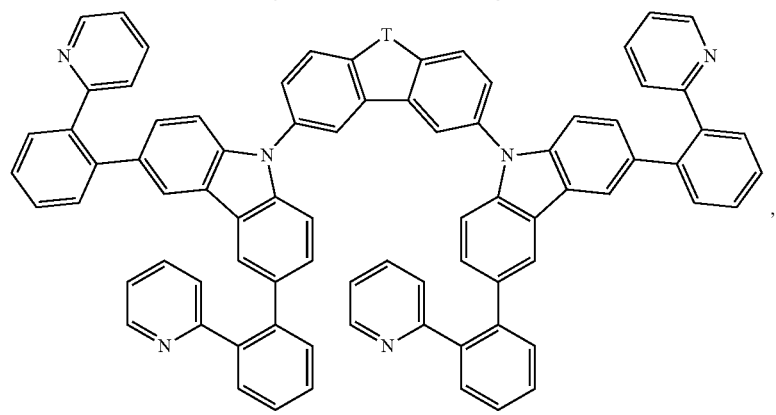
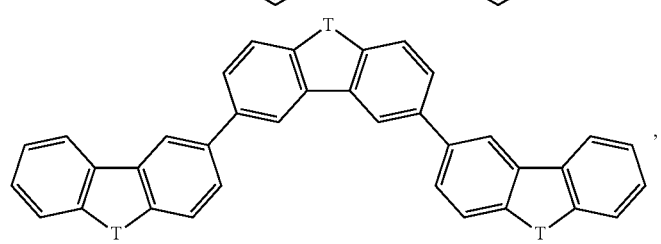

151 152
-continued
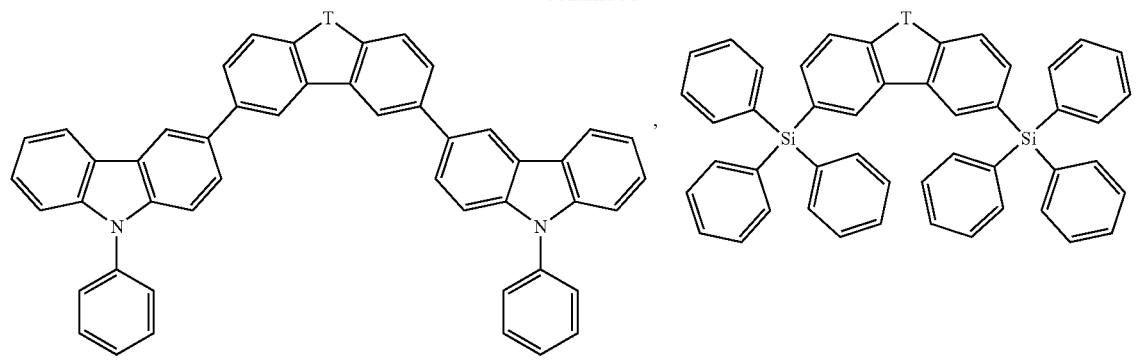
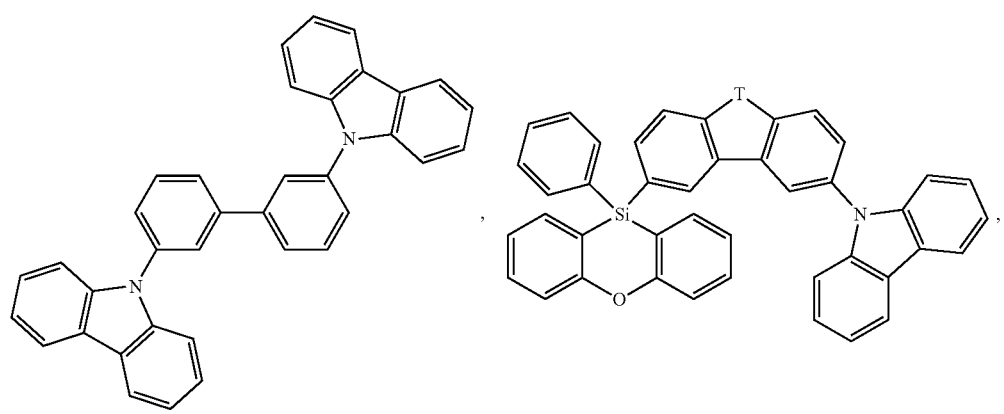
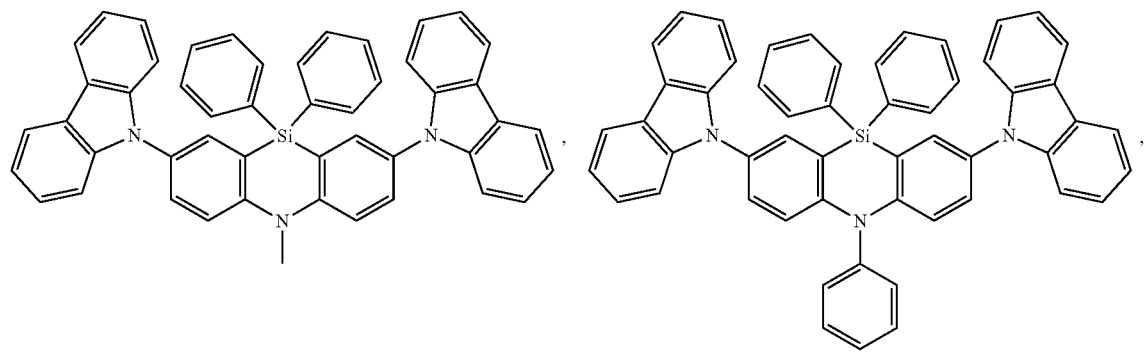
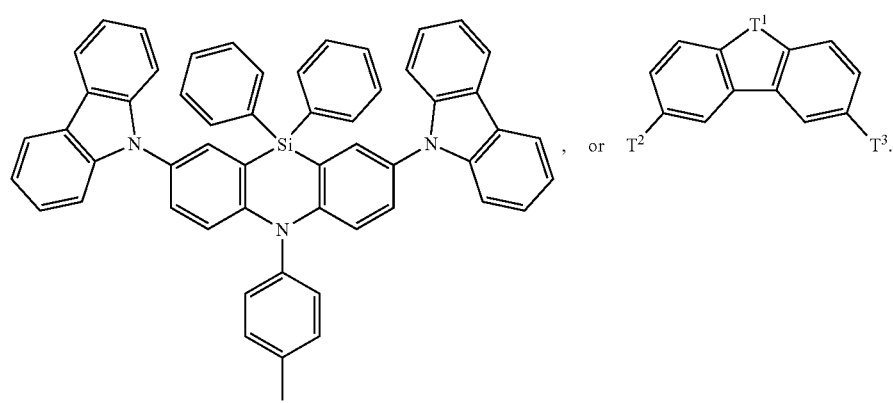

In the above-mentioned compounds T is O, or S, preferably O. If T occurs more than one time in a molecule, all groups T have the same meaning. $T^1$ is O, or S, preferably O. $T^1$ and $T^2$ are independently of each other
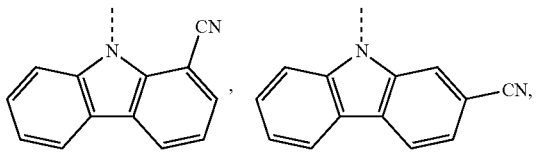
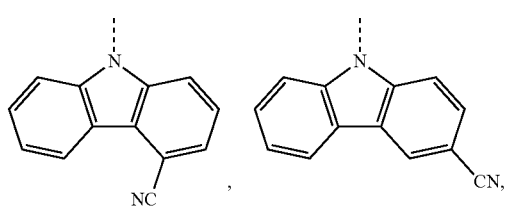
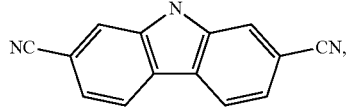
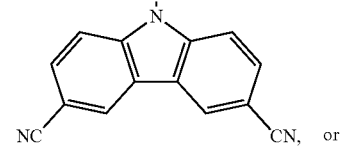
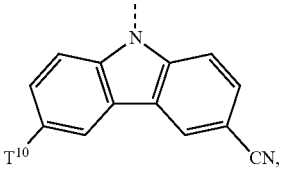
wherein $T^{10}$ is a $C_1$-$C_{25}$alkyl group. Compounds
(SH-1)
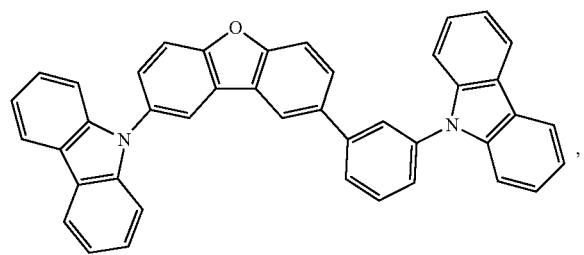
(SH-2)
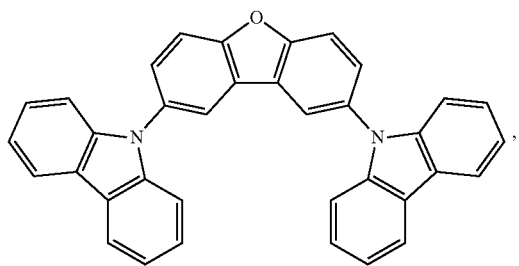
(SH-3), SH-4, SH-5, SH-6
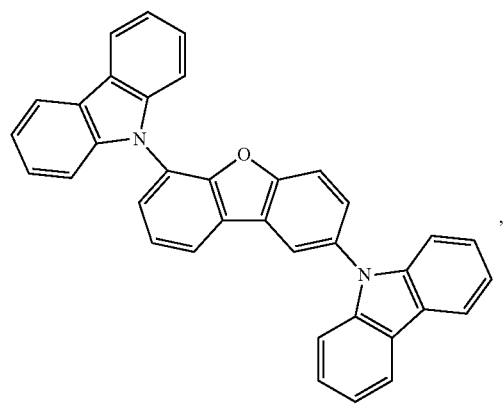
(SH-7)
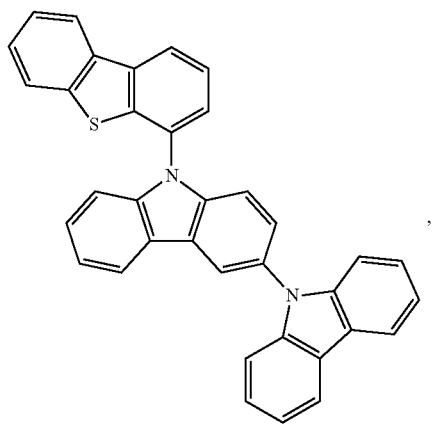

-continued

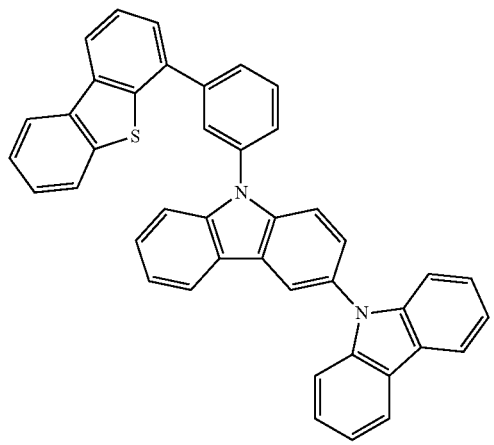
(SH-8)

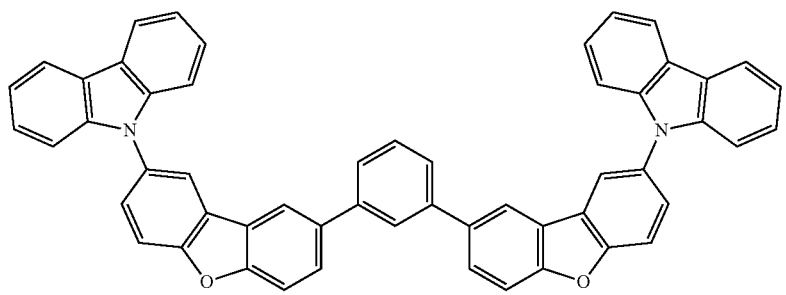
(SH-9)

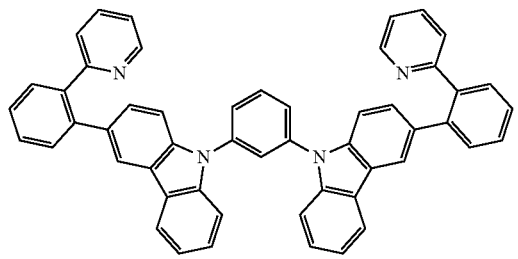
(SH-10)
and

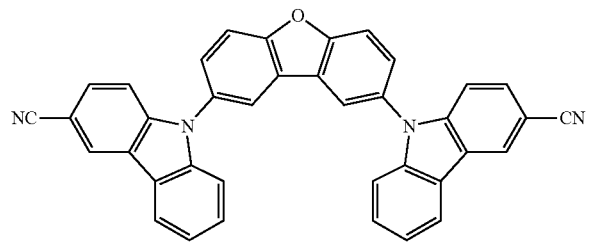
(SH-11)

are most preferred.

Hole/Exciton Blocking Layer (f):

Blocking layers may be used to reduce the number of charge carriers (electrons or holes) and/or excitons that leave the emissive layer. The hole blocking layer may be disposed between the emitting layer (e) and electron transport layer (g), to block holes from leaving layer (e) in the direction of electron transport layer (g). Blocking layers may also be used to block excitons from diffusing out of the emissive layer.

Additional hole blocker materials typically used in OLEDs are 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato) aluminum(III) (BAlq), phenothiazine S,S-dioxide derivates and 1,3,5-tris(N-phenyl-2-benzylimidazolyl)benzene) (TPBI), TPBI also being suitable as electron-transport material. Further suitable hole blockers and/or electron conductor materials are 2,2',2''-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl)borane, 2,9-bis(naphthalene-2-yl)-4,7-diphenyl-1,10-phenanthroline, 1-methyl-2-(4-(naphthalene-2-yl)phenyl)-1H-imidazo[4,5-f][1,10]phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications WO2009/003919 and WO2009003898 and disilyl compounds as disclosed in WO2008/034758, as a blocking layer for holes/excitons (f).

In another preferred embodiment compounds (SH-1), (SH-2), (SH-3), SH-4, SH-5, SH-6, (SH-7), (SH-8), (SH-9), (SH-10) and (SH-11) may be used as hole/exciton blocking materials.

In another preferred embodiment of the present invention, at least one compound of the formula I, especially a compound of formula (Ib-1), or (Ib-2), very especially a compound of the formula (Ib-1a), or (Ib-2a), such as, for example, compound (E-3), is used as hole/exciton blocker material.

Electron Transport Layer (g):

Electron transport layer may include a material capable of transporting electrons. Electron transport layer may be intrinsic (undoped), or doped. Doping may be used to enhance conductivity. Suitable electron-transporting materials for layer (g) of the inventive OLEDs comprise metals chelated with oxinoid compounds, such as tris(8-hydroxyquinolato)aluminum (Alq3), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

It is likewise possible to use mixtures of at least two materials in the electron-transporting layer, in which case at least one material is electron-conducting. Preferably, in such mixed electron-transport layers, at least one phenanthroline compound is used, preferably BCP, or at least one pyridine compound according to the formula (VIII) below, preferably a compound of the formula (VlIIaa) below. More preferably, in mixed electron-transport layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula VII). Reference is made to WO2011/157779.

The electron-transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transport layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $Rb_2CO_3$, dipotassium phthalate, $W(hpp)_4$ from EP1786050, or with compounds described in EP1837926B1, EP1837927, EP2246862 and WO2010132236.

In a preferred embodiment, the electron-transport layer comprises at least one compound of the general formula (VII)

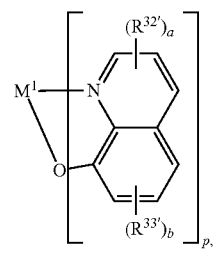

in which
$R^{32'}$ and $R^{33'}$ are each independently F, $C_1$-$C_8$-alkyl, or $C_6$-$C_{14}$-aryl, which is optionally substituted by one or more $C_1$-$C_8$-alkyl groups, or
two $R^{32'}$ and/or $R^{33'}$ substituents together form a fused benzene ring which is optionally substituted by one or more $C_1$-$C_8$-alkyl groups;
a and b are each independently 0, or 1, 2 or 3,
$M^1$ is an alkaline metal atom or alkaline earth metal atom,
p is 1 when $M^1$ is an alkali metal atom, p is 2 when $M^1$ is an earth alkali metal atom.

A very particularly preferred compound of the formula (VII) is

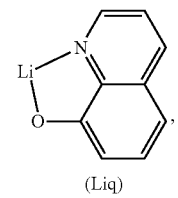

(Liq)

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transport layer comprises at least one compound of the formula (VIII),

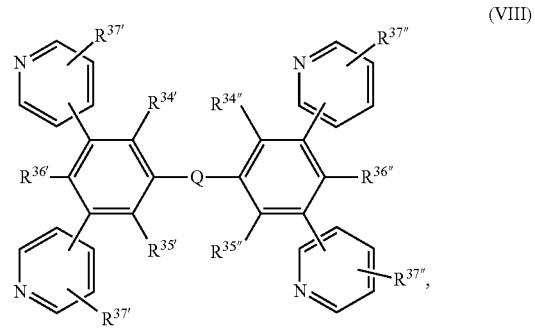

in which
$R^{34''}$, $R^{35''}$, $R^{36''}$, $R^{37''}$, $R^{34'}$, $R^{35'}$, $R^{36'}$, and $R^{37'}$ are each independently H, $C_1$-$C_{18}$alkyl, $C_1$-$C_{18}$ alkyl which is substituted by E' and/or interrupted by D', $C_6$-$C_{24}$-aryl, $C_6$-$C_{24}$-aryl which is substituted by G', $C_2$-$C_{20}$-heteroaryl or $C_2$-$C_{20}$-heteroaryl which is substituted by G', Q is an arylene or heteroarylene group, each of which is optionally substituted by G';
D' is —CO—; —COO—; —S—; —SO—; —SO$_2$—; —O—; —NR$^{40'}$—; —SiR$^{45'}$R$^{46'}$—; —POR$^{47'}$—; —CR$^{38'}$=CR$^{39'}$—; or —C≡C—;

E' is —OR$^{44'}$; —SR$^{44'}$; —NR$^{40'}$R$^{41'}$; —COR$^{43'}$; —COOR$^{42'}$; —CONR$^{40'}$R$^{41'}$; —CN; or F;

G' is E', $C_1$-$C_{18}$-alkyl, $C_1$-$C_{18}$-alkyl which is interrupted by D', $C_1$-$C_{18}$-perfluoroalkyl, $C_1$-$C_{18}$-alkoxy, or $C_1$-$C_{18}$-alkoxy which is substituted by E' and/or interrupted by D', in which R$^{38'}$ and R$^{39'}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;

R$^{40'}$ and R$^{41'}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or R$^{40'}$ and R$^{41'}$ together form a 6-membered ring;

R$^{42'}$ and R$^{43'}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, R$^{44'}$ is $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, R$^{45'}$ and R$^{46'}$ are each independently $C_1$-$C_{18}$-alkyl, $C_6$-$C_{18}$-aryl or $C_6$-$C_{18}$-aryl which is substituted by $C_1$-$C_{18}$-alkyl, R$^{47'}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (VIII) are compounds of the formula (VIIIa) in which Q is:

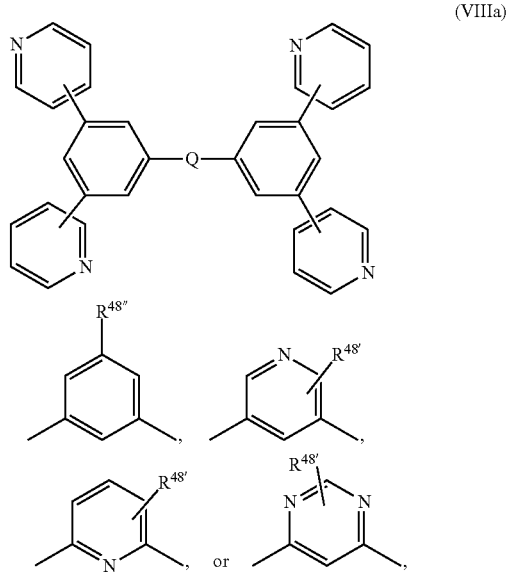

(VIIIa)

R$^{48'}$ is H or $C_1$-$C_{18}$-alkyl and

R$^{48''}$ is H, $C_1$-$C_{18}$-alkyl or

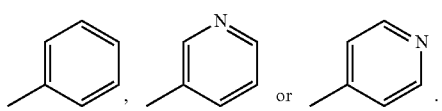

Particular preference is given to a compound of the formula

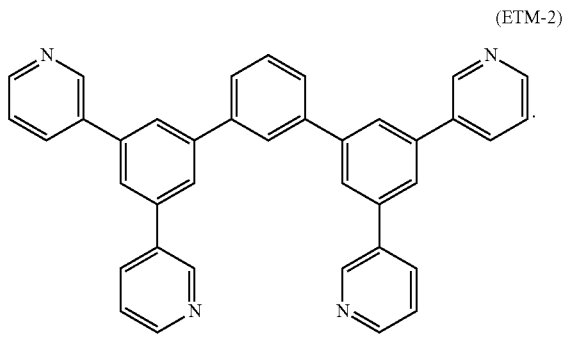 [SMILES: c1cncc(-c2cc(-c3cccnc3)cc(-c3cccc(-c4cc(-c5cccnc5)cc(-c5cccnc5)c4)c3)c2)c1]

(ETM-2)

In a further, very particularly preferred embodiment, the electron-transport layer comprises a compound Liq and a compound ETM-2.

In a preferred embodiment, the electron-transport layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008/127326, or the compounds can be prepared analogously to the processes disclosed in the aforementioned documents.

It is likewise possible to use mixtures of alkali metal hydroxyquinolate complexes, preferably Liq, and dibenzofuran compounds in the electron-transport layer. Reference is made to WO2011/157790. Dibenzofuran compounds A-1 to A-36 and B-1 to B-22 described in WO2011/157790 are preferred, wherein dibenzofuran compound

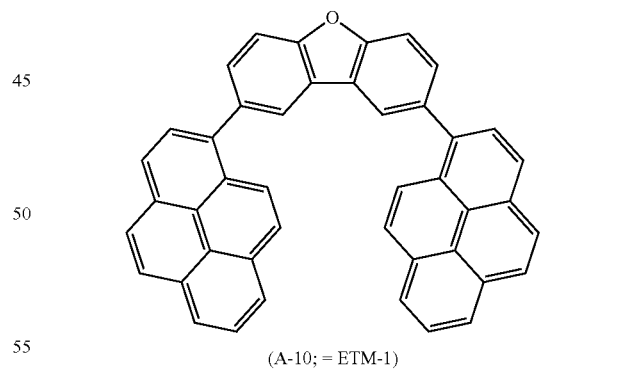

(A-10; = ETM-1)

is most preferred.

In a preferred embodiment, the electron-transport layer comprises Liq in an amount of 99 to 1% by weight, preferably 75 to 25% by weight, more preferably about 50% by weight, where the amount of Liq and the amount of the dibenzofuran compound(s), especially ETM-1, adds up to a total of 100% by weight.

In a preferred embodiment, the electron-transport layer comprises at least one phenanthroline derivative and/or pyridine derivative.

In a further preferred embodiment, the electron-transport layer comprises at least one phenanthroline derivative and/or pyridine derivative and at least one alkali metal hydroxyquinolate complex.

In a further preferred embodiment, the electron-transport layer comprises at least one of the dibenzofuran compounds A-1 to A-36 and B-1 to B-22 described in WO2011/157790, especially ETM-1.

In a further preferred embodiment, the electron-transport layer comprises a compound described in WO2012/111462, WO2012/147397, WO2012014621, such as, for example, a compound of formula (ETM-3)

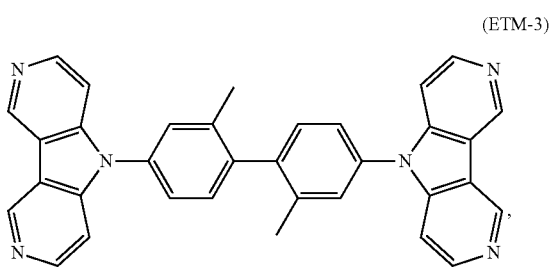 [SMILES: Cc1cc(-n2c3ccncc3c3cnccc32)ccc1-c1ccc(-n2c3ccncc3c3cnccc32)cc1C]

US2012/0261654, such as, for example, a compound of formula (ETM-4)

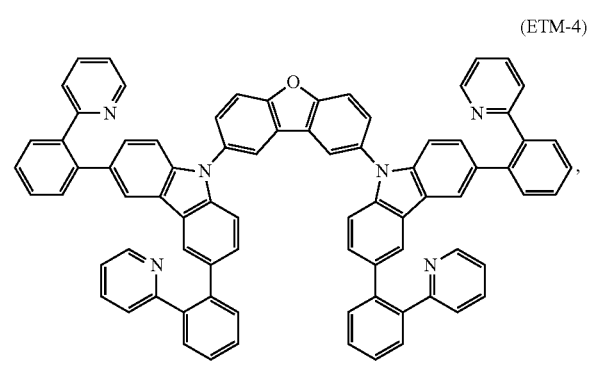 [SMILES: c1ccc(-c2ccccc2-c2ccc3c(c2)c2cc(-c4ccccc4-c4ccccn4)ccc2n3-c2ccc3oc4ccc(-n5c6ccc(-c7ccccc7-c7ccccn7)cc6c6cc(-c7ccccc7-c7ccccn7)ccc65)cc4c3c2)nc1]

and WO2012/115034, such as for example, such as, for example, a compound of formula (ETM-5)

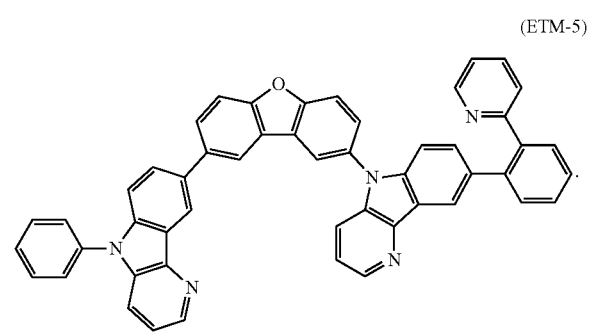 [SMILES: c1ccc(-n2c3ccc(-c4ccc5oc6ccc(-n7c8ccc(-c9ccccc9-c9ccccn9)cc8c8ncccc87)cc6c5c4)cc3c3ncccc32)cc1]

Electron Injection Layer (h):

The electron injection layer may be any layer that improves the injection of electrons into an adjacent organic layer. Lithium-comprising organometallic compounds such as 8-hydroxyquinolatolithium (Liq), CsF, NaF, KF, $Cs_2CO_3$ or LiF may be applied between the electron transport layer (g) and the cathode (i) as an electron injection layer (h) in order to reduce the operating voltage.

Cathode (i):

The cathode (i) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used.

In general, the different layers, if present, have the following thicknesses:

anode (a): 500 to 5000 Å (ångström), preferably 1000 to 2000 Å;

hole injection layer (b): 50 to 1000 Å, preferably 200 to 800 Å, hole-transport layer (c): 50 to 1000 Å, preferably 100 to 800 Å, exciton blocking layer (d): 10 to 500 Å, preferably 50 to 100 Å, light-emitting layer (e): 10 to 1000 Å, preferably 50 to 600 Å, hole/exciton blocking layer (f): 10 to 500 Å, preferably 50 to 100 Å, electron-transport layer (g): 50 to 1000 Å, preferably 200 to 800 Å, electron injection layer (h): 10 to 500 Å, preferably 20 to 100 Å, cathode (i): 200 to 10 000 Å, preferably 300 to 5000 Å.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semi-conductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

Use of the compounds of the formula I in at least one layer of the OLED, preferably in the light-emitting layer (preferably as a matrix material), charge transport layer and/or in the charge/exciton blocking layer makes it possible to obtain OLEDs with high efficiency and with low use and operating voltage. Frequently, the OLEDs obtained by the use of the compounds of the formula I additionally have high lifetimes. The efficiency of the OLEDs can additionally be improved by optimizing the other layers of the OLEDs. For example, high-efficiency cathodes such as Ca or Ba, if appropriate in combination with an intermediate layer of LiF, can be used. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight. The following examples are included for illustrative purposes only and do not limit the scope of the claims. Unless otherwise stated, all parts and percentages are by weight.

EXAMPLES

Example 1

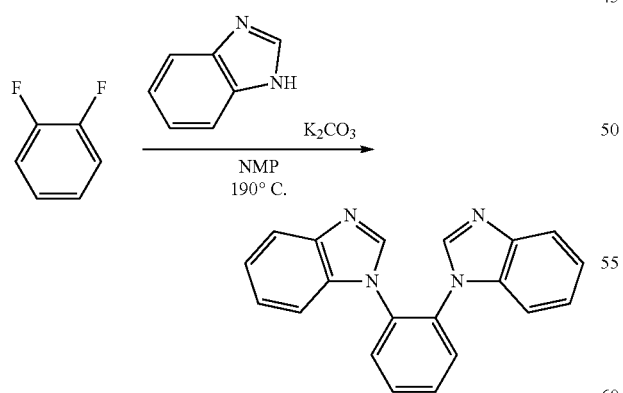

a) 5.0 g (43.8 mmol) of 1,2-difluoro-benzene, 10.4 g (87.7 mmol) of benzimidazole and 15.1 g (109.6 mmol) of potassium carbonate in 100 ml of N-methylpyrrolidone (NMP) are stirred for 24 h at 190° C. The reaction mixture is cooled at room temperature and added water, then the precipitate is filtered off and dried. Yield 12.1 g (89%).

$^1$H NMR (400 MHz, CDCl$_3$): δ 7.86-7.74 (m, 8H); 7.35-7.29 (m, 2H); 7.27-7.19 (m, 4H).

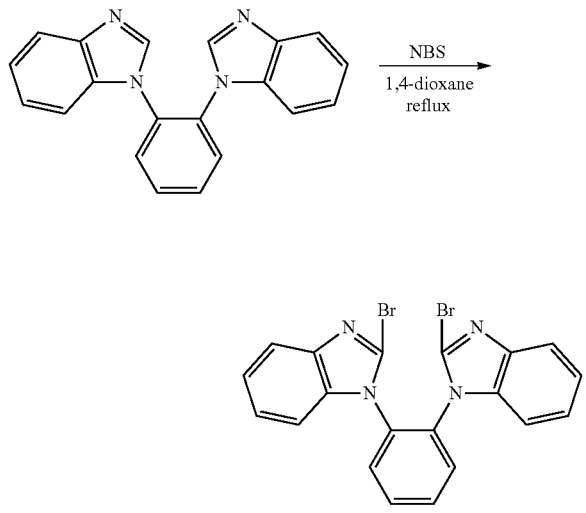

b) 10.6 g (34.2 mmol) of benzimidazole compound and 12.2 g (68.3 mmol) of N-bromosuccinimide (NBS) in 120 ml of 1,4-dioxane are reflux for 1 h. The reaction mixture is cooled at room temperature and added water, then the product is extracted with di-chloromethane. The organic layer is dried over sodium sulfate and concentrated in vacuo. Gradient column chromatography on silica gel with dichloromethane/ethyl acetate (di-chloromethane 100%, 95/5) gives the product as a mixture of the isomers. Yield 11.6 g (73%)

$^1$H NMR (400 MHz, CDCl$_3$): δ 7.87-7.81 (m, 2H); 7.73-7.67 (m, 2H); 7.57-7.51 (m, 2H); 7.23-7.13 (m, 6H).

$^1$H NMR (400 MHz, CDCl$_3$): δ 7.87-7.81 (m, 2H); 7.75-7.70 (m, 2H); 7.61 (dt, J=8.1, 0.9 Hz, 2H); 7.21-7.14 (m, 2H); 7.03-6.91 (m, 4H).

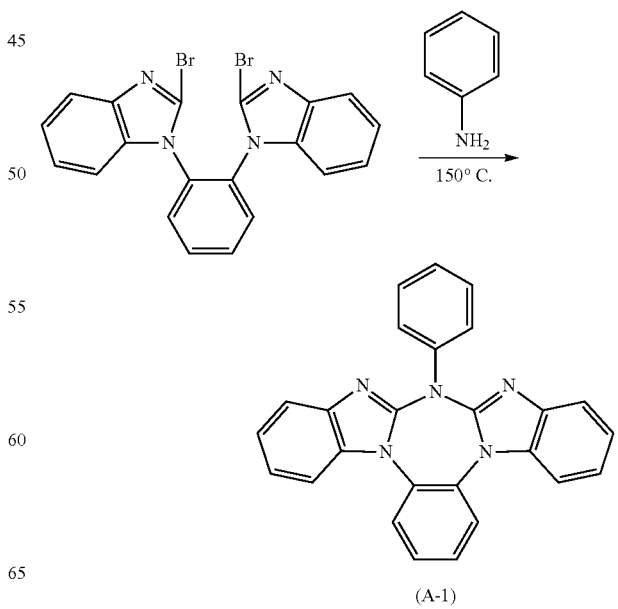

(A-1)

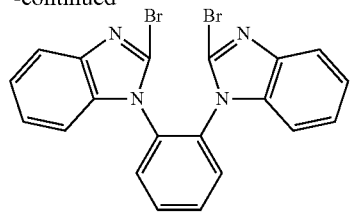

c) 0.50 g (1.07 mmol) of dibromo compound and 0.50 g (5.35 mmol) of aniline are stirred for 2 h at 150° C. The reaction mixture is cooled at room temperature and added 5 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 19/1) gives the product. Yield 0.25 g (58%).

¹H NMR (400 MHz, CDCl₃): δ 8.00-7.93 (m, 2H); 7.93-7.87 (m, 2H); 7.83-7.76 (m, 2H); 7.68-7.57 (m, 4H); 7.51-7.44 (m, 2H); 7.38-7.30 (m, 5H).

Example 2

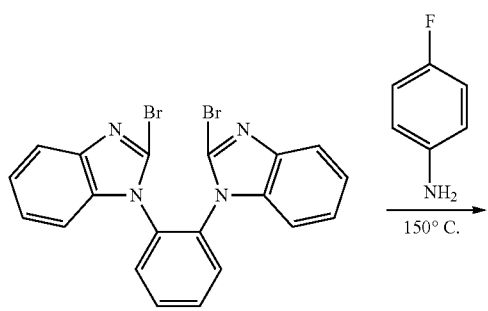

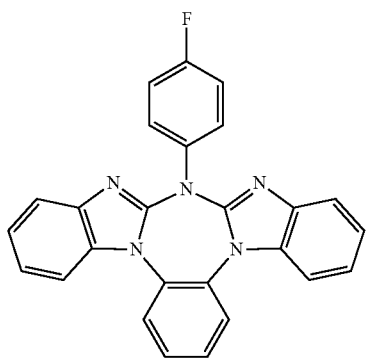

(I-1)

1.00 g (2.14 mmol) of dibromo compound and 1.20 g (10.7 mmol) of 4-fluoro-aniline are stirred for 2 h at 150° C. The reaction mixture is cooled at room temperature and added 10 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 9/1) gives the product. Yield 0.88 g (99%).

¹H NMR (400 MHz, CDCl₃): δ 7.99-7.93 (m, 2H); 7.93-7.87 (m, 2H); 7.78-7.72 (m, 2H); 7.67-7.58 (m, 4H); 7.36-7.30 (m, 4H); 7.22-7.15 (m, 2H).

Example 3

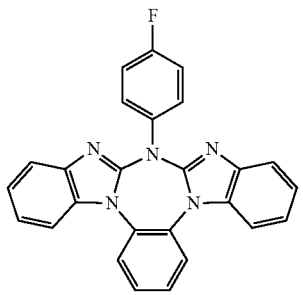
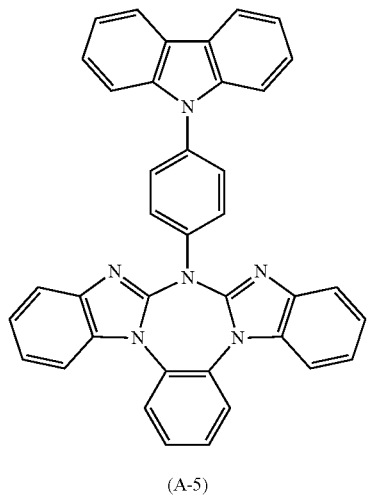

(A-5)

0.50 g (1.20 mmol) of fluoro-compound, 0.22 g (1.32 mmol) of carbazole and 0.20 g (1.44 mmol) of potassium carbonate in 10 ml of NMP are stirred for 48 h at 190° C. The reaction mixture is cooled at room temperature and added water. The precipitate is filtered off, then the product is extracted with dichloromethane. The organic layer is dried over sodium sulfate and concentrated in vacuo. Gradient column chromatography on silica gel with di-chloromethane/ethyl acetate (dichloromethane 100%, 20/1) gives the product. Yield 0.15 g (22%).

¹H NMR (400 MHz, CDCl₃): δ 8.20-8.12 (m, 4H); 8.06-7.98 (m, 2H); 7.89-7.81 (m, 2H); 7.73-7.60 (m, 6H); 7.49 (dt, J=8.3, 1.1 Hz, 2H); 7.46-7.35 (m, 6H); 7.34-7.27 (m, 2H).

Example 4

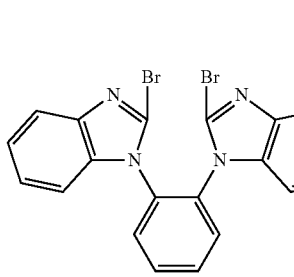
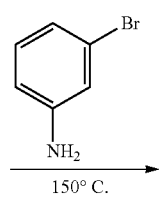

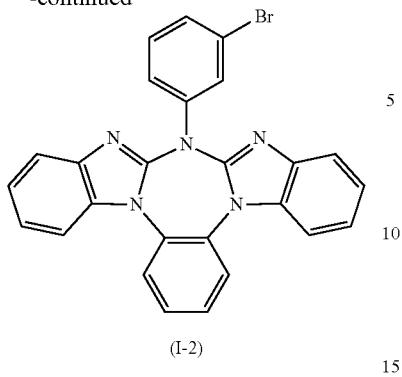

(I-2)

2.00 g (4.27 mmol) of dibromo compound and 3.67 g (21.4 mmol) of 3-bromo-aniline are stirred for 2 h at 150° C. The reaction mixture is cooled at room temperature and added 20 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 2.02 g (99%).

$^1$H NMR (400 MHz, CDCl$_3$): δ 8.03-7.92 (m, 4H); 7.85-7.78 (m, 2H); 7.69-7.59 (m, 4H); 7.44-7.30 (m, 6H).

Example 5

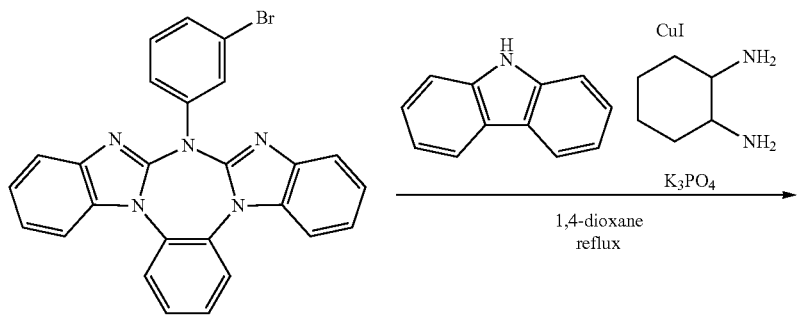

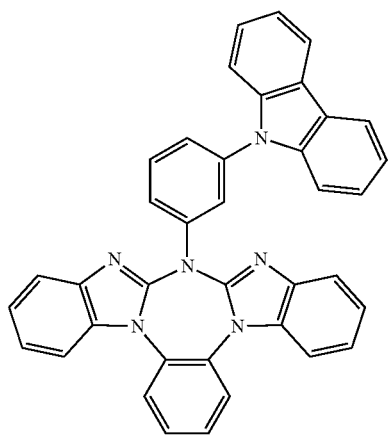

(A-4)

4.3 g (8.99 mmol) of bromo compound, 1.8 g (10.8 mmol) of carbazole, 0.51 g (2.7 mmol) of copper(I) iodide, 0.46 g (4.0 mmol) of trans-1,2-cyclohexanediamine and 5.7 g (27 mmol) of tripotassium phosphate in 70 ml of 1,4-dioxane are reflux for 24 h. The reaction mixture is cooled at room temperature and added 50 ml of 1N aqueous hydrochloric acid. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5) gives the product. Yield 4.6 g (91%).

$^1$H NMR (400 MHz, CDCl$_3$): δ 8.16-8.08 (m, 3H); 8.06 (dd, J=8.4, 2.2 Hz, 1H); 7.97-7.90 (m, 2H); 7.82-7.75 (m, 2H); 7.68-7.59 (m, 5H); 7.59-7.53 (m, 2H); 7.48 (dd, J=7.8, 1.8 Hz, 1H); 7.41 (t, J=7.7 Hz, 2H); 7.36-7.30 (m, 4H); 7.29-7.23 (m, 2H).

Example 6

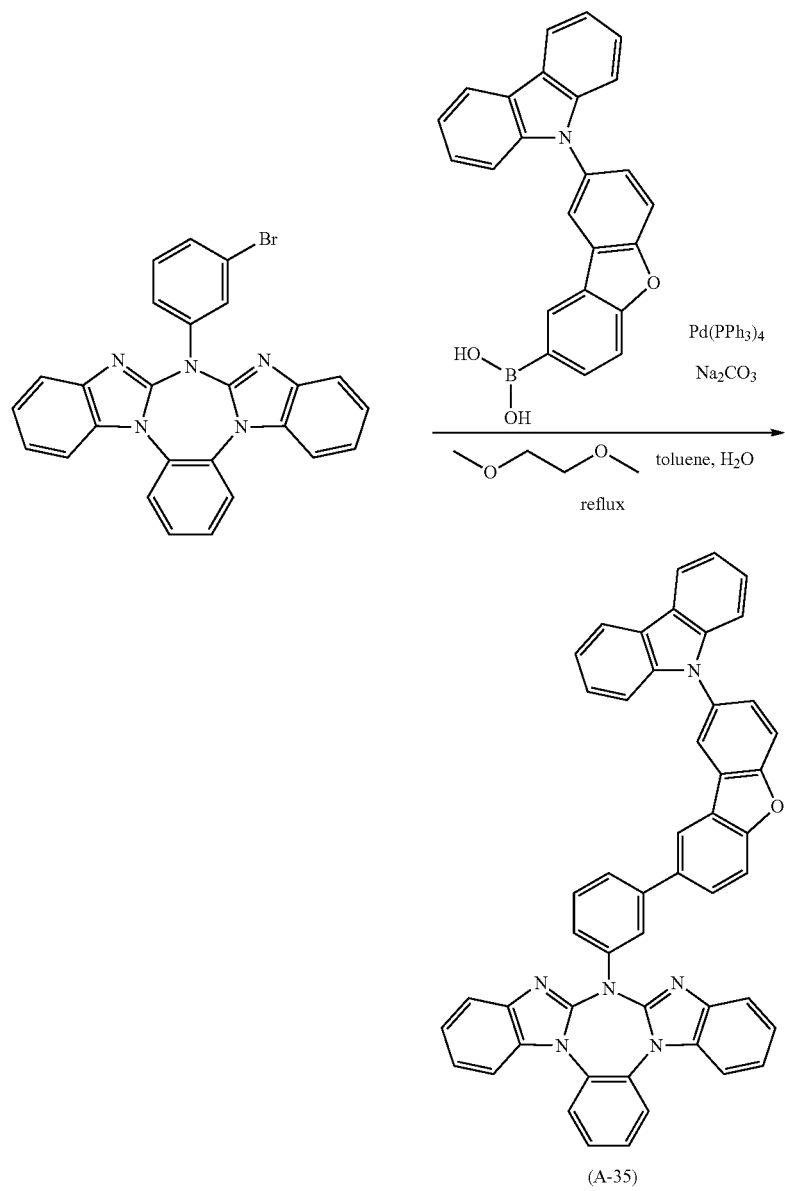

(A-35)

3.35 g (7.0 mmol) of bromo compound, 4.0 g (10.5 mmol) of 2-(8-N-carbazolyl-dibenzofuranyl)-boronic acid, 0.40 g (0.35 mmol) of tetrakis(triphenylphosphine) palladium and 1.5 g (14 mmol) of sodium carbonate in 120 ml of 1,2-dimethoxy-ethane, 80 ml of toluene and 7 ml of water are reflux for 2 h. The reaction mixture is cooled at room temperature and added water, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 4.6 g (90%).

$^1$H NMR (400 MHz, CDCl$_3$): δ 8.16 (d, J=7.8 Hz, 2H); 8.12 (d, J=2.0 Hz, 2H); 8.07 (t, J=1.7 Hz, 1H); 7.98 (dt, J=6.7, 2.4 Hz, 1H); 7.95-7.89 (m, 2H); 7.79-7.71 (m, 4H); 7.65 (d, J=8.7 Hz, 1H); 7.63-7.51 (m, 7H); 7.43-7.35 (m, 4H); 7.33-7.25 (m, 6H).

Example 7

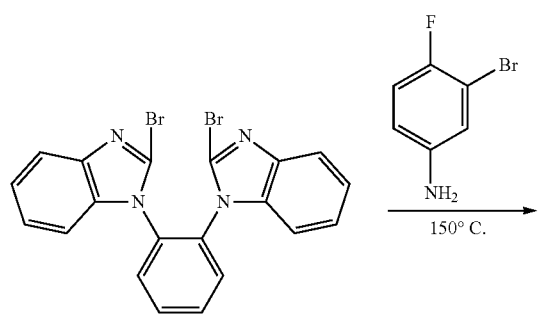

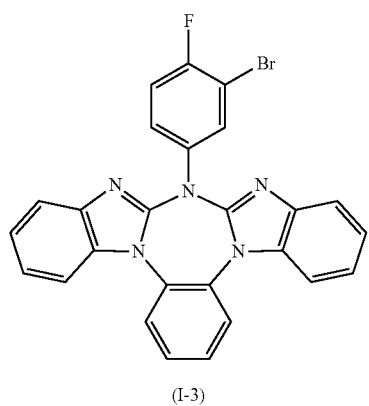

(I-3)

7.00 g (15.0 mmol) of dibromo compound and 14.2 g (74.8 mmol) of 3-bromo-4-fluoro-aniline are stirred for 3 h at 150° C. The reaction mixture is cooled at room temperature and added 70 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 7.32 g (99%).

$^1$H NMR (400 MHz, CDCl$_3$): δ 8.09 (dd, J=6.0, 2.7 Hz, 1H); 8.01-7.93 (m, 3H); 7.79-7.73 (m, 2H); 7.68-7.58 (m, 4H); 7.38-7.31 (m, 4H); 7.24 (dd, J=8.9, 8.1 Hz, 1H).

Example 8

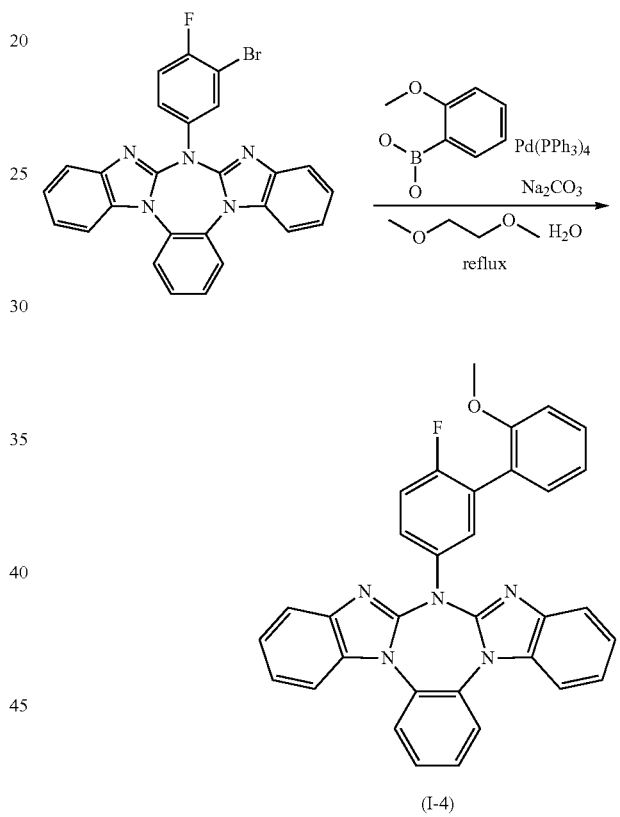

(I-4)

7.32 g (14.7 mmol) of bromo compound, 2.47 g (16.2 mmol) of 2-methoxy-benzene boronic acid, 0.17 g (0.15 mmol) of tetrakis(triphenylphosphine) palladium and 3.90 g (36.8 mmol) of sodium carbonate in 100 ml of 1,2-dimethoxy-ethane and 50 ml of water are reflux for 2 h. The reaction mixture is cooled at room temperature and added water, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 7.70 g.

$^1$H NMR (400 MHz, CDCl$_3$): δ 8.09 (ddd, J=8.9, 4.4, 2.8 Hz, 1H); 7.98-7.91 (m, 2H); 7.79-7.73 (m, 2H); 7.70 (dd, J=6.4, 2.8 Hz, 1H); 7.66-7.61 (m, 2H); 7.60-7.55 (m, 2H); 7.39-7.30 (m, 6H); 7.25 (d, J=9.1 Hz, 1H); 7.03-6.99 (m, 1H); 6.98-6.95 (m, 1H); 3.80 (s, 3H).

Example 9

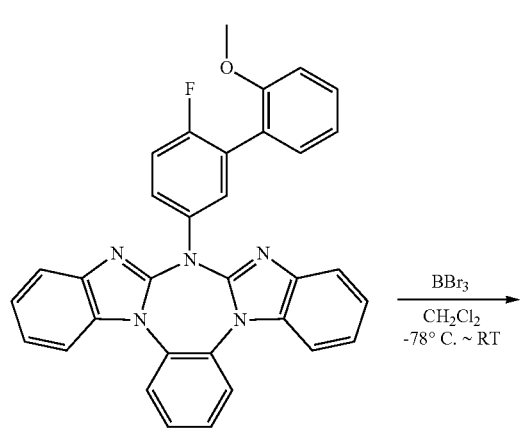

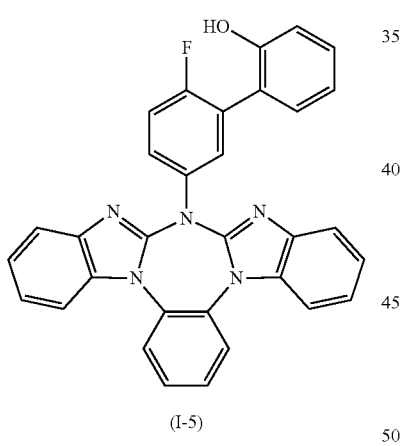

(I-5)

51 ml of 1M borontribromide in dichloromethane is added to 7.70 g (14.7 mmol) of methoxy compound in 15 ml of dichloromethane at −78° C., then the reaction mixture is warmed at room temperature and stirred for 1 h. Water is added to the reaction mixture, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 7.49 g.

$^1$H NMR (400 MHz, CDCl$_3$): δ 7.99-7.92 (m, 4H); 7.76-7.69 (m, 2H); 7.67-7.57 (m, 4H); 7.38-7.26 (m, 7H); 7.06-6.95 (m, 2H).

Example 10

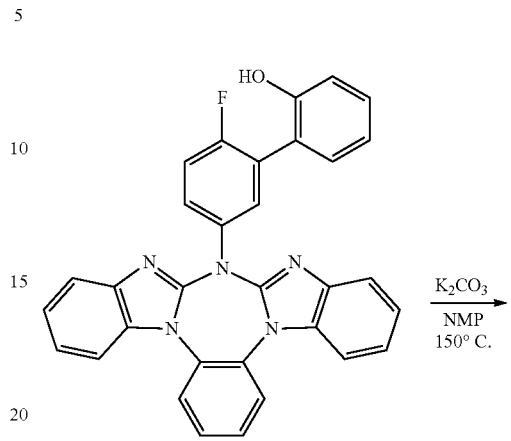

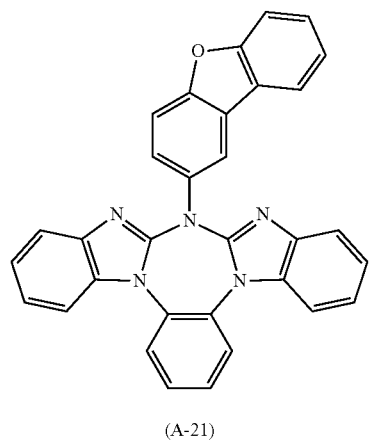

(A-21)

7.49 g (14.7 mmol) of fluoro-compound and 4.06 g (29.4 mmol) of potassium carbonate in 50 ml of NMP are stirred for 2 h at 150° C. The reaction mixture is cooled at room temperature and added water. The precipitate is filtered off, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 4.20 g (58%).

$^1$H NMR (400 MHz, CDCl$_3$): δ 8.57 (dd, J=2.3, 0.5 Hz, 1H); 8.03-7.98 (m, 3H); 7.95 (dd, J=8.8, 2.3 Hz, 1H); 7.76-7.71 (m, 2H); 7.70-7.58 (m, 6H); 7.49 (ddd, J=8.4, 7.3, 1.3 Hz, 1H); 7.39-7.29 (m, 5H).

Example 11

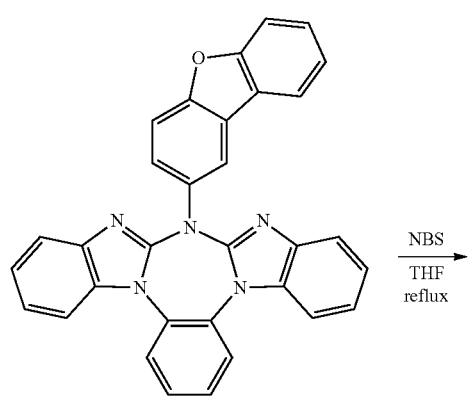

NBS
THF
reflux

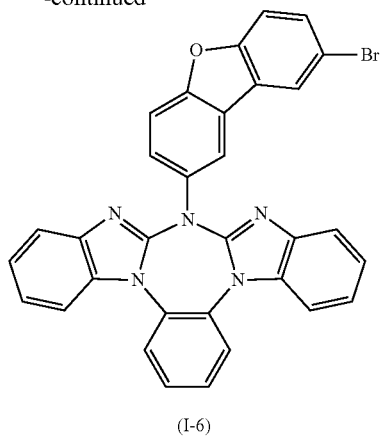

(I-6)

4.10 g (8.38 mmol) of dibenzofuran-compound and 4.47 g (25.1 mmol) of NBS in 50 ml of tetrahydrofuran (THF) are reflux for 2 h. The reaction mixture is cooled at room temperature and added aqueous sodium sulfite. The precipitate is filtered off, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the crude product. Yield 4.20 g.

Example 12

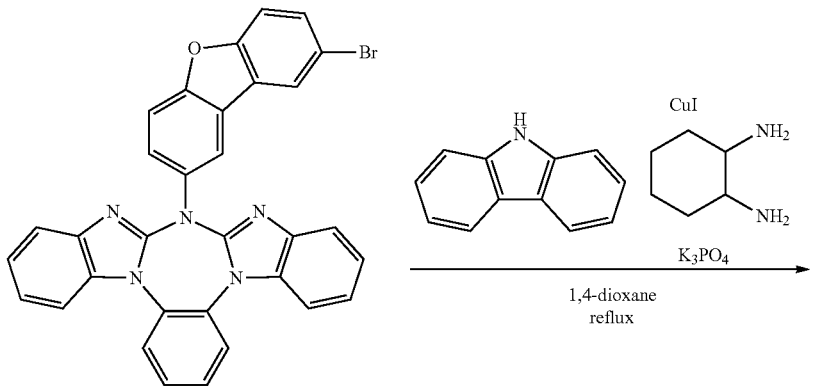

K$_3$PO$_4$
1,4-dioxane
reflux

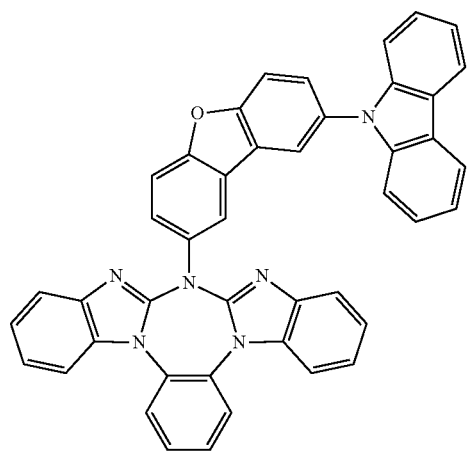

(A-25)

4.20 g of bromo compound, 1.36 g (8.13 mmol) of carbazole, 0.070 g (0.36 mmol) of copper(I) iodide, 0.17 g (1.48 mmol) of trans-1,2-cyclohexanediamine and 3.29 g (15.5 mmol) of tripotassium phosphate in 50 ml of 1,4-dioxane are reflux for 24 h. The reaction mixture is cooled at room temperature and added 25 ml of 1N aqueous hydrochloric acid. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5) gives the product. Yield 2.00 g.

$^1$H NMR (400 MHz, CDCl$_3$): δ 8.61 (dd, J=2.3, 0.5 Hz, 1H); 8.19 (dt, J=7.7, 1.0 Hz, 2H); 8.07-7.97 (m, 3H); 7.96-7.89 (m, 2H); 7.82 (dd, J=2.0, 0.6 Hz, 1H); 7.79-7.70 (m, 2H); 7.70-7.48 (m, 6H); 7.47-7.29 (m, 9H).

Example 13

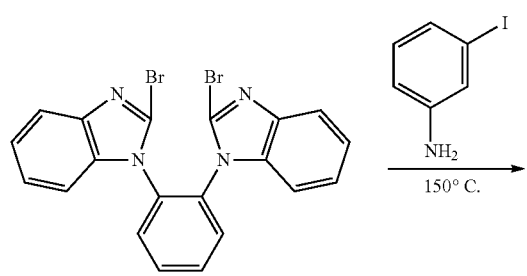

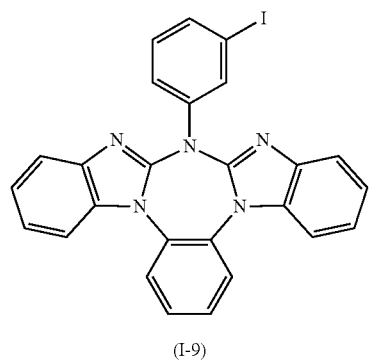

(I-9)

5.00 g (11 mmol) of dibromo compound and 11.7 g (53 mmol) of 3-iodo-aniline are stirred for 2 h at 150° C. The reaction mixture is cooled at room temperature and added 50 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 3.0 g (53%).

Example 14

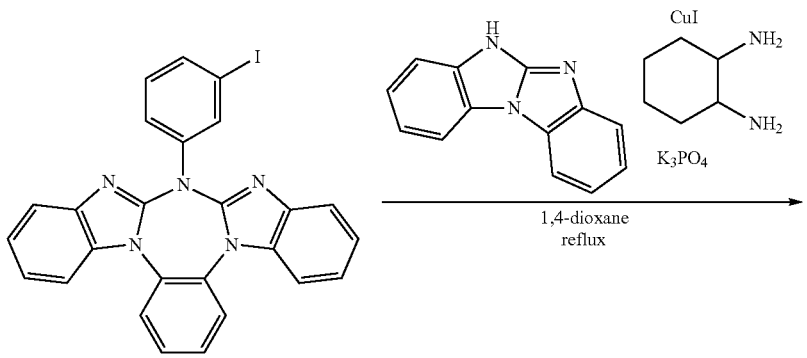

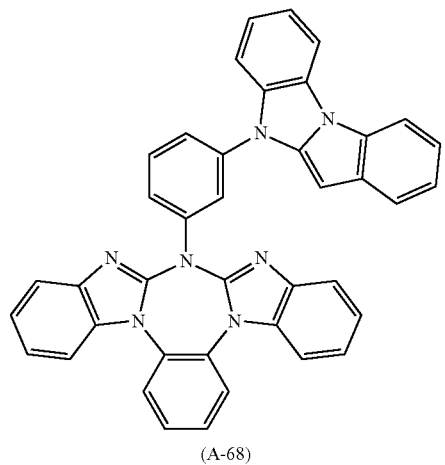

(A-68)

2.6 g (4.9 mmol) of iodo compound, 1.23 g (5.9 mmol) of 6H-benzimidazolo[1,2-a]benzimidazole, 0.28 g (1.5 mmol) of copper(I) iodide, 10 g (88 mmol) of trans-1,2-cyclohexanediamine and 2.2 g (10 mmol) of tripotassium phosphate in 17 ml of 1,4-dioxane are reflux for 24 h. The reaction mixture is cooled at room temperature and added 150 ml of 1N aqueous hydrochloric acid. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5, 1/1) gives the product. Yield 2.0 g (67%).

$^1$H NMR (400 MHz, CDCl$_3$): δ 8.49 (t, J=2.1 Hz, 1H); 8.01-7.95 (m, 3H); 7.94-7.74 (m, 7H); 7.70-7.59 (m, 5H); 7.46-7.30 (m, 8H).

Example 15

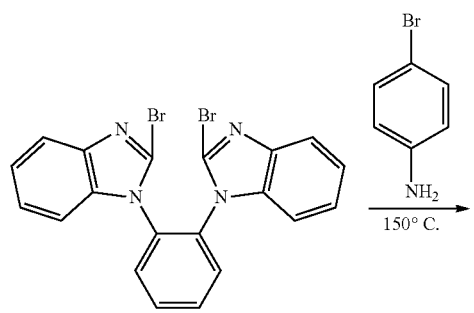

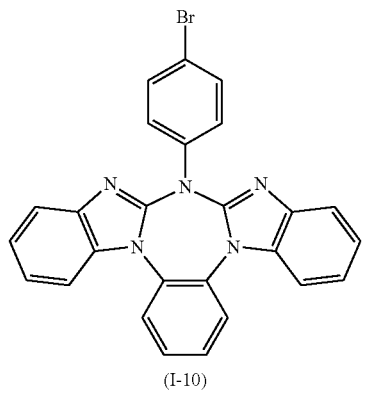

(I-10)

5.00 g (11 mmol) of dibromo compound and 9.20 g (53 mmol) of 4-bromo-aniline are stirred for 2 h at 150° C. The reaction mixture is cooled at room temperature and added 50 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 3.3 g (65%).

$^1$H NMR (400 MHz, CDCl$_3$): δ 8.01-7.91 (m, 2H); 7.84-7.73 (m, 4H); 7.69-7.54 (m, 6H); 7.38-7.31 (m, 4H).

Example 16

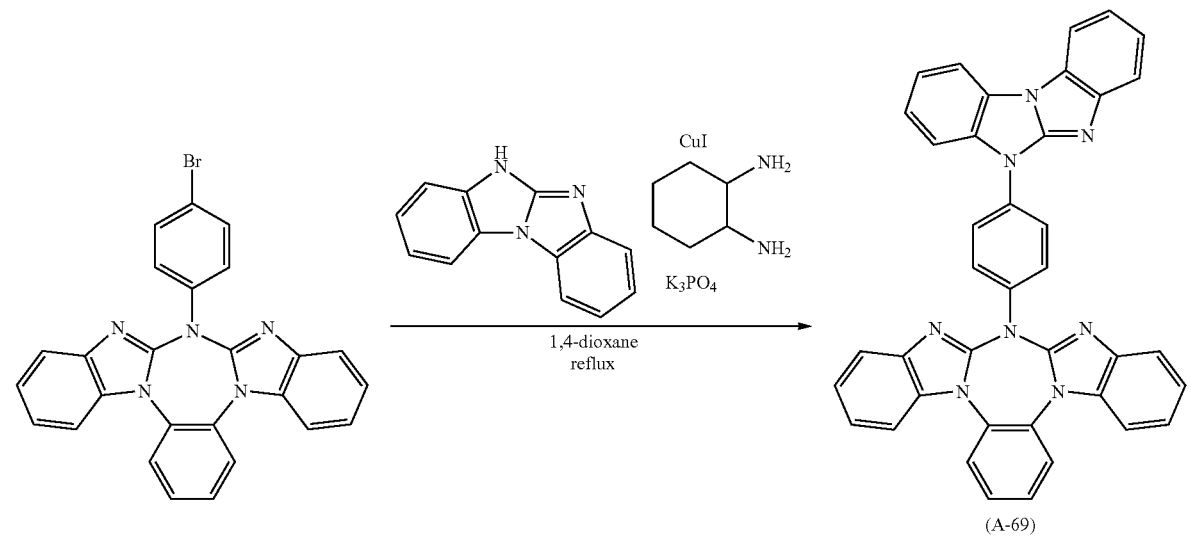

(A-69)

3.3 g (6.9 mmol) of bromo compound, 2.1 g (10 mmol) of 6H-benzimidazolo[1,2-a]benzimidazole, 0.39 g (2.1 mmol) of copper(I) iodide, 14 g (123 mmol) of trans-1,2-cyclohexanediamine and 4.8 g (23 mmol) of tripotassium phosphate in 30 ml of 1,4-dioxane are reflux for 24 h. The reaction mixture is cooled at room temperature and added 200 ml of 1N aqueous hydrochloric acid. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5, 1/1) gives the product. Yield 2.4 g (58%).

$^1$H NMR (400 MHz, CDCl$_3$): δ 8.18-8.10 (m, 2H); 8.04-7.96 (m, 2H); 7.94-7.87 (m, 2H); 7.87-7.79 (m, 4H); 7.78-7.73 (m, 1H); 7.71-7.59 (m, 5H); 7.43-7.32 (m, 7H); 7.31-7.27 (m, 1H).

Example 17

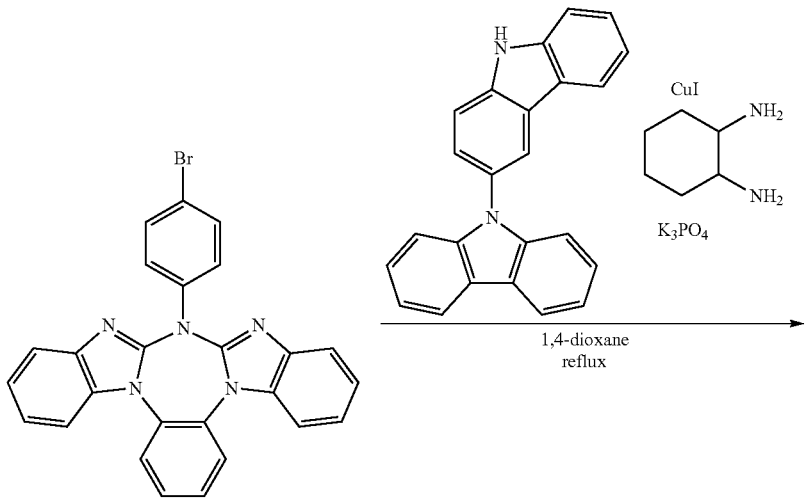

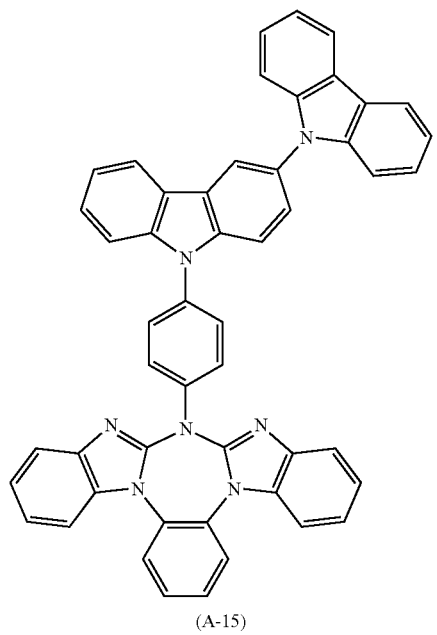

(A-15)

2.0 g (4.18 mmol) of bromo compound, 1.67 g (5.02 mmol) of 3-carbazolyl-carbazole, 0.040 g (0.21 mmol) of copper(I) iodide, 0.05 ml (0.42 mmol) of trans-1,2-cyclohexanediamine and 1.01 g (8.36 mmol) of tripotassium phosphate in 70 ml of 1,4-dioxane are reflux for 24 h. The reaction mixture is cooled at room temperature and added 30 ml of 1N aqueous hydrochloric acid. The inorganic solids are filtered, then the filtrate is extracted with di-chloromethane. The organic layer is dried over sodium sulfate and concentrated in vacuo. Gradient column chromatography on silica gel with dichloromethane/ethyl acetate (di-chloromethane 100%, 95/5) gives the product. Yield 2.1 g (69%).

$^1$H NMR (400 MHz, CDCl$_3$): δ 8.27 (d, J=1.9 Hz, 1H); 8.23-8.16 (m, 4H); 8.10 (d, J=7.6 Hz, 1H); 8.04-7.98 (m, 2H); 7.87-7.81 (m, 2H); 7.72-7.60 (m, 7H); 7.56-7.50 (m, 2H); 7.49-7.44 (m, 1H); 7.44-7.34 (m, 8H); 7.33-7.26 (m, 3H).

Example 18

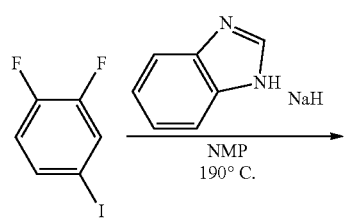

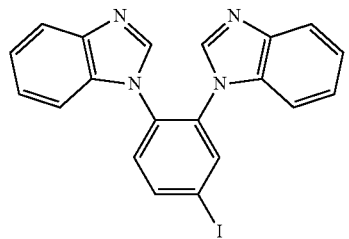

a) 7.40 g (62.5 mmol) of benzimidazole is added to 2.50 g (62.5 mmol) of 60% sodium hydride in 100 ml of NMP at room temperature, then 7.50 g (31.3 mmol) of 1,2-difluoro-4-iodo-benzene is added at room temperature and stirred for 24 h at 190° C. The reaction mixture is cooled at room temperature and added water, then the precipitate is filtered off, washed with ethyl acetate and dried. Yield 10.8 g (79%).

$^1$H NMR (400 MHz, CDCl$_3$): δ 8.10 (d, J=1.9 Hz, 1H); 8.08 (dd, J=8.3, 2.0 Hz, 1H); 7.76 (dd, J=7.9, 1.1 Hz, 2H); 7.67-7.58 (m, 2H); 7.48 (d, J=8.3 Hz, 1H); 7.33-7.16 (m, 6H).

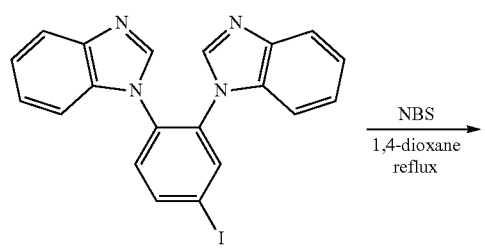

-continued

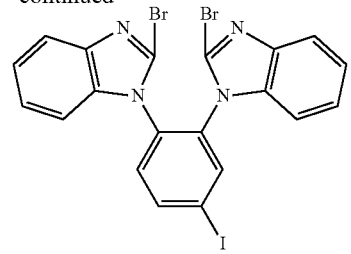

b) 10.3 g (23.6 mmol) of benzimidazole compound and 8.4 g (47.2 mmol) of N-bromosuccinimide (NBS) in 100 ml of 1,4-dioxane are reflux for 1 h. The reaction mixture is cooled at room temperature and added water, then the product is extracted with dichloromethane. The organic layer is dried over sodium sulfate and concentrated in vacuo. Gradient column chromatography on silica gel with dichloromethane/ethyl acetate (dichloromethane 100%, 90/10) gives the product as a mixture of the isomers. Yield 7.00 g (50%)

$^1$H NMR (400 MHz, CDCl$_3$): δ 8.15 (dd, J=8.4, 2.0 Hz, 1H); 8.04 (d, J=2.0 Hz, 1H); 7.57-7.51 (m, 2H); 7.41 (d, J=8.4 Hz, 1H); 7.25-7.11 (m, 6H).

$^1$H NMR (400 MHz, CDCl$_3$): δ 8.15 (dd, J=8.4, 2.0 Hz, 1H); 8.06 (d, J=2.0 Hz, 1H); 7.63-7.58 (m, 2H); 7.44 (d, J=8.4 Hz, 1H); 7.22-7.14 (m, 2H); 7.06-7.00 (m, 1H); 7.00-6.94 (m, 2H); 6.93-6.88 (m, 1H).

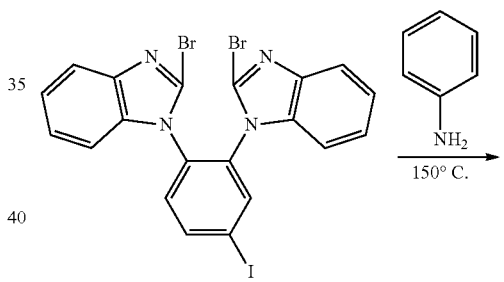

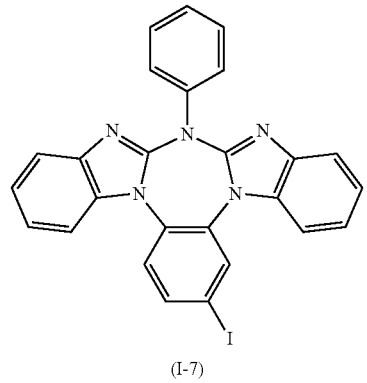

(I-7)

c) 4.00 g (6.73 mmol) of dibromo compound and 3.14 g (33.7 mmol) of aniline are stirred for 2 h at 150° C. The reaction mixture is cooled at room temperature and added 30 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 3.50 g (99%).

$^1$H NMR (400 MHz, CDCl$_3$): δ 8.27 (d, J=1.9 Hz, 1H); 7.93-7.85 (m, 3H); 7.78-7.73 (m, 2H); 7.68 (d, J=8.6 Hz, 1H); 7.64-7.60 (m, 1H); 7.60-7.57 (m, 1H); 7.51-7.45 (m, 2H); 7.40-7.31 (m, 5H).

Example 19

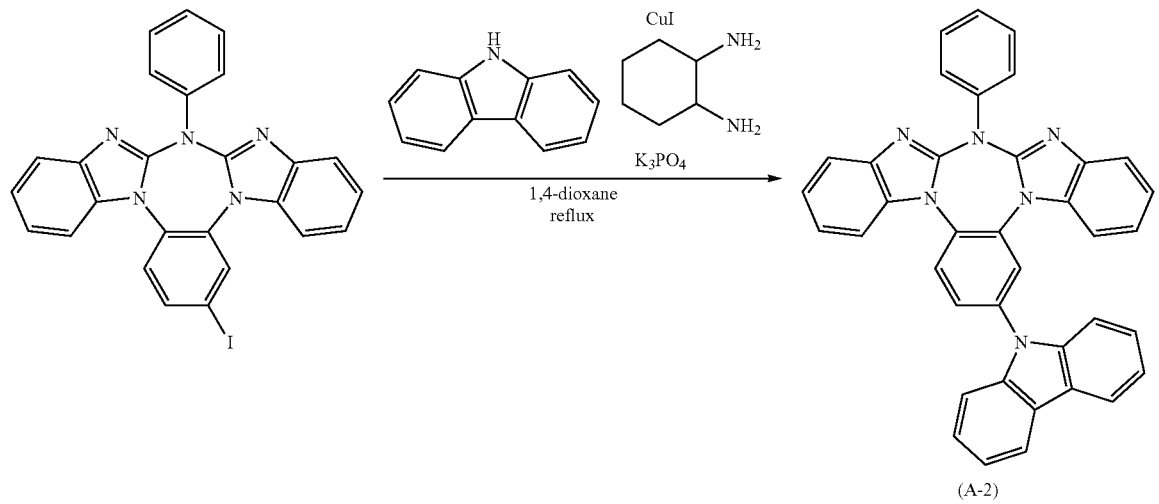

7.50 g (14.3 mmol) of iodo compound, 2.86 g (17.1 mmol) of carbazole, 0.136 g (0.71 mmol) of copper(I) iodide, 0.2 ml (1.43 mmol) of trans-1,2-cyclohexanediamine and 3.46 g (28.6 mmol) of tripotassium phosphate in 200 ml of 1,4-dioxane are reflux for 24 h. The reaction mixture is cooled at room temperature and added 100 ml of 1N aqueous hydrochloric acid. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5) gives the product. Yield 6.70 g (83%).

$^1$H NMR (400 MHz, CDCl$_3$): δ 8.22-8.12 (m, 4H); 7.96 (d, J=7.9 Hz, 2H); 7.84-7.77 (m, 2H); 7.76-7.71 (m, 2H); 7.62-7.54 (m, 3H); 7.50 (t, J=7.8 Hz, 4H); 7.40-7.31 (m, 5H); 7.30-7.22 (m, 2H).

Example 20

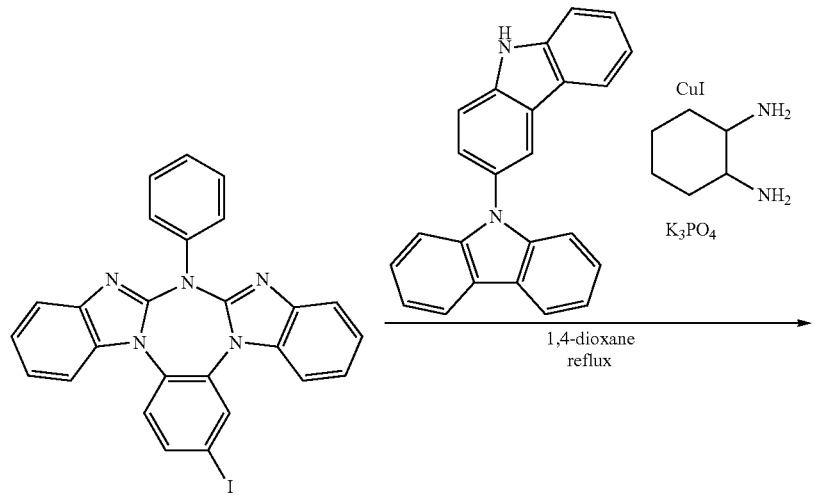

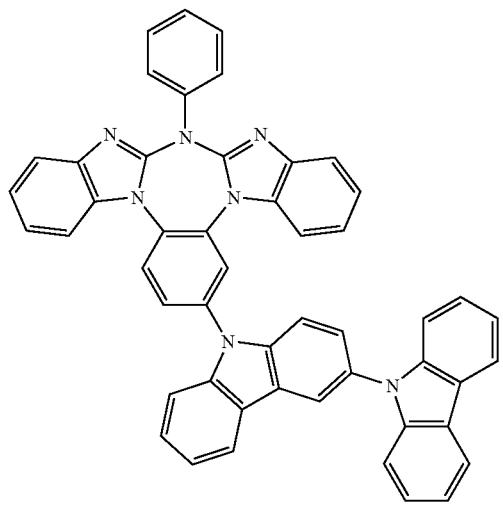

(A-17)

7.50 g (14.3 mmol) of iodo compound, 5.69 g (17.1 mmol) of 3-carbazolyl-carbazole, 0.136 g (0.71 mmol) of copper(I) iodide, 0.2 ml (1.43 mmol) of trans-1,2-cyclohexanediamine and 3.46 g (28.6 mmol) of tripotassium phosphate in 200 ml of 1,4-dioxane are reflux for 24 h. The reaction mixture is cooled at room temperature and added 100 ml of 1N aqueous hydrochloric add. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5) gives the product. Yield 9.90 g (95%).

$^1$H NMR (400 MHz, CDCl$_3$): δ 8.33 (d, J=1.9 Hz, 1H); 8.26-8.13 (m, 5H); 7.97 (d, J=8.2 Hz, 2H); 7.89 (dd, J=8.6, 2.2 Hz, 1H); 7.82-7.72 (m, 4H); 7.67-7.61 (m, 3H); 7.57 (t, J=7.6 Hz, 1H); 7.51 (t, J=7.9 Hz, 2H); 7.45-7.27 (m, 12H).

Example 21

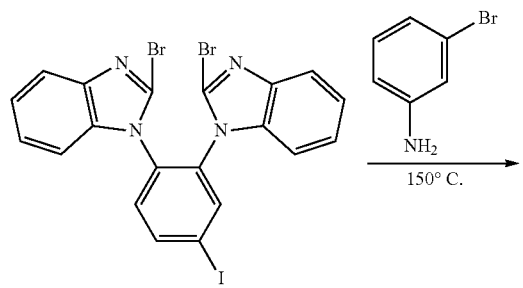

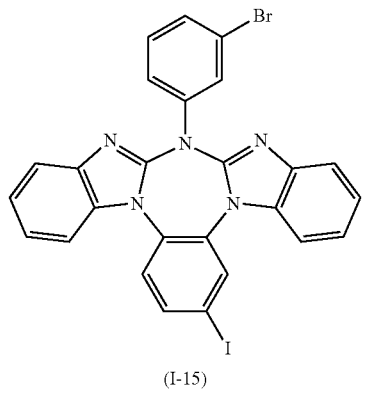

(I-15)

5.00 g (8.42 mmol) of dibromo compound and 7.24 g (42.1 mmol) of 3-bromo-aniline are stirred for 2 h at 150° C. The reaction mixture is cooled at room temperature and added 40 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 4.90 g (96%).

$^1$H NMR (400 MHz, CDCl$_3$): δ 8.28 (d, J=1.9 Hz, 1H); 7.99 (t, J=2.0 Hz, 1H); 7.94-7.88 (m, 2H); 7.81-7.75 (m, 2H); 7.69 (d, J=8.5 Hz, 1H); 7.65-7.55 (m, 2H); 7.45-7.34 (m, 5H); 7.32 (d, J=8.0 Hz, 1H).

Example 22

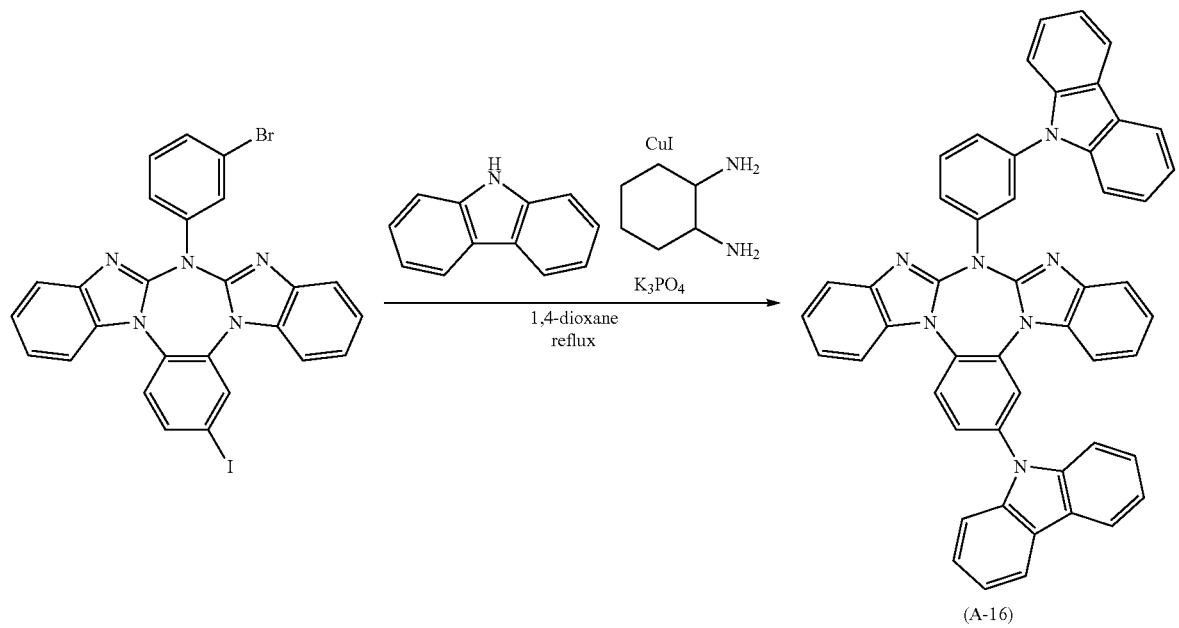

(A-16)

4.80 g (7.94 mmol) of bromo-iodo compound, 2.91 g (17.4 mmol) of carbazole, 0.079 g (0.41 mmol) of copper(I) iodide, 0.19 g (1.66 mmol) of trans-1,2-cyclohexanediamine and 7.21 g (33.9 mmol) of tripotassium phosphate in 150 ml of 1,4-dioxane are reflux for 24 h. The reaction mixture is cooled at room temperature and added 50 ml of 1N aqueous hydrochloric add. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5) gives the product. Yield 2.55 g (44%).

$^1$H NMR (400 MHz, CDCl$_3$): δ 8.24 (t, J=2.1 Hz, 1H); 8.23-8.12 (m, 7H); 7.88-7.69 (m, 8H); 7.65-7.61 (m, 1H); 7.60-7.55 (m, 3H); 7.53-7.30 (m, 11H).

LC MS: 730.33 [M+1]

Example 23

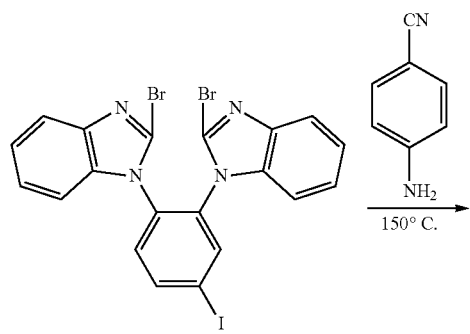

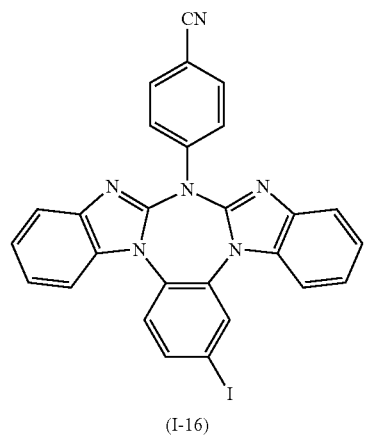

(I-16)

5.00 g (8.42 mmol) of dibromo compound and 4.97 g (42.1 mmol) of 4-amino-benzonitrile are stirred for 2 h at 150° C. The reaction mixture is cooled at room temperature and added 40 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 4.20 g (91%).

LC MS: 550.97 [M+1]

Example 24

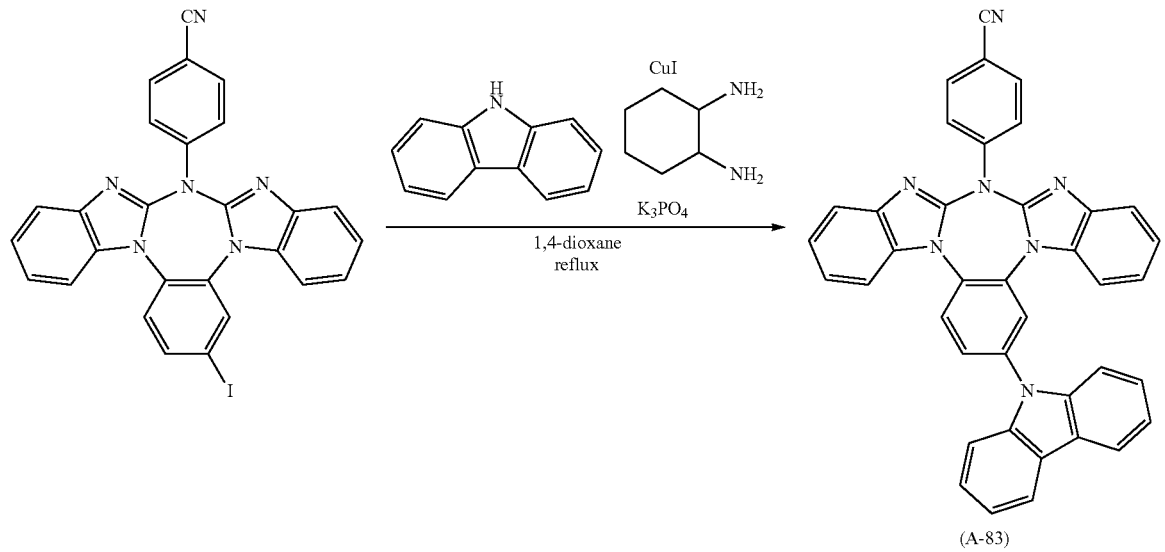

(A-83)

2.40 g (4.36 mmol) of iodo compound, 0.80 g (4.80 mmol) of carbazole, 0.042 g (0.22 mmol) of copper(I) iodide, 0.10 g (0.87 mmol) of trans-1,2-cyclohexanediamine and 1.94 g (9.16 mmol) of tripotassium phosphate in 25 ml of 1,4-dioxane are reflux for 24 h. The reaction mixture is cooled at room temperature and added 25 ml of 1N aqueous hydrochloric acid. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5) gives the product. Yield 1.70 g (66%).

$^1$H NMR (400 MHz, CDCl$_3$): δ 8.25-8.19 (m, 4H); 8.12-8.06 (m, 2H); 7.92-7.86 (m, 2H); 7.85-7.77 (m, 2H); 7.76-7.71 (m, 2H); 7.68-7.63 (m, 1H); 7.58 (d, J=8.2 Hz, 2H); 7.55-7.49 (m, 2H); 7.48-7.44 (m, 2H); 7.42-7.34 (m, 4H).

Example 25

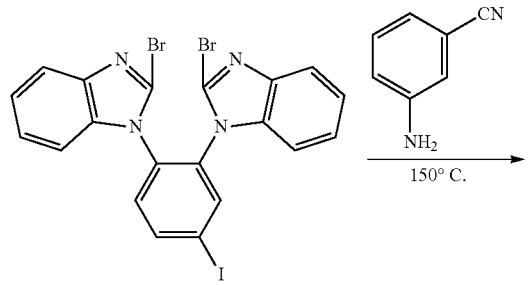

-continued

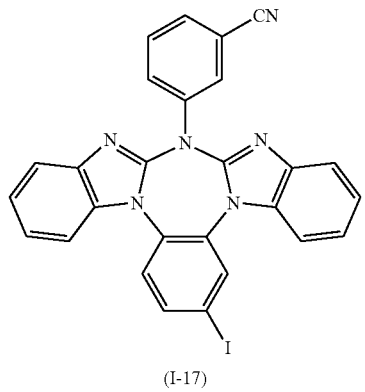

(I-17)

5.00 g (8.42 mmol) of dibromo compound and 4.97 g (42.1 mmol) of 3-amino-benzonitrile are stirred for 2 h at 150° C. The reaction mixture is cooled at room temperature and added 40 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 3.25 g (70%).

$^1$H NMR (400 MHz, CDCl$_3$): δ 8.33-8.28 (m, 2H); 8.15 (dt, J=7.0, 2.3 Hz, 1H); 7.94 (dd, J=8.5, 1.9 Hz, 1H); 7.82-7.76 (m, 2H); 7.71 (d, J=8.5 Hz, 1H); 7.66-7.52 (m, 4H); 7.45-7.35 (m, 4H).

Example 26

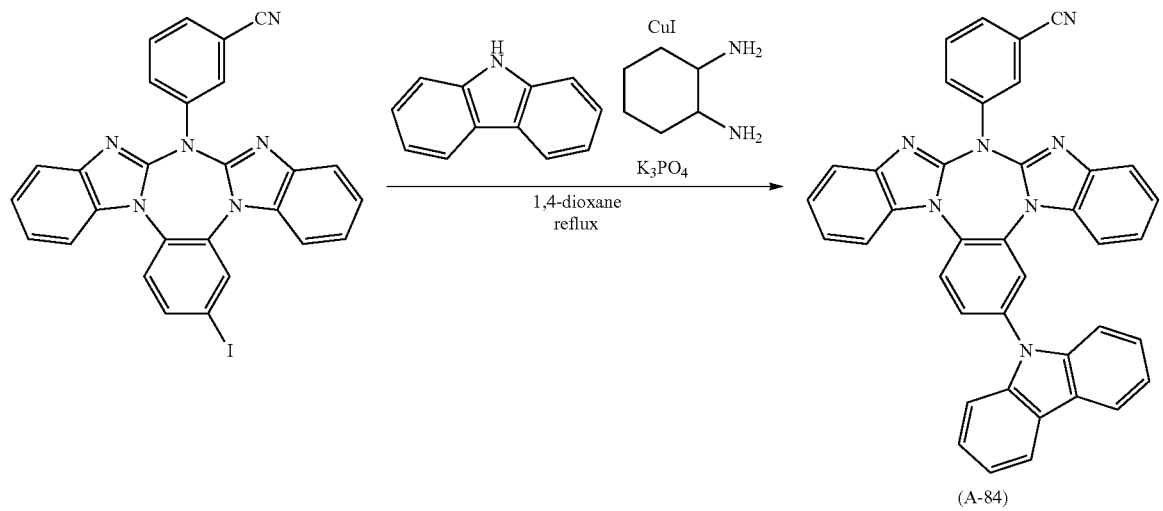

(A-84)

3.20 g (5.81 mmol) of iodo compound, 1.07 g (6.40 mmol) of carbazole, 0.055 g (0.29 mmol) of copper(I) iodide, 0.13 g (1.16 mmol) of trans-1,2-cyclohexanediamine and 2.59 g (12.2 mmol) of tripotassium phosphate in 30 ml of 1,4-dioxane are reflux for 24 h. The reaction mixture is cooled at room temperature and added 25 ml of 1N aqueous hydrochloric acid. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5) gives the product. Yield 2.60 g (76%).

$^1$H NMR (400 MHz, CDCl$_3$): δ 8.44-8.39 (m, 1H); 8.29-8.24 (m, 1H); 8.24-8.18 (m, 4H); 7.91-7.82 (m, 2H); 7.81-7.76 (m, 2H); 7.67-7.63 (m, 1H); 7.62-7.57 (m, 4H); 7.52 (ddd, J=8.3, 7.1, 1.2 Hz, 2H); 7.47-7.30 (m, 6H).

Example 27

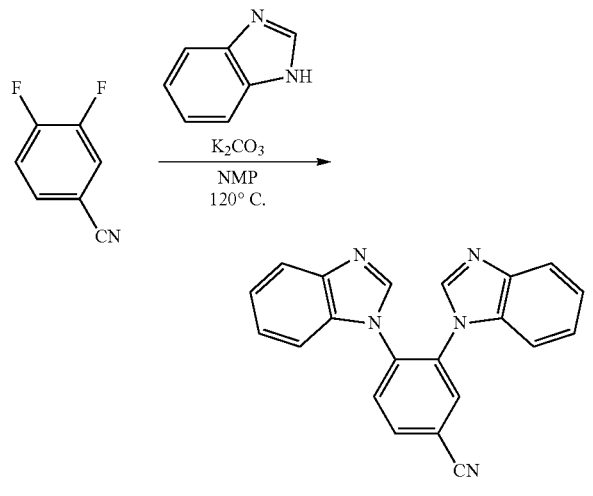

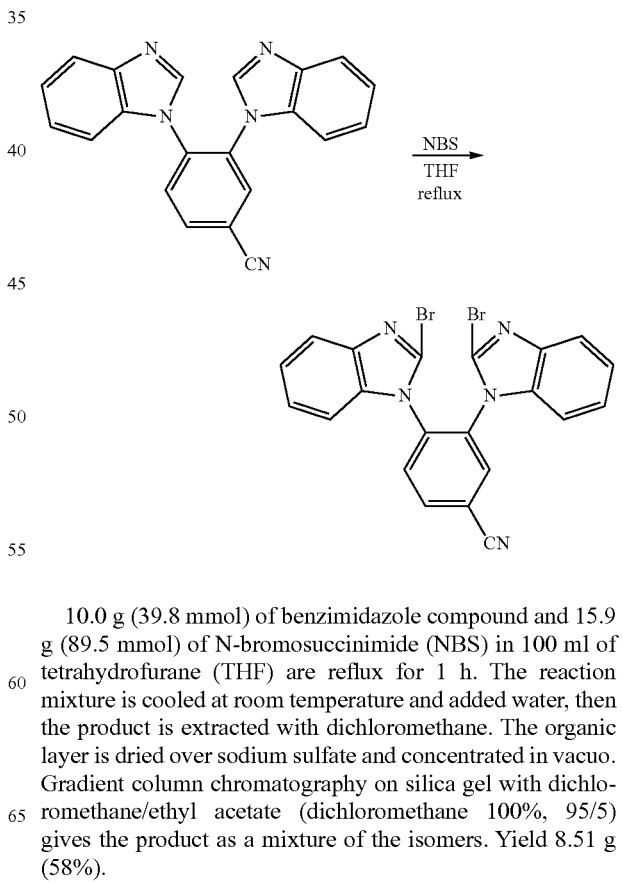

20.0 g (144 mmol) of 3,4-difluoro-benzonitrile, 34.0 g (288 mmol) of benzimidazole and 49.7 g (360 mmol) of potassium carbonate in 340 ml of N-methylpyrrolidone (NMP) are stirred for 24 h at 120° C. The reaction mixture is cooled at room temperature and added water, then the precipitate is filtered off and dried. Yield 43 g (89%).

10.0 g (39.8 mmol) of benzimidazole compound and 15.9 g (89.5 mmol) of N-bromosuccinimide (NBS) in 100 ml of tetrahydrofurane (THF) are reflux for 1 h. The reaction mixture is cooled at room temperature and added water, then the product is extracted with dichloromethane. The organic layer is dried over sodium sulfate and concentrated in vacuo. Gradient column chromatography on silica gel with dichloromethane/ethyl acetate (dichloromethane 100%, 95/5) gives the product as a mixture of the isomers. Yield 8.51 g (58%).

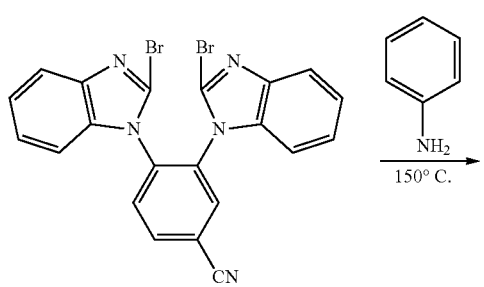
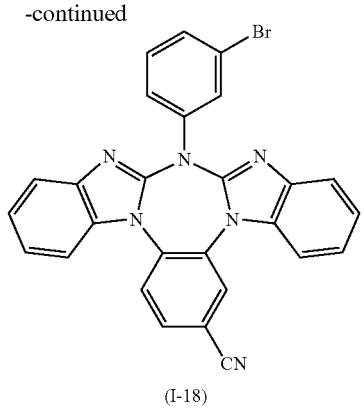

(I-18)

7.5 g (15.2 mmol) of dibromo compound and 11.6 ml (106 mmol) of 3-bromo-aniline are stirred for 2 h at 150° C. The reaction mixture is cooled at room temperature and added 120 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 5.3 g (69%).

Example 29

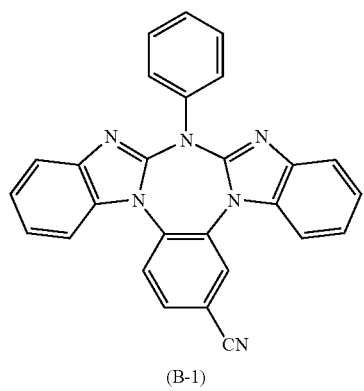

(B-1)

12.3 g (25 mmol) of dibromo compound and 11.4 ml (125 mmol) of aniline are stirred for 2 h at 150° C. The reaction mixture is cooled at room temperature and added 150 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 6.8 g (64%).

$^1$H NMR (400 MHz, CDCl$_3$): δ 8.23 (d, J=1.8 Hz, 1H); 8.06 (d, J=8.3 Hz, 1H); 7.87-7.81 (m, 3H); 7.76-7.71 (m, 2H); 7.60-7.54 (m, 2H); 7.51-7.45 (m, 2H); 7.40-7.31 (m, 5H).

Example 28

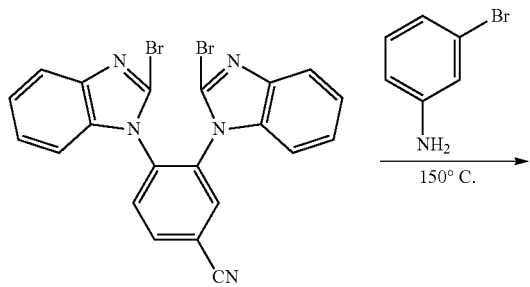

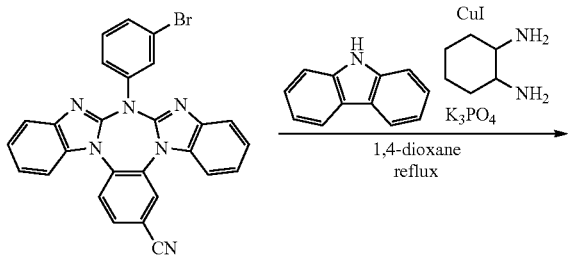

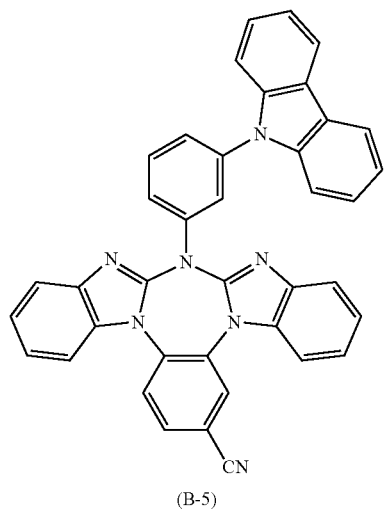

(B-5)

5.3 g (10.5 mmol) of bromo compound, 3.2 g (18.9 mmol) of carbazole, 0.90 g (8.5 mmol) of copper(I) iodide, 0.9 ml (7.1 mmol) of trans-1,2-cyclohexanediamine and 10.0 g (47.3 mmol) of tripotassium phosphate in 90 ml of 1,4-dioxane are reflux for 24 h. The reaction mixture is cooled at room temperature and added 25 ml of 1N aqueous hydrochloric acid. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5) gives the product. Yield 3.55 g (57%).

¹H NMR (400 MHz, CDCl₃): δ 8.24 (d, J=1.9 Hz, 1H); 8.14-8.10 (m, 3H); 8.07 (d, J=8.4 Hz, 1H); 8.01 (dd, J=8.4, 2.1 Hz, 1H); 7.84 (dd, J=8.3, 1.9 Hz, 1H); 7.80-7.76 (m, 2H); 7.67 (dd, J=16.8, 8.2 Hz, 3H); 7.60-7.56 (m, 3H); 7.44-7.35 (m, 6H); 7.29 (d, J=7.4 Hz, 2H).

Example 30

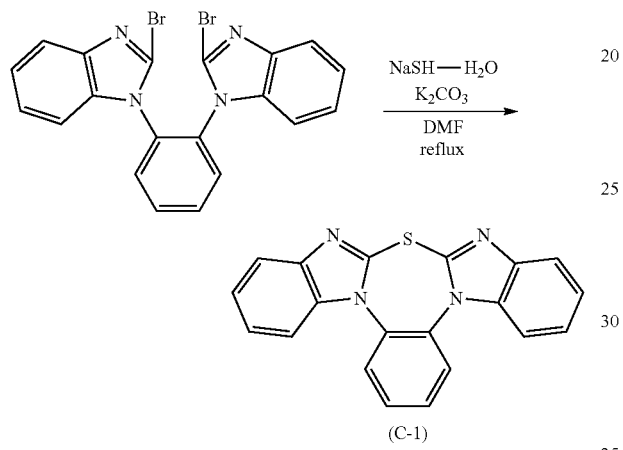

(C-1)

0.50 g (1.07 mmol) of dibromo compound, 0.09 g (1.61 mmol) of sodium hydrosulfide monohydrate and 0.89 g (6.42 mmol) of potassium carbonate in 5 ml of dimethylformamide (DMF) are reflux for 24 h. The reaction mixture is cooled at room temperature and added 20 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 0.20 g (56%).

¹H NMR (400 MHz, CDCl₃): δ 7.97-7.91 (m, 2H); 7.89-7.84 (m, 2H); 7.75-7.70 (m, 2H); 7.61-7.55 (m, 2H); 7.41-7.35 (m, 4H).

Example 31

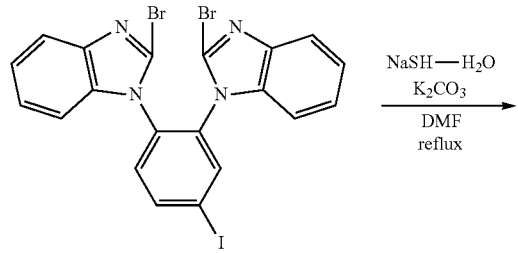

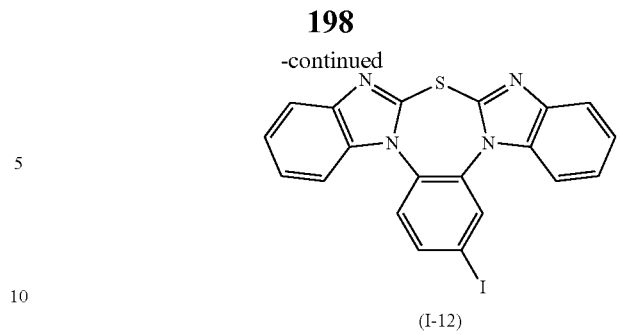

(I-12)

3.00 g (5.05 mmol) of dibromo compound, 0.42 g (7.58 mmol) of sodium hydrosulfide monohydrate and 4.19 g (30.3 mmol) of potassium carbonate in 25 ml of dimethylformamide (DMF) are reflux for 3 h. The reaction mixture is cooled at room temperature and added 100 ml of 1N HCl, then the product is extracted with dichloromethane. The organic layer is dried over sodium sulfate and concentrated in vacuo. Gradient column chromatography on silica gel with dichloromethane/ethyl acetate (dichloromethane 100%, 20/1) gives the product. Yield 1.50 g (64%).

¹H NMR (400 MHz, CDCl₃): δ 8.26 (d, J=1.9 Hz, 1H); 8.06-8.00 (m, 1H); 7.89-7.84 (m, 2H); 7.65 (d, J=8.5 Hz, 1H); 7.60-7.56 (m, 1H); 7.56-7.51 (m, 1H); 7.47-7.37 (m, 4H).

Example 32

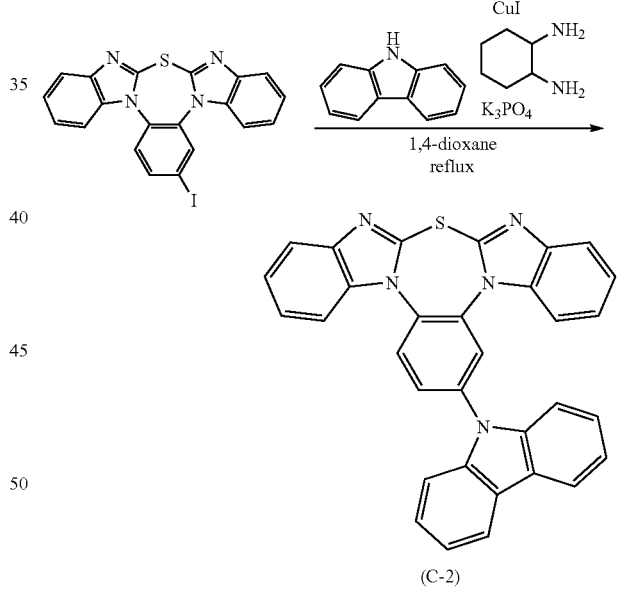

(C-2)

4.80 g (7.94 mmol) of bromo-iodo compound, 2.91 g (17.4 mmol) of carbazole, 0.079 g (0.41 mmol) of copper(I) iodide, 0.19 g (1.66 mmol) of trans-1,2-cyclohexanediamine and 7.21 g (33.9 mmol) of tripotassium phosphate in 150 ml of 1,4-dioxane are reflux for 24 h. The reaction mixture is cooled at room temperature and added 100 ml of 1N aqueous hydrochloric acid. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5) gives the product. Yield 2.55 g (44%).

¹H NMR (400 MHz, CDCl₃): δ 8.24 (t, J=2.1 Hz, 1H); 8.23-8.12 (m, 7H); 7.88-7.69 (m, 8H); 7.65-7.61 (m, 1H); 7.60-7.55 (m, 3H); 7.53-7.30 (m, 11H).

LC MS: 730.33 [M+1]

Example 33

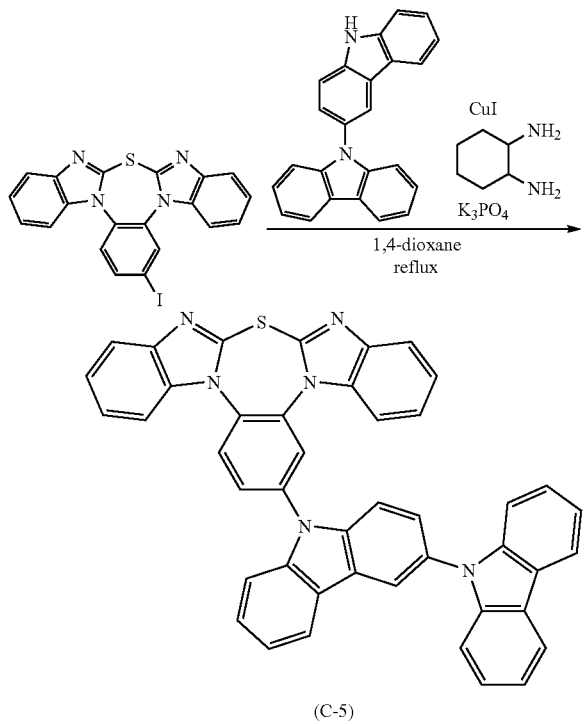

(C-5)

2.72 g (5.83 mmol) of bromo-iodo compound, 2.33 g (7.00 mmol) of 3-carbazolyl-carbazole, 0.056 g (0.29 mmol) of copper(I) iodide, 0.07 ml (0.58 mmol) of trans-1,2-cyclohexanediamine and 1.41 g (11.7 mmol) of tripotassium phosphate in 100 ml of 1,4-dioxane are reflux for 24 h. The reaction mixture is cooled at room temperature and added 50 ml of 1N aqueous hydrochloric acid. The inorganic solids are filtered, then the filtrate is extracted with dichloromethane. The organic layer is dried over sodium sulfate and concentrated in vacuo. Gradient column chromatography on silica gel with dichloromethane/ethyl acetate (dichloromethane 100%, 95/5) gives the product. Yield 4.3 g (93%).

¹H NMR (400 MHz, CDCl₃): δ 8.34 (d, J=1.9 Hz, 1H); 8.25-8.14 (m, 5H); 8.03 (dd, J=8.4, 2.4 Hz, 1H); 7.89 (d, J=7.5 Hz, 1H); 7.87-7.83 (m, 1H); 7.80 (d, J=8.7 Hz, 1H); 7.71 (d, J=7.8 Hz, 1H); 7.69-7.64 (m, 2H); 7.64-7.55 (m, 2H); 7.48-7.39 (m, 7H); 7.38-7.29 (m, 4H).

Comparative Application Example 1

A glass substrate with 120 nm-thick indium-tin-oxide (ITO) transparent electrode used as an anode is first cleaned with isopropanol in an ultrasonic bath for 10 min. To eliminate any possible organic residues, the substrate is exposed to an ultraviolet light and ozone for further 30 min. This treatment also improves the hole injection properties of the ITO. The cleaned substrate is mounted on a substrate holder and loaded into a vacuum chamber. Thereafter, the organic materials specified below are applied by vapor deposition to the ITO substrate at a rate of approx. 0.2-1 Å/sec at about 10⁻⁶-10⁻⁸ mbar. As a hole injection layer, As a hole injection layer, compound

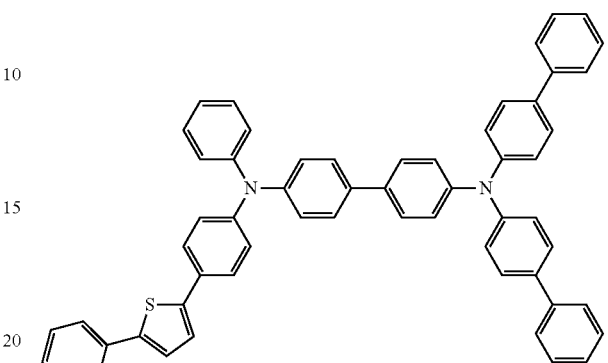

with 30 nm thickness is applied. As a hole transport, compound (SH-1)

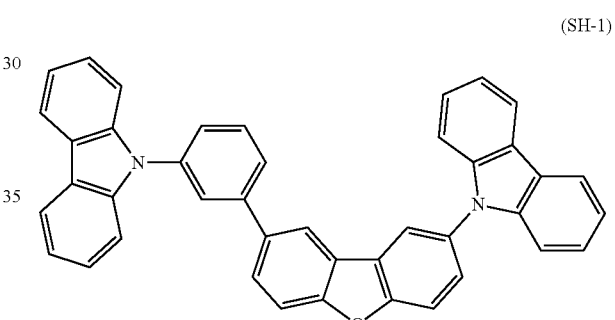

is applied by vapor deposition in a thickness of 60 nm doped with MoO$_x$ (~10%) to improve the conductivity. As exciton and electron blocker, (SH-1) is applied to the substrate with a thickness of 10 nm. Subsequently, a mixture of 20% by weight of emitter compound, (BE-1)

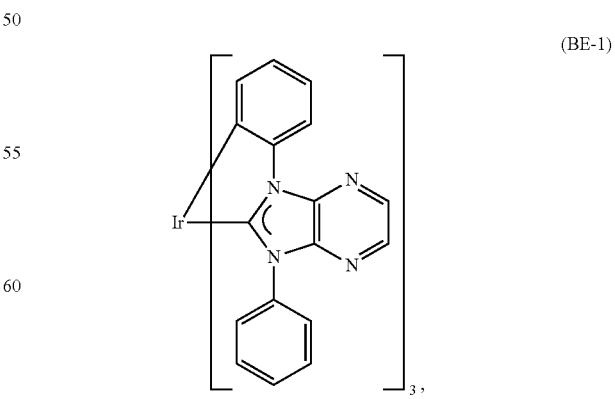

80% by weight of host compound

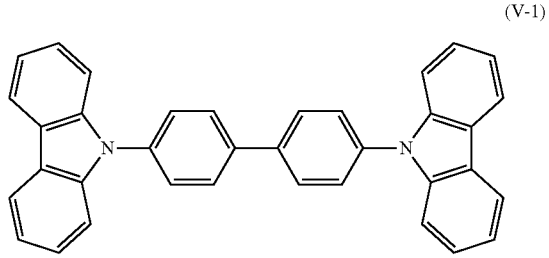 [SMILES: c1ccc2c(c1)c1ccccc1n2-c1ccc(-c2ccc(-n3c4ccccc4c4ccccc43)cc2)cc1]
(V-1)

are applied by vapor deposition in a thickness of 40 nm as an emitting layer. Subsequently, material

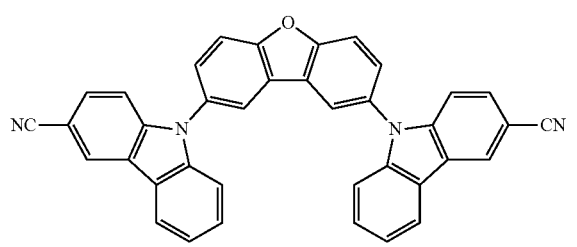 [SMILES: N#Cc1ccc2c(c1)c1ccccc1n2-c1ccc2oc3ccc(-n4c5ccccc5c5cc(C#N)ccc54)cc3c2c1]

(SH-2) is applied by vapour deposition with a thickness of 5 nm as an exciton and hole blocker. Thereafter, compound

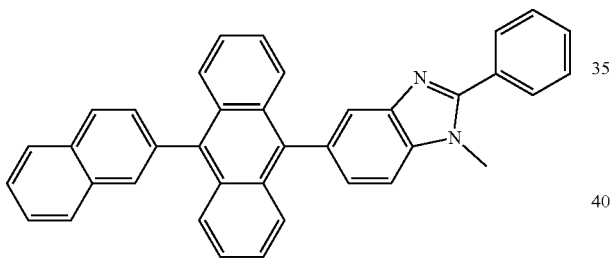

with 20 nm thickness is deposited as an electron transport layer. Finally, 1 nm-thick LiF is deposited as an electron injection layer and 80 nm-thick Al is then deposited as a cathode to complete the device. The device is sealed with a glass lid and a getter in an inert nitrogen atmosphere with less than 1 ppm of water and oxygen.

Comparative Application Example 2

Comparative Application Example 1 is repeated except that the host compound (V-1) is replaced by compound

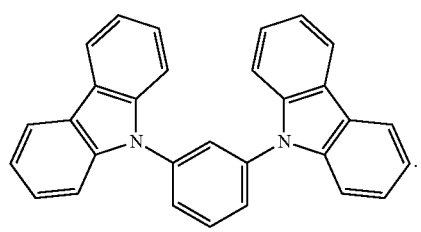
(V-2)

OLED Characterization

To characterize the OLED, electroluminescence spectra are recorded at various currents and voltages. In addition, the current-voltage characteristic is measured in combination with the luminance to determine luminous efficiency and external quantum efficiency (EQE). EQE are given at luminance (L)=1000 cd/m$^2$.

Application Examples 1, 2, 3, 4, 5 and 6

Comparative Application Example 1 is repeated except that the host (V-1) is replaced by compound

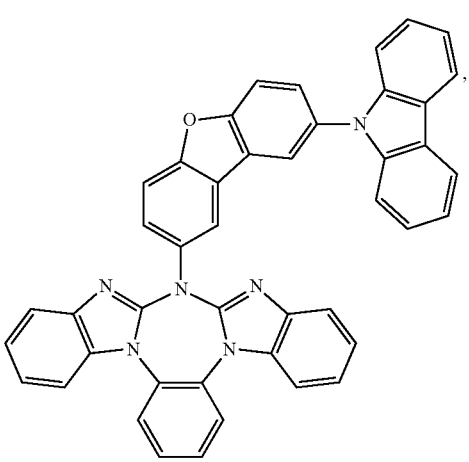
(A-25)

compound

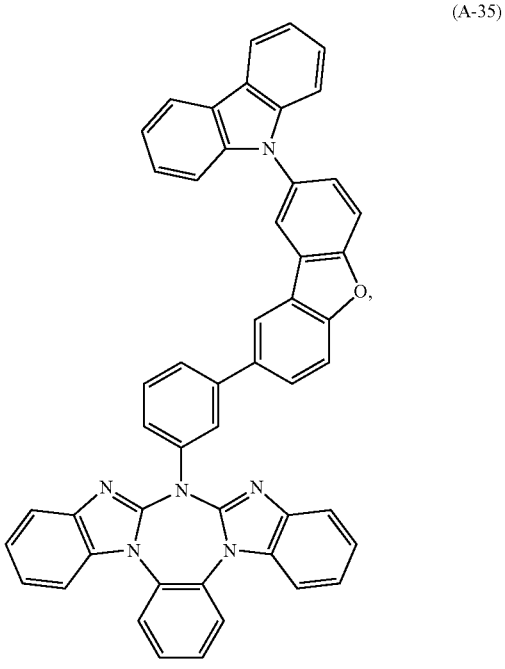 [SMILES: c1cc(-c2ccc3oc4ccc(-n5c6ccccc6c6ccccc65)cc4c3c2)cc(-n2c3nc4ccccc4n3c3ccccc3n3c4ccccc4nc23)c1]
(A-35)

compound (A-16)

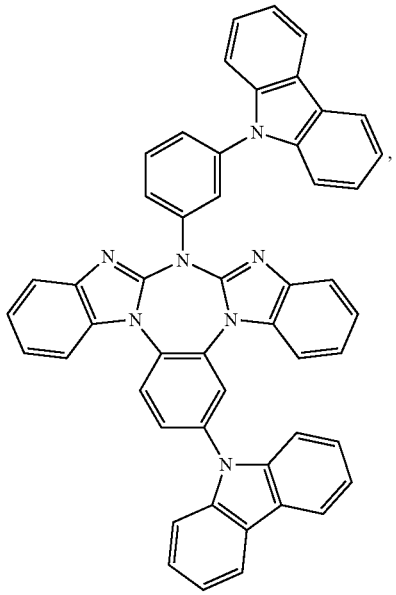

compound (B-1)

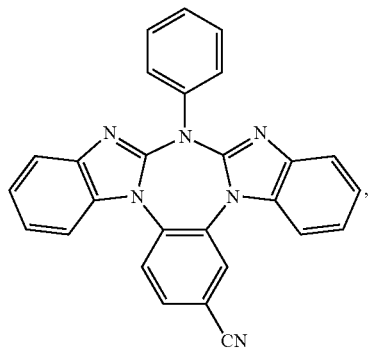

compound (B-5)

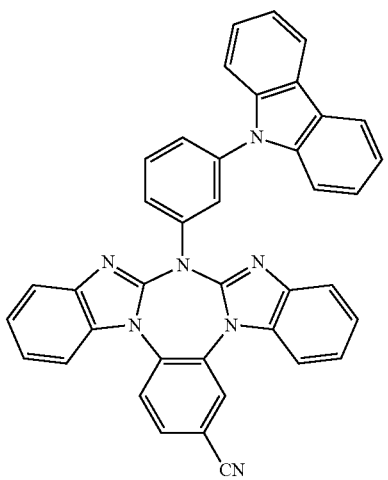

or compound (C-2)

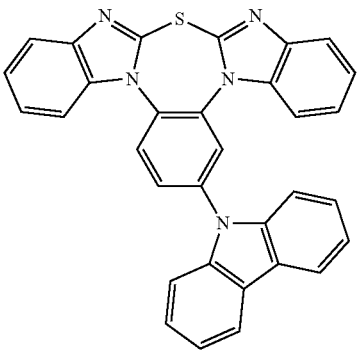

for Application Example 1, 2, 3, 4, 5 and 6 respectively. The device results are shown in Table 1.

TABLE 1

| Appl. Ex. | Host | EQE [%] |
| --- | --- | --- |
| 1 | (A-25) | 8.0 |
| 2 | (A-35) | 10.4 |
| 3 | (A-16) | 8.6 |
| 4 | (B-1) | 16.6 |
| 5 | (B-5) | 12.2 |
| 6 | (C-2) | 10.4 |
| Comp. Appl. Ex. 1 | (V-1) | 0.5 |
| Comp. Appl. Ex. 2 | (V-2) | 7.9 |

The results shown in Table 1 demonstrate that the EQE is improved when compounds (A-25), (A-35), (A-16), (B-1), (B-5) and (C-2) are used as a host instead of reference compounds (V-1) and (V-2).

The invention claimed is:

1. A compound of formula

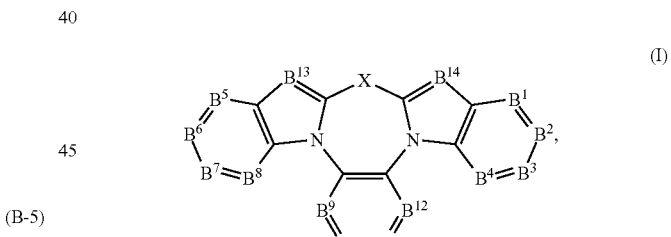

(I)

wherein $B^1$ is N or a $CR^{81}$ group,
$B^2$ is N or a $CR^{82}$ group,
$B^3$ is N or a $CR^{83}$ group,
$B^4$ is N or a $CR^{84}$ group,
$B^5$ is N or a $CR^{85}$ group,
$B^6$ is N or a $CR^{86}$ group,
$B^7$ is N or a $CR^{87}$ group,
$B^8$ is N or a $CR^{88}$ group,
$B^9$ is N or a $CR^{89}$ group,
B10 is N or a $CR^{90}$ group,
$B^{11}$ is N or a $CR^{91}$ group,
$B^{12}$ is N or a $CR^{92}$ group,
$B^{13}$ is N or a $CR^{93}$ group,
$B^{14}$ is N or a $CR^{94}$ group, and
X is an $NR^{95}$ group, S or O,
wherein $R^{81}$, $R^{82}$, $R^{83}$, $R^{84}$, $R^{85}$, $R^{86}$, $R^{87}$, $R^{88}$, $R^{89}$, $R^{90}$, $R^{91}$, $R^{92}$, $R^{93}$ and $R^{94}$ are each independently:

H; F; CN; a $C_1$-$C_{25}$ alkyl group, which can optionally be substituted by E and/or interrupted by D; a $C_6$-$C_{24}$ aryl group, which can optionally be substituted by G; a $C_2$-$C_{30}$ heteroaryl group, which can optionally be substituted by G; or a -$(A^5)_s$-$(A^6)_t$-$(A^7)_u$-$(A^8)_v$-$R^{17}$ group, and $R^{95}$ is a -$(A^1)_o$-$(A^2)_p$-$(A^3)_q$-$(A^4)_r$-$R^{16}$ group, wherein o, p, q, r, s, t, u and v are each independently 0 or 1, $R^{16}$ and $R^{17}$ are each independently: H; an —$NR^{10}R^{11}$ group; a —$C(=O)R^{15}$ group; an —$Si(R^{12})(R^{13})(R^{14})$ group; a $C_6$-$C_{24}$ aryl group, which can optionally be substituted by G; or a $C_2$-$C_{30}$ heteroaryl I group, which can optionally be substituted by G, wherein $R^{10}$, $R^{11}$ and $R^{15}$ are each independently: a $C_6$-$C_{24}$ aryl group, which can optionally be substituted by G; or a $C_2$-$C_{30}$ heteroaryl group, which can optionally be substituted by G, and if o, p, q and r are each 0, then $R^{16}$ is neither H nor the —$NR^{10}R^{11}$ group, $A^1$, $A^2$, $A^3$, $A^4$, $A^5$, $A^6$, $A^7$ and $A^8$ are each independently: an —$Si(R^{12'})(R^{13'})$— group; a $C_6$-$C_{24}$ arylene group, which can optionally be substituted by G: or a $C_2$-$C_{30}$ heteroarylene group, which can optionally be substituted by G, and $R^{12}$, $R^{13}$, $R^{12'}$, $R^{13'}$ and $R^{14}$ are each independently: a $C_1$-$C_{25}$ alkyl group, which can optionally be substituted by E and/or interrupted by D; a $C_6$-$C_{24}$ aryl group, which can optionally be substituted by G; or a $C_2$-$C_{30}$ heteroaryl group, which can optionally be substituted by G, each D is independently: —CO—, —COO—, —S—, —SO—, —$SO_2$—, —O—, an —$NR^{65}$— group, an —$SiR^{70}R^{71}$— group, a —$POR^{72}$— group, a —$CR^{63}=CR^{64}$— group or —C≡C—, each E is independently: an —$OR^{69}$ group, an —$SR^{69}$ group, an —$NR^{65}R^{66}$ group, a —$COR^{68}$ group, a —$COOR^{67}$ group, a —$CONR^{65}R^{66}$ group, —CN or F, each G is independently: E; an —$Si(R^{71})(R^{74})(R^{75})$ group; a $C_1$-$C_{18}$ alkyl group; a $C_6$-$C_{24}$ aryl group; a $C_6$-$C_{24}$ aryl group that is substituted by F, by a $C_1$-$C_{18}$ alkyl group or by a $C_1$-$C_{18}$ alkyl group that is interrupted by O; a $C_2$-$C_{30}$ heteroaryl group; or a $C_2$-$C_{30}$ heteroaryl group that is substituted by F, by a $C_1$-$C_{18}$ alkyl group or by a $C_1$-$C_{18}$ alkyl group that is interrupted by O, E, wherein $R^{63}$ and $R^{64}$ are each independently: H; a $C_6$-$C_{18}$ aryl group; a $C_6$-$C_{18}$ aryl group that is substituted by a $C_1$-$C_{18}$ alkyl group or a $C_1$-$C_{18}$ alkoxy group; a $C_1$-$C_{18}$ alkyl group; or a $C_1$-$C_{18}$ alkyl group that is interrupted by —O—, $R^{65}$ and $R^{66}$ are each independently: a $C_6$-$C_{18}$ aryl group; a $C_6$-$C_{18}$ aryl group that is substituted by a $C_1$-$C_{18}$ alkyl group or a $C_1$-$C_{18}$ alkoxy group; a $C_1$-$C_{18}$ alkyl group; or a $C_1$-$C_{18}$ alkyl group that is interrupted by —O—; or $R^{65}$ and $R^{66}$ together form a five or six membered ring, $R^{67}$ is a $C_6$-$C_{18}$ aryl group; a $C_6$-$C_{18}$ aryl group that is substituted by a $C_1$-$C_{18}$ alkyl group or a $C_1$-$C_{18}$ alkoxy group; a $C_1$-$C_{18}$ alkyl group; or a $C_1$-$C_{18}$ alkyl group that is interrupted by —O—, $R^{68}$ is H; a $C_6$-$C_{18}$ aryl group; a $C_6$-$C_{18}$ aryl group that is substituted by a $C_1$-$C_{18}$ alkyl group or a $C_1$-$C_{18}$ alkoxy group; a $C_1$-$C_{18}$ alkyl group; or a $C_1$-$C_{18}$ alkyl group that is interrupted by —O—, $R^{69}$ is a $C_6$-$C_{18}$ aryl group; a $C_6$-$C_{18}$ aryl group that is substituted by a $C_1$-$C_{18}$ alkyl group or a $C_1$-$C_{18}$ alkoxy group; a $C_1$-$C_{18}$ alkyl group; or a $C_1$-$C_{18}$ alkyl group that is interrupted by —O—, $R^{70}$ and $R^{71}$ are each independently: a $C_1$-$C_{18}$ alkyl group; a $C_6$-$C_{18}$ aryl group; or a $C_6$-$C_{18}$ aryl group that is substituted by a $C_1$-$C_{18}$ alkyl group, $R^{72}$ is a $C_1$-$C_{18}$ alkyl group; a $C_6$-$C_{18}$ aryl group; or a $C_6$-$C_{18}$ aryl group that is substituted by a $C_1$-$C_{18}$ alkyl group, and $R^{73}$, $R^{74}$ and $R^{75}$ are each independently: a $C_1$-$C_{25}$ alkyl group, which can optionally be interrupted by O; a $C_6$-$C_{24}$ aryl group, which can optionally be substituted by one or more $C_1$-$C_{18}$ alkyl groups; or a $C_2$-$C_{30}$ heteroaryl group, which can optionally be substituted by one or more $C_1$-$C_{18}$ alkyl groups, not more than two of $B^1$, $B^2$, $B^3$ and $B^4$ are N, and not more than two of $B^5$, $B^6$, $B^7$ and $B^8$ are N.

2. The compound of claim 1, wherein the compound satisfies formula

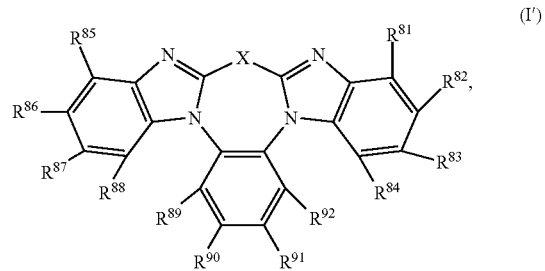

(I′)

wherein X, $R^{81}$, $R^{82}$, $R^{83}$, $R^{84}$, $R^{85}$, $R^{86}$, $R^{87}$, $R^{88}$, $R^{89}$, $R^{90}$, $R^{91}$ and $R^{92}$ are defined as in claim 1.

3. The compound of claim 1, wherein the compound satisfies formula

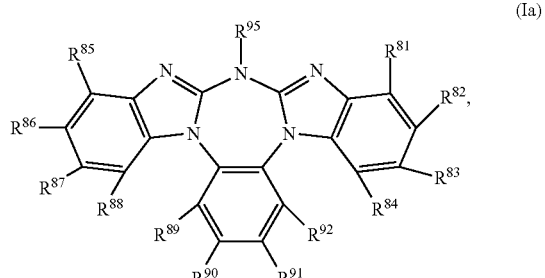

(Ia)

wherein $R^{95}$, $R^{81}$, $R^{82}$, $R^{83}$, $R^{84}$, $R^{85}$, $R^{86}$, $R^{87}$, $R^{88}$, $R^{89}$, $R^{90}$, $R^{91}$ and $R^{92}$ are defined as in claim 1.

4. The compound of claim 1, wherein the compound satisfies formula

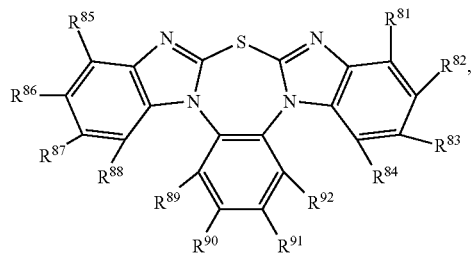
(Ib)

wherein $R^{81}$, $R^{82}$, $R^{83}$, $R^{84}$, $R^{85}$, $R^{86}$, $R^{87}$, $R^{88}$, $R^{89}$, $R^{90}$, $R^{91}$ and $R^{92}$ are defined as in claim 1.

5. The compound of claim 1, wherein $R^{81}$, $R^{82}$, $R^{83}$, $R^{84}$, $R^{85}$, $R^{86}$, $R^{87}$, $R^{88}$, $R^{89}$ and $R^{92}$ are H.

6. The compound of claim 1, wherein $R^{90}$ and $R^{91}$ are H, CN or a -$(A^5)_s$-$(A^6)_t$-$(A^7)_u$-$(A^8)_v$-$R^{17}$ group,
wherein s, t, u, v, $R^{17}$, $A^5$, $A^6$, $A^7$ and $A^8$ are defined as in claim 1.

7. The compound of claim 1, wherein $A^1$, $A^2$, $A^3$, $A^4$, $A^5$, $A^6$, A7 and $A^8$ are each independently:

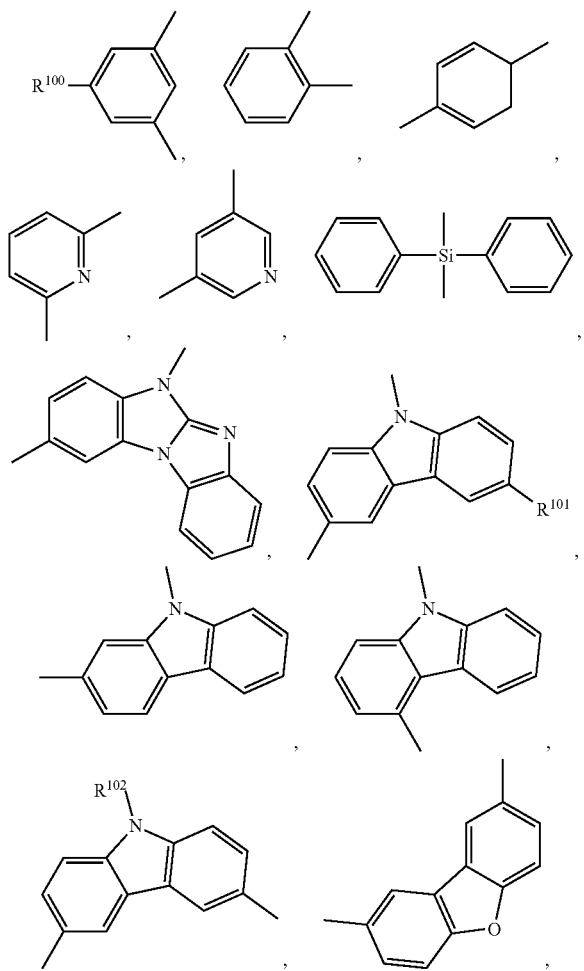

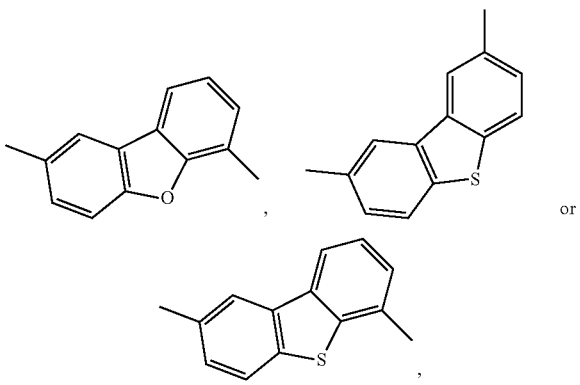

wherein $R^{100}$ is H, Si(Ph)$_3$ or

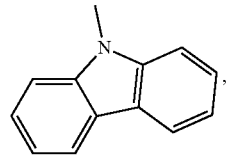

$R^{101}$ is H or CN, $R^{102}$ is a phenyl group, and o, p, q, r and $R^{16}$ are defined as in claim 1.

8. The compound of claim 1, wherein $R^{16}$ is: CN,

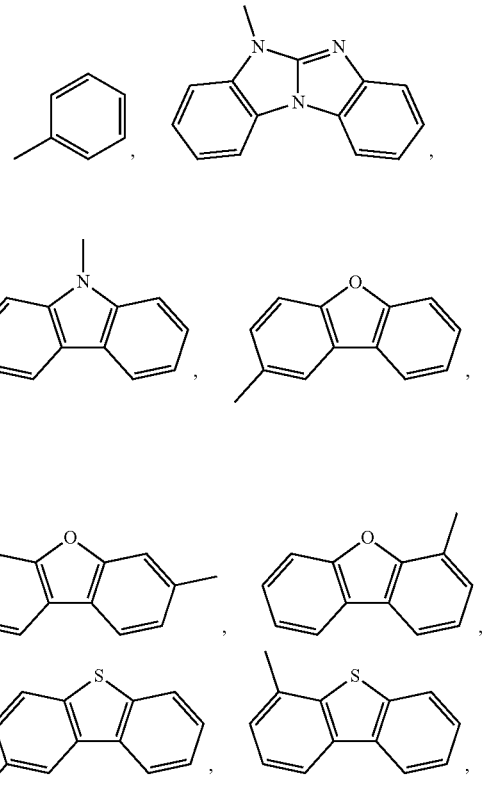

209
-continued
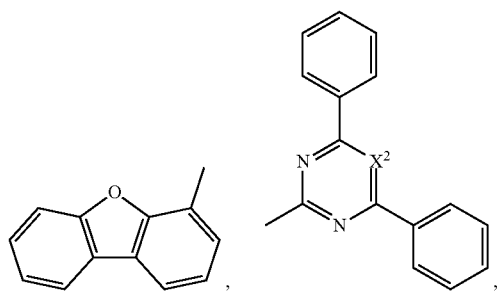
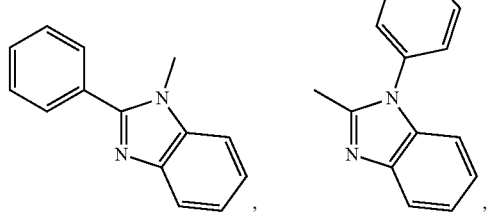
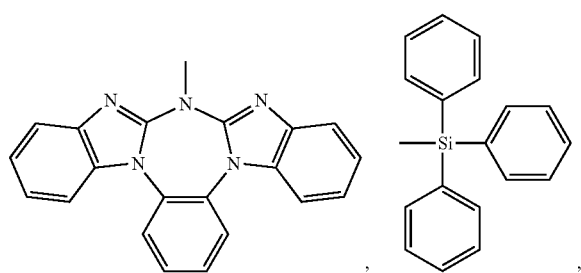
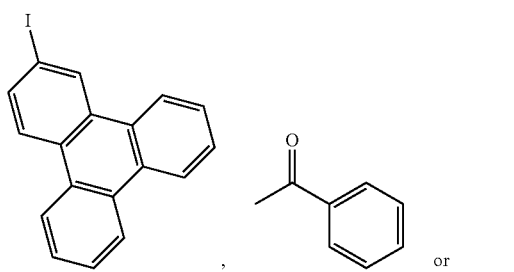
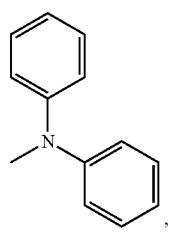
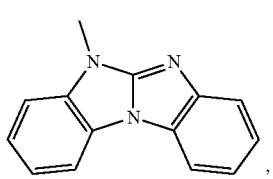
wherein $X^2$ is N or CH, and
o is 1 if $R^{16}$ is: CN,
210
-continued
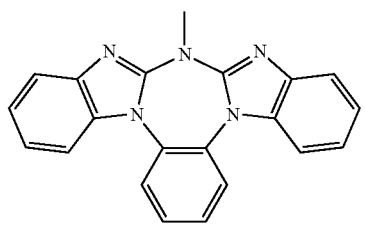
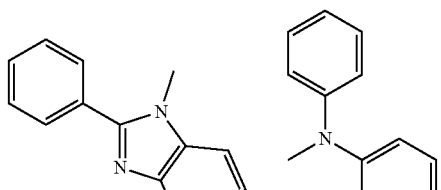
9. The compound of claim 1, wherein $R^{17}$ is: CN,
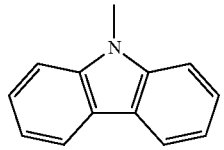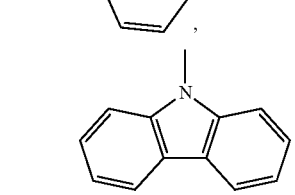
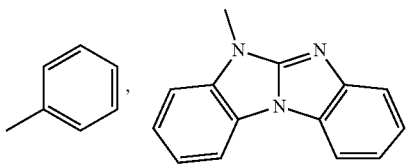
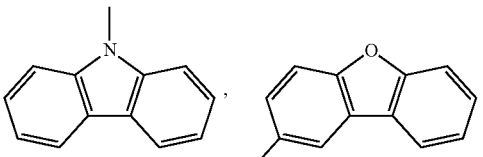
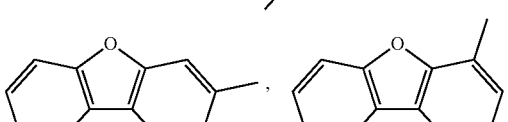
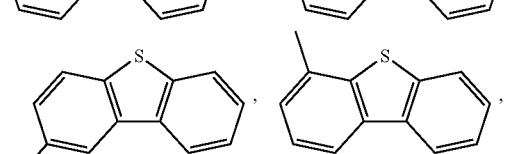
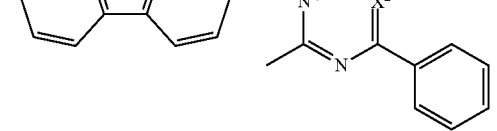

-continued
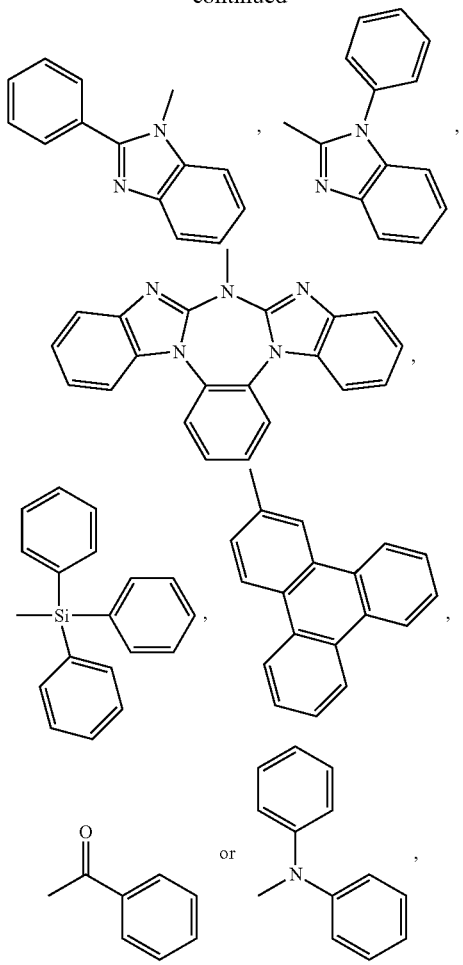
wherein $X^{2'}$ is N or CH.
10. The compound of claim 1, wherein the compound satisfies formula
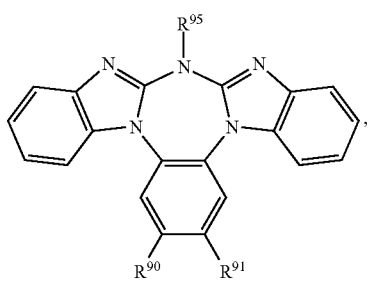
(Ia-1)
wherein $R^{95}$ is a $-(A^1)_o-(A^2)_p-(A^3)_q-(A^4)_r-R^{16}$ group, wherein $A^1$, $A^2$, $A^3$ and $A^4$ are each independently:
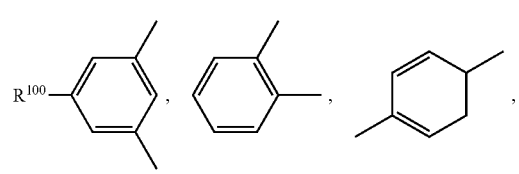
-continued
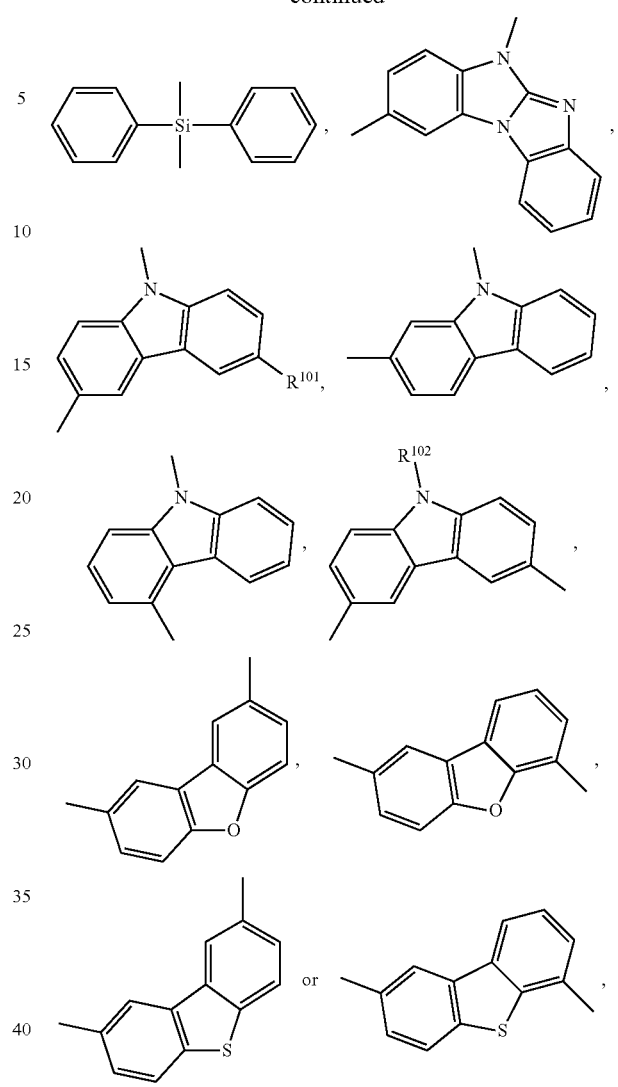
wherein $R^{100}$ is H, Si(Ph)$_3$ or
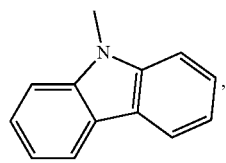
$R^{101}$ is H or CN, and
$R^{102}$ is a phenyl group,
$R^{16}$ is: CN,
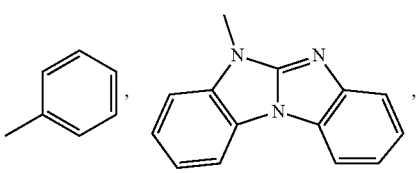

213
-continued
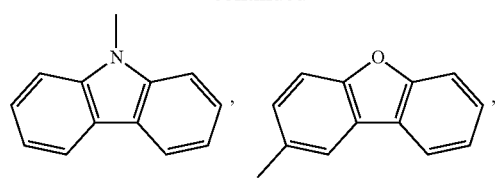
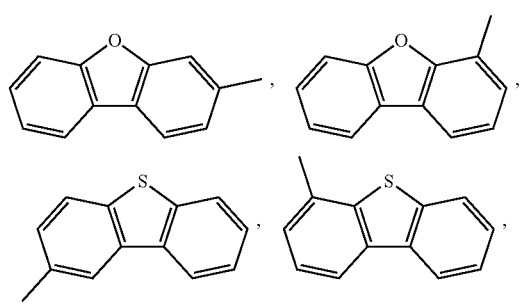
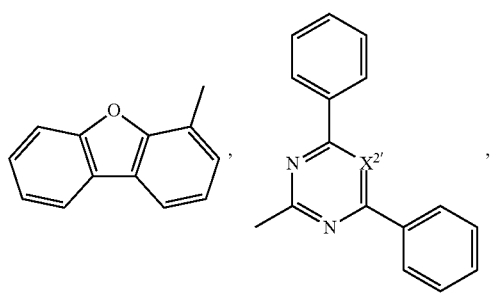
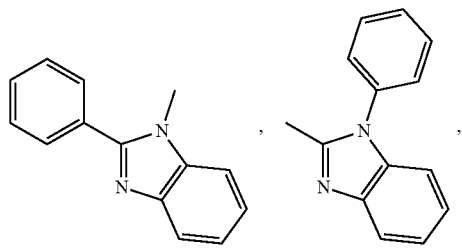
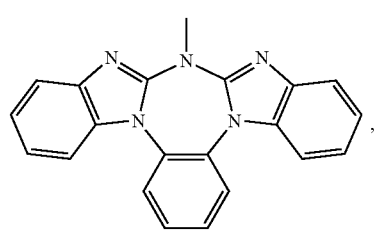
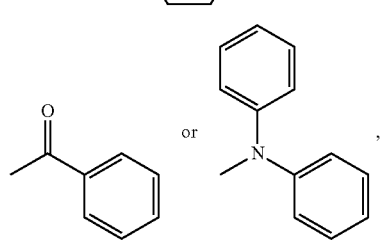
214
wherein $X^2$ is N or CH, and
o, p, q and r are each independently 0 or 1,
wherein o is 1 if $R^{16}$ is: CN,
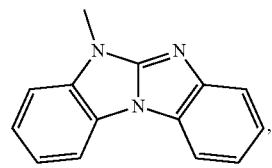
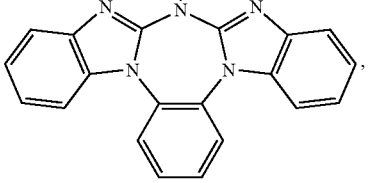
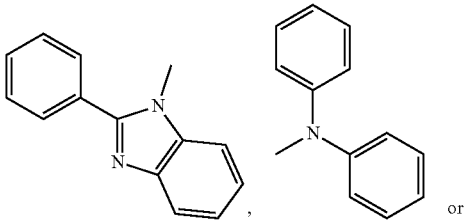
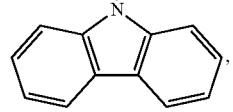
$R^{90}$ and $R^{91}$ are H; or $R^{90}$ and $R^{91}$ are CN; or one of $R^{90}$ and $R^{91}$ is H and the other is CN; or one of $R^{90}$ and $R^{91}$ is H and the other is a $-(A^5)_s-(A^6)_t-(A^7)_u-(A^8)_v-R^{17}$ group,
wherein s, t, u and v are each independently 0 or 1,
$A^5$, $A^6$, $A^7$ and $A^8$ are each independently:
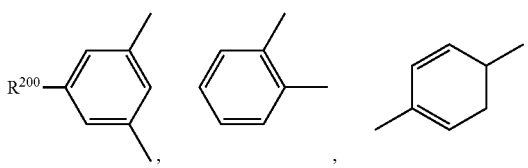
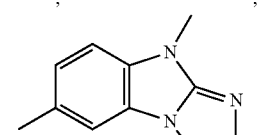
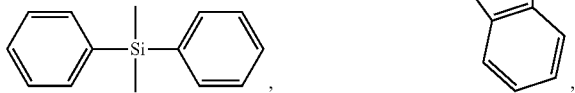
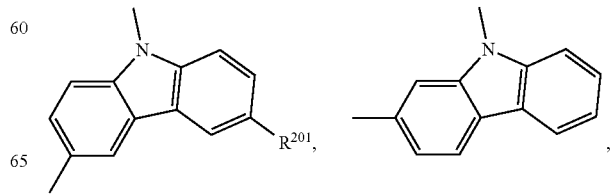

-continued

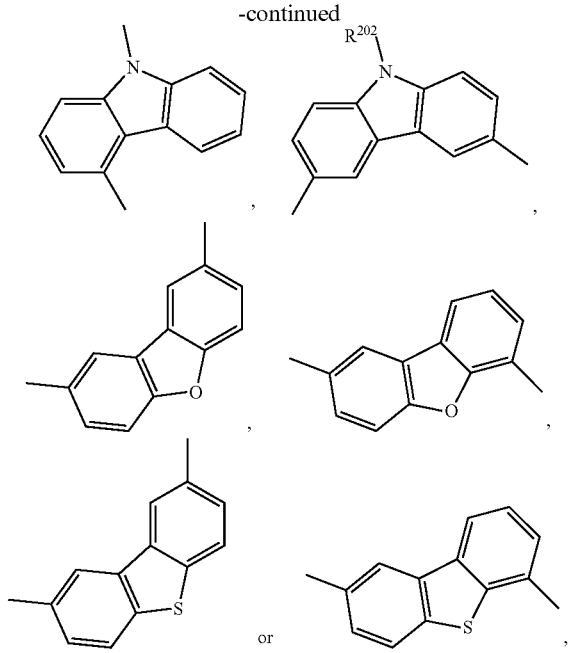

wherein $R^{200}$ is H, Si(Ph)$_3$ or

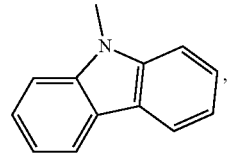

$R^{201}$ is H or CN, and
$R^{202}$ is a phenyl group, and
$R^{17}$ is: CN,

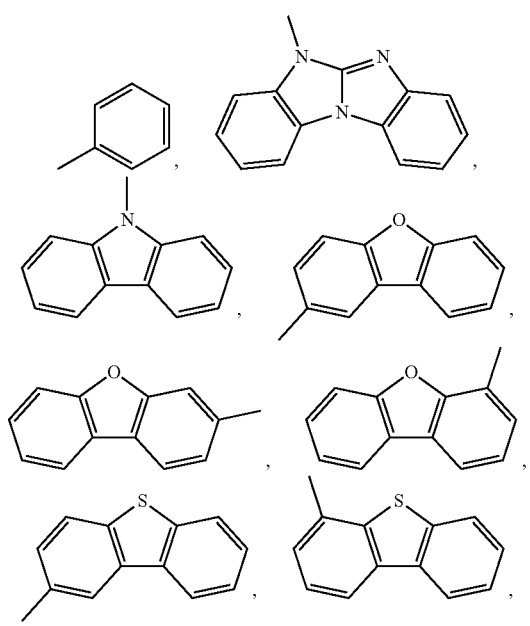

-continued

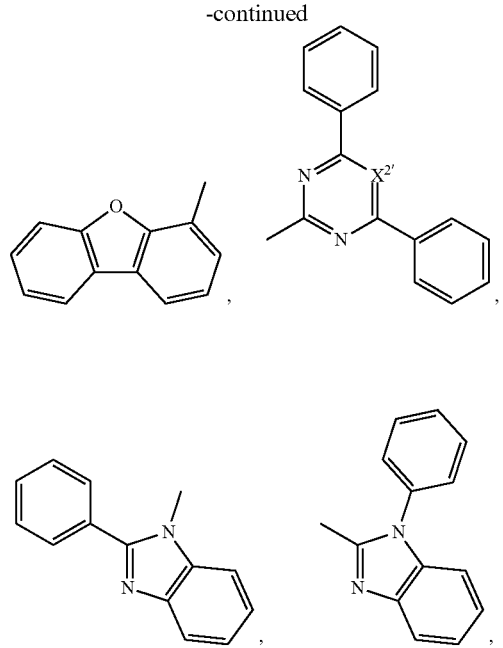

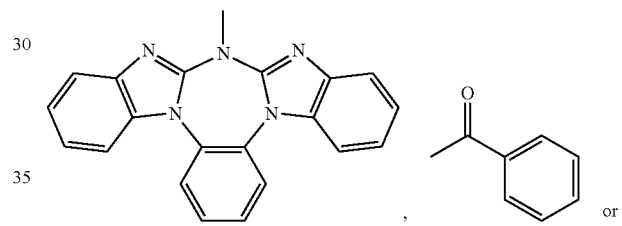

wherein $X^{2'}$ is N or CH.

11. The compound of claim 1, wherein the compound satisfies formula

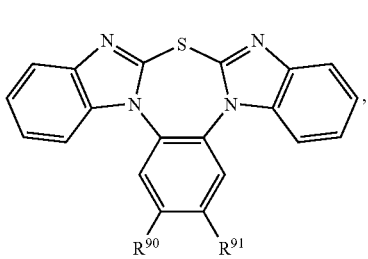

(Ib-1)

wherein $R^{90}$ and $R^{91}$ are H; or $R^{90}$ and $R^{91}$ are CN; or one of $R^{90}$ and $R^{91}$ is H and the other is CN; or one of $R^{90}$ and $R^{91}$ is H and the other is a -(A$^5$)$_s$-(A$^6$)$_t$-(A$^7$)$_u$-(A$^8$)$_v$-R$^{17}$ group, wherein s, t, u and v are each independently 0 or 1

217

$A^5$, $A^6$, $A^7$ and $A^8$ are each independently:

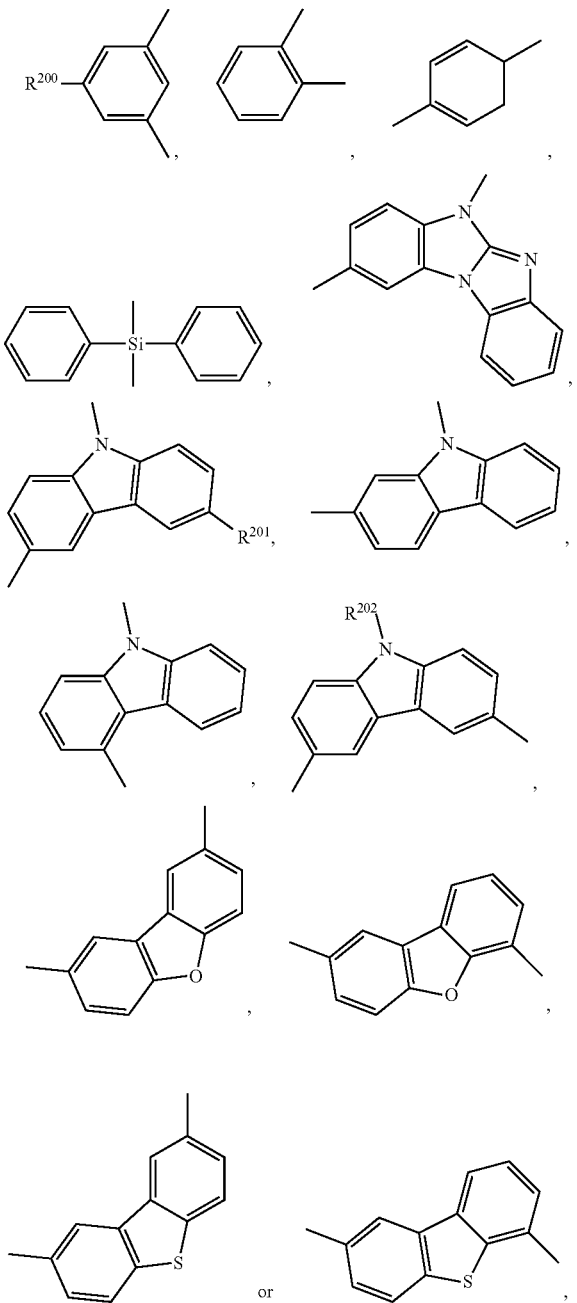

wherein $R^{200}$ is H, Si(Ph)$_3$ or

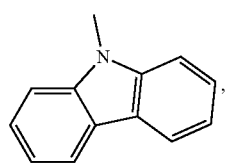

$R^{201}$ is H or CN, and $R^{202}$ is a phenyl group.

218

12. A compound of formula

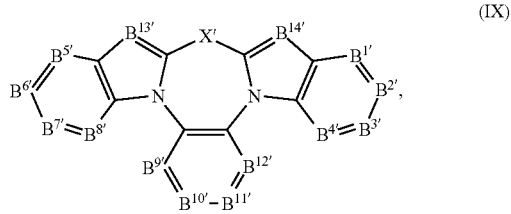

(IX)

wherein $B^{1'}$ is N or a $CR^{81'}$ group,
$B^{2'}$ is N or a $CR^{82'}$ group,
$B^{3'}$ is N or a $CR^{83'}$ group,
$B^{4'}$ is N or a $CR^{84'}$ group,
$B^{5'}$ is N or a $CR^{85'}$ group,
$B^{6'}$ is N or a $CR^{86'}$ group,
$B^{7'}$ is N or a $CR^{87'}$ group,
$B^{8'}$ is N or a $CR^{88'}$ group,
$B^{9'}$ is N or a $CR^{89'}$ group,
$B^{10'}$ is N or a $CR^{90'}$ group,
$B^{11'}$ is N or a $CR^{91'}$ group,
$B^{12'}$ is N or a $CR^{92'}$ group,
$B^{13'}$ is N or a $CR^{93'}$ group,
$B^{14'}$ is N or a $CR^{94'}$ group, and
X' is an $NR^{95'}$ group, S or O,
  wherein $R^{81'}$, $R^{82'}$, $R^{83'}$, $R^{84'}$, $R^{85'}$, $R^{86'}$, $R^{87'}$, $R^{88'}$, $R^{89'}$, $R^{90'}$, $R^{91'}$, $R^{92'}$, $R^{93'}$ and $R^{94'}$ are each independently:
  H; CN; a $C_1$-$C_{25}$ alkyl group, which can optionally be substituted by E and/or interrupted by D; a $C_6$-$C_{24}$ aryl group, which can optionally be substituted by G; a $C_2$-$C_{30}$ heteroaryl group, which can optionally be substituted by G; or a -$(A^5)_s$-$(A^6)_t$-$(A^7)_u$-$(A^8)_v$-$R^{17'}$ group,
$R^{95'}$ is a -$(A^1)_o$-$(A^2)_p$-$(A^3)_q$-$(A^4)_r$-$R^{16'}$ group,
  wherein o is 1,
  $R^{16'}$ and $R^{17'}$ are each independently: F, Cl, Br, I, —B(OH)$_2$, —B(OY$^1$)$_2$,

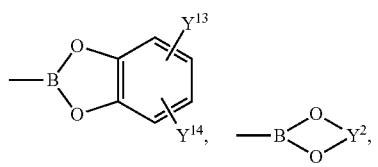

—BF$_4$Na or —BF$_4$K,
  wherein each $Y^1$ is independently a $C_1$-$C_{18}$ alkyl group; each $Y^2$ is independently a $C_2$-$C_{10}$ alkylene group; and each $Y^{13}$ and each $Y^{14}$ are independently H or a $C_1$-$C_{18}$ alkyl group,
at least one of $B^{1'}$ to $B^{14'}$ is different from N,
at least one of $R^{81'}$, $R^{82'}$, $R^{83'}$, $R^{84'}$, $R^{85'}$, $R^{86'}$, $R^{87'}$, $R^{88'}$, $R^{89'}$, $R^{90'}$, $R^{91'}$, $R^{92'}$, $R^{93'}$ and $R^{94'}$ is a -$(A^5)_s$-$(A^6)_t$-$(A^7)_u$-$(A^8)_v$-$R^{17'}$ group and/or $R^{95'}$ is a -$(A^1)_o$-$(A^2)_p$-$(A^3)_q$-$(A^4)_r$-$R^{16'}$ group, and p, q, r, s, t, u, v, D, E, G, $A^1$, $A^2$, $A^3$, $A^4$, $A^5$, $A^6$, $A^7$ and $A^8$ are defined as in claim 1.

13. An electronic device comprising the compound of claim 1.

14. The electronic device of claim 13, wherein the electronic device is an electroluminescent device.

15. A layer, wherein the layer is a charge transport layer, a charge/exciton blocker layer, or an emitting layer; and wherein the layer comprises the compound of claim 1.

16. An emitting layer, comprising the compound of claim 1 as a host material in combination with a phosphorescent emitter.

17. An apparatus selected from the group consisting of a stationary visual display unit, a mobile visual display unit, an illumination unit, a keyboard, an item of clothing, an item of furniture, and a wallpaper; wherein the apparatus comprises the electronic device of claim 13.

18. An apparatus selected from the group consisting of an electrophotographic photoreceptor, a photoelectric converter, an organic solar cell, a switching element, an organic light emitting field effect transistor, an image sensor, a dye laser and an electroluminescent device; wherein the apparatus comprises the compound of claim 1.

19. A compound satisfying formula

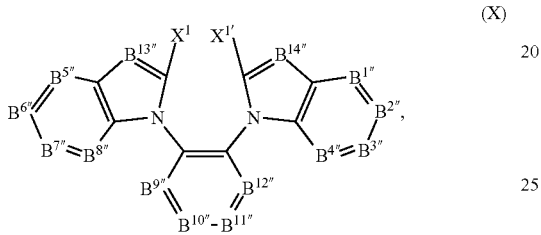

(X)

wherein $X^1$ and $X^{1'}$ are each independently: Cl, Br or I, $B^{1''}$ is N or a $CR^{81''}$ group,
$B^{2''}$ is N or a $CR^{82''}$ group,
$B^{3''}$ is N or a $CR^{83''}$ group,
$B^{4''}$ is N or a $CR^{84''}$ group,
$B^{5''}$ is N or a $CR^{85''}$ group,
$B^{6''}$ is N or a $CR^{86''}$ group,
$B^{7''}$ is N or a $CR^{87''}$ group,
$B^{8''}$ is N or a $CR^{88''}$ group,
$B^{9''}$ is N or a $CR^{89''}$ group,
$B^{10''}$ is N or a $CR^{90''}$ group,
$B^{11''}$ is N or a $CR^{91''}$ group,
$B^{12''}$ is N or a $CR^{92''}$ group,
$B^{13''}$ is N or a $CR^{93''}$ group, and
$B^{14''}$ is N or a $CR^{94''}$ group, wherein $R^{81'}$, $R^{82'}$, $R^{83'}$, $R^{84'}$, $R^{85'}$, $R^{86'}$, $R^{87'}$, $R^{88'}$, $R^{89'}$, $R^{90'}$, $R^{91'}$, $R^{92'}$, $R^{93'}$ and $R^{94'}$ are each independently: H; CN; a $C_1$-$C_{25}$ alkyl group, which can optionally be substituted by E and/or interrupted by D; a $C_6$-$C_{24}$ aryl group, which can optionally be substituted by G; a $C_2$-$C_3$ heteroaryl group, which can optionally be substituted by G; a -$(A^5)_s$-$(A^6)_t$-$(A^7)_u$-$(A^8)_v$-$R^{17'}$ group, a -$(A^5)_s$-$(A^6)_t$-$(A^7)_u$-$(A^8)_v$-$R^{17}$ group, wherein s, t, u and v are each independently 0 or 1, $R^{17}$ is: H; an —$NR^{10}R^{11}$ group: a —$C(=O)R^{15}$ group: an —$Si(R^{12})(R^{13})(R^{14})$ group; a $C_6$-$C_{24}$ aryl group, which can optionally be substituted by G; or a $C_2$-$C_{30}$ heteroaryl 1 group, which can optionally be substituted by G, wherein $R^{10}$, $R^{11}$ and $R^{15}$ are each independently: a $C_6$-$C_{24}$ aryl group, which can optionally be substituted by G; or a $C_2$-$C_{30}$ heteroaryl group, which can optionally be substituted by G, wherein each $R^{17'}$ is independently: F, Cl, Br, I, —$B(OH)_2$, —$B(OY^1)_2$,

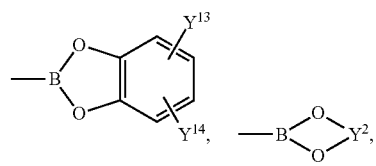

—$BF_4Na$ or —$BF_4K$, wherein each $Y^1$ is independently a $C_1$-$C_{18}$ alkyl group; each $Y^2$ is independently a $C_2$-$C_{10}$ alkylene group; and each $Y^{13}$ and each $Y^{14}$ are independently H or a $C_1$-$C_{18}$ alkyl group, and $A^5$, $A^6$, $A^7$ and $A^8$ are each independently: an —Si $(R^{12'})(R^{13'})$— group; a $C_6$-$C_{24}$ arylene group, which can optionally be substituted by G; or a $C_2$-$C_{30}$ heteroarylene group, which can optionally be substituted by G, $R^{12}$, $R^{13}$, $R^{12'}$, $R^{13'}$ and $R^{14}$ are each independently: a $C_1$-$C_{25}$ alkyl group, which can optionally be substituted by E and/or interrupted by D; a $C_6$-$C_{24}$ aryl group, which can optionally be substituted by G; or a $C_2$-$C_{30}$ heteroaryl group, which can optionally be substituted by G, each D is independently: —CO—, —COO—, —S—, —SO—, —SO$_2$—, —O—, an —$NR^{65}$— group, an —$SiR^{70}R^{71}$— group, a —$POR^{72}$— group, a —$CR^{63}=CR^{64}$— group or —C≡C—, each E is independently: an —$OR^{69}$ group, an —$SR^{69}$ group, an —$NR^{65}R^{66}$ group, a —$COR^{67}$ group, a —$COOR^{67}$ group, a —$CONR^{65}R^{66}$ group, —CN or F, each G is independently: E; an —$Si(R^{73})(R^{74})(R^{75})$ group; a $C_1$-$C_{18}$ alkyl group; a $C_6$-$C_{24}$ aryl group; a $C_6$-$C_{24}$ aryl group that is substituted by F, by a $C_1$-$C_{18}$ is alkyl group or by a $C_1$-$C_{18}$ alkyl group that is interrupted by O; a $C_2$-$C_{30}$ heteroaryl group; or a $C_2$-$C_{30}$ heteroaryl group that is substituted by F, by a $C_1$-$C_{18}$ alkyl group or by a $C_1$-$C_{18}$ alkyl group that is interrupted by O, E, wherein $R^{63}$ and $R^{64}$ are each independently: H; a $C_6$-$C_{18}$ aryl group; a $C_6$-$C_{18}$ aryl group that is substituted by a $C_1$-$C_{18}$ alkyl group or a $C_1$-$C_{18}$ alkoxy group; a $C_1$-$C_{18}$ alkyl group; or a $C_1$-$C_{18}$ alkyl group that is interrupted by —O—, $R^{65}$ and $R^{66}$ are each independently: a $C_6$-$C_{18}$ aryl group; a $C_6$-$C_{18}$ aryl group that is substituted by a $C_1$-$C_{18}$ alkyl group or a $C_1$-$C_{18}$ alkoxy group; a $C_1$-$C_{18}$ alkyl group; or a $C_1$-$C_{18}$ alkyl group that is interrupted by —O—; or $R^{65}$ and $R^{66}$ together form a five or six membered ring, $R^{67}$ is a $C_6$-$C_{18}$ aryl group; a $C_6$-$C_{18}$ aryl group that is substituted by a $C_1$-$C_{18}$ alkyl group or a $C_1$-$C_{18}$ alkoxy group; a $C_1$-$C_{18}$ alkyl group; or a $C_1$-$C_{18}$ alkyl group that is interrupted by —O—, $R^{68}$ is H; a $C_6$-$C_1$-$C_{18}$ aryl group; a $C_6$-$C_{18}$ aryl group that is substituted by a $C_1$-$C_{18}$ alkyl group or a $C_1$-$C_{18}$ alkoxy group; a $C_1$-$C_{18}$ alkyl group: or a $C_1$-$C_{18}$ alkyl group that is interrupted by —O—, $R^{69}$ is a $C_6$-$C_{18}$ aryl group; a $C_6$-$C_{18}$ aryl group that is substituted by a $C_1$-$C_{18}$ alkyl group or a $C_1$-$C_{18}$ alkoxy group; a $C_1$-$C_{18}$ alkyl group; or a $C_1$-$C_{18}$ alkyl group that is interrupted by —O—, $R^{70}$ and $R^{71}$ are each independently: a $C_1$-$C_{18}$ alkyl group; a $C_6$-$C_{18}$ aryl group: or a $C_6$-$C_{18}$ aryl group that is substituted by a $C_1$-$C_{18}$ alkyl group, $R^{72}$ is a $C_1$-$C_{18}$ alkyl group; a $C_6$-$C_{18}$ aryl group; or a $C_6$-$C_{18}$ aryl group that is substituted by a $C_1$-$C_{18}$ alkyl group, and $R^{73}$, $R^{74}$ and $R^{75}$ are each independently: a $C_1$-$C_{25}$ alkyl group, which can optionally be interrupted by O; a $C_6$-$C_{24}$ aryl group, which can optionally be substituted by one or more $C_1$-$C_{18}$ alkyl groups; or a $C_2$-$C_{30}$ heteroaryl group, which can optionally be substituted by one or more $C_1$-$C_{18}$ alkyl groups.

20. The compound of claim 19, wherein the compound satisfies formula

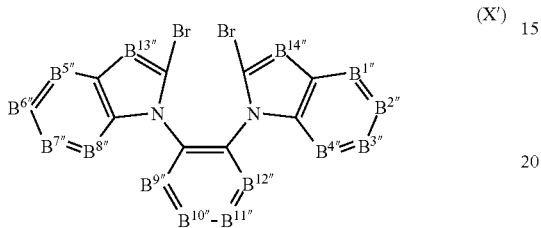

(X')

wherein $B^{1''}$ to $B^{14''}$ are defined as in claim 19.

21. A process of producing (i) a compound of formula

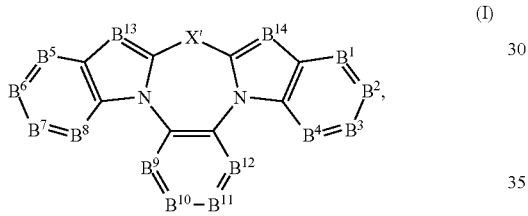

(I)

wherein X is an $NR^{95}$ group or S, or
(ii) a compound of formula

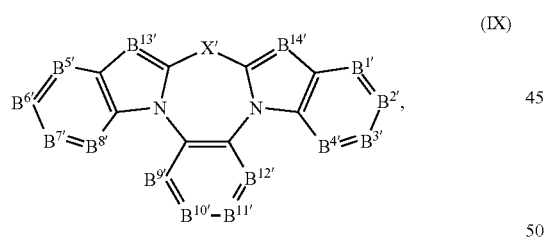

(IX)

wherein X' is an $NR^{95'}$ group or S,
wherein the process comprises:
reacting a compound of formula

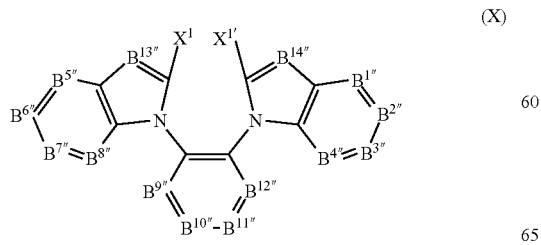

(X)

with:
(A) a compound of formula $NH_2R^{95}$ (XIIIa), optionally in a solvent at elevated temperature,
wherein $R^{95}$ is a $-(A^1)_o-(A^2)_p-(A^3)_q-(A^4)_r-R^{16}$ group
(B) a compound of formula $NH_2R^{95'}$ (XIIIb), optionally in a solvent at elevated temperature,
wherein $R^{95'}$ is a $-(A^1)_o-(A^2)_p-(A^3)_q-(A^4)_r-R^{16'}$ group, or
(C) natrium hydrogensulfite in a solvent at elevated temperature,
wherein o, p, q, r, s, $R^{16}$, $R^{95}$, $A^1$, $A^2$, $A^3$ and $A^4$ are defined as in claim 1,
wherein $X^1$ and $X^{1'}$ are each independently Cl, Br or I
wherein $B^{1'}$ is N or a $CR^{81'}$ group,
$B^{2'}$ is N or a $CR^{82'}$ group,
$B^{3'}$ is N or a $CR^{83'}$ group,
$B^{4'}$ is N or a $CR^{84'}$ group,
$B^{5'}$ is N or a $CR^{85'}$ group,
$B^{6'}$ is N or a $CR^{86'}$ group,
$B^{7'}$ is N or a $CR^{87'}$ group,
$B^{8'}$ is N or a $CR^{88'}$ group,
$B^{9'}$ is N or a $CR^{89'}$ group,
$B^{10'}$ is N or a $CR^{90'}$ group,
$B^{11'}$ is N or a $CR^{91'}$ group,
$B^{12'}$ is N or a $CR^{92'}$ group,
$B^{13'}$ is N or a $CR^{93'}$ group, and
$B^{14'}$ is N or a $CR^{94'}$ group,
wherein $R^{81'}$, $R^{82'}$, $R^{83'}$, $R^{84'}$, $R^{85'}$, $R^{86'}$, $R^{87'}$, $R^{88'}$, $R^{89'}$, $R^{90'}$, $R^{91'}$, $R^{92'}$, $R^{93'}$ and $R^{94'}$ are each independently: H; CN; a $C_1$-$C_{25}$ alkyl group, which can optionally be substituted by E and/or interrupted by D; a $C_6$-$C_{24}$ aryl group, which can optionally be substituted by G; a $C_2$-$C_{30}$ heteroaryl group, which can optionally be substituted by G; or a $-(A^5)_s-(A^6)_t-(A^7)_u-(A^8)_v-R^{17'}$ group,
$R^{95'}$ is a $-(A^1)_o-(A^2)_p-(A^3)_q-(A^4)_r-R^{16'}$ group,
wherein o is 1,
$R^{16'}$ and $R^{17'}$ are each independently: F, Cl, Br, I, $—B(OH)_2$, $—B(OY^1)_2$,

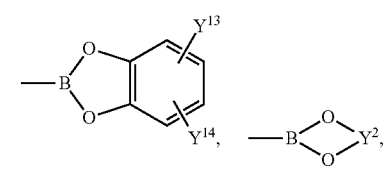

$—BF_4Na$ or $—BF_4K$,
wherein each $Y^1$ is independently a $C_1$-$C_{18}$ alkyl group; each $Y^2$ is independently a $C_2$-$C_{10}$ alkylene group; and each $Y^{13}$ and each $Y^{14}$ are independently H or a $C_1$-$C_{18}$ alkyl group,
at least one of $B^{1'}$ to $B^{14'}$ is different from N,
at least one of $R^{81'}$, $R^{82'}$, $R^{83'}$, $R^{84'}$, $R^{85'}$, $R^{86'}$, $R^{87'}$, $R^{88'}$, $R^{89'}$, $R^{90'}$, $R^{91'}$, $R^{92'}$, $R^{93'}$ and $R^{94'}$ is a $-(A^5)_s-(A^6)_t-(A^7)_u-(A^8)_v-R^{17'}$ group and/or $R^{95'}$ is a $-(A^1)_o-(A^2)_p-(A^3)_q-(A^4)_r-R^{16'}$ group, and p, q, r, s, t, u, v, D, E, G, $A^1$, $A^2$, $A^3$, $A^4$, $A^5$, $A^6$, $A^7$ and $A^8$ are defined as in claim 1, and
wherein $B^{1''}$ is N or a $CR^{81''}$ group,
$B^{2''}$ is N or a $CR^{82''}$ group,
$B^{3''}$ is N or a $CR^{83''}$ group,
$B^{4''}$ is N or a $CR^{84''}$ group,
$B^{5''}$ is N or a $CR^{85''}$ group,
$B^{6''}$ is N or a $CR^{86''}$ group,
$B^{7''}$ is N or a $CR^{87''}$ group, $B^{8''}$ is N or a $CR^{88''}$ group,
$B^{9''}$ is N or a $CR^{89''}$ group,
$B^{10''}$ is N or a $CR^{90''}$ group,
$B^{11''}$ is N or a $CR^{91''}$ group,
$B^{12''}$ is N or a $CR^{92''}$ group,
$B^{13''}$ is N or a $CR^{93''}$ group, and
$B^{14''}$ is N or a $CR^{94''}$ group,
wherein $R^{81'}$, $R^{82'}$, $R^{83'}$, $R^{84'}$, $R^{85'}$, $R^{86'}$, $R^{87'}$, $R^{88'}$, $R^{89'}$, $R^{90'}$, $R^{91'}$, $R^{92'}$, $R^{93'}$ and $R^{94'}$ are each independently: H; CN; a $C_1$-$C_{25}$ alkyl group, which can optionally be substituted by E and/or interrupted by D; a $C_6$-$C_{24}$ aryl group, which can optionally be substituted by G; a $C_2$-$C_{30}$ heteroaryl group, which can optionally be substituted by G; a -$(A^5)_s$-$(A^6)_t$-$(A^7)_u$-$(A^8)_v$-$R^{17'}$ group; or a -$(A^5)_s$-$(A^6)_t$-$(A^7)_u$-$(A^8)_v$-$R^{17}$ group, wherein each $R^{17'}$ is independently: F, Cl, Br, I, —$B(OH)_2$, —$B(OY^1)_2$,

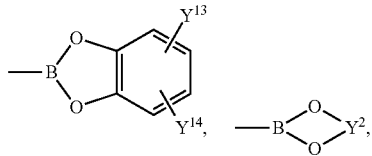

—$BF_4Na$ or —$BF_4K$,
wherein each $Y^1$ is independently a $C_1$-$C_{18}$ alkyl group; each $Y^2$ is independently a $C_2$-$C_{10}$ alkylene group; and each $Y^{13}$ and each $Y^{14}$ are independently H or a $C_1$-$C_{18}$ alkyl group, and s, t, u, v, D, E, G, $R^{17}$, $A^5$, $A^6$, $A^7$ and $A^8$ are defined as in claim 1.

22. An electronic device, comprising the compound of claim 12.

23. The electronic device of claim 22, wherein the electronic device is an electroluminescent device.

24. A layer, wherein the layer is a charge transport layer, a charge/exciton blocker layer, or an emitting layer; and wherein the layer comprises the compound of claim 12.

25. An emitting layer, comprising the compound of claim 12 as a host material in combination with a phosphorescent emitter.

26. An apparatus selected from the group consisting of a stationary visual display unit, a mobile visual display unit, an illumination unit, a keyboard, an item of clothing, an item of furniture, and a wallpaper; wherein the apparatus comprises the electronic device of claim 22.

27. An apparatus selected from the group consisting of a stationary visual display unit, a mobile visual display unit, an illumination unit, a keyboard, an item of clothing, an item of furniture, and a wallpaper: wherein the apparatus comprises the layer of claim 15.

28. An apparatus selected from the group consisting of a stationary visual display unit, a mobile visual display unit, an illumination unit, a keyboard, an item of clothing, an item of furniture, and a wallpaper, wherein the apparatus comprises the layer of claim 24.

29. An apparatus selected from the group consisting of an electrophotographic photoreceptor, a photoelectric converter, an organic solar cell, a switching element, an organic light emitting field effect transistor, an image sensor, a dye laser and an electroluminescent device; wherein the apparatus comprises the compound of claim 12.

* * * * *